United States Patent
Bigi et al.

(10) Patent No.: US 12,247,015 B2
(45) Date of Patent: Mar. 11, 2025

(54) 3-AMINO-4H-BENZO[E][1,2,4]THIADIAZINE 1,1-DIOXIDE DERIVATIVES AS INHIBITORS OF MRGX2

(71) Applicant: Solent Therapeutics, LLC, Wellesley, MA (US)

(72) Inventors: Simone Bigi, San Diego, CA (US); Alison L. Chambers, San Diego, CA (US); Tony Gibson, San Diego, CA (US); Jason Pickens, San Diego, CA (US); Steve Swann, San Diego, CA (US); Angie Vassar, San Diego, CA (US); Feng Zhou, San Diego, CA (US); Mitsunori Kono, Kanagawa (JP); Masaki Seto, Kanagawa (JP); Zenyu Shiokawa, Kanagawa (JP)

(73) Assignee: SOLENT THERAPEUTICS, LLC, Palo Alto, CA (US)

( * ) Notice: Subject to any disclaimer, the term of this patent is extended or adjusted under 35 U.S.C. 154(b) by 747 days.

(21) Appl. No.: 17/605,962

(22) PCT Filed: Apr. 28, 2020

(86) PCT No.: PCT/US2020/030305
§ 371 (c)(1),
(2) Date: Oct. 22, 2021

(87) PCT Pub. No.: WO2020/223255
PCT Pub. Date: Nov. 5, 2020

(65) Prior Publication Data
US 2022/0119361 A1 Apr. 21, 2022

Related U.S. Application Data

(60) Provisional application No. 62/840,344, filed on Apr. 29, 2019.

(51) Int. Cl.
*C07D 285/24* (2006.01)
*C07D 417/10* (2006.01)
*A61K 45/06* (2006.01)

(52) U.S. Cl.
CPC ......... *C07D 285/24* (2013.01); *C07D 417/10* (2013.01); *A61K 45/06* (2013.01)

(58) Field of Classification Search
CPC .................................................. C07D 285/24
See application file for complete search history.

(56) References Cited

U.S. PATENT DOCUMENTS

2016/0096874 A1   4/2016   Golz et al.

FOREIGN PATENT DOCUMENTS

| CN | 201810140937 | | 2/2018 |
|---|---|---|---|
| EP | 105732 | A2 | 9/1983 |
| EP | 386931 | A1 | 2/1990 |
| EP | 2457906 | A1 | 5/2012 |
| JP | 2013083504 | | 5/2013 |
| WO | WO-9111172 | A1 | 8/1991 |
| WO | WO-9402518 | A1 | 2/1994 |
| WO | 1997049692 | A1 | 12/1997 |
| WO | WO-9855148 | A1 | 12/1998 |
| WO | 1999042456 | A2 | 2/1999 |
| WO | 99/32467 | A1 | 7/1999 |
| WO | 2003004604 | A2 | 1/2003 |
| WO | 2003073107 | A2 | 9/2003 |
| WO | 2003087089 | A1 | 10/2003 |
| WO | 2003091245 | A1 | 11/2003 |
| WO | 2004000999 | A2 | 12/2003 |
| WO | 2005/019191 | A2 | 3/2005 |
| WO | 2005028667 | A1 | 3/2005 |
| WO | 2005/067933 | A1 | 7/2005 |
| WO | 2006033972 | A2 | 3/2006 |
| WO | 2006062316 | A1 | 3/2006 |
| WO | 2006089286 | A2 | 8/2006 |
| WO | 2006108581 | A2 | 10/2006 |
| WO | 2006118328 | A1 | 11/2006 |

(Continued)

OTHER PUBLICATIONS

Innes et al. (Aus. J. Chem., 2018, 71, pp. 610-623).* Pettus, et al., Discovery and Optimization of Quinazolinone-pyrrolopyrrolones as Potent and Orally Bioavailable Pan-Pim Kinase Inhibitors, J. Med. Chem. 2016, 59, pp. 6407-6430.
Jensen et al. Phosphorus Pentoxide in Organic Synthesis, Chemica Scripta, vol. 20, No. 5, Jan. 1, 1982, pp. 248-250.
Takeshi Nanjo et al., Divergent and Scalable Synthesis of alpha-hydroxy/keto-beta- amino acid analogues by the catalytic enantioselective addition of glyoxylate cyanohydrin to imines, ACS Catalysis, vol. 9, No. 11, Nov. 24, 2019, pp. 10087-10092.
Innes et al., N, N-Dialkyl-N'-Chlorosulfonyl Chloroformamidines in Heterocyclic Synthesis. Part XV .* Some Unexpected Reactions with Anilines. Aus. J. Chem., 2018, 71, pp. 610-623.
Tullio, et al. -Alkylamino-4H-1,2,4-benzothiadiazine 1,1-Dioxides as ATP-Sensitive Potassium Channel Openers: Effect of 6,7-Disubstitution on Potency and Tissue Selectivity, journal of Medicinal Chemistry, 2005, vol. 48, No. 15 4993.

(Continued)

*Primary Examiner* — Valerie Rodriguez-Garcia
(74) *Attorney, Agent, or Firm* — WILSON SONSINI GOODRICH & ROSATI

(57) ABSTRACT

Disclosed are compounds of Formula (1), tautomers thereof, and pharmaceutically acceptable salts of the compounds or tautomers, wherein L, $R^1$, $R^2$, $R^3$, $R^4$ and $R^5$ are defined in the specification. This disclosure also relates to materials and methods for preparing compounds of Formula (1), to pharmaceutical compositions which contain them, and to their use for treating diseases, disorders or conditions associated with MRGX2.

(1)

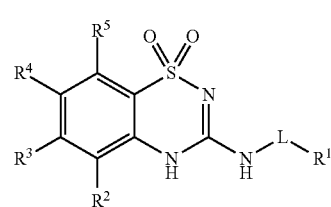

22 Claims, No Drawings

(56) References Cited

FOREIGN PATENT DOCUMENTS

| | | | |
|---|---|---|---|
| WO | 2007032793 A1 | 3/2007 | |
| WO | 2007053514 A2 | 5/2007 | |
| WO | 2007058336 A1 | 5/2007 | |
| WO | 2008043561 A2 | 4/2008 | |
| WO | 2008052072 A2 | 5/2008 | |
| WO | 2008061209 A2 | 5/2008 | |
| WO | 2008/124450 A1 | 10/2008 | |
| WO | 2009072882 A1 | 6/2009 | |
| WO | 2010147117 A1 | 12/2010 | |
| WO | 2011028945 A1 | 3/2011 | |
| WO | 2013130411 A1 | 9/2013 | |
| WO | 2020016434 A1 | 9/2013 | |
| WO | 2014055955 A1 | 4/2014 | |
| WO | 2015117024 A1 | 8/2015 | |
| WO | 2015157093 A1 | 10/2015 | |
| WO | 2016118632 A1 | 7/2016 | |
| WO | 2017/095759 A1 | 6/2017 | |
| WO | 2017098421 A1 | 6/2017 | |
| WO | 2018185266 | 10/2018 | |
| WO | 2018213934 A1 | 11/2018 | |
| WO | 2020/006018 A1 | 1/2020 | |
| WO | WO-2020223255 A1 | 11/2020 | |

OTHER PUBLICATIONS

Sharma, et al. A QSAR Study On Atp-Sensitive Potassium Channel Openers : The Derivatives Of 3-Alkylamiino-4H-1, 2, 4-Benzothiadiazine 1, 1-Dioxide, Int. J. Chem. Sci.: 7(2), 2009, 655-671.

Sharma, et al. Quantitative structure-activity relationship study of ATP-sensitive potassium channel openers: derivatives of 3-alkylamino-4H-1,2,4-benzothiadiazine 1,1-dioxide, J Enzyme Inhib Med Chem Feb. 2008;23(1):1-6. doi: 10.1080/14756360701442381.

Tullio, et al. Three-dimensional quantitative structure-activity relationships of ATP-sensitive potassium (KATP) channel openers belonging to the 3-alkylamino-4H-1,2,4-benzo- and 3-alkylamino-4H-1,2,4-pyridothiadiazine 1,1-dioxide families, J Med Chem. Nov. 16, 2006;49(23):6779-88. doi: 10.1021/jm060534w.

Petersen, H J. Synthesis of 3-amino- and 3-substituted amino-2H-1,2,4-benzothiadiazine 1,1-dioxides. Acta Chem Scand. 1973;27(7):2655-60. doi: 10.3891/acta.chem.scand.27-2655.

Battisti, et al. 5-Arylbenzothiadiazine Type Compounds as Positive Allosteric Modulators of AMPA/Kainate Receptors. ACS Med Chem Lett. Nov. 14, 2011;3(1):25-9. doi: 10.1021/ml200184w. eCollection Jan. 12, 2012.

Wang, et al. 3-Arylamino-2H-1,2,4-benzothiadiazin-5-ol 1,1-dioxides as novel and selective CXCR2 antagonists. Bioorg Med Chem Lett. Jul. 15, 2007;17(14):3864-7. doi: 10.1016/j.bmcl.2007. 05.011. Epub May 10, 2007.

Blackburn, et al. Synthesis of 3-amino-1,2,4-benzothiadi- azine 1,1-dioxides via a tandem aza-Wittig/heterocumulene annulation. J Org Chem. Nov. 25, 2005;70(24):10206-9. doi: 10.1021/jo051843h.

Carosati, et al., Virtual screening for novel openers of pancreatic K(ATP) channels. J Med Chem May 3, 2007;50(9):2117-26. doi: 10.1021/jm061440p. Epub Apr. 11, 2007.

Almarsson et al. Crystal engineering of the composition of pharmaceutical phases. Do pharmaceutical co-crystals represent a new path to improved medicines? Chem. Commun. 17:1889-1896 (2004).

Berge et al. Pharmaceutical Salts. Journal of Pharmaceutical Sciences 66(1):1-19 (Jan. 1977).

Finnin et al. Transdermal penetration enhancers: Applications, limitations, and potential. J Pharm. Sci. 88(10):955-958 (1999).

Fujisawa et al. Expression of Mas-related gene X2 on mast cells is upregulated in the skin of patents with severe chronic urticaria. J Allergy Clin Immunol 134(3):622-633.e9 (2014).

Haleblian. Characterization of Habits and Crystalline Modification of Solids and Their Pharmaceutical Applications. Journal of Pharmaceutical Sciences 64(8):1269-1288 (1975).

Jensen et al. Phosphorus Pentoxide in Organic Synthesis. Chemica Scripta 20(5):248-250 (1982).

Kashem et al. G protein coupled receptor specificity for C3a and compound 48/80-induced degranulation in human mast cells: roles of Mas-related genes MrgX1 and MrgX2. Eur J Pharmacol 668(1-2):299-304 (2011).

Liang et al. Fast-dissolving intraoral drug delivery. Expert Opinion in Therapeutic Patents 11(6):981-986 (2001).

McNeil et al. Identification of a mast-cell-specific receptor crucial for pseudo-allergic drug reactions. Nature, 519(7542):237-41 (2015).

Nanjo et al. Divergent and Scalable Synthesis of [alpha]-Hydroxy/KetoibetaFamino Acid Analogues by the Catalytic Enantioselective Addition of Glyoxylate Cyanohydrin to Imines. ACS Catalysis 9(11):10087-10092 (2019).

PCT/US2020/030305 International Preliminary Report on Patentability dated Nov. 11, 2021.

PCT/US2020/030305 International Search Report and Written Opinion dated Jul. 14, 2020.

Robas et al. MrgX2 is a high potency cortistatin receptor expressed in dorsal root ganglion. J Biol Chem, 278(45):44400-4 (2003).

Subramanian et al. Mas-related gene X2 (MrgX2) is a novel G protein-coupled receptor for the antimicrobial peptide LL-37 in human mast cells: resistance to receptor phosphorylation, desensitization, and internalization. J Biol Chem 286(52):44739-49 (2011).

Subramanian et al. PMX-53 as a dual CD88 antagonist and an agonist for Mas-related gene 2 (MrgX2) in human mast cells. Mol Pharmacol 79(6):1005-13 (2011).

Subramanian et al. Roles of Mas-related G protein-coupled receptor X2 on mast cell-mediated host defense, pseudoallergic drug reactions, and chronic inflammatory diseases. J Allergy Clin Immunol 138(3):700-10 (2016).

Tatemoto et al. Immunoglobulin E-independent activation of mast cell is mediated by Mrg receptors . Biochem Biophys Res Commun 349(4):1322-8 (2006).

Verma et al. Current Status of Drug Delivery Technologies and Future Directions. Pharmaceutical Technology On-line 25(2):1-14 (2001).

Kamal, Ahmed et al.: "Anti-tubercular agents. Part 3. Benzothiadiazine as a novel scaffold for anti-*Mycobacterium* activity", Bioorganic & Medicinal Chemistry, Elsevier, Oct. 3, 2005, pp. 650-658, doi: 10.1016/j.bmc.2005.

* cited by examiner

3-AMINO-4H-BENZO[E][1,2,4]THIADIAZINE 1,1-DIOXIDE DERIVATIVES AS INHIBITORS OF MRGX2

FIELD OF THE INVENTION

This invention relates to 3-amino-5-methyl-4H-benzo[e][1,2,4]thiadiazine 1,1-dioxide derivatives which are inhibitors of Mas-related gene X2 (MRGX2), to pharmaceutical compositions which contain them, and to their use to treat diseases, disorders, or conditions associated with MRGX2.

BACKGROUND OF THE INVENTION

Mas-related gene X2 (MRGX2, MRGPRX2, TGR12) is a member of the X subfamily of the Mas family of G-protein coupled receptors (GPCRs). This subfamily is specific to human, macaques, and rhesus monkey and MRGX2 is expressed specifically in mast cells (H. Subramanian et al., *J Allergy Clin Immunol,* 138(3):700-10 (2016); K. Tatemoto et al., *Biochem Biophys Res Commun,* 349(4):1322-8 (2006)). Activators of MRGX2 include a wide range of basic secretagogues including: neuropeptides (substance P, PAMP, cortistatin, VIP, PACAP, SST), eosinophil granule proteins (MBP, EPO), antimicrobial peptides (LL-37, β-defensin), and others such as anaphylatoxin and various venom peptides (H. Subramanian et al., *Mol Pharmacol,* 79(6):1005-13 (2011); K. Tatemoto et al., *Biochem Biophys Res Commun,* 349(4):1322-8; N. Robas et al., *J Biol Chem,* 278(45): 44400-4 (2003); S. Kashem et al., *Eur J Pharmacol,* 668 (1-2):299-304 (2011)). Studies of MRGX2 ligands have been conducted in LAD2 human mast cell line and CD34+ cell-derived human primary mast cells, both of which endogenously express MRGX2. These ligands induce degranulation of the mast cell through MRGX2 in an IgE-independent manner and the release of mediators such as histamine and tryptase (K. Tatemoto et al., *Biochem Biophys Res Commun,* 349(4):1322-8 (2006)). In addition to degranulation, activation of MRGX2 results in the release of cytokines (TNF-α, IL-6, IL-1α, IL-1β, GM-CSF, M-CSF, etc.) and chemokines (MCP-1, MIP-1 α/β, RANTES, IL-8, etc.), contributing to acute and chronic inflammatory responses.

MRGX2 is Gq-coupled and induces the mobilization of intracellular $Ca^{2+}$ upon activation by ligands. MRGX2 is a non-canonical GPCR in the sense that it does not internalize and desensitize following agonist-induced activation (H. Subramanian et al., *J Biol Chem,* 286(52):44739-49 (2011)). In addition, MRGX2 is expressed intracellularly in the cytoplasm of LAD2 cells and in human adult peripheral blood-derived cultured mast cells (D. Fujisawa et al., *J Allergy Clin Immunol,* 134(3):622-33.e9 (2014)). Mrg receptors are not well-conserved across species, with human and mouse sharing only 45-65% amino acid sequence homology. The mouse ortholog of the human MRGX2 receptor has been reported to be Mrgprb2 (B. D. McNeil et al., *Nature,* 519(7542):237-41 (2015)).

MRGX2 is potentially involved in host defense, drug-induced anaphylactoid reactions, neurogenic inflammation, pain, itch, and chronic inflammatory diseases (H. Subramanian et al., *J Allergy Clin Immunol,* 138(3):700-10 (2016)). MRGX2 and its ligands have been implicated in human disease states where mast cells are involved, including atopic dermatitis, chronic urticaria, and asthma (H. Subramanian et al., *J Allergy Clin Immunol,* 138(3):700-10 (2016); D. Fujisawa et al., *J Allergy Clin Immunol,* 134(3): 622-33.e9 (2014)). Selective inhibition of MRGX2, resulting in reduced activation and prevention of subsequent degranulation of mast cells, is a therapeutic strategy for disorders driven by mast cell pathophysiology.

SUMMARY OF THE INVENTION

This invention provides 3-amino-5-methyl-4H-benzo[e][1,2,4]thiadiazine 1,1-dioxide derivatives and pharmaceutical compositions which contain them. The 3-amino-5-methyl-4H-benzo[e][1,2,4]thiadiazine 1,1-dioxides are inhibitors of Mas-related gene X2 (MRGX2) and may be used to treat diseases, disorders or conditions associated with MRGX2, including atopic dermatitis, chronic urticaria and asthma, among others.

One aspect of the invention provides a compound of Formula 1:

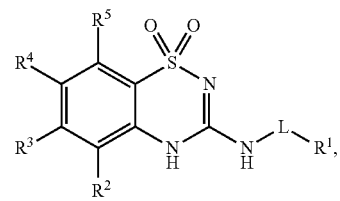

or a tautomer thereof, or a pharmaceutically acceptable salt of the compound of Formula 1 or tautomer thereof, wherein:

L is selected from a bond and $C_{1-4}$ alkanediyl;

$R^1$ is selected from (a) $C_{1-4}$ alkyl which is substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; and (b) a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

$R^2$ is selected from (a) $C_{1-4}$ alkyl which is substituted with from 0 to 3 optional substituents independently selected from halo, hydroxy, cyano, $C_{1-4}$ alkoxy and amino; and (b) a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

$R^3$, $R^4$, and $R^5$ are each independently selected from hydrogen, halo, cyano, and $C_{1-3}$ alkyl; wherein each of the aforementioned heterocyclyl and heteroaryl moieties independently has 1 to 4 heteroatoms as ring members, each independently selected from N, O, and S.

Another aspect of the invention provides a compound which is selected from the group of compounds described in the examples, tautomers thereof, and pharmaceutically acceptable salts of the compounds in the examples and tautomers thereof.

A further aspect of the invention provides a pharmaceutical composition which includes a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraph; and a pharmaceutically acceptable excipient.

An additional aspect of the invention provides a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs, for use as a medicament.

Another aspect of the invention provides a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs, for treatment of a disease, disorder or condition associated with MRGX2.

A further aspect of the invention provides a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs, for the manufacture of a medicament for the treatment of a disease, disorder or condition associated with MRGX2.

An additional aspect of the invention provides a method of treating a disease, disorder or condition associated with MRGX2, the method comprising administering to the subject an effective amount of a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs.

Another aspect of the invention provides a method for inhibiting MRGX2 in a subject, the method comprising administering to the subject an effective amount of a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs.

A further aspect of the invention provides a method of treating a disease, disorder or condition in a subject, the method comprising administering to the subject an effective amount of a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs, wherein the disease, disorder or condition is selected from systemic lupus erythematosus (SLE), psoriasis, psoriatic arthritis, rosacea, chronic urticaria, atopic dermatitis, rheumatoid arthritis, bronchial asthma, irritable bowel syndrome (IBS), systemic mastocytosis, cutaneous mastocytosis, mastocytic enterocolitis, mast cell activation syndrome (MCAS), interstitial cystitis, food allergy, pruiritis, allergic rhinitis, microbial infection, eosinophilic esophagitis (EOE) and chronic pain.

An additional aspect of the invention provides an effective amount of a compound of Formula 1, a tautomer thereof, or a pharmaceutically acceptable salt of the compound of Formula 1 or tautomer thereof, or any one of the compounds, tautomers or pharmaceutically acceptable salts defined in the preceding paragraphs; and at least one additional pharmacologically active agent.

DETAILED DESCRIPTION OF THE INVENTION

Unless otherwise indicated, this disclosure uses definitions provided below.

"Substituted," when used with a chemical substituent or moiety (e.g., a $C_{1-6}$ alkyl group), means that one or more hydrogen atoms of the substituent or moiety have been replaced with one or more non-hydrogen atoms or groups, provided valence requirements are met and a chemically stable compound results from the substitution.

"About" or "approximately," when used with a measurable numerical variable, refers to the indicated value of the variable and to all values of the variable that are within the experimental error of the indicated value or within +10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having from 1 to 4 (i.e., 1, 2, 3 or 4) carbon atoms, $C_{1-6}$ alkyl refers to an alkyl group having from 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having from 1 to 4 (i.e., 1, 2, 3 or 4) carbon atoms, $C_{1-6}$ alkanediyl refers to an alkanediyl group having from 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms.

Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Alkoxy" refers to straight chain and branched saturated hydrocarbon groups attached through an oxygen atom, generally having a specified number of carbon atoms (e.g., $C_{1-4}$ alkoxy refers to an alkoxy group having from 1 to 4 (i.e., 1, 2, 3 or 4) carbon atoms, $C_{1-6}$ alkoxy refers to an alkoxy group having from 1 to 6 carbon atoms, and so on). Examples of alkoxy groups include methoxy, ethoxy, n-propoxy, i-propoxy, n-butoxy, s-butoxy, i-butoxy, t-butoxy, pent-1-yloxy, pent-2-yloxy, pent-3-yloxy, 3-methylbut-1-yloxy, 3-methylbut-2-yloxy, 2-methylbut-2-yloxy, 2,2,2-trimethyleth-1-yloxy, n-hexoxy, and the like.

"Amino" refers to —$NH_2$, which when indicated may optionally include one or two non-hydrogen substituents that may be the same or different.

"Aminocarbonyl" refers to —$C(O)NH_2$, which when indicated, may optionally include one or two non-hydrogen substituents that may be the same or different.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one, two, three or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-6}$ cycloalkyl refers to a cycloalkyl group having from 3 to 6 carbon atoms as ring members, $C_{3-8}$ cycloalkyl refers to a cycloalkyl group having from 3 to 8 carbon atoms as ring members, and so on). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having from 3 to 6 carbon atoms as ring members, $C_{3-8}$ cycloalkylidene refers to a cycloalkylidene group having from 3 to 8 carbon atoms as ring members, and so on). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-10}$ aryl refers to an aryl group having from 6 to 10 carbon atoms as ring members, $C_{6-14}$ aryl refers to an aryl group having from 6 to 14 carbon atoms as ring members, and so on). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having from 2 to 6 carbon atoms and from 1 to 4 heteroatoms as ring members, $C_{2-9}$ heterocyclyl refers to a heterocyclyl group having from 2 to 9 carbon atoms and from 1 to 4 heteroatoms as ring members, and so on). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having from 2 to 6 carbon atoms and from 1 to 4 heteroatoms as ring members, $C_{2-9}$ heterocycle-diyl refers to a heterocycle-diyl group having from 2 to 9 carbon atoms and from 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-5}$ heteroaryl refers to a heteroaryl group having 1 to 5 carbon atoms and from 1 to 4 heteroatoms as ring members, $C_{1-9}$ heteroaryl refers to a heteroaryl group having from 1 to 9 carbon atoms and from 1 to 4 heteroatoms as ring members, and so on) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. For the purposes of this disclosure, 2-pyridone and 4-pyridone, 2-quinolone and 4-quinolone, and the like, are considered to be 2-oxo- and 4-oxo-substituted derivatives of the corresponding heteroaromatic group (pyridine, quinoline, and the like).

Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c] pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

Other examples of include heteroaryl groups also include bicyclic groups 2,3-dihydrobenzofuranyl, 2-oxo-1,2,5,6,7,8-hexahydroquinolinyl, 4-oxo-4H-pyrido[1,2-a]pyrimidinyl, 5,6,7,8-tetrahydropyrazolo[5,1-b][1,3]oxazepinyl, 5,6-dihydro-4H-pyrrolo[1,2-b]pyrazolyl, 5-oxo-5H-thiazolo[3,2-a]pyrimidinyl, 6,7-dihydro-5H-cyclopenta[b]pyridinyl, 6,7-dihydro-5H-pyrazolo[5,1-b][1,3]oxazinyl, and pyrrolo[1,2-c]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members).

Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Disease, disorder or condition associated with MRGX2" and similar phrases relate to a disease, disorder or condition in a subject for which inhibition of MRGX2 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (effective concentration at half maximal response); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); $K_d$ (dissociation constant); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-pyrrolidone); OTf (triflate); $Pd(amphos)Cl_2$ (bis(di-tert-butyl(4-dimethylaminophenyl)phosphine)dichloropalladium(II)); PE (petroleum ether); Ph (phenyl); $pEC_{50}$ ($-\log_{10}(EC_{50})$, where $EC_{50}$ is given in molar (M) units); $pIC_{50}$ ($-\log_{10}(IC_{50})$, where $IC_{50}$ is given in molar (M) units); pKd ($-\log_{10}(K_d)$, where $K_d$ is given in molar (M) units); Pr (propyl); c-Pr (cyclopropyl); i-Pr (isopropyl); PTFE (polytetrafluoroethylene); RT (room temperature, approximately 20° C. to 25° C.); T3P (2,4,6-tripropyl-1,3,5,2,4,6-trioxatriphosphinane 2,4,6-trioxide); TCEP (tris(2-carboxyethyl) phosphine); TFA (trifluoroacetic acid); TFAA (2,2,2-trifluoroacetic anhydride); THF (tetrahydrofuran); TMEDA ($N^1,N^1,N^2,N^2$-tetramethylethane-1,2-diamine); TMS (trimethylsilyl); and Tris buffer (2-amino-2-hydroxymethylpropane-1,3-diol buffer).

As described, below, this disclosure concerns compounds of Formula 1, tautomers thereof, and pharmaceutically acceptable salts of the compounds and tautomers thereof, and pharmaceutically acceptable salts of the compounds of Formula 1 and tautomers thereof. This disclosure also concerns materials and methods for preparing compounds of Formula 1, pharmaceutical compositions which contain them, and the use of compounds of Formula 1, tautomers thereof, and pharmaceutically acceptable salts of the compounds of Formula 1 and tautomers thereof (optionally in combination with other pharmacologically active agents) for treating diseases, disorders or conditions associated with MRGX2.

In addition to the specific compounds in the examples, the compounds of Formula 1,

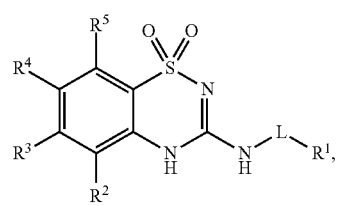

1 tautomers thereof, or pharmaceutically acceptable salts of the compounds of Formula 1 or tautomers thereof, include those in which:

(1) L is selected from a bond and $C_{1-4}$ alkanediyl;
$R^1$ is selected from
(a) $C_{1-4}$ alkyl which is substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; and
(b) a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;
$R^2$ is selected from
(a) $C_{1-4}$ alkyl which is substituted with from 0 to 3 optional substituents independently selected from halo, hydroxy, cyano, $C_{1-4}$ alkoxy and amino; and
(b) a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;
$R^3$, $R^4$, and $R^5$ are each independently selected from hydrogen, halo, cyano, and $C_{1-3}$ alkyl;
wherein each of the aforementioned heterocyclyl and heteroaryl moieties independently has 1 to 4 heteroatoms as ring members, each independently selected from N, O, and S.

In addition to embodiment (1) in the preceding paragraph, compounds of Formula 1 include those in which:
(2) $R^1$ is $C_{1-4}$ alkyl which is substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition, or as an alternative, to embodiment (2) in the preceding paragraph, compounds of Formula 1 include those in which:
(3) the $R^1$ $C_{1-4}$ alkyl is selected from methyl, ethyl, propyl and isopropyl, each substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;
(4) the $R^1$ $C_{1-4}$ alkyl is selected from methyl or ethyl, each substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or
(5) the $R^1$ $C_{1-4}$ alkyl is methyl substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition, or as an alternative, to any one of embodiments (2) through (5) in the preceding paragraphs, compounds of Formula 1 include those in which:
(6) the $R^1$ $C_{1-4}$ alkyl is substituted with from 0 to 3 optional substituents independently selected from halo, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;
(7) the $R^1$ $C_{1-4}$ alkyl is substituted with from 0 to 3 optional substituents independently selected from halo, $C_{1-4}$ alkoxy and aminocarbonyl, wherein each of the $C_{1-4}$ alkoxy optional substituents is independently substituted with from 0 to 3 substituents independently selected from halo, and wherein each of the aminocarbonyl optional substituents is independently substituted with from 0 to 2 substituents independently selected from $C_{1-4}$ alkyl;
(8) the $R^1$ $C_{1-4}$ alkyl is substituted with from 0 to 3 optional substituents independently selected from halo and $C_{1-4}$ alkoxy, wherein each of the $C_{1-4}$ alkoxy optional substituents is independently substituted with from 0 to 3 substituents independently selected from halo;
(9) the $R^1$ $C_{1-4}$ alkyl is substituted with from 0 to 3 optional substituents independently selected from halo;
(10) the $R^1$ $C_{1-4}$ alkyl is substituted with from 0 to 3 optional substituents independently selected from fluoro and chloro;
(11) the $R^1$ $C_{1-4}$ alkyl is substituted with from 0 to 3 fluoro substituents;

(12) the $R^1$ $C_{1-4}$ alkyl is substituted with from 0 to 3 optional substituents independently selected from $C_{1-4}$ alkoxy, wherein each of the $C_{1-4}$ alkoxy optional substituents is independently substituted with from 0 to 3 substituents independently selected from halo;

(13) the $R^1$ $C_{1-4}$ alkyl is substituted with $C_{1-4}$ alkoxy, wherein the $C_{1-4}$ alkoxy substituent is substituted with from 0 to 3 substituents independently selected from halo;

(14) the $R^1$ $C_{1-4}$ alkyl is substituted with $C_{1-4}$ alkoxy, wherein the $C_{1-4}$ alkoxy substituent is substituted with from 0 to 3 fluoro substituents;

(15) the $R^1$ $C_{1-4}$ alkyl is substituted with $C_{1-4}$ alkoxy, wherein the $C_{1-4}$ alkoxy substituent is unsubstituted;

(16) the $R^1$ $C_{1-4}$ alkyl is substituted with methoxy, which is unsubstituted; or

(17) the $R^1$ $C_{1-4}$ alkyl is unsubstituted.

In addition to embodiment (1) above, compounds of Formula 1 include those in which:

(18) $R^1$ is a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition to embodiment (1) above, compounds of Formula 1 include those in which:

(19) $R^1$ is a cyclic group which is $C_{3-8}$ cycloalkyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(20) $R^1$ is a cyclic group which is $C_{3-6}$ cycloalkyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(21) $R^1$ is a cyclic group which is cyclopropyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or

(22) $R^1$ is a cyclic group which is cyclobutyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition to embodiment (1) above, compounds of Formula 1 include those in which:

(23) $R^1$ is a cyclic group which is $C_{2-9}$ heterocyclyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(24) $R^1$ is a cyclic group which is $C_{2-6}$ heterocyclyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or

(25) $R^1$ is a cyclic group which is $C_{1-4}$ heterocyclyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition, or as an alternative, to any one of embodiments (23) to (25) in the preceding paragraph, compounds of Formula 1 include those in which:

(26) the $R^1$ cyclic group has 1 or 2 heteroatoms as ring members, each independently selected from N, O, and S;

(27) the $R^1$ cyclic group has 1 or 2 heteroatoms as ring members, each independently selected from N and O; or

(28) the $R^1$ cyclic group has 1 heteroatom as a ring member, which is selected from N and O.

In addition, or as an alternative, to any one of embodiments (23) to (28) in the preceding paragraphs, compounds of Formula 1 include those in which:

(29) the $R^1$ cyclic group is monocyclic.

In addition to embodiment (1) above, compounds of Formula 1 include those in which:

(30) $R^1$ is a cyclic group which is selected from tetrahydrofuranyl and morpholinyl, each substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition to embodiment (1) above, compounds of Formula 1 include those in which:

(31) $R^1$ is a cyclic group which is $C_{6-14}$ aryl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(32) $R^1$ is a cyclic group which is $C_{6-10}$ aryl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or

(33) $R^1$ is a cyclic group which is phenyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition to embodiment (1) above, compounds of Formula 1 include those in which:

(34) $R^1$ is a cyclic group which is $C_{1-9}$ heteroaryl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(35) $R^1$ is a cyclic group which is $C_{1-5}$ heteroaryl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or

(36) $R^1$ is a cyclic group which is $C_{3-5}$ heteroaryl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition, or as an alternative, to any one of embodiments (34) through (36) in the preceding paragraphs, compounds of Formula 1 include those in which:

(37) $R^1$ cyclic group has 1 or 2 heteroatoms as ring members, each independently selected from N, O, and S.

In addition to embodiment (1) above, compounds of Formula 1 include those in which:

(38) $R^1$ is a cyclic group which is selected from pyrrolyl, furanyl, thienyl, pyrazolyl, imidazolyl, isoxazolyl, oxazolyl, isothiazolyl, thiazolyl, 1,2,3-triazolyl, 1,3,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridinyl, pyridazinyl, pyrimidinyl, and pyrazinyl, each substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

(39) $R^1$ is a cyclic group which is selected from pyrrolyl, furanyl, thienyl, pyrazolyl, imidazolyl, isoxazolyl, oxazolyl, isothiazolyl, thiazolyl, pyridinyl, pyridazinyl, pyrimidinyl, and pyrazinyl, each substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; or

(40) $R^1$ is a cyclic group which is selected from furanyl, pyrazolyl, oxazolyl, isothiazolyl, thiazolyl, pyridinyl, and pyrimidinyl, each substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

In addition, or as an alternative, to any one of embodiments (18) to (40) in the preceding paragraphs, compounds of Formula 1 include those in which:

(41) $R^1$ cyclic group is substituted with from 0 to 3 optional substituents independently selected from halo, hydroxy, cyano, $C_{1-4}$ alkyl, and $C_{1-4}$ alkoxy, wherein each of the $C_{1-4}$ alkyl and $C_{1-4}$ alkoxy optional substituents is independently substituted with from 0 to 3 substituents independently selected from halo; or

(42) $R^1$ cyclic group is substituted with from 0 to 3 optional substituents independently selected from fluoro, chloro, hydroxy, cyano, $C_{1-4}$ alkyl, and $C_{1-4}$ alkoxy, wherein each of the $C_{1-4}$ alkyl and $C_{1-4}$ alkoxy optional substituents is independently substituted with from 0 to 3 substituents independently selected from halo.

In addition, or as an alternative, to any one of embodiments (41) and (42) in the preceding paragraph, compounds of Formula 1 include those in which:

(43) each of the $C_{1-4}$ alkyl and $C_{1-4}$ alkoxy optional substituents on the $R^1$ cyclic group is independently substituted with from 0 to 3 substituents independently selected from fluoro and chloro;
(44) each of the $C_{1-4}$ alkyl and $C_{1-4}$ alkoxy optional substituents on the $R^1$ cyclic group is independently substituted with from 0 to 3 substituents selected from fluoro; or
(45) each of the $C_{1-4}$ alkyl and $C_{1-4}$ alkoxy optional substituents on the $R^1$ cyclic group is unsubstituted.

In addition, or as an alternative, to any one of embodiments (41) to (45) in the preceding paragraphs, compounds of Formula 1 include those in which:
(46) each of the $C_{1-4}$ alkyl optional substituents on the $R^1$ cyclic group is independently selected from methyl, ethyl, and isopropyl; or
(47) each of the $C_{1-4}$ alkoxy optional substituents on the $R^1$ cyclic group is independently selected from methoxy and ethoxy.

In addition, or as an alternative, to any one of embodiments (18) to (47) in the preceding paragraphs, compounds of Formula 1 include those in which:
(48) the $R^1$ cyclic group is substituted with from 0 to 2 optional substituents; or
(49) the $R^1$ cyclic group is substituted with 0 or 1 optional substituent.

In addition, or as an alternative, to any one of embodiments (18) to (40) in the preceding paragraphs, compounds of Formula 1 include those in which:
(50) the $R^1$ cyclic group is unsubstituted.

In addition, or as an alternative, to any one of embodiments (1) to (50) in the preceding paragraphs, compounds of Formula 1 include those in which:
(51) L is selected from a bond, —$CH_2$—, —$CH_2CH_2$—, and —$CH(CH_3)$—;
(52) L is selected from a bond, —$CH_2$—, and —$CH_2CH_2$—;
(53) L is selected from a bond and —$CH_2$—;
(54) L is —$CH_2$—; or
(55) L is a bond.

In addition, or as an alternative, to any one of embodiments (1) to (55) in the preceding paragraphs, compounds of Formula 1 include those in which:
(56) $R^2$ is $C_{1-4}$ alkyl which is substituted with from 0 to 3 optional substituents independently selected from halo, hydroxy, cyano, $C_{1-4}$ alkoxy and amino.

In addition to embodiment (56) in the preceding paragraph, compounds of Formula 1 include those in which:
(57) the $R^2$ $C_{1-4}$ alkyl is selected from methyl, ethyl, propyl and isopropyl, each substituted with from 0 to 3 optional substituents independently selected from halo, hydroxy, cyano, $C_{1-4}$ alkoxy and amino;
(58) the $R^2$ $C_{1-4}$ alkyl is selected from methyl, ethyl and isopropyl, each substituted with from 0 to 3 optional substituents independently selected from halo, hydroxy, cyano, $C_{1-4}$ alkoxy and amino;
(59) the $R^2$ $C_{1-4}$ alkyl is selected from methyl and ethyl, each substituted with from 0 to 3 optional substituents independently selected from halo, hydroxy, cyano, $C_{1-4}$ alkoxy and amino;
(60) the $R^2$ $C_{1-4}$ alkyl is methyl which is substituted with from 0 to 3 optional substituents independently selected from halo, hydroxy, cyano, $C_{1-4}$ alkoxy and amino; or
(61) the $R^2$ $C_{1-4}$ alkyl is methyl which is substituted with from 0 to 3 optional substituents independently selected from halo, hydroxy and $C_{1-4}$ alkoxy.

In addition, or as an alternative, to any one of embodiments (56) to (61) in the preceding paragraphs, compounds of Formula 1 include those in which:
(62) the $R^2$ $C_{1-4}$ alkyl is substituted with from 0 to 3 optional substituents independently selected from halo and $C_{1-4}$ alkoxy;
(63) the $R^2$ $C_{1-4}$ alkyl is substituted with from 0 to 3 optional substituents independently selected from fluoro, chloro, methoxy and ethoxy;
(64) the $R^2$ $C_{1-4}$ alkyl is substituted with from 0 to 3 optional substituents independently selected from fluoro and methoxy; or
(65) the $R^2$ $C_{1-4}$ alkyl is unsubstituted.

In addition, or as an alternative, to any one of embodiments (56) to (61) in the preceding paragraphs, compounds of Formula 1 include those in which:
(66) the $R^2$ $C_{1-4}$ alkyl is substituted with $C_{1-4}$ alkoxy;
(67) the $R^2$ $C_{1-4}$ alkyl is substituted with methoxy or ethoxy; or
(68) the $R^2$ $C_{1-4}$ alkyl is substituted with methoxy.

In addition, or as an alternative, to any one of embodiments (1) to (55) in the preceding paragraphs, compounds of Formula 1 include those in which:
(69) $R^2$ is a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or
(70) $R^2$ is a cyclic group selected from $C_{3-8}$ cycloalkyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{1-4}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (1) to (55) in the preceding paragraphs, compounds of Formula 1 include those in which:
(71) $R^2$ is a cyclic group which is $C_{3-8}$ cycloalkyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(72) $R^2$ is a cyclic group which is $C_{3-6}$ cycloalkyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(73) $R^2$ is a cyclic group which is cyclopropyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or

(74) $R^2$ is a cyclic group which is cyclobutyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (1) to (55) in the preceding paragraphs, compounds of Formula 1 include those in which:

(75) $R^2$ is a cyclic group which is $C_{2-9}$ heterocyclyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(76) $R^2$ is a cyclic group which is $C_{2-6}$ heterocyclyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or

(77) $R^2$ is a cyclic group which is $C_{3-5}$ heterocyclyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (75) to (77) in the preceding paragraph, compounds of Formula 1 include those in which:

(78) the $R^2$ cyclic group has 1 or 2 heteroatoms as ring members, each independently selected from N, O, and S;

(79) the $R^2$ cyclic group has 1 or 2 heteroatoms as ring members, each independently selected from N and O; or

(80) the $R^2$ cyclic group has 1 heteroatom as a ring member, which is selected from N and O.

In addition, or as an alternative, to any one of embodiments (75) to (80) in the preceding paragraphs, compounds of Formula 1 include those in which:

(81) the $R^2$ cyclic group is monocyclic.

In addition, or as an alternative, to any one of embodiments (1) to (55) in the preceding paragraphs, compounds of Formula 1 include those in which:

(82) $R^2$ is a cyclic group which is $C_{6-14}$ aryl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(83) $R^2$ is a cyclic group which is $C_{6-10}$ aryl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-7}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or

(84) $R^2$ is a cyclic group which is phenyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-7}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (1) to (55) in the preceding paragraphs, compounds of Formula 1 include those in which:

(85) $R^2$ is a cyclic group which is $C_{1-9}$ heteroaryl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(86) $R^2$ is a cyclic group which is $C_{1-5}$ heteroaryl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or

(87) $R^2$ is a cyclic group which is $C_{3-5}$ heteroaryl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (85) to (87) in the preceding paragraph, compounds of Formula 1 include those in which:

(88) the $R^2$ cyclic group has 1 or 2 heteroatoms as ring members, each independently selected from N, O, and S; or

(89) the $R^2$ cyclic group has 1 or 2 heteroatoms as ring members, each being N.

In addition, or as an alternative, to any one of embodiments (1) to (55) in the preceding paragraphs, compounds of Formula 1 include those in which:

(90) $R^2$ is a cyclic group which is selected from pyrrolyl, furanyl, thienyl, pyrazolyl, imidazolyl, isoxazolyl, oxazolyl, isothiazolyl, thiazolyl, 1,2,3-triazolyl, 1,3,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridinyl, pyridazinyl, pyrimidinyl, and pyrazinyl, each substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(91) $R^2$ is a cyclic group which is selected from pyrrolyl, furanyl, thienyl, pyrazolyl, imidazolyl, isoxazolyl, oxazolyl, isothiazolyl, thiazolyl, pyridinyl, pyridazinyl, pyrimidinyl, and pyrazinyl, each substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(92) $R^2$ is a cyclic group which is selected from pyrazolyl, pyridinyl, and pyrimidinyl, each substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

(93) $R^2$ is a cyclic group which is pyrazolyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl; or

(94) $R^2$ is a cyclic group which is pyridinyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{1-4}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

In addition, or as an alternative, to any one of embodiments (69) to (94) in the preceding paragraphs, compounds of Formula 1 include those in which:
- (95) the $R^2$ cyclic group is substituted with from 0 to 3 optional substituents independently selected from halo, cyano, $C_{1-4}$ alkyl, $C_{1-4}$ alkoxy, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo; or (96) the $R^2$ cyclic group is substituted with from 0 to 3 optional substituents independently selected from fluoro, chloro, cyano, $C_{1-4}$ alkyl, $C_{1-4}$ alkoxy, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo.

In addition, or as an alternative, to any one of embodiments (95) and (96) in the preceding paragraph, compounds of Formula 1 include those in which:
- (97) each of the $C_{1-4}$ alkyl, $C_{1-4}$ alkoxy, $C_{3-8}$ cycloalkyl and $C_{3-5}$ heterocyclyl optional substituents on the $R^2$ cyclic group is independently substituted with from 0 to 3 substituents independently selected from fluoro and chloro;
- (98) each of the $C_{1-4}$ alkyl, $C_{1-4}$ alkoxy, $C_{3-8}$ cycloalkyl and $C_{3-5}$ heterocyclyl optional substituents on the $R^2$ cyclic group is independently substituted with from 0 to 3 substituents independently selected from fluoro; or
- (99) each of the $C_{1-4}$ alkyl, $C_{1-4}$ alkoxy, $C_{3-8}$ cycloalkyl and $C_{3-5}$ heterocyclyl optional substituents on the $R^2$ cyclic group is unsubstituted.

In addition, or as an alternative, to any one of embodiments (95) to (99) in the preceding paragraphs, compounds of Formula 1 include those in which:
- (100) each of the $C_{1-4}$ alkyl optional substituents on the $R^2$ cyclic group is independently selected from methyl, ethyl, and isopropyl;
- (101) each of the $C_{1-4}$ alkoxy optional substituents on the $R^2$ cyclic group is independently selected from methoxy and ethoxy;
- (102) the $C_{3-8}$ cycloalkyl optional substituent on the $R^2$ cyclic group is selected from cyclopropyl and cyclobutyl;
- (103) the $C_{3-5}$ heterocyclyl optional substituent on the $R^2$ cyclic group has 1 or 2 heteroatoms as ring members, each independently selected from N, O, and S; or
- (104) the $C_{3-5}$ heterocyclyl optional substituent on the $R^2$ cyclic group has 1 heteroatom as a ring member, which is selected from N and O.

In addition, or as an alternative, to any one of embodiments (95) to (99), (103) and (104) in the preceding paragraphs, compounds of Formula 1 include those in which:
- (105) the $C_{3-5}$ heterocyclyl optional substituent on the $R^2$ cyclic group is monocyclic.

In addition, or as an alternative, to any one of embodiments (95) to (99) in the preceding paragraphs, compounds of Formula 1 include those in which:
- (106) the $C_{3-5}$ heterocyclyl optional substituent on the $R^2$ cyclic group is oxetanyl.

In addition, or as an alternative, to any one of embodiments (1) to (106) in the preceding paragraphs, compounds of Formula 1 include those in which:
- (107) $R^3$, $R^4$ and $R^5$ are each independently selected from hydrogen, halo and $C_{1-3}$ alkyl;
- (108) $R^3$, $R^4$ and $R^5$ are each independently selected from hydrogen, fluoro and $C_{1-3}$ alkyl;
- (109) $R^3$, $R^4$ and $R^5$ are each independently selected from hydrogen, fluoro and methyl;
- (110) $R^3$ and $R^4$ are each independently selected from hydrogen, fluoro and methyl, and $R^5$ is hydrogen;
- (111) $R^4$ is selected from hydrogen and fluoro, and $R^3$ and $R^5$ are each hydrogen; or
- (112) $R^3$, $R^4$ and $R^5$ are each hydrogen.

Compounds of Formula 1 include embodiments (1) through (112) described in the preceding paragraphs and all compounds specifically named above and in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J Pharm. Sci.* (1975) 64(8): 1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —COO$^-$Na$^+$, —COO$^-$K$^+$, —SO$_3^-$Na$^+$) or polar non-ionic moiety (such as —N$^-$N$^+$(CH$_3$)$_3$). See, e.g., N. H. Hartshome and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, Stereochemistry of Organic Compounds (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, Comprehensive Organic Transformations (1999), and the multi-volume series edited by Michael B. Smith and others, Compendium of Organic Synthetic Methods (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., L, $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^2$ substituent having a potentially reactive amine. In such cases, $R^2$ would include the moiety with or without, say, a Boc or Cbz group attached to the amine.

Scheme A shows a general method for preparing compounds of Formula 1. In accordance with the method, a 2-haloaniline (A-1, X=bromo, iodo) is reacted with a boronic acid or ester (A-2 in which, e.g., each $R^6$ is H or $C_{1-4}$ alkyl) in the presence of a palladium catalyst (e.g., $PdCl_2$(dppf), $PdCl_2$(dppf)·$CH_2Cl_2$, Pd(PPh$_3$)$_4$, Pd(amphos)Cl$_2$, etc.), a base (e.g., $K_2CO_3$, KHCO$_3$, Na$_2$CO$_3$, NaHCO$_3$, CsF, KF, etc.) and one or more polar solvents (e.g., dioxane, DMF, water, etc.) at elevated temperature (e.g., 75-130° C.) to give an $R^2$-substituted aniline (A-3). The $R^2$-substituted aniline is reacted with sulfurisocyanatidic chloride in the presence of a polar solvent (nitromethane) at reduced temperature (e.g., −40 to 0° C.) to give a urea intermediate (not shown) which is subsequently treated with aluminum trichloride at reduced temperature (e.g., −20 to 0° C.) and then at elevated temperature (e.g., 100 to 120° C.) to give a 3-hydroxy-4H-benzo[e][1,2,4]thiadiazine 1,1-dioxide intermediate (A-4), which may exist as a corresponding tautomer, a 2H-benzo[e][1,2,4]thiadiazin-3(4H)-one 1,1-dioxide derivative. Following ring closure, the 2H-benzo[e][1,2,4]thiadiazin-3(4H)-one 1,1-dioxide derivative (A-4) is reacted with POCl$_3$ in a compatible solvent at elevated temperature (e.g., 120° C.) to give a 3-chloro-4H-benzo[e][1,2,4]thiadiazine 1,1-dioxide intermediate (A-5) which is subsequently reacted with an R$^1$-L-substituted amine (A-6) in the presence of a non-nucleophilic base (e.g., DIPEA, Et$_3$N, K$_2$CO$_3$, Cs$_2$CO$_3$, etc.) and polar solvent (e.g., ACN, DMA, DMSO, MeOH, EtOH, i-PrOH, i-BuOH, etc.) at elevated temperature (e.g., 60-150° C.). The reaction gives the compound of Formula 1 directly or indirectly, e.g., after removal of protecting groups, further elaboration of functional groups, salt formation, etc.

Scheme A

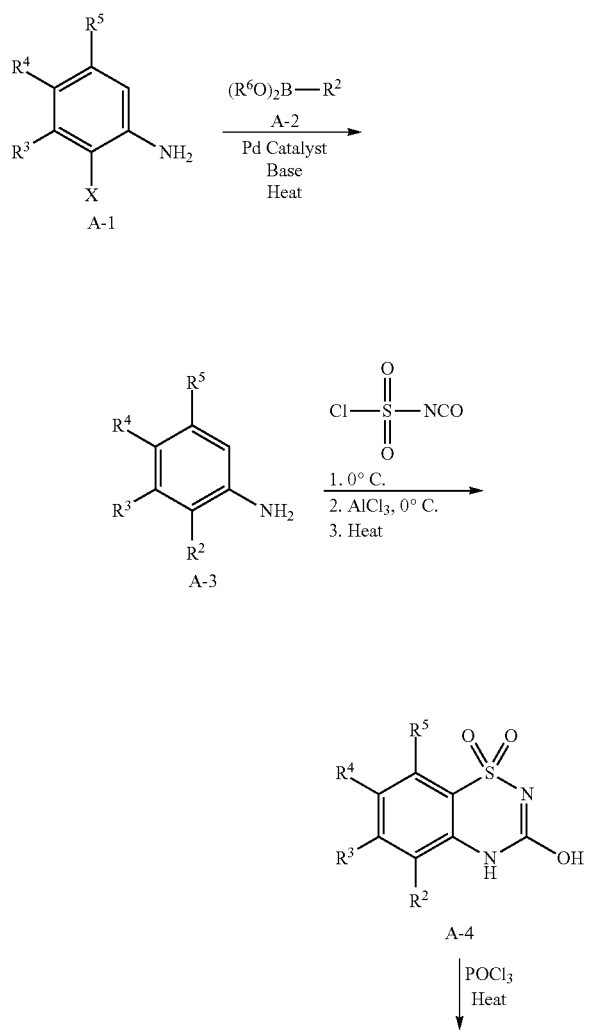

-continued

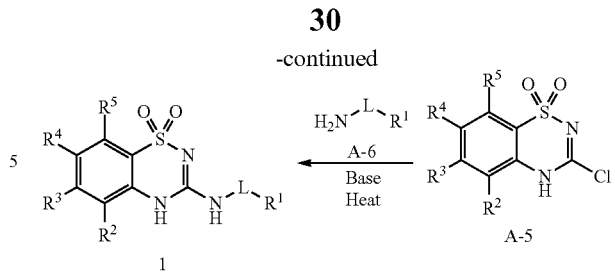

Scheme B shows a general method for preparing compounds of Formula 1. Like Scheme A, the method starts with a 2-haloaniline (A-1, X=bromo, iodo) but it is reacted with sulfurisocyanatidic chloride, in the presence of a polar solvent (nitromethane) at reduced temperature (e.g., −40 to 0° C.) to give a urea intermediate (not shown) which is subsequently treated with AlCl$_3$ at reduced temperature (e.g., −20 to 0° C.) and then at elevated temperature (e.g., 100 to 120° C.) to give a 3-hydroxy-4H-benzo[e][1,2,4]thiadiazine 1,1-dioxide intermediate (B-1) or its corresponding tautomer, a 2H-benzo[e][1,2,4]thiadiazin-3(4H)-one 1,1-dioxide derivative. Following ring closure, the 2H-benzo[e][1,2,4]thiadiazin-3(4H)-one 1,1-dioxide derivative (B-1) is reacted with POCl$_3$ in a compatible solvent at elevated temperature (e.g., 120° C.) to give a 3-chloro-4H-benzo[e][1,2,4]thiadiazine 1,1-dioxide intermediate (B-2) which is subsequently reacted with an R$^1$-L-substituted amine (A-6) in the presence of a non-nucleophilic base (e.g., DIPEA, Et$_3$N, K$_2$CO$_3$, Cs$_2$CO$_3$, etc.) and polar solvent (e.g., ACN, DMA, DMSO, MeOH, EtOH, i-PrOH, i-BuOH, etc.) at elevated temperature (e.g., 60-150° C.). The resulting R$^1$-L-substituted intermediate (B-3) is subsequently reacted with a boronic acid or ester (A-2 in which, e.g., each R$^6$ is H or C$_{1-4}$ alkyl) in the presence of a palladium catalyst (e.g., PdCl$_2$(dppf), PdCl$_2$(dppf)·CH$_2$Cl$_2$, Pd(PPh$_3$)$_4$, Pd(amphos)Cl$_2$, etc.), a base (e.g., K$_2$CO$_3$, KHCO$_3$, Na$_2$CO$_3$, NaHCO$_3$, CsF, KF, etc.) and one or more polar solvents (e.g., dioxane, DMF, water, etc.). The palladium catalyzed cross-coupling reaction is typically carried out at elevated temperature (e.g., 75-130° C.) and gives the compound of Formula 1 directly or indirectly, e.g., after removal of protecting groups, further elaboration of functional groups, salt formation, etc. Alternatively, the R$^2$-substituent may be installed via Negishi coupling (e.g., reacting B-3 with R$^2$ZnX in a compatible solvent and catalytic amounts of S-Phos and Pd(OAc)$_2$) or Ullman reaction (e.g., reacting B-3 with R$^2$—H in the presence of a non-nucleophilic base, Cu(I) iodide catalyst and compatible solvent).

Scheme B

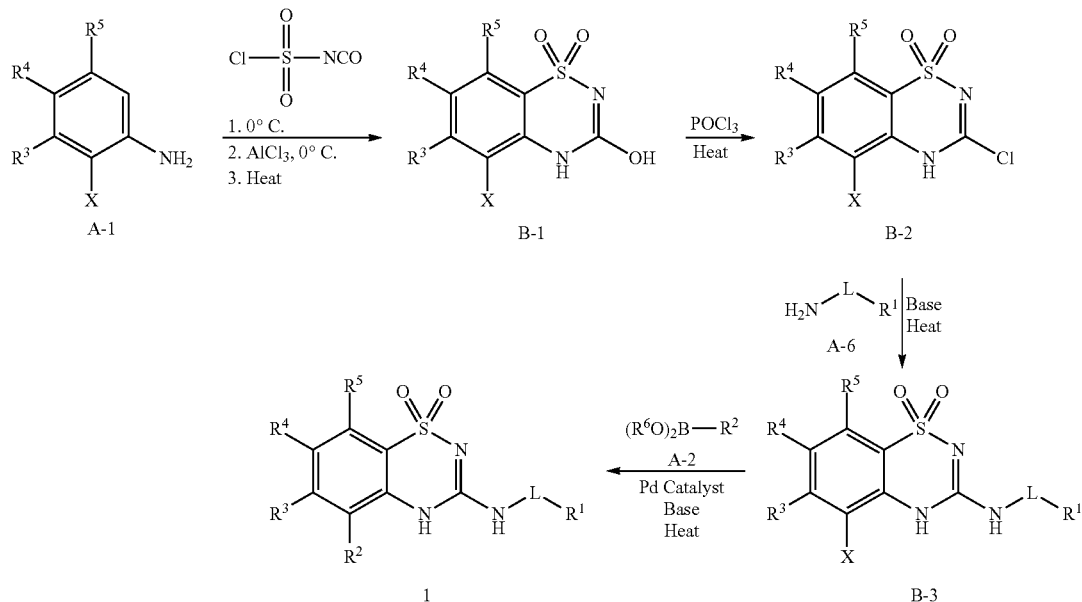

The methods depicted in the schemes may be varied as desired. For example, protecting groups may be added or removed and products (including intermediates) may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named in the specification, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively, or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see R. K. Verma and S. Garg, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration.

Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., B. C. Finnin and T. M. Morgan, *J Pharm. Sci.* 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically acceptable complexes, salts, solvates and hydrates, may be combined with each other or with one or more other active pharmaceutically active compounds to treat various diseases, conditions or disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., pediatric patient) whose mass falls outside of this mass range.

The compounds of Formula 1 may be used to treat diseases, disorders or conditions for which inhibition of MRGX2 is indicated. These diseases, disorders or conditions include systemic lupus erythematosus (SLE), psoriasis, psoriatic arthritis, rosacea, chronic urticaria, atopic dermatitis, rheumatoid arthritis, bronchial asthma, irritable bowel syndrome (IBS), systemic mastocytosis, cutaneous mastocytosis, mastocytic enterocolitis, mast cell activation syndrome (MCAS), interstitial cystitis, food allergy, pruiritis, allergic rhinitis, microbial infection, eosinophilic esophagitis (EOE) and chronic pain.

The claimed and disclosed compounds may be combined with one or more other pharmacologically active compounds or therapies to treat one or more diseases, disorders or conditions associated with MRGX2. Such combinations may offer significant therapeutic advantages, including fewer side effects, improved ability to treat underserved patient populations, or synergistic activity. For example, compounds of Formula 1 or tautomers thereof, including compounds specifically named in the specification, and their pharmaceutically acceptable complexes, salts, solvates and hydrates, may be administered simultaneously, sequentially or separately in combination with one or more anti-inflammatory agents, analgesics, biological response modifiers, disease modifying antirheumatic drugs (DMARDs), antihistamines, mast cell stabilizers, prokinetic agents, antidiarrheals, prosecretory agents, antibiotics, antidepressants, anxiolytics, antipsychotics and anticonvulsants, among others.

The compounds of Formula 1 may be combined with anti-inflammatory agents, which include nonsteroidal anti-inflammatory drugs (NSAIDs) and corticosteroids. Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate and sulindac. Representative corticosteroids include betamethasone, cortisone acetate, dexamethasone, hydrocortisone, methylprednisolone, prednisolone and prednisone.

Alternatively or additionally, the compounds of Formula 1 may be combined with analgesics, biological response modifiers, DMARDs or some combination thereof. Representative analgesics include acetaminophen and morphine sulfate, as well as codeine, hydrocodone, oxycodone, propoxyphene, and tramadol, all with or without acetaminophen. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept. Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, sulfasalazine, and JAK3 inhibitor (e.g., tofacitinib).

Useful combinations include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

Additionally or alternatively, the compounds of Formula 1 may be combined with antihistamines, mast cell stabilizers, prokinetic agents, antidiarrheals, prosecretory agents, antibiotics or some combination thereof. Representative antihistamines include $H_1$-antihistamines (e.g. acrivastine, azelastine, bilastine, bromodiphenhydramine, brompheniramine, buclizine, carbinoxamine, cetirizine, chlorodiphenhydramine, chlorpheniramine, clemastine, cyclizine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocabastine, levocetirizine, loratadine, meclizine, olopatadine, orphenadrine, phenindamine, pheniramine, phenyltoloxamine, promethazine, rupatadine, tripelennamine and triprolidine), $H_1$ inverse agonists (e.g. levocetirizine, desloratadine and pyrilamine), $H_2$-antihistamines (e.g. cimetidine, famotidine, lafutidine, nizatidine, ranitidine and roxatidine), $H_3$-antihistamines (e.g. clobenpropit, ciproxifan, conessine and thioperamide), and $H_4$-antihistamines (e.g. thioperamide).

Representative mast cell stabilizers include azelastine, 32 adrenergic receptor agonists (e.g. abediterol, arformoterol, bambuterol, bitolterol, carmoterol, clenbuterol, fenoterol, formoterol, indacaterol, isoprenaline, isoxsuprine, levosalbutamol, mabuterol, olodaterol, orciprenaline, pirbuterol, procaterol, ritodrine, salbutamol, terbutaline, vilanterol and zilpaterol), cromoglicic acid, ketotifen, mepolizumab, nedocromil, olopatadine, omalizumab, palmitoylethanolamide, pemirolast, quercetin, rupatadine, tranilast and vitamin D.

Representative prokinetic agents include cinitapride, cisapride, domperidone, itopride, levosulpiride, linaclotide, metoclopramide, mitemcinal, mosapride, prucalopride, renzapride and tegaserod. Representative antidiarrheals include bismuth subsalicylate, crofelemer, difenoxin HCl/atropine, diphenoxylate HCl/atropine, loperamide, loperamide/simethicone, octreotide and paregoric. Representative prosecretory agents include lubiprostone, linaclotide, plecanatide and elobixibat. Representative antiobiotics include tetracycline, amoxicillin clavulanate, metronidazole, fluoroquinolones (e.g. norfloxacin) and rifaximin.

Additionally or alternatively, the compounds of Formula 1 may be combined with antidepressants, antipsychotics, anxiolytics, anticonvulsants or other medications that are used to treat neurological or psychiatric diseases. For example, the compounds of Formula 1 may be combined with antidepressants, which include tricyclic antidepressants, selective seretonin reuptake inhibitors (SSRIs) or selective serotonin and norepinephrine reuptake inhibitors (SNRIs), or with antipsychotics, including atypical antipsychotics, or some combination thereof. Representative antidepressants include amitriptyline, amoxapine, bupropion, citalopram, desvenlafaxine, doxepin, duloxetine, escitalopram, fluoxetine, imipramine, isocarboxazid, levomilnacipran, mirtazapine, nefazodone, nortriptyline, paroxetine, phenelzine, protriptyline, selegiline, sertraline, tranylcypromine, trazodone, trimipramine, venlafaxine, vilazodone and vortioxetine. Representative antipsychotics include aripiprazole, asenapine, chlorpromazine, clozapine, desipramine, fluphenazine, haloperidol, iloperidone, lurasidone, olanzapine, paliperidone, perphenazine, quetiapine, risperidone and ziprasidone.

Likewise, the compounds of Formula 1 may be combined with one or more agents for treating anxiety (anxiolytics) or for treating epilepsy (antiepileptics or anticonvulsants) or some combination thereof. Representative anxiolytics include benzodiazepines (e.g. alprazolam, chlordiazepoxide, clobazepam, clonazepam, clorazepate, diazepam, estazolam, flurazepam, lorazepam, midazolam, oxazepam, prazepam, quazepam, temazepam and triazolam), non-benzodiazepines (e.g. eszopiclone, zaleplon, zolpidem and zopiclone) and buspirone. Representative anticonvulsants include acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The activity of the example compounds may be determined by a variety of methods, including in vitro and in vivo methods.

In Vitro Inhibition ($EC_{50}$) of Intracellular Calcium Flux

The release of intracellular calcium following stimulation of cells with substance P in the presence or absence of inhibitor compounds was measured using the FLIPR Tetra® system. CHO-K1 cells overexpressing MRGX2 were seeded into 384-well plates (Black clear bottom, TC-treated, Fisher #07-200-655) and incubated overnight to allow for cell attachment. Media was removed, and 1× loading buffer (FLIPR® Calcium 5 assay solution, Molecular Devices, per manufacturer specifications) was added. The plates were incubated at 37° C. for 30 minutes. Test compounds were added to cells (11-point dose response, 10 □M maximum concentration) and fluorescence measured (120 seconds, in real time) using the FLIPR Tetra® system. Immediately following, MRGX2 ligand substance P was added at a final concentration of 1 □M and fluorescence measured (120 seconds, in real time) using the FLIPR Tetra® system. The data for the examples are reported as $pEC_{50}$.

In vitro Radioligand Binding Assay ($K_d$)

Equilibrium dissociation constants, $K_d$, for many of the compounds described in the Examples section ("test compounds") are determined in the presence cellular membrane prepared from SF9 cell lines overexpressing the human MRGX2 receptor. The assay is carried out in a 96-well plate (Greiner V-Bottom #651201). To each well is admixed fixed amounts of cell membrane preparation (75 µg/well, final concentration) and a $^3$H-labeled ligand, 3-(((furan-2-yl-4,5-t2)methyl)amino)-5-(o-tolyl)-4H-benzo[e][1,2,4]thiadiazine 1,1-dioxide (Quotient Bioresearch, 40 µM final concentration), along with a range of the (unlabeled) test compound (eight-point dose response curve, 10 µM maximum concentration, 4-fold serial dilution) in 50 mM HEPES buffer containing 10 mM $MgCl_2$, 0.01% Triton X-100, 200 µM EDTA at pH 7.4. The assay mixtures, which comprise MRGX2 receptor, radiolabeled ligand and test compound, are incubated at room temperature (~22° C.) for 60 minutes to reach equilibrium. After incubation, the assay mixtures are collected on a filter mat (Filtermat A, Perkin Elmer) using a cell harvester (Harvester 96, TOMTEC). The filter mat is completely dried. A solid scintillant (Meltilex, Perkin Elmer) is added to each filter membrane and the level of radioactivity ("Signal") from each well (assay mixture) is recorded using a scintillation counter (Trilux Microbeta, PerkinElmer). $K_d$ is determined by curve-fitting the dose response data ([I], Signal) for each set of samples to the equation, $$\text{Signal} = 100\% \left( 1 + \frac{1}{1 + \frac{[I]}{K_d}} \right),$$

where [I] is the concentration of the test compound. The data are reported as $pK_d$

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, products of certain preparations and examples are purified by mass-triggered HPLC (e.g., Pump: Waters™ 2525; MS: ZQ™; Software: MassLynx™) flash chromatography or preparative thin layer chromatography (TLC). Reverse phase chromatography is typically carried out on a column (e.g., Phenomenex Gemini™ 5µ, C18, 30 mm×150 mm; Axia™, 5µ, 30 mm×75 mm) under acidic conditions ("acid mode") eluting with $CH_3CN$ and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., H2) atmosphere are typically carried out at a pressure of about 1 atmosphere (14.7 psi).

Preparation 1: 3-chloro-5-(2-chloro-3-fluorophenyl)-4H-benzo[e][1,2,4]thiadiazine 1,1-dioxide

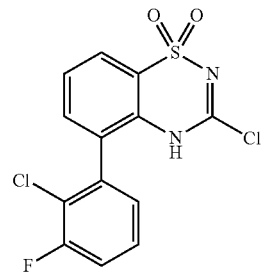 [SMILES: O=S1(=O)N=C(Cl)Nc2c(-c3cccc(F)c3Cl)cccc21]

To a suspension of 3-chloro-5-iodo-4H-benzo[e][1,2,4]thiadiazine 1,1-dioxide (3 g, 8.76 mmol) and (2-chloro-3-fluorophenyl)boronic acid (1.833 g, 10.51 mmol) in dioxane (20 mL) and saturated (aq) $NaHCO_3$ (20 mL) was added $PdCl_2$(dppf) (0.641 g, 0.876 mmol). The mixture was heated in a microwave reactor at 75° C. for 30 minutes. The residue was diluted with EtOAc and washed with saturated (aq) $NH_4Cl$ (3×). The combined organic layers were dried over $MgSO_4$, filtered, and concentrated in vacuo. The resulting residue was purified by column chromatography (Teledyne ISCO CombiFlash™, 120 g column) eluting with a gradient of 30-100% EtOAc in hexanes. The title compound was isolated as a brown solid (1.00 g, 33%).

Preparation 2: 3-chloro-5-(2-chloro-3-fluorophenyl)-7-fluoro-4H-benzo[e][1,2,4]thiadiazine 1,1-dioxide

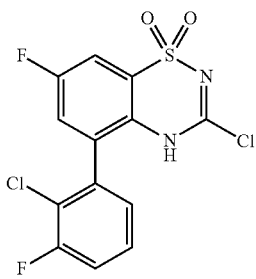 [SMILES: O=S1(=O)N=C(Cl)Nc2c(-c3cccc(F)c3Cl)cc(F)cc21]

Step A: 2'-chloro-3',5-difluoro-[1,1'-biphenyl]-2-amine

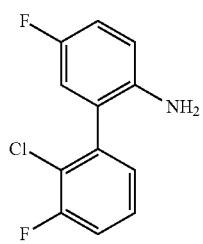 [SMILES: Nc1ccc(F)cc1-c1cccc(F)c1Cl]

To a 300 mL heavy-walled flask were added (2-chloro-3-fluorophenyl)boronic acid (5.51 g, 31.6 mmol), 2-bromo-4-fluoroaniline (5 g, 26.3 mmol) and PdCl$_2$(dppf) (1.925 g, 2.63 mmol) in dioxane (60 mL) and saturated (aq) NaHCO$_3$ (60.0 mL) to give an orange solution. The flask was sealed, heated to 100° C. and stirred for 18 hours. The reaction mixture was partially concentrated, then diluted with EtOAc, and washed with saturated (aq) NH$_4$Cl (3×100 mL). The combined organic layers were dried over MgSO$_4$, filtered, and concentrated in vacuo. The product was purified by column chromatography (Teledyne ISCO CombiFlash™, 120 g column) eluting with a gradient of 10-90% EtOAc in hexanes. The title compound was isolated as a red oil (3.75 g, 60%); ESI-MS m/z [M+H]$^+$ 239.4.

Step B: 5-(2-chloro-3-fluorophenyl)-7-fluoro-3-hydroxy-4H-benzo[e][1,2,4]thiadiazine 1,1-dioxide

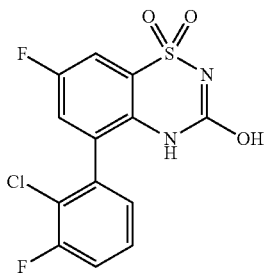 [SMILES: O=S1(=O)N=C(O)Nc2c(-c3cccc(F)c3Cl)cc(F)cc21]

To a 200 mL round-bottomed flask were added sulfurisocyanatidic chloride (1.907 mL, 21.91 mmol) and nitromethane (10 mL). The mixture was cooled to 0° C. Next, 2'-chloro-3',5-difluoro-[1,1'-biphenyl]-2-amine (3.75 g, 15.7 mmol) in nitromethane (40 mL) was added dropwise to give a yellow solution. The reaction mixture was stirred at 0° C. for 30 minutes. Aluminum trichloride (3.13 g, 23.47 mmol) was added and the reaction mixture was heated to 120° C. for 1.5 hours. Following reaction, the mixture was concentrated and diluted with EtOAc and washed with saturated (aq) NH$_4$Cl (3×80 mL). The combined organic layers were dried over MgSO$_4$, filtered, and concentrated in vacuo to give a brown solid. The product was purified by column chromatography (Teledyne ISCO CombiFlash™, 120 g column) eluting with a gradient of 30-100% EtOAc in hexanes. The title compound was isolated as a tan solid (2.57 g, 48%). $^1$H NMR (400 MHz, DMSO-d$_6$), δ ppm 7.27 (d, J=7.07 Hz, 1H), 7.42-7.63 (m, 3H), 7.79 (dd, J=7.07, 2.53 Hz, 1H), 10.20 (br s, 1H).

Step C: 3-chloro-5-(2-chloro-3-fluorophenyl)-7-fluoro-4H-benzo[e][1,2,4]thiadiazine 1,1-dioxide To a 200 mL round-bottomed flask were added 5-(2-chloro-3-fluorophenyl)-7-fluoro-3-hydroxy-4H-benzo[e][1,2,4]thiadiazine 1,1-dioxide (2.57 g, 7.46 mmol) in POCl$_3$ (50 mL, 536 mmol) and N,N-diethylaniline (1.716 mL, 10.73 mmol) to give a black solution. The reaction mixture was heated to 120° C. and stirred for 5 hours, was subsequently cooled to ambient temperature, and left to stir overnight. The reaction mixture was poured into ice water and stirred for 2 hours. The black oil eventually formed a brown precipitate that was collected by vacuum filtration and dried under vacuum to give the title compound as a brown solid (2.55 g, 65%). The product was used without further purification.

Preparation 3: (3-fluoropyridin-2-yl)methanamine

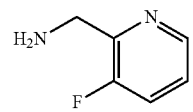

A stirred solution of 3-fluoropicolinonitrile (500 mg, 4.10 mmol) in EtOH (25 mL) and hydrochloric acid (12 M, 1.02 mL) was reacted with H2 in the presence of a catalyst (10% Pd/C, 200 mg) at 50 psi for 16 hours. The progress of the hydrogenation reaction was monitored by TLC. Following completion of the reaction, the mixture was filtered to remove the catalyst. The solvents were removed under reduced pressure and the resulting solid was suspended in acetonitrile and filtered to give an HCl salt of the title compound (700 mg), which was used without further purification. $^1$H NMR (400 MHz, CDCl$_3$) δ ppm 8.54 (br s, 2H), 8.49 (d, J=4.8 Hz, 1H), 7.83 (dt, J=1.1, 9.2 Hz, 1H), 7.54 (td, J=4.4, 8.4 Hz, 1H), 4.40-4.12 (m, 2H).

Preparation 4: 3-(((3-fluoropyridin-2-yl)methyl)amino)-5-iodo-4H-benzo[e][1,2,4]thiadiazine 1,1-dioxide

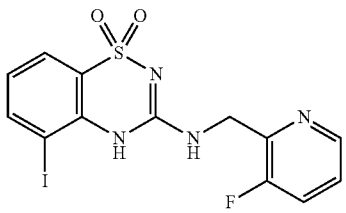 [SMILES: O=S1(=O)N=C(NCc2ncccc2F)Nc2c(I)cccc21]

To a solution of (3-fluoropyridin-2-yl)methanamine (1.06 g, 3.08 mmol) and 3-chloro-5-iodo-4H-benzo[e][1,2,4]thiadiazine 1,1-dioxide (500 mg, 3.08 mmol) in 10 mL isopropanol was added Et$_3$N (1.28 mL, 9.24 mmol) with stirring at 80° C. The reaction mixture was stirred at 80° C. for 30 minutes at which time TLC monitoring (DCM/MeOH=10:1 mobile phase) showed the reaction was complete. The volatiles were removed in vacuo. The resulting residue was purified by silica gel column chromatography, eluting with a gradient of 50-80% EtOAc in petroleum ether, to give the title compound as a light-yellow solid (1.20 g). $^1$H NMR (400 MHz, DMSO-d$_6$) δ ppm 9.62 (s, 1H), 8.84 (t, J=4.8 Hz, 1H), 8.46 (d, J=4.8 Hz, 1H), 8.09 (dd, J=1.2, 7.8 Hz, 1H), 7.78 (t, J=9.2 Hz, 1H), 7.71 (d, J=7.8 Hz, 1H), 7.48 (td, J=4.4, 8.4 Hz, 1H), 7.08 (t, J=7.8 Hz, 1H), 4.68 (d, J=3.6 Hz, 2H); ESI-MS m/z [M+H]$^+$ 433.0.

Preparation 5: 3-chloro-5-(2-chlorophenyl)-7-fluoro-4H-benzo[e][1,2,4]thiadiazine 1,1-dioxide

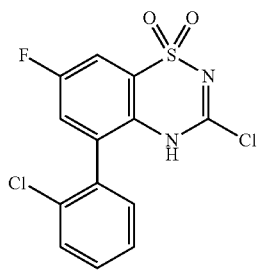 [SMILES: O=S1(=O)N=C(Cl)Nc2c(-c3ccccc3Cl)cc(F)cc21]

Step A: 2'-chloro-5-fluoro-[1,1'-biphenyl]-2-amine

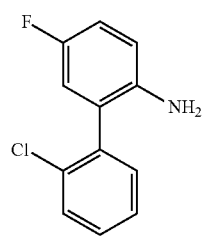 [SMILES: Nc1ccc(F)cc1-c1ccccc1Cl]

To a solution of 2-bromo-4-fluoro-aniline (5.00 g, 26.31 mmol) and (2-chlorophenyl)boronic acid (4.53 g, 28.94 mmol) in dioxane (50.00 mL) was added Pd(dppf)Cl$_2$ (962.56 mg, 1.32 mmol) and NaHCO$_3$ (4.42 g, 52.62 mmol) in H$_2$O (10.00 mL). The mixture was purged with N$_2$ (3×) and heated to 120° C. for 2 hours. The solvent was removed in vacuo and the residue was partitioned between H$_2$O (80 mL) and EtOAc (50 mL). The aqueous layer was extracted with EtOAc (3×30 mL). The organic layers were combined, washed with brine (50 mL) and dried over Na$_2$SO$_4$. The crude product was purified by column chromatography (ISCO 80 g column) eluting with a gradient of EtOAc/petroleum ether (1:50-1:8) to give the title compound as a yellow oil (5.18 g, 89%). $^1$H NMR (400 MHz, CDCl$_3$) δ ppm 3.44 (br s, 2H), 6.73 (dd, J=4.9, 8.8 Hz, 1H), 6.81 (dd, J=2.9, 9.0 Hz, 1H), 6.94 (dt, J=2.9, 8.5 Hz, 1H), 7.42-7.29 (m, 3H), 7.57-7.48 (m, 1H).

Step B: 5-(2-chlorophenyl)-7-fluoro-3-hydroxy-4H-benzo[e][1,2,4]thiadiazine 1,1-dioxide

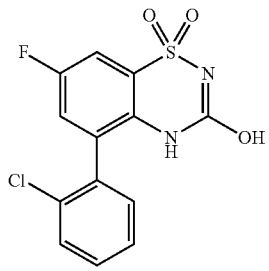 [SMILES: O=S1(=O)N=C(O)Nc2c(-c3ccccc3Cl)cc(F)cc21]

To a solution of sulfurisocyanatidic chloride (4.96 g, 35.06 mmol) in nitromethane (60.00 mL) was added 2'-chloro-5-fluoro-[1,1'-biphenyl]-2-amine (5.18 g, 23.37 mmol) at −5° C. to 0° C. The resulting mixture was stirred at −5° C. to 0° C. for 30 minutes and then AlCl$_3$ (6.23 g, 46.74 mmol, 2.55 mL) was added. The reaction mixture was heated to 120° C. for 1.5 hours, then cooled to 25° C., poured into ice water (200 mL) and stirred for 30 minutes. A precipitant was collected by filtration. The collected solid was dissolved in EtOAc (50 mL) and washed with saturated (aq) NaHCO$_3$ solution (3×50 mL). The aqueous layers were combined, adjusted to pH 1 with concentrated (aq) HCl, and extracted with EtOAc (3×30 mL). The combined organic layers were dried over Na$_2$SO$_4$, filtered, and concentrated to give the title compound as a dark solid (3.80 g, 50%). $^1$H NMR (400 MHz, DMSO-d$_6$) δ ppm 7.55-7.39 (m, 4H), 7.65-7.57 (m, 1H), 7.79 (dd, J=2.8, 7.1 Hz, 1H), 10.32 (s, 1H).

Step C: 3-chloro-5-(2-chlorophenyl)-7-fluoro-4H-benzo[e][1,2,4]thiadiazine 1,1-dioxide To a solution of 5-(2-chlorophenyl)-7-fluoro-3-hydroxy-4H-benzo[e][1,2,4]thiadiazine 1,1-dioxide (1.00 g, 3.06 mmol) in POCl$_3$ (15.00 mL) was added N,N-diethylaniline (456.74 mg, 3.06 mmol, 491.12 µL). The solution was heated to 120° C. for 20 hours, then cooled to 25° C., poured into ice water (100 mL), and stirred for 1 hour. The mixture was extracted with EtOAc (3×30 mL). The organic layers were combined, dried over Na$_2$SO$_4$, filtered, and concentrated in vacuo to afford the title compound as a dark solid (900 mg, 85%). The product was used without further purification.

Preparation 6: 3-chloro-5-(2,3-difluorophenyl)-4H-benzo[e][1,2,4]thiadiazine 1,1-dioxide

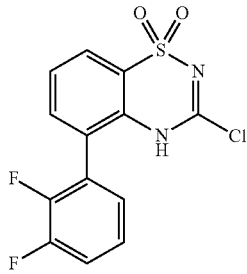 [SMILES: O=S1(=O)N=C(Cl)Nc2c(-c3cccc(F)c3F)cccc21]

To a 20 mL microwave vial equipped with a stirring device were added (2,3-difluorophenyl)boronic acid (0.507 g, 3.21 mmol), 3-chloro-5-iodo-4H-benzo[e][1,2,4]thiadiazine 1,1-dioxide (1.00 g, 2.92 mmol), $Cs_2CO_3$ (2M, 3.65 mL, 7.30 mmol), and $Pd(dppf)_2 \cdot CH_2Cl_2$ adduct (0.238 g, 0.292 mmol) dissolved in dioxane (14.60 mL). The reaction mixture was heated in a microwave reactor at 120° C. for 30 minutes and then diluted in deionized water (~100 mL). Next 1 N (aq) HCl was added dropwise until a precipitate formed. The solids were collected by vacuum filtration through a Kiriyama Rohto SB-40 glass filter funnel while washing with copious amounts of deionized water followed by hexanes. The filter cake was dried in a vacuum oven to afford the title compound as a (crude) solid (1.164 g).

Preparation 7: 3-chloro-5-(2-chloro-3,5-difluorophenyl)-4H-benzo[e][1,2,4]thiadiazine 1,1-dioxide

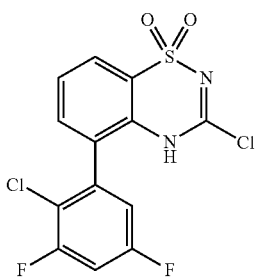 [SMILES: O=S1(=O)N=C(Cl)Nc2c(-c3cc(F)cc(F)c3Cl)cccc21]

The title compound was prepared in a manner similar to Preparation 6, using (2-chloro-3,5-difluorophenyl)boronic acid (90 mg, 0.467 mmol), 3-chloro-5-iodo-4H-benzo[e][1,2,4]thiadiazine 1,1-dioxide (80 mg, 0.234 mmol), $Cs_2CO_3$ (2M, 0.292 mL, 0.584 mmol), and $Pd(dppf)_2 \cdot CH_2Cl_2$ adduct (19.07 mg, 0.023 mmol) dissolved in dioxane (1168 μL), and was isolated as a (crude) solid (56.2 mg). ESI-MS m/z [M+H]+ 362.9.

Preparation 8: 5-iodo-3-((2-methoxyethyl)amino)-4H-benzo[e][1,2,4]thiadiazine 1,1-dioxide

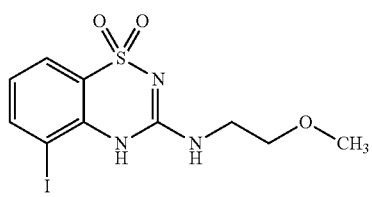 [SMILES: COCCNC1=NS(=O)(=O)c2cccc(I)c2N1]

To a flask containing a solution of 3-chloro-5-iodo-4H-benzo[e][1,2,4]thiadiazine 1,1-dioxide (2 g, 5.84 mmol) and $K_2CO_3$ (0.807 g, 5.84 mmol) in DMA (11.68 mL) was added 2-methoxyethanamine (0.554 mL, 6.42 mmol). The reaction mixture was heated at 100° C. for 2 hours and then cooled and diluted with water (300 mL). An organic phase (oil) pooled at the bottom of the flask. The aqueous phase was decanted and extracted with DCM (3×50 mL). The organic layers were combined with the oil and concentrated to give the title compound as an orange-brown solid (1.8 g, 81%).

Preparation 9: 3-chloro-5-(2-chlorophenyl)-4H-benzo[e][1,2,4]thiadiazine 1,1-dioxide

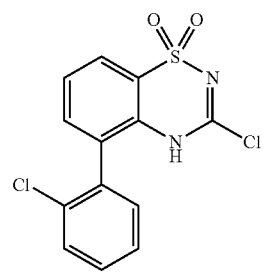 [SMILES: O=S1(=O)N=C(Cl)Nc2c(-c3ccccc3Cl)cccc21]

To a 20 mL microwave vial equipped for stirring and charged with 3-chloro-5-iodo-4H-benzo[e][1,2,4]thiadiazine 1,1-dioxide (1.000 g, 2.92 mmol), (2-chlorophenyl)boronic acid (0.479 g, 3.07 mmol), $Cs_2CO_3$ (5.84 mL, 11.68 mmol) and dioxane (14.60 mL), was added $Pd(dppf)_2 \cdot CH_2Cl_2$ adduct (0.238 g, 0.292 mmol) under nitrogen. The reaction mixture was heated to 120° C. for 15 minutes in a microwave reactor and then poured into water (200 mL). 1N HCl (aq) was added until a tan solid began to form. The solid was filtered and washed with copious amounts of water followed by hexanes to afford the title compound (0.95 g, 99%). ESI-MS m/z [M+H]+ 326.9.

Preparation 10: 3-chloro-5-(3-chloro-2-fluoropyridin-4-yl)-4H-benzo[e][1,2,4]thiadiazine 1,1-dioxide

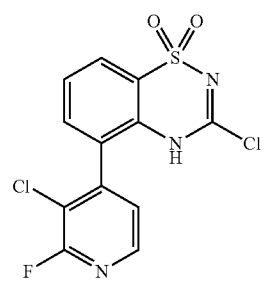

To a 20 mL pressurized microwave vial equipped with a stirring bar were added 3-chloro-2-fluoro-4-(4,4,5,5-tetramethyl-1,3,2-dioxaborolan-2-yl)pyridine (750 mg, 2.91 mmol), 3-chloro-5-iodo-4H-benzo[e][1,2,4]thiadiazine 1,1-dioxide (907 mg, 2.65 mmol), cesium fluoride (aq) (1.006 g, 6.62 mmol), and $Pd(dppf)_2 \cdot CH_2Cl_2$ adduct (216 mg, 0.265 mmol) dissolved in dioxane (8.826 mL). The reaction mixture was heated in a microwave reactor at 120° C. for 30 minutes. Next 1 N (aq) HCl was added, causing solids to precipitate out of solution. The solids were collected by vacuum filtration through a Kiriyama Rohto SB-21 glass filter funnel while washing with copious amounts of deionized water followed by hexanes. The filter cake was dried in a vacuum oven to afford the title compound as a (crude) solid (933.8 mg, 2.70 mmol) that was used to prepare Examples 48, 49, 50, and 51.

In an effort to lower the Pd content, a portion of the crude product (400 mg) was dispersed in EtOH (5 mL), and 1,4-diazabicyclo[2,2,2]octane-activated charcoal (10% by weight, 40 mg) was added, and the mixture was heated at 60° C. for 2.5 hours. The mixture was subsequently filtered through a RediSep® pre-packed plug with MeOH rinse and concentrated under vacuum to give the title compound (296.3 mg) which was used to prepare Examples 52, 53, 54, and 55.

Preparation 11: 3-chloro-5-(1,3-dimethyl-1H-pyrazol-4-yl)-4H-benzo[e][1,2,4]thiadiazine 1,1-dioxide

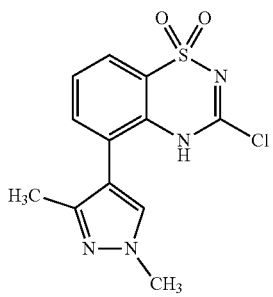 [SMILES: Cc1nn(C)cc1-c1cccc2c1NC(Cl)=NS2(=O)=O]

A 20 mL microwave vial equipped for stirring was charged with 1,3-dimethyl-4-(4,4,5,5-tetramethyl-1,3,2-dioxaborolan-2-yl)-1H-pyrazole (421 mg, 1.898 mmol), 3-chloro-5-iodo-4H-benzo[e][1,2,4]thiadiazine 1,1-dioxide (500 mg, 1.460 mmol), $Cs_2CO_3$ (2.919 mL, 5.84 mmol), and $Pd(dppf)_2 \cdot CH_2Cl_2$ adduct (119 mg, 0.146 mmol) and dioxane (7.298 mL). The reaction mixture was heated in a microwave reactor at 120° C. for 30 minutes, then diluted in deionized water (75 mL) and extracted with DCM/IPA (4×). Only a nominal amount of product went into the organic phase. The aqueous phase was concentrated with 60-angstrom silica gel and the residue was purified by normal phase column chromatography (RediSep® half-column) eluting with 80/20 DCM/MeOH. The product-containing fractions were collected, concentrated, and dried under vacuum to afford the title compound as the major product (549.8 mg). ESI-MS m/z [M+H]$^+$ 311.0.

Preparation 12: 3-chloro-5-(3,5-difluorophenyl)-4H-benzo[e][1,2,4]thiadiazine 1,1-dioxide

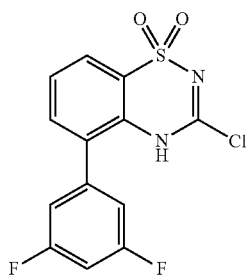 [SMILES: O=S1(=O)N=C(Cl)Nc2c(-c3cc(F)cc(F)c3)cccc21]

A 20 mL pressurized microwave vial equipped for stirring was charged with 3-chloro-5-iodo-4H-benzo[e][1,2,4]thiadiazine 1,1-dioxide (700 mg, 2.044 mmol), (3,5-difluorophenyl)boronic acid (355 mg, 2.248 mmol), $Cs_2CO_3$ (2.55 mL, 5.11 mmol), and $Pd(dppf)_2 \cdot CH_2Cl_2$ adduct (167 mg, 0.204 mmol) dissolved in dioxane (10.2 mL). The reaction mixture was heated in a microwave reactor at 120° C. for 30 minutes and then diluted in about 100 mL of deionized water. To the mixture was added 1N HCl (about 3 mL) dropwise until a precipitate formed. The solid was collected by vacuum filtration through a Kiriyama Rohto SB-40 glass funnel while washing with copious amounts of deionized water followed by hexanes to afford the title compound as a pale pink solid (779.6 mg). The crude product was dried in the vacuum oven prior to use.

Preparation 13: 5-iodo-3-(methylamino)-4H-benzo[e][1,2,4]thiadiazine 1,1-dioxide

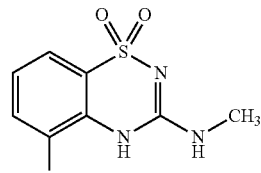

To a 20 mL vial were added 3-chloro-5-iodo-4H-benzo[e][1,2,4]thiadiazine 1,1-dioxide (800 mg, 2.34 mmol), methanamine (2M in MeOH, 1.518 mL, 3.04 mmol) and DIPEA (0.408 mL, 2.335 mmol) in DMA (7 mL) to give a yellow solution. The reaction mixture was heated to 80° C. and stirred overnight. LC/MS indicated the reaction was complete. The reaction mixture was subsequently diluted with EtOAc and washed with saturated (aq) $NH_4Cl$ (3×). The organic layers were combined, dried over $MgSO_4$, filtered, and concentrated. The product was purified by column chromatography (ISCO 40 g column) eluting with a gradient of 30-100% EtOAc in hexane to give the title compound as a brown oil (356 mg, 45%). ESI-MS m/z [M+H]$^+$ 338.

Preparation 14: 3-chloro-5-(2-chloro-3-fluorophenyl)-7-methyl-4H-benzo[e][1,2,4]thiadiazine 1,1-dioxide

Step A: 5-bromo-3-hydroxy-7-methyl-4H-benzo[e][1,2,4]thiadiazine 1,1-dioxide

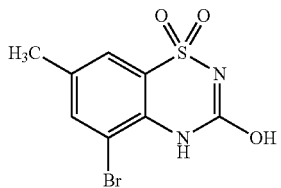

To a 25 mL round-bottomed flask were added 2-bromo-4-methylaniline (700 mg, 3.76 mmol) in nitromethane (5 mL) and the reaction mixture was cooled to −40° C. Sulfurisocyanatidic chloride (0.425 mL, 4.89 mmol) was added and the reaction mixture was allowed to slowly warm to 25° C. and stirred for another 30 minutes. Next aluminum trichloride (602 mg, 4.51 mmol) was added. The reaction mixture was heated at 100° C. for 1.5 hours, cooled to 25° C., poured into ice water, and sonicated to afford a tan precipitate. The solids were collected by vacuum filtration and dried under vacuum to give the title compound (685 mg, 63%). $^1$H NMR (400 MHz, DMSO-d$_6$), δ ppm 2.4 (s, 3H), 4.4 (s, 1H), 7.6 (s, 1H), 7.8 (s, 1H), 10.3 (s, 1H).

Step B: 5-bromo-3-chloro-7-methyl-4H-benzo[e][1,2,4]thiadiazine 1,1-dioxide

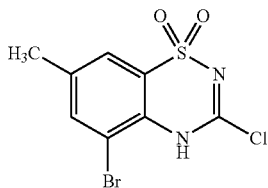

To a 50 mL round-bottomed flask was added 5-bromo-3-hydroxy-7-methyl-4H-benzo[e][1,2,4]thiadiazine 1,1-dioxide (685 mg, 2.353 mmol) in nitromethane (12 mL). To the resulting brown solution, was added POCl$_3$ (1.382 mL, 14.82 mmol) alone with N,N-diethylaniline (0.151 mL, 0.941 mmol). The reaction mixture was heated to 100° C. for 16 hours, then cooled to 0° C., quenched with water, and sonicated to give a precipitate. The solids were collected by vacuum filtration to give the title compound as a tan solid (160 mg, 22%). The product was used without purification. $^1$H NMR (400 MHz, DMSO-d$_6$), δ ppm 2.4 (s, 3H), 7.5 (s, 1H), 7.7 (s, 1H).

Step C: 3-chloro-5-(2-chloro-3-fluorophenyl)-7-methyl-4H-benzo[e][1,2,4]thiadiazine 1,1-dioxide To a 5 mL microwave vial were added 5-bromo-3-chloro-7-methyl-4H-benzo[e][1,2,4]thiadiazine 1,1-dioxide (160 mg, 0.517 mmol), Pd$_2$Cl$_2$(dppf) (3.78 mg, 5.17 μmol), (2-chloro-3-fluorophenyl)boronic acid (108 mg, 0.620 mmol), and saturated (aq) NaHCO$_3$ (3.0 mL) in dioxane (3.0 mL). The reaction mixture was heated in a microwave reactor for 1 hour at 75° C., then diluted in EtOAc, and washed with saturated (aq) NH$_4$Cl (3×). The organic layers were combined, dried over MgSO$_4$, filtered, and concentrated in vacuo. The product was purified by column chromatography (ISCO 4 g column) eluting with a gradient of 30-100% EtOAc in hexane to give the title compound as a yellow oil (44 mg, 24%). ESI-MS m/z [M+H]$^+$ 359.0.

Preparation 15: 5-iodo-3-((4-isopropylphenyl)amino)-4H-benzo[e][1,2,4]thiadiazine 1,1-dioxide

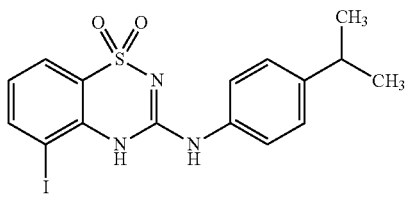 [SMILES: CC(C)c1ccc(NC2=NS(=O)(=O)c3cccc(I)c3N2)cc1]

A 100 mL round-bottomed flask was charged with 3-chloro-5-iodo-4H-benzo[e][1,2,4]thiadiazine 1,1-dioxide (750 mg, 2.190 mmol), 4-isopropylaniline (0.449 mL, 3.28 mmol), Et$_3$N (0.916 ml, 6.57 mmol) and EtOH (20 mL). The resulting brown solution was heated to 65° C. and stirred overnight. LC/MS showed the reaction was not yet complete. The reaction mixture was allowed to stir overnight again, after which LC/MS showed the reaction was mostly complete. The reaction mixture was subsequently concentrated, taken up in EtOAc, and washed with saturated (aq) NH$_4$Cl (3×). The organic layers were combined, dried over MgSO$_4$, filtered, and concentrated. The product was purified by column chromatography (ISCO 40 g column) eluting with a gradient of 30-100% EtOAc in hexane to give the title compound as a purple solid. ESI-MS m/z [M+H]$^+$ 442.

Preparation 16: 5-iodo-3-((3-isopropylphenyl)amino)-4H-benzo[e][1,2,4]thiadiazine 1,1-dioxide

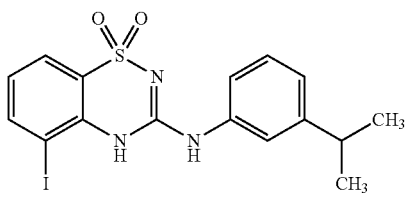 [SMILES: CC(C)c1cccc(NC2=NS(=O)(=O)c3cccc(I)c3N2)c1]

To a solution of 3-chloro-5-iodo-4H-benzo[e][1,2,4]thiadiazine 1,1-dioxide (125 mg, 0.365 mmol) in EtOH (mL) was added 3-isopropylaniline (74.0 mg, 0.547 mmol) followed by Et$_3$N (0.102 mL, 0.730 mmol). The reaction mixture was heated at 80° C. for 2 days and set aside (first reaction mixture). To a 10 mL vial was added 3-chloro-5-iodo-4H-benzo[e][1,2,4]thiadiazine 1,1-dioxide (125 mg, 0.365 mmol), 3-isopropylaniline (64.1 mg, 0.474 mmol) and DIPEA (0.127 mL, 0.730 mmol) in DMA (3.5 mL). The second reaction mixture was heated to 100° C. and stirred for 18 hours. The second reaction mixture was combined with the first reaction mixture, diluted with EtOAc and washed with saturated (aq) NH$_4$Cl (3×). The organic layers were combined, dried over MgSO$_4$, filtered, and concentrated. The product was purified by column chromatography (ISCO) eluting with a gradient of 20-70% EtOAc in hexane to give the title compound (118 mg, 37%). ESI-MS m/z [M+H]$^+$ 442.1.

Preparation 17: 5-iodo-3-((6-isopropylpyridin-3-yl)amino)-4H-benzo[e][1,2,4]thiadiazine 1,1-dioxide

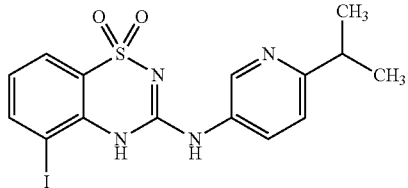 [SMILES: CC(C)c1ccc(NC2=NS(=O)(=O)c3cccc(I)c3N2)cn1]

To a solution of 3-chloro-5-iodo-4H-benzo[e][1,2,4]thiadiazine 1,1-dioxide (125 mg, 0.365 mmol) in EtOH (3.5 mL) was added 6-isopropylpyridin-3-amine (74.5 mg, 0.547 mmol) followed by Et$_3$N (0.102 mL, 0.730 mmol). The reaction mixture was heated at 80° C. for 3 days to give a first batch of product (about 50% conversion of starting material). To a 10 mL vial was added 3-chloro-5-iodo-4H-benzo[e][1,2,4]thiadiazine 1,1-dioxide (125 mg, 0.365 mmol), 6-isopropylpyridin-3-amine (64.6 mg, 0.474 mmol) and DIPEA (0.127 mL, 0.730 mmol) in DMA (3.5 mL). The reaction mixture was heated to 100° C. and stirred for 2 days to give a second batch of product (about 50% conversion). The first and second batches were combined, diluted with EtOAc and washed with saturated (aq) NH$_4$Cl (3×). The organic layers were combined, dried over MgSO$_4$, filtered, and concentrated. The product was purified by column chromatography (ISCO) eluting with a gradient of 40-95% EtOAc in hexane to give the title compound as a mixture with starting material (87 mg). ESI-MS m/z [M+H]$^+$ 443.0.

Preparation 18: 5-iodo-3-(((6-methoxypyridin-2-yl)methyl)amino)-4H-benzo[e][1,2,4]thiadiazine 1,1-dioxide

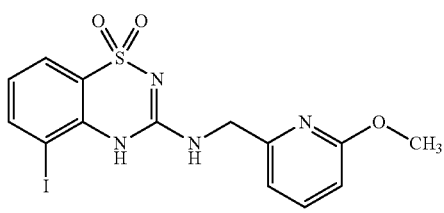 [SMILES: COc1cccc(CNC2=NS(=O)(=O)c3cccc(I)c3N2)n1]

To a 10 mL vial were added 3-chloro-5-iodo-4H-benzo[e][1,2,4]thiadiazine 1,1-dioxide (250 mg, 0.730 mmol), (6-methoxypyridin-2-yl)methanamine (131 mg, 0.949 mmol) and DIPEA (0.255 mL, 1.460 mmol) in DMA (3.5 mL). The reaction mixture was heated to 100° C. and stirred for 5 hours. The reaction mixture was subsequently diluted with EtOAc and washed with saturated (aq) NH$_4$Cl (3×). The organic layers were combined, dried over MgSO$_4$, filtered, and concentrated. The product was purified by column chromatography (ISCO NH column) eluting with a gradient of 0-10% MeOH in DCM. The title compound was isolated as a pale yellow solid (167 mg, 52%). ESI-MS m/z [M+H]$^+$ 445.0.

Preparation 19: 3-(((3-fluoropyridin-2-yl)methyl)amino)-5-iodo-4H-benzo[e][1,2,4]thiadiazine 1,1-dioxide

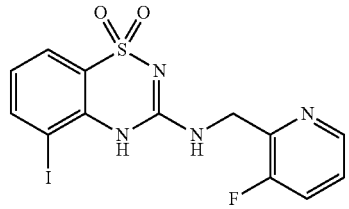 [SMILES: O=S1(=O)N=C(NCc2ncccc2F)Nc2c(I)cccc21]

The title compound was prepared in a manner similar to Preparation 18, using 3-chloro-5-iodo-4H-benzo[e][1,2,4]thiadiazine 1,1-dioxide (175 mg, 0.511 mmol), (3-fluoropyridin-2-yl)methanamine (97 mg, 0.766 mmol) and DIPEA (0.178 mL, 1.022 mmol) in DMA (2 mL), and was isolated as a pale yellow solid (53 mg, 24%). ESI-MS m/z [M+H]$^+$ 433.0.

Preparation 20: 5-iodo-3-(phenylamino)-4H-benzo[e][1,2,4]thiadiazine 1,1-dioxide

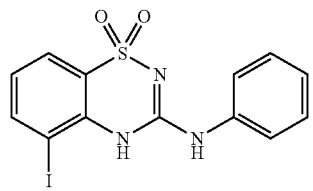 [SMILES: O=S1(=O)N=C(Nc2ccccc2)Nc2c(I)cccc21]

The title compound was prepared in a manner similar to Preparation 18, using 3-chloro-5-iodo-4H-benzo[e][1,2,4]thiadiazine 1,1-dioxide (0.200 g, 0.584 mmol) and aniline (0.800 mL, 8.76 mmol), and was isolated as a pale pink solid (35 mg, 15%). ESI-MS m/z [M+H]$^+$ 400.0.

Preparation 21: 5-iodo-3-((thiazol-2-ylmethyl)amino)-4H-benzo[e][1,2,4]thiadiazine 1,1-dioxide

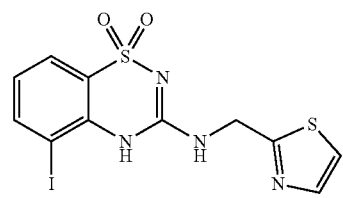 [SMILES: O=S1(=O)N=C(NCc2nccs2)Nc2c(I)cccc21]

To a 2-5 mL microwave vial were added 3-chloro-5-iodo-4H-benzo[e][1,2,4]thiadiazine 1,1-dioxide (200 mg, 0.584 mmol), thiazol-2-ylmethanamine (120 mg, 0.796 mmol) and K$_2$CO$_3$ (81 mg, 0.584 mmol) in DMA (1.168 mL). The reaction mixture was heated at 100° C. for 2 hours, then poured into water, and extracted with EtOAc (3×). The organic layers were combined, dried over MgSO$_4$, filtered, and concentrated to give the title compound as a light brown oil, which was used without further purification. ESI-MS m/z [M+H]$^+$ 421.2.

Preparation 22: 5-iodo-3-((2-methoxypropyl)amino)-4H-benzo[e][1,2,4]thiadiazine 1,1-dioxide

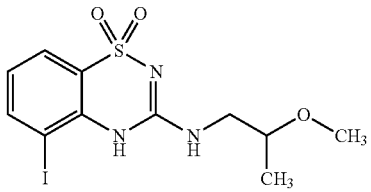 [SMILES: COC(C)CNC1=NS(=O)(=O)c2cccc(I)c2N1]

To a 2-5 mL microwave vial were added 3-chloro-5-iodo-4H-benzo[e][1,2,4]thiadiazine 1,1-dioxide (200 mg, 0.584 mmol), 2-methoxypropan-1-amine hydrochloride (81 mg, 0.642 mmol) and K$_2$CO$_3$ (81 mg, 0.584 mmol) in DMA (1.168 mL). The reaction mixture was heated at 100° C. for 2 hours, then poured into water, and extracted with EtOAc (3×). The organic layers were combined, dried over MgSO$_4$, filtered, and concentrated to give the title compound as a light brown oil, which was used without further purification. ESI-MS m/z [M+H]$^+$ 396.0.

Preparation 23: 3-((cyclobutylmethyl)amino)-5-iodo-4H-benzo[e][1,2,4]thiadiazine 1,1-dioxide

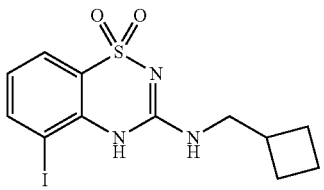 [SMILES: O=S1(=O)N=C(NCC2CCC2)Nc2c(I)cccc21]

The title compound was prepared in a manner similar to Preparation 22, using 3-chloro-5-iodo-4H-benzo[e][1,2,4]thiadiazine 1,1-dioxide (200 mg, 0.584 mmol), cyclobutylmethanamine hydrochloride (78 mg, 0.642 mmol), and K$_2$CO$_3$ (81 mg, 0.584 mmol) in DMA (1.168 mL), and was isolated as an oil. ESI-MS m/z [M+H]$^+$ 391.9.

Preparation 24: 5-iodo-3-((pyridin-2-ylmethyl)amino)-4H-benzo[e][1,2,4]thiadiazine 1,1-dioxide

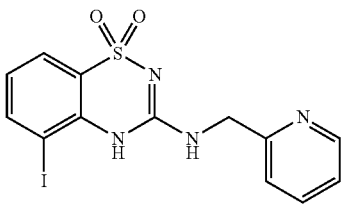 [SMILES: O=S1(=O)N=C(NCc2ccccn2)Nc2c(I)cccc21]

To a stirred solution of pyridin-2-ylmethanamine (0.020 mL, 0.200 mmol) in MeOH (0.125 mL) was added 3-chloro-5-iodo-2H-benzo[e][1,2,4]thiadiazine 1,1-dioxide (0.034 g, 0.1 mmol). During addition of the benzo[e][1,2,4]thiadiazine 1,1-dioxide the mixture was cooled in an ice bath. Following the addition, the reaction mixture was stirred at room temperature overnight. One drop of Et$_3$N was added and the reaction mixture was stirred at room temperature for 1 hour and then at 65° C. for another hour. Additional pyridin-2-ylmethanamine (0.020 mL, 0.200 mmol) was added and the mixture was stirred at 65° C. for 6 hours. This first reaction mixture was set aside. To a stirred solution of pyridin-2-ylmethanamine (40.9 µL, 0.400 mmol) in 2-propanol (250 µL) was added Et$_3$N (84 µL, 0.600 mmol) followed by 3-chloro-5-iodo-2H-benzo[e][1,2,4]thiadiazine 1,1-dioxide (68.5 mg, 0.2 mmol). The reaction mixture was cooled in an ice bath during addition of the base and the benzo[e][1,2,4]thiadiazine 1,1-dioxide and was subsequently stirred at room temperature for 96 hours. The first and second reaction mixtures were combined and purified by preparative HPLC, eluting with a gradient of 5-95% ACN in water (formic acid conditions). The title compound was isolated as an off-white solid (42 mg, 51%). ESI-MS m/z [M+H]$^+$ 415.0.

Preparation 25: 3-chloro-5-(1-methyl-1H-pyrazol-4-yl)-4H-benzo[e][1,2,4]thiadiazine 1,1-dioxide

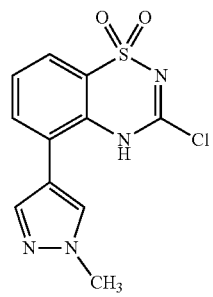 [SMILES: Cn1cc(-c2cccc3c2NC(Cl)=NS3(=O)=O)cn1]

To a stirring solution of 3-chloro-5-iodo-4H-benzo[e][1,2,4]thiadiazine 1,1-dioxide (1.250 g, 3.65 mmol) and 1-methyl-4-(4,4,5,5-tetramethyl-1,3,2-dioxaborolan-2-yl)-1H-pyrazole (1.139 g, 5.47 mmol) in water (10 mL) and dioxane (30 mL), were added PdCl$_2$(dppf)·CH$_2$Cl$_2$ adduct (298 mg, 0.365 mmol) and K$_2$CO$_3$ (1.110 g, 8.03 mmol). The reaction mixture was heated at 100° C. for 1.5 hours, then cooled to room temperature, and poured into water (50 mL). A tan precipitate formed. A 1N HCl (aq) solution was added to adjust the pH from 8 to 5, precipitating more solids. The mixture was filtered, but only a trace amount of material was recovered. The filtrate was extracted with EtOAc (3×) forming an emulsion, which was separated and extracted with DCM. The product was exclusively in the water layers, which were concentrated. The solids were rinsed with ACN and the salts were filtered off. The filtrate was concentrated and dried in the vacuum oven to give the title compound as a tan solid, which was used without further purification (1.16 g, 95% purity by LC/MS). ESI-MS m/z [M+H]$^+$ 297.0.

Preparation 26: 3-chloro-5-(2,5-difluorophenyl)-4H-benzo[e][1,2,4]thiadiazine 1,1-dioxide

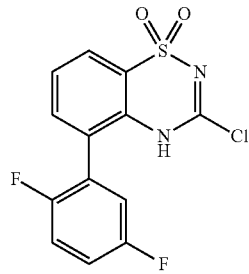 [SMILES: O=S1(=O)N=C(Cl)Nc2c(-c3cc(F)ccc3F)cccc21]

To a solution of 3-chloro-5-iodo-4H-benzo[e][1,2,4]thiadiazine 1,1-dioxide (1 g, 2.92 mmol) and (2,5-difluorophenyl)boronic acid (2 g, 12.67 mmol) in dioxane (30 mL) was added PdCl$_2$(dppf) (50 mg, 0.068 mmol). The mixture was sparged with nitrogen. Saturated (aq) NaHCO$_3$ (5 mL) was added and the reaction mixture was stirred and heated at 140° C. in a microwave reactor. The solvents were removed under high vacuum. The crude material was suspended in DMA (30 mL) and the residual solids were removed by filtration. The filtrate was used as a stock solution of the title compound (3 mmol/mL). ESI-MS m/z [M+H]$^+$ 329.0.

Preparation 27: 2-(3-chloro-1,1-dioxido-4H-benzo[e][1,2,4]thiadiazin-5-yl)benzonitrile

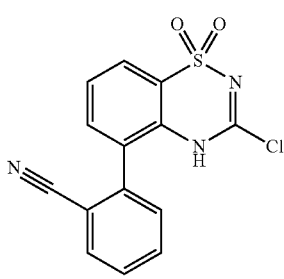 [SMILES: N#Cc1ccccc1-c1cccc2c1NC(Cl)=NS2(=O)=O]

To a mixture of 3-chloro-5-iodo-4H-benzo[e][1,2,4]thiadiazine 1,1-dioxide (0.461 g, 1.34 mmol), 2-(4,4,5,5-tetramethyl-1,3,2-dioxaborolan-2-yl)benzonitrile (0.28 g, 1.2 mmol), Cs$_2$CO$_3$ (2.445 mL, 4.89 mmol) and dioxane (6.11 mL) in a 20 mL microwave vial equipped for stirring, was added Pd(dppf)$_2$·CH$_2$Cl$_2$ adduct (0.100 g, 0.122 mmol) under nitrogen. The reaction mixture was heated in a microwave reactor to 120° C. for 20 minutes, then cooled, poured into water (150 mL) and acidified with 1N HCl (aq) until a brown precipitate formed. The solid was filtered and washed with copious amounts of water followed by hexanes to give the (crude) title compound (0.42 g). ESI-MS m/z [M+H]$^+$ 318.0.

Preparation 28: 2-(3-chloro-1,1-dioxido-4H-benzo[e][1,2,4]thiadiazin-5-yl)-6-fluorobenzonitrile

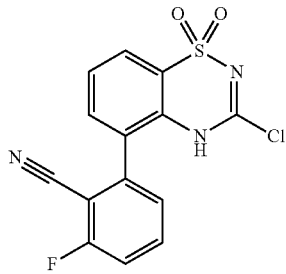 [SMILES: N#Cc1c(F)cccc1-c1cccc2c1NC(Cl)=NS2(=O)=O]

A 20 mL microwave vial equipped for stirring was charged with 3-chloro-5-iodo-4H-benzo[e][1,2,4]thiadiazine 1,1-dioxide (0.55 g, 1.606 mmol), 2-fluoro-6-(4,4,5,5-tetramethyl-1,3,2-dioxaborolan-2-yl)benzonitrile (0.436 g, 1.766 mmol), Cs$_2$CO$_3$ (3.21 mL, 6.42 mmol) and dioxane (8.03 mL). Next, Pd(dppf)$_2$·CH$_2$Cl$_2$ adduct (0.131 g, 0.161 mmol) was added under nitrogen. The reaction mixture was heated in a microwave reactor to 120° C. for 20 minutes, then cooled, poured into water (150 mL) and acidified with 1N HCl (aq) until a brown precipitate formed. The solid was filtered and washed with copious amounts of water followed by hexanes to give the title compound which was used without further purification (0.42 g, 78%).

Preparation 29: 3-chloro-5-(2-cyclopropyl-3-fluorophenyl)-4H-benzo[e][1,2,4]thiadiazine 1,1-dioxide

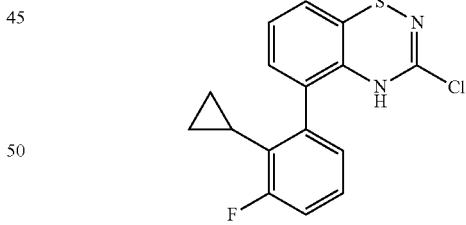

To a 20 mL microwave vial equipped for stirring and charged with 3-chloro-5-iodo-4H-benzo[e][1,2,4]thiadiazine 1,1-dioxide (0.297 g, 0.867 mmol), 2-(2-cyclopropyl-3-fluorophenyl)-4,4,5,5-tetramethyl-1,3,2-dioxaborolane (0.25 g, 0.954 mmol), Cs$_2$CO$_3$ (1.734 mL, 3.47 mmol) and dioxane (4.34 mL), was added Pd(dppf)$_2$·CH$_2$Cl$_2$ adduct (0.071 g, 0.087 mmol) under nitrogen. The reaction mixture was heated to 120° C. for 20 minutes in a microwave reactor and then cooled, poured into water (150 mL) and acidified with 1N HCl (aq) until a brown precipitate formed. The solid was filtered while washing with copious amounts of water followed by hexanes to give the title compound (0.2 g, 66%).

Example 1: 5-(2-chloro-3-fluorophenyl)-3-(methylamino)-4H-benzo[e][1,2,4]thiadiazine 1,1-dioxide

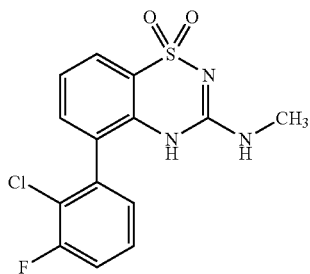 [SMILES: CNC1=NS(=O)(=O)c2cccc(-c3cccc(F)c3Cl)c2N1]

To a mixture of 3-chloro-5-(2-chloro-3-fluorophenyl)-4H-benzo[e][1,2,4]thiadiazine 1,1-dioxide (300 mg, 0.869 mmol) and Et₃N (0.363 mL, 2.61 mmol) in EtOH (7.00 mL) was added methanamine (2 M MeOH solution, 0.869 mL, 1.74 mmol). The mixture was heated at 65° C. for 12 hours. The solvent was subsequently removed in vacuo, and the residue was suspended in DCM and washed with saturated (aq) NH₄Cl (3×). The combined organic layers were dried over MgSO₄, filtered, and concentrated in vacuo. The resulting residue was purified by column chromatography (Teledyne ISCO CombiFlash™, 24 g column) eluting with a gradient of 40-100% EtOAc in hexanes. The fractions containing the product were combined and the solvent removed to give a white solid, which was dissolved in EtOAc and IPA upon heating and sonication. The solution was cooled in an ice bath and allowed to equilibrate at room temperature over a 12-hour period during which white crystals were formed. The solution was decanted and the crystals were collected by vacuum filtration while washing with IPA. The crystalline solid was dried for several hours at 35° C. under vacuum to give the title compound as a white, crystalline solid (85.0 mg, 29.1%). $^1$H NMR (400 MHz, DMSO-$d_6$) δ ppm 2.74 (d, J=4.55 Hz, 3H), 7.21 (br s, 1H), 7.28-7.45 (m, 3H), 7.52-7.66 (m, 2H), 7.78 (dd, J=7.71, 1.14 Hz, 1H), 9.05 (s, 1H); ESI-MS m/z [M+H]⁺ 340.0.

Example 2: 5-(2-chloro-3-fluorophenyl)-3-((2-methoxyethyl)amino)-4H-benzo[e][1,2,4]thiadiazine 1,1-dioxide

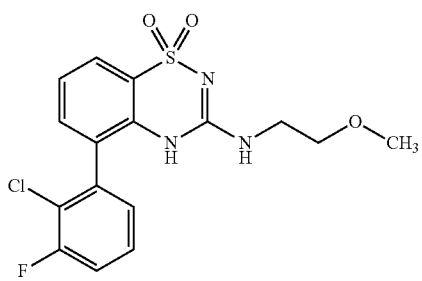

The title compound was prepared in a manner similar to Example 1, using 3-chloro-5-(2-chloro-3-fluorophenyl)-4H-benzo[e][1,2,4]thiadiazine 1,1-dioxide (120 mg, 0.348 mmol), DIPEA (0.121 mL, 0.695 mmol), and methoxyethanamine (31.3 mg, 0.417 mmol) in DMA (0.695 mL), and was isolated as a pale beige solid (76.8 mg, 57.6%). $^1$H NMR (400 MHz, DMSO-$d_6$) δ ppm 3.27 (s, 3H), 3.39 (dd, J=10.99, 4.67 Hz, 2H), 3.44 (d, J=4.55 Hz, 2H), 3.98 (s, 1H), 7.33-7.40 (m, 2H), 7.42-7.49 (m, 2H), 7.58-7.65 (m, 2H), 7.80 (dd, J=7.58, 1.26 Hz, 1H), 9.09 (s, 1H); ESI-MS m/z [M+H]⁺ 384.0.

Example 3: 5-(2-chloro-3-fluorophenyl)-7-fluoro-3-(methylamino)-4H-benzo[e][1,2,4]thiadiazine 1,1-dioxide

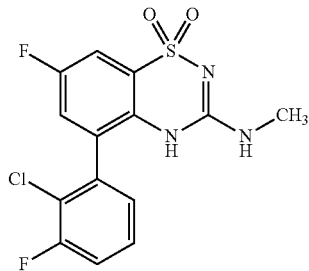 [SMILES: CNC1=NS(=O)(=O)c2cc(F)cc(-c3cccc(F)c3Cl)c2N1]

To a 20 mL vial were added 3-chloro-5-(2-chloro-3-fluorophenyl)-7-fluoro-4H-benzo[e][1,2,4]thiadiazine 1,1-dioxide (300 mg, 0.826 mmol) in EtOH (9 mL) along with methanamine (33% in MeOH, 0.134 mL, 1.074 mmol) and Et₃N (0.345 mL, 2.48 mmol). The resulting yellow solution was heated to 65° C. and stirred for 4 hours. The mixture was subsequently concentrated, diluted with EtOAc, and washed with saturated (aq) NH₄Cl (3×20 mL). The combined organic layers were dried over MgSO₄, filtered, and concentrated in vacuo. The product was purified by column chromatography (Teledyne ISCO CombiFlash™, 12 g column) eluting with a gradient of 20-100% EtOAc in hexanes. The title compound was isolated as an off-white solid (44 mg, 15%). $^1$H NMR (400 MHz, DMSO-$d_6$), δ ppm 2.73 (d, J=4.55 Hz, 3H), 7.22 (br s, 1H), 7.34 (d, J=7.07 Hz, 1H), 7.44 (dd, J=8.84, 2.78 Hz, 1H), 7.52-7.70 (m, 3H), 9.01-9.24 (m, 1H); ESI-MS m/z [M+H]⁺ 358.0; mp 241-243° C.

Example 4: 5-(2-chloro-3-fluorophenyl)-7-fluoro-3-((2-methoxyethyl)amino)-4H-benzo[e][1,2,4]thiadiazine 1,1-dioxide

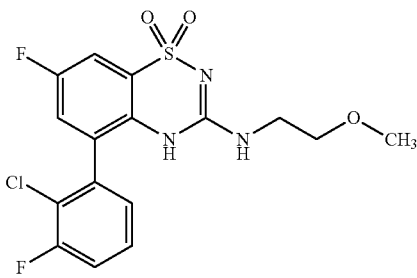 [SMILES: COCCNC1=NS(=O)(=O)c2cc(F)cc(-c3cccc(F)c3Cl)c2N1]

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), 2-methoxyethanamine (26.9 mg, 0.358 mmol) and Et₃N (0.115 mL, 0.826 mmol), and was isolated as a yellow film (19 mg, 17%); ESI-MS m/z [M+H]⁺ 402.2.

Example 5: 5-(2-chloro-3-fluorophenyl)-7-fluoro-3-((thiazol-2-ylmethyl)amino)-4H-benzo[e][1,2,4]thiadiazine 1,1-dioxide

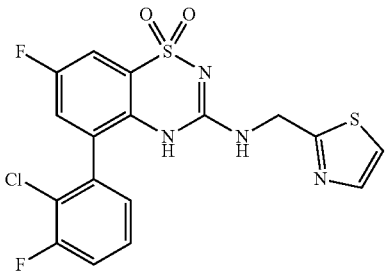

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), thiazol-2-ylmethanamine hydrochloride (53.9 mg, 0.358 mmol) and Et₃N (0.115 mL, 0.826 mmol), and was isolated as a yellow film (15 mg, 12%). ¹H NMR (400 MHz, CD₃OD) δ ppm 4.61 (s, 1H), 4.82 (br s, 2H), 7.25-7.36 (m, 2H), 7.39-7.58 (m, 3H), 7.61-7.68 (m, 1H), 7.71 (br s, 1H); ESI-MS m/z [M+H]⁺ 441.2.

Example 6: 5-(2-chloro-3-fluorophenyl)-3-(ethylamino)-7-fluoro-4H-benzo[e][1,2,4]thiadiazine 1,1-dioxide

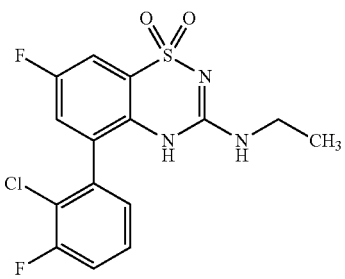 [SMILES: CCNC1=NS(=O)(=O)c2cc(F)cc(-c3cccc(F)c3Cl)c2N1]

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), ethanamine (2 M in THF, 0.179 mL, 0.358 mmol) and Et₃N (0.115 mL, 0.826 mmol), and was isolated as a brown oil (10 mg, 10%); ESI-MS m/z [M+H]⁺ 371.9.

Example 7: 5-(2-chloro-3-fluorophenyl)-3-((cyclopropylmethyl)amino)-7-fluoro-4H-benzo[e][1,2,4]thiadiazine 1,1-dioxide

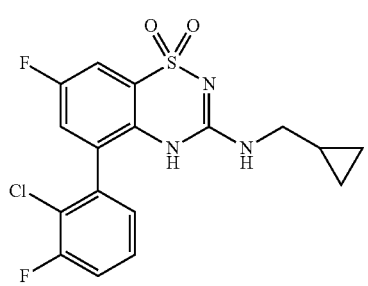 [SMILES: O=S1(=O)N=C(NCC2CC2)Nc2c(-c3cccc(F)c3Cl)cc(F)cc21]

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), cyclopropylmethanamine (25.5 mg, 0.358 mmol) and Et₃N (0.115 mL, 0.826 mmol), and was isolated as a yellow oil (25 mg, 23%). ¹H NMR (400 MHz, CD₃OD) δ ppm 0.23 (q, J=4.55 Hz, 2H), 0.46-0.56 (m, 2H), 0.94-1.08 (m, 1H), 3.16 (d, J=7.33 Hz, 2H), 7.23-7.32 (m, 2H), 7.42-7.49 (m, 1H), 7.50-7.58 (m, 1H), 7.61 (dd, J=7.07, 3.03 Hz, 1H), 7.87 (s, 1H); ESI-MS m/z [M+H]⁺ 398.1.

Example 8: 5-(2-chloro-3-fluorophenyl)-7-fluoro-3-((1-(thiazol-2-yl)ethyl)amino)-4H-benzo[e][1,2,4]thiadiazine 1,1-dioxide

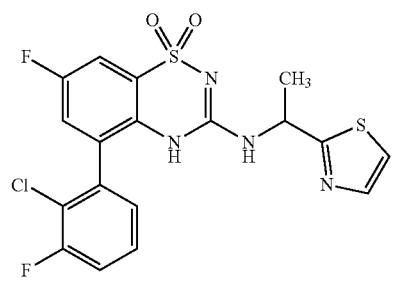 [SMILES: CC(NC1=NS(=O)(=O)c2cc(F)cc(-c3cccc(F)c3Cl)c2N1)c1nccs1]

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), 1-(thiazol-2-yl)ethanamine hydrochloride (58.9 mg, 0.358 mmol) and Et₃N (0.115 mL, 0.826 mmol), and was isolated as a brown film (8.0 mg, 6%). ¹H NMR (400 MHz, CD₃OD) δ ppm 1.61 (t, J=6.69 Hz, 3H), 5.40 (m, 1H), 7.17-7.37 (m, 2H), 7.41-7.60 (m, 3H), 7.63 (dd, J=6.95, 2.91 Hz, 1H), 7.71 (br s, 1H); ESI-MS m/z [M+H]⁺ 455.0.

Example 9: 5-(2-chloro-3-fluorophenyl)-7-fluoro-3-((1-(thiazol-4-yl)ethyl)amino)-4H-benzo[e][1,2,4]thiadiazine 1,1-dioxide

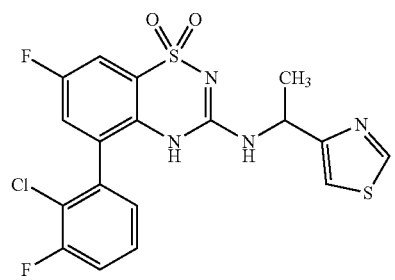 [SMILES: CC(NC1=NS(=O)(=O)c2cc(F)cc(-c3cccc(F)c3Cl)c2N1)c1cscn1]

The title compound was prepared in a manner similar to Example 3, using 3-chloro-5-(2-chloro-3-fluorophenyl)-7-fluoro-4H-benzo[e][1,2,4]thiadiazine 1,1-dioxide (100 mg, 0.275 mmol) in EtOH (3 mL), 1-(thiazol-4-yl)ethanamine (45.9 mg, 0.358 mmol) and Et₃N (0.115 mL, 0.826 mmol), and was isolated as a brown film (4 mg, 3%); ESI-MS m/z [M+H]⁺ 454.9.

Example 10: 5-(2-chloro-3-fluorophenyl)-3-((2,2-difluoroethyl)amino)-7-fluoro-4H-benzo[e][1,2,4]thiadiazine 1,1-dioxide

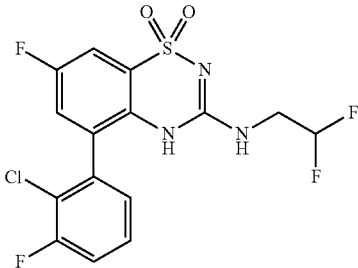 [SMILES: O=S1(=O)N=C(NCC(F)F)Nc2c(-c3cccc(F)c3Cl)cc(F)cc21]

The title compound was prepared in a manner similar to Example 3, using 3-chloro-5-(2-chloro-3-fluorophenyl)-7-fluoro-4H-benzo[e][1,2,4]thiadiazine 1,1-dioxide (50 mg, 0.138 mmol) in EtOH (0.688 mL), 2,2-difluoroethanamine, HCl (24.27 mg, 0.207 mmol) and Et$_3$N (57.6 µL, 0.413 mmol), and was isolated as a pale, beige solid (19.1 mg, 34%). $^1$H NMR (400 MHz, DMSO-d$_6$), δ ppm 3.72 (d, J=3.28 Hz, 2H), 5.98-6.33 (m, 1H), 7.36-7.43 (m, 1H), 7.52 (dd, J=8.84, 2.78 Hz, 1H), 7.58-7.75 (m, 4H), 9.30 (s, 1H); ESI-MS m/z [M+H]$^+$ 408.0.

Example 11: 5-(2-chloro-3-fluorophenyl)-7-fluoro-3-((2-fluoroethyl)amino)-4H-benzo[e][1,2,4]thiadiazine 1,1-dioxide

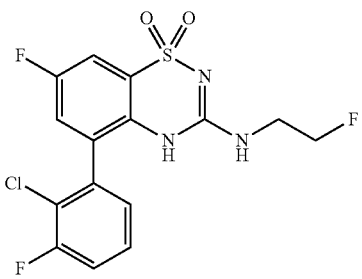 [SMILES: O=S1(=O)N=C(NCCF)Nc2c(-c3cccc(F)c3Cl)cc(F)cc21]

The title compound was prepared in a manner similar to Example 3, using 3-chloro-5-(2-chloro-3-fluorophenyl)-7-fluoro-4H-benzo[e][1,2,4]thiadiazine 1,1-dioxide (50 mg, 0.138 mmol) in EtOH (0.688 mL), 2-fluoroethanamine, HCl (20.56 mg, 0.207 mmol) and Et$_3$N (57.6 µL, 0.413 mmol), and was isolated as a yellow film (10.8 mg, 20.6%). $^1$H NMR (400 MHz, DMSO-d$_6$) δ ppm 3.50-3.61 (m, 2H), 4.47-4.63 (m, 2H), 7.37-7.41 (m, 1H), 7.50 (dd, J=8.84, 3.03 Hz, 1H), 7.59-7.72 (m, 4H), 9.19 (s, 1H); ESI-MS m/z [M+H]$^+$ 390.0.

Example 12: 5-(2-chloro-3-fluorophenyl)-3-(((3-fluoropyridin-2-yl)methyl)amino)-4H-benzo[e][1,2,4]thiadiazine 1,1-dioxide

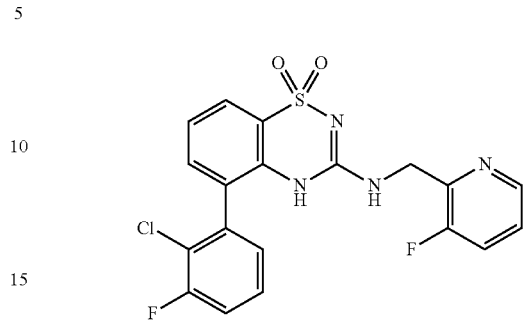

To a solution of 3-(((3-fluoropyridin-2-yl)methyl)amino)-5-iodo-4H-benzo[e][1,2,4]thiadiazine 1,1-dioxide (500 mg, 1.16 mmol) and 2-chloro-3-fluorophenyl)boronic acid (202 mg, 1.16 mmol) in dioxane (10 mL) and water (2 mL) was added Pd(dppf)Cl$_2$ (84.9 mg, 116 µmol) and NaHCO$_3$ (244 mg, 2.90 mmol) under N2 atmosphere. The reaction mixture was stirred at 110° C. for 2 hours, then diluted with water (20 mL) and extracted with EtOAc (3×20 mL). The combined organic phase was washed with water (3×20 mL) and then brine (1×15 mL), dried over anhydrous Na$_2$SO$_4$, filtered, and concentrated. The crude product was purified by preparative HPLC to give the title compound as a light-yellow solid (225 mg, 44.3%). $^1$H NMR (400 MHz, DMSO-d$_6$) δ ppm 9.40 (br s, 1H), 8.41 (br s, 1H), 8.00 (br s, 1H), 7.86-7.72 (m, 2H), 7.67-7.53 (m, 2H), 7.48-7.27 (m, 4H), 4.72-4.54 (m, 2H); ESI-MS m/z [M+H]$^+$ 435.0.

Example 13: 5-(2-chlorophenyl)-7-fluoro-3-(methylamino)-4H-benzo[e][1,2,4]thiadiazine 1,1-dioxide

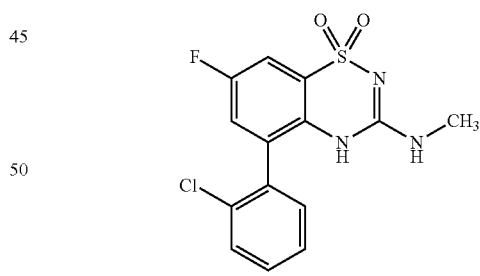

The title compound was prepared in a manner similar to Example 3, using 3-chloro-5-(2-chlorophenyl)-7-fluoro-4H-benzo[e][1,2,4]thiadiazine 1,1-dioxide (500 mg, 1.45 mmol) and methanamine (2M in THF, 10.0 mL, 20.0 mmol), except the reaction mixture was heated to 80° C. for 1 hour. The solvent was removed under vacuum and the crude product was purified by preparative HPLC (Phenomenex Gemini® C18, 10 µm, ID 50×250 mm column) eluting with a gradient of 30-55% ACN in water (0.1% TFA). The title compound was isolated as a brown solid (323.87 mg, 63%). $^1$H NMR (400 MHz, DMSO-d$_6$) δ ppm 9.07 (s, 1H), 7.74-7.27 (m, 7H), 2.73 (d, J=4.6 Hz, 3H) ESI-MS m/z [M+H]$^+$ 340.1

Example 14: 5-(2-chlorophenyl)-7-fluoro-3-((2-methoxyethyl)amino)-4H-benzo[e][1,2,4]thiadiazine 1,1-dioxide

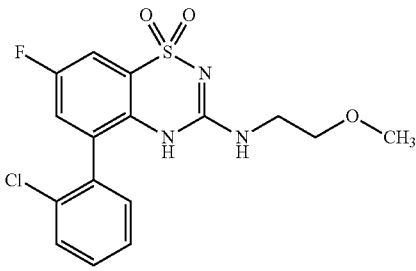 [SMILES: COCCNC1=NS(=O)(=O)c2cc(F)cc(-c3ccccc3Cl)c2N1]

The title compound was prepared in a manner similar to Example 3, using 3-chloro-5-(2-chlorophenyl)-7-fluoro-4H-benzo[e][1,2,4]thiadiazine 1,1-dioxide (100 mg, 0.290 mmol), methoxyethanamine (34.81 mg, 0.463 mmol) and Et$_3$N (115 μL, 0.826 mmol) in EtOH (3 mL), and was isolated as a white solid (30.14 mg, 34%). $^1$H NMR (400 MHz, CD3CN) δ ppm 2.96-3.70 (m, 7H), 6.24 (br s, 1H), 7.26 (dd, J=2.4, 8.8 Hz, 1H), 7.40-7.69 (m, 7H), 8.02 (br s, 1H); ESI-MS m/z [M+H]$^+$ 384.0.

Example 15: 5-(2-chlorophenyl)-3-(ethylamino)-7-fluoro-4H-benzo[e][1,2,4]thiadiazine 1,1-dioxide

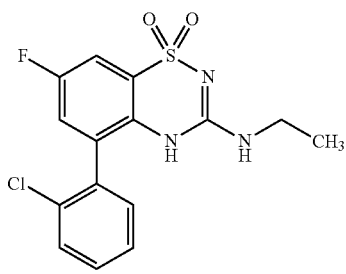 [SMILES: CCNC1=NS(=O)(=O)c2cc(F)cc(-c3ccccc3Cl)c2N1]

The title compound was prepared in a manner similar to Example 3, using 3-chloro-5-(2-chlorophenyl)-7-fluoro-4H-benzo[e][1,2,4]thiadiazine 1,1-dioxide (100 mg, 0.290 mmol), ethanamine (52.24 mg, 1.16 mmol) and Et$_3$N (151 μL, 0.826 mmol) in EtOH (3 mL), and was isolated as a white solid (17 mg, 20%). $^1$H NMR (400 MHz, CD3CN) δ ppm 1.11 (t, J=7.2 Hz, 3H), 3.28 (dd, J=5.4, 7.2 Hz, 2H), 5.93 (br s, 1H), 7.22 (dd, J=2.9, 8.8 Hz, 1H), 7.39-7.44 (m, 1H), 7.46-7.60 (m, 3H), 7.63 (dd, J=1.3, 7.8 Hz, 1H), 7.84 (br s, 1H); ESI-MS m/z [M+H]$^+$ 354.0.

Example 16: 5-(2-chlorophenyl)-7-fluoro-3-(((3-fluoropyridin-2-yl)methyl)amino)-4H-benzo[e][1,2,4]thiadiazine 1,1-dioxide

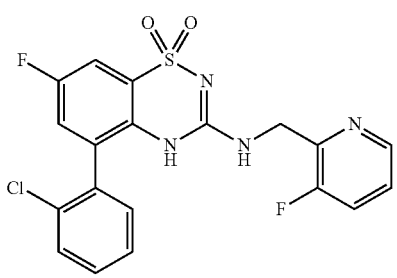 [SMILES: O=S1(=O)N=C(NCc2ncccc2F)Nc2c(-c3ccccc3Cl)cc(F)cc21]

The title compound was prepared in a manner similar to Example 3, using 3-chloro-5-(2-chlorophenyl)-7-fluoro-4H-benzo[e][1,2,4]thiadiazine 1,1-dioxide (100 mg, 0.290 mmol), (3-fluoropyridin-2-yl)methanamine (61.39 mg, 486.70 μmol) and Et$_3$N (151 μL, 0.826 mmol) in EtOH (3 mL), and was isolated as a white solid (24.87 mg, 14%). $^1$H NMR (400 MHz, DMSO-d$_6$) δ ppm 4.61 (br s, 2H), 7.17-7.83 (m, 9H), 8.21-8.57 (m, 1H); ESI-MS m/z [M+H]$^+$ 435.0.

Example 17: 5-(2-chloro-3-fluorophenyl)-3-((cyclobutylmethyl)amino)-4H-benzo[e][1,2,4]thiadiazine 1,1-dioxide

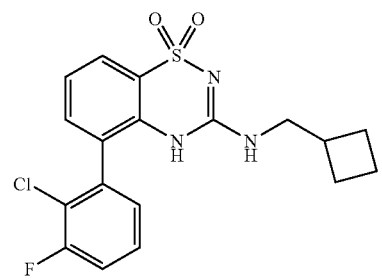 [SMILES: O=S1(=O)N=C(NCC2CCC2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 μL, 0.232 mmol), and cyclobutylmethanamine, HCl (16.91 mg, 0.139 mmol) in DMA (0.232 mL), and was isolated as a brown-orange solid (22.8 mg, 50%). $^1$H NMR (400 MHz, DMSO-d$_6$) δ ppm 1.60-1.73 (m, 2H), 1.81-1.91 (m, 2H), 1.95-2.05 (m, 2H), 2.40-2.49 (m, 1H), 3.22-3.31 (m, 2H), 7.27-7.39 (m, 3H), 7.41-7.45 (m, 1H), 7.57-7.67 (m, 2H), 7.80 (dd, J=7.83, 1.26 Hz, 1H), 8.98 (s, 1H); ESI-MS m/z [M+H]$^+$ 394.0.

Example 18: 5-(2-chloro-3-fluorophenyl)-3-(((6-methoxypyridin-2-yl)methyl)amino)-4H-benzo[e][1,2,4]thiadiazine 1,1-dioxide

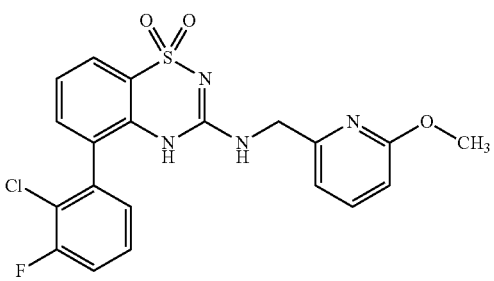 [SMILES: COc1cccc(CNC2=NS(=O)(=O)c3cccc(-c4cccc(F)c4Cl)c3N2)n1]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), DIPEA (30.4 μL, 0.174 mmol), and (6-methoxypyridin-2-yl)methanamine (14.41 mg, 0.104 mmol) in DMA (0.174 mL), and was isolated as a pale, yellow oil (24.5 mg, 63%). $^1$H NMR (400 MHz, DMSO-d$_6$) δ ppm 3.84 (s, 3H), 4.46 (d, J=5.81 Hz, 2H), 6.73 (d, J=8.34 Hz, 1H), 6.92 (d, J=7.33 Hz, 1H), 7.35-7.41 (m, 2H), 7.45-7.48 (m, 1H), 7.58-7.67 (m, 2H), 7.70 (dd, J=8.08, 7.33 Hz, 1H), 7.78-7.83 (m, 2H), 9.28 (s, 1H); ESI-MS m/z [M+H]+ 447.0.

Example 19: 5-(2,3-difluorophenyl)-3-(((6-methoxypyridin-2-yl)methyl)amino)-4H-benzo[e][1,2,4]thiadiazine 1,1-dioxide

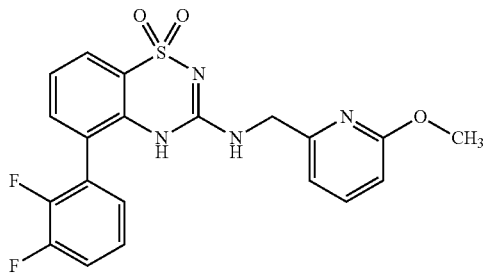 [SMILES: COc1cccc(CNC2=NS(=O)(=O)c3cccc(-c4cccc(F)c4F)c3N2)n1]

To a 2 mL conical microwave vial equipped with a stirring device were added 3-chloro-5-(2,3-difluorophenyl)-4H-benzo[e][1,2,4]thiadiazine 1,1-dioxide (40 mg, 0.122 mmol), DIPEA (42.5 µL, 0.243 mmol), and (6-methoxypyridin-2-yl)methanamine (20.18 mg, 0.146 mmol) dissolved in DMA (243 µL). The reaction mixture was heated at 90° C. for 4 hours and was subsequently purified by mass-triggered preparative-LC/MS (Waters SunFire® C18, 5 µm, ID 30×75 mm column) eluting with a gradient of 35-60% ACN in water (acid mode). The product-containing fractions were collected, concentrated, and dried in vacuo to afford the title compound as a pale, yellow solid (27.4 mg, 52%). $^1$H NMR (400 MHz, DMSO-$d_6$) δ ppm 3.85 (s, 3H), 4.47 (d, J=5.56 Hz, 2H), 6.73 (d, J=8.08 Hz, 1H), 6.94 (d, J=7.07 Hz, 1H), 7.31-7.36 (m, 1H), 7.38-7.47 (m, 2H), 7.54 (dd, J=7.58, 1.26 Hz, 1H), 7.61-7.68 (m, 1H), 7.71 (dd, J=8.08, 7.33 Hz, 1H), 7.81-7.87 (m, 2H), 9.46 (s, 1H); ESI-MS m/z [M+H]+ 431.0.

Example 20: 3-(((5-(2,3-difluorophenyl)-1,1-dioxido-4H-benzo[e][1,2,4]thiadiazin-3-yl)amino)methyl)-1-methylpyridin-2(1H)-one

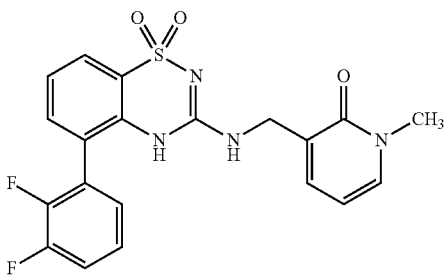 [SMILES: Cn1cccc(CNC2=NS(=O)(=O)c3cccc(-c4cccc(F)c4F)c3N2)c1=O]

The title compound was prepared in a manner similar to Example 19, using 3-chloro-5-(2,3-difluorophenyl)-4H-benzo[e][1,2,4]thiadiazine 1,1-dioxide (40 mg, 0.122 mmol), DIPEA (42.5 µL, 0.243 mmol), and 3-(aminomethyl)-1-methylpyridin-2(1H)-one (20.18 mg, 0.146 mmol) in DMA (243 µL), and was isolated as a pale, yellow solid (1.2 mg, 2%). $^1$H NMR (400 MHz, DMSO-$d_6$) δ ppm 3.47 (s, 3H), 4.20 (br s, 2H), 6.25 (t, J=6.69 Hz, 1H), 7.31 (d, J=7.07 Hz, 1H), 7.40 (dd, J=15.41, 7.07 Hz, 3H), 7.51 (d, J=6.32 Hz, 1H), 7.64 (d, J=9.35 Hz, 1H), 7.70 (d, J=6.82 Hz, 1H), 7.81 (d, J=6.82 Hz, 2H), 9.32 (s, 1H); ESI-MS m/z [M+H]+ 431.1.

Example 21: 5-(2,3-difluorophenyl)-3-((2-fluoroethyl)amino)-4H-benzo[e][1,2,4]thiadiazine 1,1-dioxide

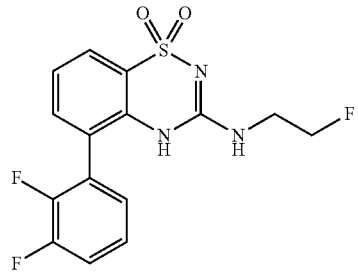 [SMILES: O=S1(=O)N=C(NCCF)Nc2c(-c3cccc(F)c3F)cccc21]

The title compound was prepared in a manner similar to Example 19, using 3-chloro-5-(2,3-difluorophenyl)-4H-benzo[e][1,2,4]thiadiazine 1,1-dioxide (60 mg, 0.183 mmol), DIPEA (31.9 µL, 0.183 mmol), and 2-fluoroethanamine HCl (23.6 mg, 0.237 mmol) in DMA (365 µL), and was isolated as a tan solid (25 mg, 39%). $^1$H NMR (400 MHz, CD$_3$OD) δ ppm 3.47-3.54 (m, 1H), 3.58 (d, J=2.02 Hz, 1H), 4.48 (s, 1H), 4.60 (s, 1H), 7.27-7.33 (m, 1H), 7.39 (d, J=7.83 Hz, 2H), 7.51 (d, J=1.52 Hz, 1H), 7.60-7.69 (m, 2H), 7.79-7.84 (m, 1H), 9.26 (s, 1H).

Example 22: 3-((cyclobutylmethyl)amino)-5-(2,3-difluorophenyl)-4H-benzo[e][1,2,4]thiadiazine 1,1-dioxide

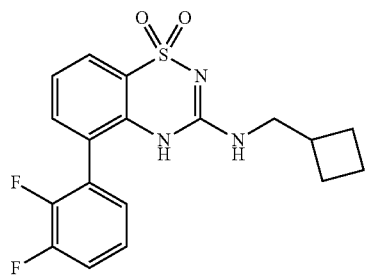 [SMILES: O=S1(=O)N=C(NCC2CCC2)Nc2c(-c3cccc(F)c3F)cccc21]

The title compound was prepared in a manner similar to Example 19, using 3-chloro-5-(2,3-difluorophenyl)-4H-benzo[e][1,2,4]thiadiazine 1,1-dioxide (60 mg, 0.183 mmol), DIPEA (31.9 µL, 0.183 mmol), and cyclobutylmethanamine HCl (28.9 mg, 0.237 mmol) in DMA (365 µL), and was isolated as a tan solid (14.2 mg, 20.6%). $^1$H NMR (400 MHz, CD$_3$OD) δ ppm 2.09 (s, 4H), 3.22-3.26 (m, 3H), 3.37-3.39 (m, 5H), 3.41-3.45 (m, 4H), 3.44 (br s, 1H), 7.31-7.39 (m, 1H), 7.42-7.51 (m, 1H), 7.61-7.68 (m, 1H), 7.73-7.82 (m, 2H), 7.88-7.93 (m, 1H), 8.94-9.00 (m, 1H).

Example 23: 5-(2,3-difluorophenyl)-3-((2-methoxypropyl)amino)-4H-benzo[e][1,2,4]thiadiazine 1,1-dioxide

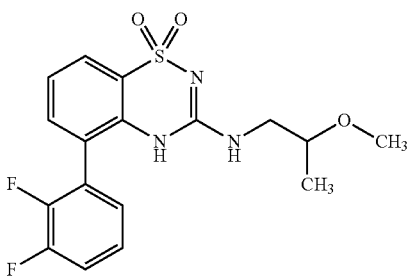 [SMILES: COC(C)CNC1=NS(=O)(=O)c2cccc(-c3cccc(F)c3F)c2N1]

The title compound was prepared in a manner similar to Example 19, using 3-chloro-5-(2,3-difluorophenyl)-4H-benzo[e][1,2,4]thiadiazine 1,1-dioxide (60 mg, 0.183 mmol), DIPEA (31.9 µL, 0.183 mmol), and 2-methoxypropan-1-amine HCl (29.8 mg, 0.237 mmol) in DMA (365 µL), and was isolated as an orange-brown oil (25.7 mg, 36.9%). $^1$H NMR (400 MHz, CD$_3$OD) δ ppm 2.09 (s, 4H), 3.22-3.26 (m, 3H), 3.37-3.39 (m, 5H), 3.41-3.45 (m, 4H), 3.44 (br s, 1H), 7.31-7.39 (m, 2H), 7.42-7.51 (m, 1H), 7.61-7.68 (m, 1H), 7.73-7.82 (m, 2H), 7.88-7.93 (m, 1H), 8.94-9.00 (m, 1H).

Example 24: (R)-5-(2,3-difluorophenyl)-3-((2-methoxypropyl)amino)-4H-benzo[e][1,2,4]thiadiazine 1,1-dioxide

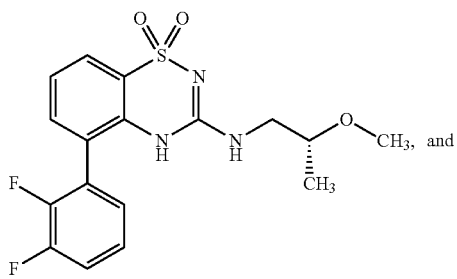 [SMILES: CO[C@H](C)CNC1=NS(=O)(=O)c2cccc(-c3cccc(F)c3F)c2N1]

Example 25: (S)-5-(2,3-difluorophenyl)-3-((2-methoxypropyl)amino)-4H-benzo[e][1,2,4]thiadiazine 1,1-dioxide

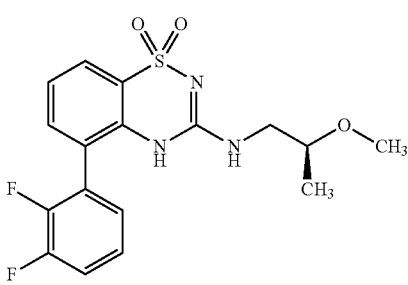 [SMILES: CO[C@@H](C)CNC1=NS(=O)(=O)c2cccc(-c3cccc(F)c3F)c2N1]

The racemate prepared in Example 23 was resolved by chiral chromatography using SFC/UV, PIC system (Chiral Technology AS-H column, 5 µm, ID 20×150 mm, flow rate at 75 mL/min) eluting with 25% MeOH. The first eluting peak was arbitrarily assigned R-stereochemical configuration (Example 24) and the second eluting peak was assign S-stereochemical configuration (Example 25). Each of the title compounds was isolated as a white solid (7 mg).

Example 26: 5-(2,3-difluorophenyl)-3-(methylamino)-4H-benzo[e][1,2,4]thiadiazine 1,1-dioxide

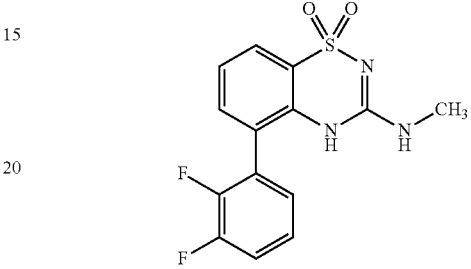

The title compound was prepared in a manner similar to Example 19, using 3-chloro-5-(2,3-difluorophenyl)-4H-benzo[e][1,2,4]thiadiazine 1,1-dioxide (60 mg, 0.183 mmol), DIPEA (31.9 µL, 0.183 mmol), and methanamine (2 M MeOH solution, 0.119 mL, 0.237 mmol) in DMA (365 µL), and was isolated as a tan solid (13 mg, 22%). $^1$H NMR (400 MHz, CD$_3$OD) δ ppm 2.75 (d, J=4.80 Hz, 3H), 7.24-7.33 (m, 2H), 7.33-7.39 (m, 1H), 7.39-7.46 (m, 1H), 7.46-7.53 (m, 1H), 7.54-7.69 (m, 1H), 7.74-7.83 (m, 1H), 9.23 (s, 1H).

Example 27: 5-(2,3-difluorophenyl)-3-((oxazol-2-ylmethyl)amino)-4H-benzo[e][1,2,4]thiadiazine 1,1-dioxide

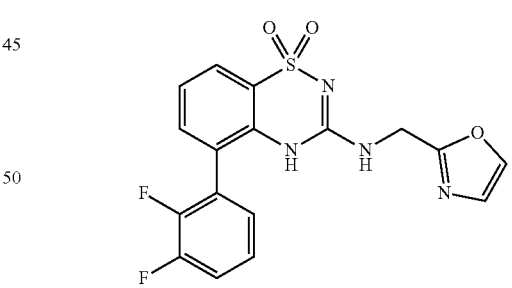

The title compound was prepared in a manner similar to Example 19, using 3-chloro-5-(2,3-difluorophenyl)-4H-benzo[e][1,2,4]thiadiazine 1,1-dioxide (40 mg, 0.122 mmol), DIPEA (42.5 µL, 0.243 mmol), and oxazol-2-ylmethanamine (14.3 mg, 0.146 mmol) in DMA (243 µL), and was isolated as a colorless oil (5 mg, 10%). $^1$H NMR (400 MHz, DMSO-d$_6$) δ ppm 4.61 (d, J=4.55 Hz, 2H), 7.20 (d, J=1.01 Hz, 1H), 7.33 (t, J=6.82 Hz, 1H), 7.42 (d, J=7.58 Hz, 2H), 7.55 (dd, J=7.58, 1.26 Hz, 1H), 7.61-7.69 (m, 1H), 7.84 (dd, J=7.96, 1.14 Hz, 1H), 7.95 (t, J=5.68 Hz, 1H), 8.12 (d, J=0.76 Hz, 1H), 9.49 (s, 1H); ESI-MS m/z [M+H]$^+$ 391.1.

Example 28: 5-(2-chloro-3-fluorophenyl)-3-((oxazol-2-ylmethyl)amino)-4H-benzo[e][1,2,4]thiadiazine 1,1-dioxide

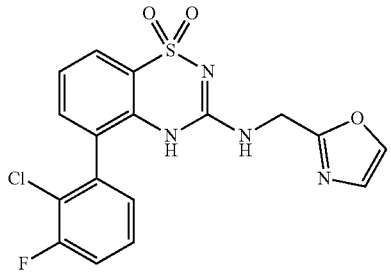

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and oxazol-2-ylmethanamine, HCl (18.71 mg, 0.139 mmol)) in DMA (0.232 mL), and was isolated as a pale, beige solid (13.0 mg, 28%). $^1$H NMR (400 MHz, DMSO-$d_6$) δ ppm 3.98 (s, 1H), 4.60 (dd, J=5.68, 1.89 Hz, 2H), 7.20 (d, J=0.76 Hz, 1H), 7.34-7.43 (m, 2H), 7.45-7.49 (m, 1H), 7.57-7.66 (m, 2H), 7.82 (dd, J=7.71, 1.14 Hz, 1H), 7.89 (t, J=5.56 Hz, 1H), 8.11 (d, J=0.76 Hz, 1H), 9.31 (s, 1H); ESI-MS m/z [M+H]$^+$ 407.0.

Example 29: 5-(2-chloro-3-fluorophenyl)-3-((cyclopropylmethyl)amino)-4H-benzo[e][1,2,4]thiadiazine 1,1-dioxide

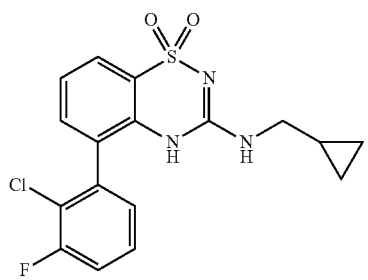

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and cyclopropylmethanamine (9.89 mg, 0.139 mmol) in DMA (0.232 mL), and was isolated as a brown, orange solid (13.6 mg, 31%). $^1$H NMR (400 MHz, DMSO-$d_6$) δ ppm 0.22 (d, J=3.79 Hz, 2H), 0.46 (dd, J=7.96, 1.64 Hz, 2H), 0.90-1.04 (m, 1H), 3.03-3.12 (m, 2H), 7.32-7.44 (m, 4H), 7.56-7.68 (m, 2H), 7.78 (dd, J=7.71, 1.39 Hz, 1H), 9.00 (s, 1H); ESI-MS m/z [M+H]$^+$ 380.0.

Example 30: 5-(2-chloro-3-fluorophenyl)-3-(((4-methyloxazol-2-yl)methyl)amino)-4H-benzo[e][1,2,4]thiadiazine 1,1-dioxide

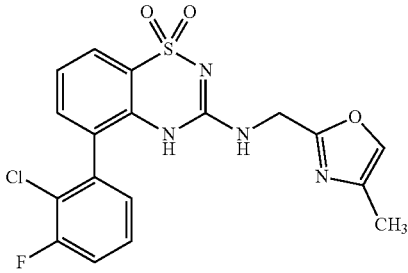 [SMILES: Cc1coc(CNC2=NS(=O)(=O)c3cccc(-c4cccc(F)c4Cl)c3N2)n1]

The title compound was prepared in a manner similar to Example 1, using 3-chloro-5-(2-chloro-3-fluorophenyl)-4H-benzo[e][1,2,4]thiadiazine 1,1-dioxide (60 mg, 0.174 mmol), DIPEA (60.7 µL, 0.348 mmol), and (4-methyloxazol-2-yl)methanamine, HCl (31.0 mg, 0.209 mmol) in DMA (0.348 mL), and was isolated as a pale, yellow solid (33.7 mg, 46%). $^1$H NMR (400 MHz, DMSO-$d_6$) δ ppm 2.07 (d, J=1.26 Hz, 3H), 4.54 (dd, J=5.43, 2.40 Hz, 2H), 7.34-7.37 (m, 1H), 7.38-7.42 (m, 1H), 7.45-7.49 (m, 1H), 7.58-7.66 (m, 2H), 7.78-7.89 (m, 3H), 9.30 (s, 1H); ESI-MS m/z [M+H]$^+$ 421.0.

Example 31: 5-(2-chloro-3-fluorophenyl)-3-((pyridin-2-ylmethyl)amino)-4H-benzo[e][1,2,4]thiadiazine 1,1-dioxide

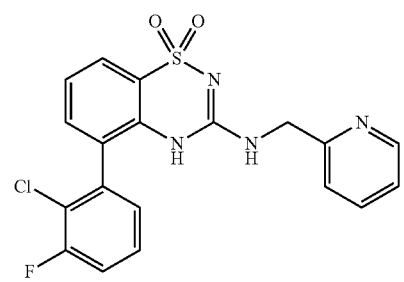

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and pyridin-2-ylmethanamine (15.04 mg, 0.139 mmol) in DMA (232 µL), and was isolated as a pale, green solid (30.4 mg, 63%). $^1$H NMR (400 MHz, DMSO-$d_6$) δ ppm 3.98 (s, 1H), 4.59 (br s, 2H), 7.36-7.42 (m, 3H), 7.44-7.48 (m, 2H), 7.59-7.66 (m, 2H), 7.82 (dd, J=7.83, 1.26 Hz, 1H), 7.90 (t, J=7.07 Hz, 1H), 7.98 (br s, 1H), 8.60 (d, J=4.55 Hz, 1H), 9.41 (s, 1H); ESI-MS m/z [M+H]$^+$ 417.0.

Example 32: 5-(2-chloro-3,5-difluorophenyl)-3-((2-methoxyethyl)amino)-4H-benzo[e][1,2,4]thiadiazine 1,1-dioxide

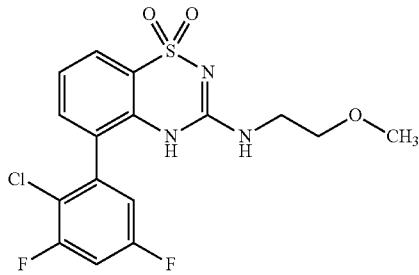 [SMILES: COCCNC1=NS(=O)(=O)c2cccc(-c3cc(F)cc(F)c3Cl)c2N1]

The title compound was prepared in a manner similar to Example 1, using 3-chloro-5-(2-chloro-3,5-difluorophenyl)-4H-benzo[e][1,2,4]thiadiazine 1,1-dioxide (56.2 mg, 0.155 mmol), DIPEA (54.1 µL, 0.309 mmol), and 2-methoxyethanamine (13.95 mg, 0.186 mmol) in DMA (500 µL), and was isolated as a clear film (7.1 mg, 11%). $^1$H NMR (400 MHz, CD$_3$OD) δ ppm 3.35 (s, 3H), 3.49 (br s, 4H), 7.15 (d, J=7.33 Hz, 1H), 7.32-7.48 (m, 3H), 7.89 (dd, J=7.58, 1.77 Hz, 1H); ESI-MS m/z [M+H]$^+$ 402.0.

Example 33: 5-(2-chloro-3-fluorophenyl)-3-((2-methoxypropyl)amino)-4H-benzo[e][1,2,4]thiadiazine 1,1-dioxide

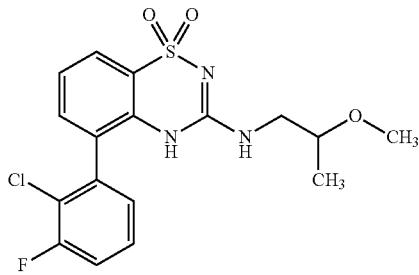

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and 2-methoxypropan-1-amine, HCl (17.47 mg, 0.139 mmol) in DMA (232 µL), and was isolated as a pale, beige solid (21.6 mg, 47%). $^1$H NMR (400 MHz, DMSO-d$_6$) δ ppm 1.06 (dd, J=6.06, 3.28 Hz, 3H), 3.14-3.22 (m, 1H), 3.24 (d, J=3.28 Hz, 3H), 3.35-3.50 (m, 2H), 7.32-7.38 (m, 2H), 7.39-7.46 (m, 2H), 7.56-7.65 (m, 2H), 7.79 (dd, J=7.58, 1.26 Hz, 1H), 9.09 (d, J=2.27 Hz, 1H); ESI-MS m/z [M+H]$^+$ 398.0.

Example 34: 5-(2-chloro-3-fluorophenyl)-3-((2,2-difluoroethyl)amino)-4H-benzo[e][1,2,4]thiadiazine 1,1-dioxide

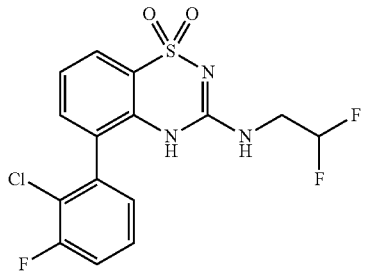

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and 2,2-difluoroethanamine, HCl (16.34 mg, 0.139 mmol) in DMA (232 µL), and was isolated as a brown, orange solid (13.5 mg, 30%). $^1$H NMR (400 MHz, DMSO-d$_6$) δ ppm 3.63-3.78 (m, 2H), 5.99-6.30 (m, 1H), 7.33-7.47 (m, 3H), 7.56-7.67 (m, 3H), 7.82 (dd, J=7.71, 1.14 Hz, 1H), 9.19 (s, 1H); ESI-MS m/z [M+H]$^+$ 390.0.

Example 35: 5-(2-chlorophenyl)-3-((2-methoxyethyl)amino)-4H-benzo[e][1,2,4]thiadiazine 1,1-dioxide

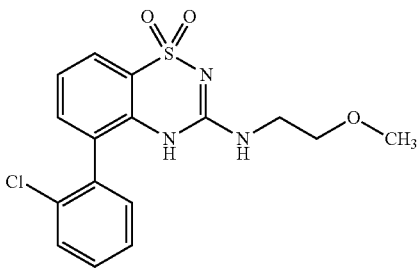 [SMILES: COCCNC1=NS(=O)(=O)c2cccc(-c3ccccc3Cl)c2N1]

A 10 mL microwave vial equipped for stirring was charged with 5-iodo-3-((2-methoxyethyl)amino)-4H-benzo[e][1,2,4]thiadiazine 1,1-dioxide (0.04 g, 0.105 mmol), (2-chlorophenyl)boronic acid (0.016 g, 0.105 mmol), Cs$_2$CO$_3$ (2M, 0.210 mL, 0.420 mmol) and dioxane (0.525 mL). To the mixture was added Pd(dppf)$_2$·CH$_2$Cl$_2$ adduct (4.28 mg, 5.25 µmol) under nitrogen. The reaction mixture was heated to 100° C. in a microwave reactor for 2 hours, then cooled, diluted with MeOH (1 mL) and filtered. The residue was purified by preparative LC/MS (Waters SunFire® C18, 5 µm, ID 30×75 mm column) eluting with a gradient of 25-90% ACN in water (acid mode). The product-containing fractions were collected, concentrated, and dried in vacuo to give the title compound as a tan solid (2 mg, 5%). $^1$H NMR (400 MHz, CD$_3$OD) δ ppm 3.48 (br s, 4H) 7.35-7.43 (m, 3H), 7.46-7.55 (m, 2H), 7.58-7.65 (m, 1H), 7.81-7.89 (m, 1H); ESI-MS m/z [M+H]$^+$ 366.0.

Example 36: 5-(3-chloro-2-fluoropyridin-4-yl)-3-((2-methoxyethyl)amino)-4H-benzo[e][1,2,4]thiadiazine 1,1-dioxide

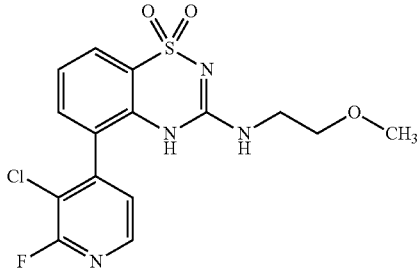 [SMILES: COCCNC1=NS(=O)(=O)c2cccc(-c3ccnc(F)c3Cl)c2N1]

The title compound was prepared in a manner similar to Example 35, using 5-iodo-3-((2-methoxyethyl)amino)-4H-benzo[e][1,2,4]thiadiazine 1,1-dioxide (60 mg, 0.157 mmol), 3-chloro-2-fluoro-4-(4,4,5,5-tetramethyl-1,3,2-dioxaborolan-2-yl)pyridine (81 mg, 0.315 mmol), cesium fluoride (aq) (59.8 mg, 0.394 mmol), and Pd(dppf)$_2$·CH$_2$Cl$_2$ adduct (12.85 mg, 0.016 mmol) in dioxane (525 μL), and was isolated as a white solid (49.7 mg, 82%). 1H NMR (400 MHz, DMSO-d$_6$) δ ppm 3.27 (s, 3H), 3.37-3.47 (m, 4H), 7.27 (br s, 1H), 7.38-7.45 (m, 1H), 7.49-7.55 (m, 1H), 7.58 (d, J=4.80 Hz, 1H), 7.86 (d, J=7.83 Hz, 1H), 8.40 (d, J=5.05 Hz, 1H), 9.20 (s, 1H); ESI-MS m/z [M+H]$^+$ 385.0.

Example 37: 5-(2,3-difluorophenyl)-3-((2-methoxyethyl)amino)-4H-benzo[e][1,2,4]thiadiazine 1,1-dioxide

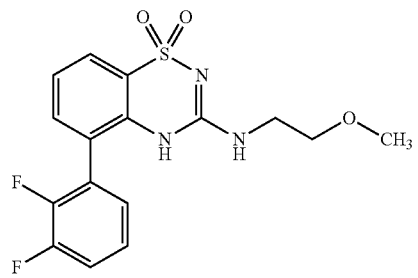 [SMILES: COCCNC1=NS(=O)(=O)c2cccc(-c3cccc(F)c3F)c2N1]

The title compound was prepared in a manner similar to Example 35, using 5-iodo-3-((2-methoxyethyl)amino)-4H-benzo[e][1,2,4]thiadiazine 1,1-dioxide (40 mg, 0.105 mmol), (2,3-difluorophenyl)boronic acid (22 mg, 0.136 mmol), Cs$_2$CO$_3$ (2M, 0.210 mL, 0.420 mmol), and Pd(dppf)$_2$·CH$_2$Cl$_2$ adduct (8.57 mg, 10.49 μmol) in dioxane (525 μL), and was isolated as a tan solid (19 mg, 49%). $^1$H NMR (400 MHz, CD$_3$OD) δ ppm 3.26 (s, 3H), 3.36-3.41 (m, 2H), 3.42-3.47 (m, 2H), 7.26-7.32 (m, 1H), 7.34-7.39 (m, 1H), 7.40-7.46 (m, 1H), 7.47-7.55 (m, 2H), 7.60-7.68 (m, 1H), 7.77-7.83 (m, 1H); ESI-MS m/z [M+H]$^+$ 368.0.

Example 38: 5-(2-chloro-3-fluorophenyl)-3-(((5-methyloxazol-2-yl)methyl)amino)-4H-benzo[e][1,2,4]thiadiazine 1,1-dioxide

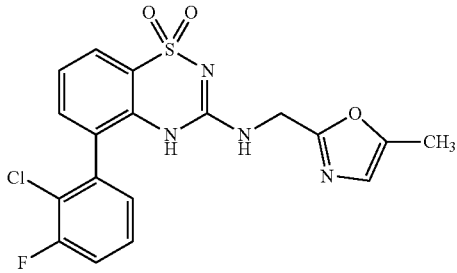 [SMILES: Cc1cnc(CNC2=NS(=O)(=O)c3cccc(-c4cccc(F)c4Cl)c3N2)o1]

The title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), DIPEA (50.6 μL, 0.290 mmol), and (5-methyloxazol-2-yl)methanamine (19.49 mg, 0.174 mmol) in DMA (290 μL), and was isolated as a yellow-orange solid (18.6 mg, 31%). $^1$H NMR (400 MHz, DMSO-d$_6$) δ ppm 2.28 (d, J=1.26 Hz, 3H), 4.53 (dd, J=5.56, 2.27 Hz, 2H), 6.80 (d, J=1.01 Hz, 1H), 7.35 (dd, J=6.44, 1.14 Hz, 1H), 7.41 (d, J=7.58 Hz, 1H), 7.45-7.48 (m, 1H), 7.59-7.68 (m, 2H), 7.81-7.89 (m, 2H), 9.29 (s, 1H); ESI-MS m/z [M+H]$^+$ 421.0.

Example 39: 5-(2-chloro-3-fluorophenyl)-3-(ethylamino)-4H-benzo[e][1,2,4]thiadiazine 1,1-dioxide The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 μL, 0.232 mmol), and ethanamine, HCl (11.34 mg, 0.139 mmol) in DMA (232 μL), and was isolated as a pale, beige solid (15.6 mg, 38%). $^1$H NMR (400 MHz, DMSO-d$_6$) δ ppm 1.10 (t, J=7.20 Hz, 3H), 3.18-3.28 (m, 2H), 7.26-7.39 (m, 3H), 7.41-7.45 (m, 1H), 7.56-7.68 (m, 2H), 7.80 (dd, J=7.58, 1.26 Hz, 1H), 8.98 (s, 1H); ESI-MS m/z [M+H]$^+$ 354.1.

Example 40: 5-(2-chlorophenyl)-3-((2-methoxypropyl)amino)-4H-benzo[e][1,2,4]thiadiazine 1,1-dioxide

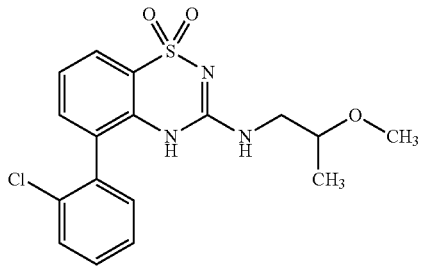 [SMILES: COC(C)CNC1=NS(=O)(=O)c2cccc(-c3ccccc3Cl)c2N1]

To a solution of 2-methoxypropan-1-amine, HCl (34.9 mg, 0.278 mmol) and DIPEA (37.4 µL, 0.214 mmol) in DMA (428 µL) was added 3-chloro-5-(2-chlorophenyl)-4H-benzo[e][1,2,4]thiadiazine 1,1-dioxide (70 mg, 0.214 mmol). The reaction mixture was heated at 70° C. for 24 hours, then diluted with MeOH (1 mL), and filtered. The residue purified by preparative LC/MS (Waters SunFire® C18, 5 µm, ID 30×75 mm column) eluting with a 25-90% gradient of ACN in water (acid mode). The product-containing fractions were collected, concentrated, and dried in vacuo to afford the title compound as a brown solid (16 mg, 20% yield). ESI-MS m/z [M+H]$^+$ 380.0.

Example 41: 5-(2-chlorophenyl)-3-((pyridin-2-ylmethyl)amino)-4H-benzo[e][1,2,4]thiadiazine 1,1-dioxide

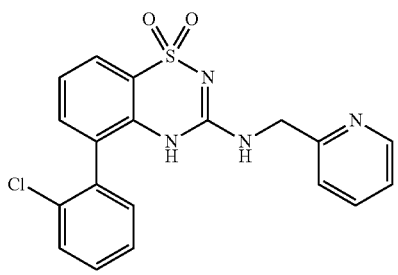 [SMILES: O=S1(=O)N=C(NCc2ccccn2)Nc2c(-c3ccccc3Cl)cccc21]

The title compound was prepared in a manner similar to Example 40, using 3-chloro-5-(2-chlorophenyl)-4H-benzo[e][1,2,4]thiadiazine 1,1-dioxide (50 mg, 0.153 mmol), pyridin-2-ylmethanamine (16.53 mg, 0.153 mmol) and DIPEA (26.7 µL, 0.153 mmol) in DMA (306 µL), and was isolated as a black oil (34 mg, 56%). $^1$H NMR (400 MHz, CD$_3$OD) δ ppm 1.10 (t, J=7.20 Hz, 3H), 3.22 (dd, J=7.33, 5.31 Hz, 2H), 7.31-7.55 (m, 6H), 7.78 (dd, J=7.83, 1.01 Hz, 1H), 9.12 (s, 1H); ESI-MS m/z [M+H]$^+$ 399.8.

Example 42: 5-(2-chlorophenyl)-3-(ethylamino)-4H-benzo[e][1,2,4]thiadiazine 1,1-dioxide

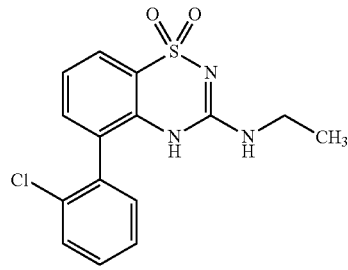 [SMILES: CCNC1=NS(=O)(=O)c2cccc(-c3ccccc3Cl)c2N1]

The title compound was prepared in a manner similar to Example 40, using 3-chloro-5-(2-chlorophenyl)-4H-benzo[e][1,2,4]thiadiazine 1,1-dioxide (60 mg, 0.183 mmol), ethanamine, HCl (19.44 mg, 0.238 mmol) and DIPEA (64.1 µL, 0.367 mmol) in DMA (367 µL), and was isolated as a pale, beige solid (14.9 mg, 24%). $^1$H NMR (400 MHz, DMSO-d$_6$) δ ppm 1.10 (t, J=7.33 Hz, 3H), 3.18-3.24 (m, 2H), 7.30-7.43 (m, 3H), 7.44-7.49 (m, 1H), 7.50-7.63 (m, 2H), 7.70 (dd, J=7.96, 1.14 Hz, 1H), 7.77 (dd, J=7.45, 1.89 Hz, 1H), 8.93 (br s, 1H); ESI-MS m/z [M+H]$^+$ 336.0.

Example 43: 5-(2-chlorophenyl)-3-(methylamino)-4H-benzo[e][1,2,4]thiadiazine 1,1-dioxide

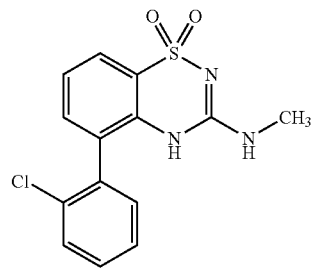 [SMILES: CNC1=NS(=O)(=O)c2cccc(-c3ccccc3Cl)c2N1]

The title compound was prepared in a manner similar to Example 40, using 3-chloro-5-(2-chlorophenyl)-4H-benzo[e][1,2,4]thiadiazine 1,1-dioxide (60 mg, 0.183 mmol), methanamine (2M in MeOH) (119 µL, 0.238 mmol) and DIPEA (64.1 µL, 0.367 mmol) in DMA (367 µL), and was isolated as a pale, beige solid (10.6 mg, 18%). $^1$H NMR (400 MHz, DMSO-d$_6$) δ ppm 2.73 (d, J=4.80 Hz, 3H), 7.12 (br s, 1H), 7.32-7.39 (m, 3H), 7.43-7.47 (m, 1H), 7.51-7.59 (m, 2H), 7.67 (dd, J=7.83, 1.26 Hz, 1H), 7.75 (dd, J=7.45, 1.89 Hz, 1H), 9.00 (br s, 1H); ESI-MS m/z [M+H]$^+$ 322.0.

Example 44: 5-(2-chlorophenyl)-3-((2,2-difluoro-ethyl)amino)-4H-benzo[e][1,2,4]thiadiazine 1,1-dioxide

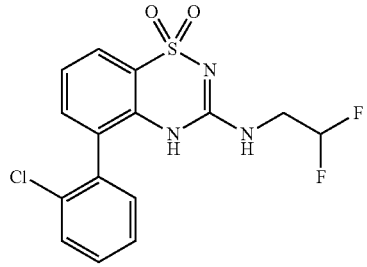 [SMILES: O=S1(=O)N=C(NCC(F)F)Nc2c(-c3ccccc3Cl)cccc21]

The title compound was prepared in a manner similar to Example 40, using 3-chloro-5-(2-chlorophenyl)-4H-benzo[e][1,2,4]thiadiazine 1,1-dioxide (60 mg, 0.183 mmol), 2,2-difluoroethanamine, HCl (28.0 mg, 0.238 mmol) and DIPEA (64.1 μL, 0.367 mmol) in DMA (367 μL), and was isolated as a pale, beige solid (9.0 mg, 13%). $^1$H NMR (400 MHz, DMSO-$d_6$) δ ppm 0.97-1.38 (m, 2H), 3.66-3.79 (m, 2H), 5.98-6.33 (m, 1H), 7.37-7.44 (m, 2H), 7.46-7.50 (m, 1H), 7.54-7.63 (m, 2H), 7.70-7.83 (m, 3H), 9.18 (br s, 1H); ESI-MS m/z [M+H]$^+$ 372.0.

Example 45: 5-(2-chlorophenyl)-3-((2-fluoroethyl)amino)-4H-benzo[e][1,2,4]thiadiazine 1,1-dioxide

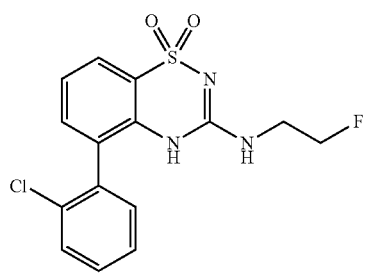 [SMILES: O=S1(=O)N=C(NCCF)Nc2c(-c3ccccc3Cl)cccc21]

The title compound was prepared in a manner similar to Example 40, using 3-chloro-5-(2-chlorophenyl)-4H-benzo[e][1,2,4]thiadiazine 1,1-dioxide (60 mg, 0.183 mmol), 2-fluoroethanamine, HCl (23.73 mg, 0.238 mmol) and DIPEA (64.1 μL, 0.367 mmol) in DMA (367 μL), and was isolated as a brown, orange solid (26.8 mg, 41%). $^1$H NMR (400 MHz, DMSO-$d_6$) δ ppm 3.48-3.59 (m, 3H), 4.48 (t, J=5.05 Hz, 1H), 4.60 (t, J=4.80 Hz, 1H), 7.34-7.43 (m, 2H), 7.46-7.50 (m, 1H), 7.53-7.63 (m, 2H), 7.71 (dd, J=7.71, 1.39 Hz, 2H), 7.79 (dd, J=7.58, 1.77 Hz, 1H), 9.07 (s, 1H); ESI-MS m/z [M+H]$^+$ 354.0.

Example 46: 3-(((5-(2-chloro-3-fluorophenyl)-1,1-dioxido-4H-benzo[e][1,2,4]thiadiazin-3-yl)amino)methyl)-1-methylpyridin-2(1H)-one

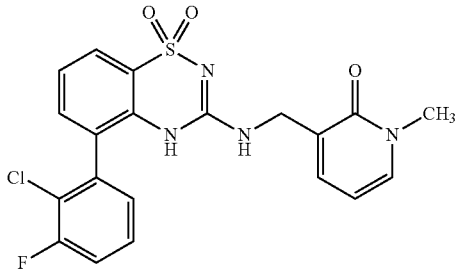 [SMILES: Cn1cccc(CNC2=NS(=O)(=O)c3cccc(-c4cccc(F)c4Cl)c3N2)c1=O]

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 μL, 0.232 mmol), and 3-(aminomethyl)-1-methylpyridin-2(1H)-one (16.01 mg, 0.116 mmol) in DMA (232 μL), and was isolated as a pale, beige solid (16.7 mg, 32%). $^1$H NMR (400 MHz, DMSO-$d_6$) δ ppm 3.47 (s, 3H), 4.14-4.25 (m, 2H), 6.25 (t, J=6.82 Hz, 1H), 7.31-7.40 (m, 2H), 7.40-7.45 (m, 2H), 7.56-7.65 (m, 2H), 7.70 (dd, J=6.69, 1.64 Hz, 1H), 7.73-7.82 (m, 2H), 9.16 (s, 1H); ESI-MS m/z [M+H]$^+$ 447.0.

Example 47: (R)-5-(2-chloro-3-fluorophenyl)-3-((2-methoxypropyl)amino)-4H-benzo[e][1,2,4]thiadiazine 1,1-dioxide

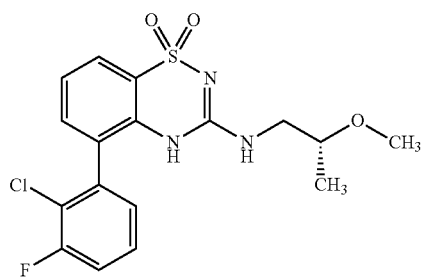 [SMILES: CO[C@H](C)CNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), DIPEA (30.4 μL, 0.174 mmol), and (R)-2-methoxypropan-1-amine, HCl (13.10 mg, 0.104 mmol) in DMA (217 μL), and was isolated as a clear film (2.6 mg, 8%). $^1$H NMR (400 MHz, CD$_3$OD) δ ppm 1.14 (br s, 3H), 3.50 (d, J=16.67 Hz, 3H), 7.25 (br s, 1H), 7.36-7.55 (m, 4H), 7.88 (d, J=8.08 Hz, 1H); ESI-MS m/z [M+H]$^+$ 398.0.

Example 48: 5-(3-chloro-2-fluoropyridin-4-yl)-3-((oxazol-2-ylmethyl)amino)-4H-benzo[e][1,2,4]thiadiazine 1,1-dioxide

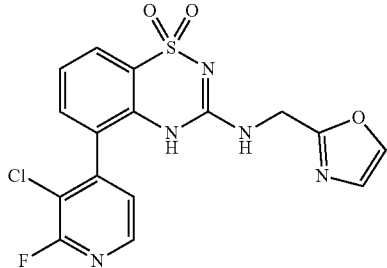 [SMILES: O=S1(=O)N=C(NCc2ncco2)Nc2c(-c3ccnc(F)c3Cl)cccc21]

To a 2 mL scintillation vial equipped with a stirring device were added 3-chloro-5-(3-chloro-2-fluoropyridin-4-yl)-4H-benzo[e][1,2,4]thiadiazine 1,1-dioxide (40 mg, 0.116 mmol), DIPEA (40.4 µL, 0.231 mmol), and oxazol-2-ylmethanamine, HCl (18.66 mg, 0.139 mmol) dissolved in DMA (385 µL). The reaction mixture was heated at 60° C. overnight, then filtered through a 12 mL fritted syringe containing a 0.5-inch pad of Celite®. The syringe was rinsed MeOH and the filtrate purified by mass-triggered preparative LC/MS (Waters® XSelect CSH Prep C18, 5 µm, ID 30×75 mm column) eluting with a gradient of 20-50% ACN in water (acid mode). The fractions were collected, concentrated, and dried in vacuo to afford the title compound as a brown-orange film (6.5 mg, 14%). $^1$H NMR (400 MHz, CD$_3$OD) δ ppm 4.69 (br s, 2H), 7.29 (br s, 1H), 7.47-7.59 (m, 3H), 7.98 (d, J=6.57 Hz, 2H), 8.35 (d, J=4.80 Hz, 1H); ESI-MS m/z [M+H]$^+$ 408.0.

Example 49: 5-(3-chloro-2-fluoropyridin-4-yl)-3-((thiazol-2-ylmethyl)amino)-4H-benzo[e][1,2,4]thiadiazine 1,1-dioxide

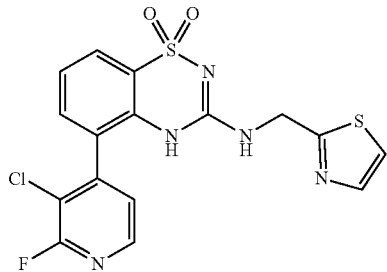 [SMILES: O=S1(=O)N=C(NCc2nccs2)Nc2c(-c3ccnc(F)c3Cl)cccc21]

The title compound was prepared in a manner similar to Example 48, using 3-chloro-5-(3-chloro-2-fluoropyridin-4-yl)-4H-benzo[e][1,2,4]thiadiazine 1,1-dioxide (30 mg, 0.087 mmol), DIPEA (30.3 µL, 0.173 mmol), and thiazol-2-ylmethanamine, HCl (15.66 mg, 0.104 mmol) dissolved in DMA (433 µL), and was isolated as a clear film (1.46 mg, 4%). 1H NMR (400 MHz, CD$_3$OD) δ ppm 4.84 (s, 2H), 7.42-7.53 (m, 3H), 7.54 (d, J=3.28 Hz, 1H), 7.72 (br s, 1H), 7.95 (dd, J=7.71, 1.64 Hz, 1H), 8.30 (d, J=4.80 Hz, 1H); ESI-MS m/z [M+H]$^+$ 424.0.

Example 50: 5-(3-chloro-2-fluoropyridin-4-yl)-3-((cyclopropylmethyl)amino)-4H-benzo[e][1,2,4]thiadiazine 1,1-dioxide

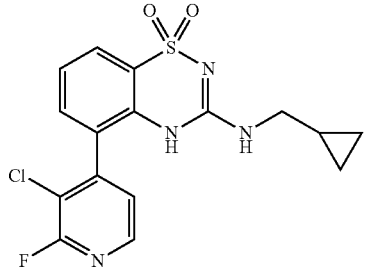 [SMILES: O=S1(=O)N=C(NCC2CC2)Nc2c(-c3ccnc(F)c3Cl)cccc21]

The title compound was prepared in a manner similar to Example 48, using 3-chloro-5-(3-chloro-2-fluoropyridin-4-yl)-4H-benzo[e][1,2,4]thiadiazine 1,1-dioxide (40 mg, 0.116 mmol), DIPEA (40.4 µL, 0.231 mmol), and cyclopropylmethanamine (9.86 mg, 0.139 mmol) dissolved in DMA (385 µL), and was isolated as a brown-orange solid (6.4 mg, 15%). $^1$H NMR (400 MHz, DMSO-d$_6$) δ ppm 0.22 (d, J=3.79 Hz, 2H), 0.44-0.47 (m, 2H), 1.23 (br s, 3H), 3.03-3.10 (m, 2H), 7.21 (d, J=8.59 Hz, 1H), 7.49-7.52 (m, 1H), 7.57 (s, 1H), 7.79 (br s, 1H), 7.85 (s, 1H), 8.22 (d, J=5.05 Hz, 1H), 8.39 (d, J=5.05 Hz, 1H), 9.15 (s, 1H); ESI-MS m/z [M+H]$^+$ 381.0.

Example 51: 5-(3-chloro-2-fluoropyridin-4-yl)-3-(((3-fluoropyridin-2-yl)methyl)amino)-4H-benzo[e][1,2,4]thiadiazine 1,1-dioxide

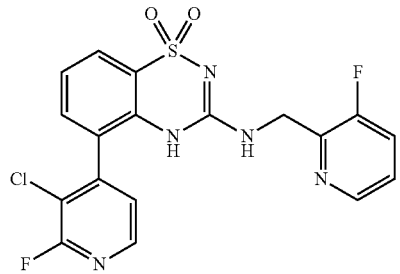 [SMILES: O=S1(=O)N=C(NCc2ncccc2F)Nc2c(-c3ccnc(F)c3Cl)cccc21]

The title compound was prepared in a manner similar to Example 48, using 3-chloro-5-(3-chloro-2-fluoropyridin-4-yl)-4H-benzo[e][1,2,4]thiadiazine 1,1-dioxide (40 mg, 0.116 mmol), DIPEA (40.4 µL, 0.231 mmol), and (3-fluoropyridin-2-yl)methanamine, HCl (22.55 mg, 0.139 mmol) dissolved in DMA (385 µL), and was isolated as a beige solid (3.3 mg, 7%). $^1$H NMR (400 MHz, CD$_3$OD) δ ppm 1.34 (s, 4H), 4.75 (br s, 2H), 7.36-7.57 (m, 4H), 7.65 (t, J=9.09 Hz, 1H), 7.99 (dd, J=7.58, 1.52 Hz, 1H), 8.28-8.44 (m, 2H); ESI-MS m/z [M+H]$^+$ 436.0.

Example 52: 5-(3-chloro-2-fluoropyridin-4-yl)-3-(ethylamino)-4H-benzo[e][1,2,4]thiadiazine 1,1-dioxide

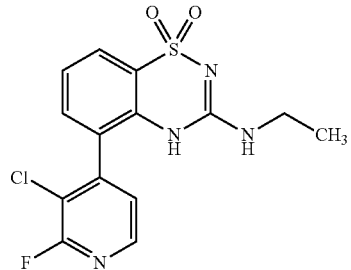 [SMILES: CCNC1=NS(=O)(=O)c2cccc(-c3ccnc(F)c3Cl)c2N1]

The title compound was prepared in a manner similar to Example 48, using 3-chloro-5-(3-chloro-2-fluoropyridin-4-yl)-4H-benzo[e][1,2,4]thiadiazine 1,1-dioxide (30 mg, 0.087 mmol), Et₃N (24.16 µL, 0.231 mmol), and ethanamine (70% in water, 7.01 µL, 0.087 mmol) dissolved in EtOH (500 µL), and was isolated as a clear film (3.3 mg, 11%). ¹H NMR (400 MHz, CD₃OD) δ ppm 1.17 (t, J=7.20 Hz, 3H), 3.33-3.38 (m, 2H), 7.38-7.51 (m, 3H), 7.93 (dd, J=7.71, 1.64 Hz, 1H), 8.29 (d, J=5.05 Hz, 1H); ESI-MS m/z [M+H]⁺ 355.0.

Example 53: 5-(3-chloro-2-fluoropyridin-4-yl)-3-((2,2-difluoroethyl)amino)-4H-benzo[e][1,2,4]thiadiazine 1,1-dioxide

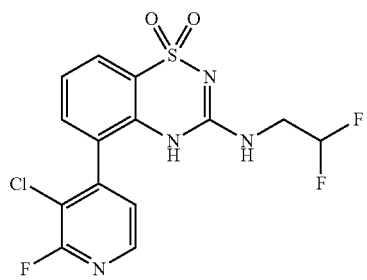 [SMILES: O=S1(=O)N=C(NCC(F)F)Nc2c(-c3ccnc(F)c3Cl)cccc21]

The title compound was prepared in a manner similar to Example 48, using 3-chloro-5-(3-chloro-2-fluoropyridin-4-yl)-4H-benzo[e][1,2,4]thiadiazine 1,1-dioxide (40 mg, 0.116 mmol), Et₃N (32.2 µL, 0.231 mmol), and 2,2-difluoroethanamine, HCl (16.30 mg, 0.139 mmol) dissolved in EtOH (500 µL), and was isolated as a clear film (6.9 mg, 15%). ¹H NMR (400 MHz, CD₃OD) δ ppm 3.69-3.78 (m, 2H), 5.85-6.18 (m, 1H), 7.41 (d, J=5.05 Hz, 1H), 7.44-7.53 (m, 2H), 7.95 (dd, J=7.58, 1.77 Hz, 1H), 8.30 (d, J=5.05 Hz, 1H); ESI-MS m/z [M+H]⁺ 391.1.

Example 54: 5-(3-chloro-2-fluoropyridin-4-yl)-3-((4-fluorobenzyl)amino)-4H-benzo[e][1,2,4]thiadiazine 1,1-dioxide

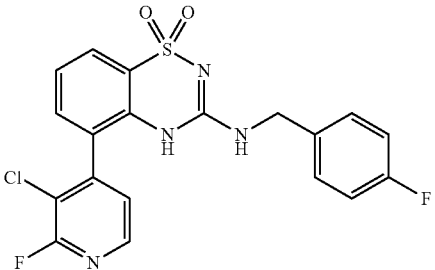 [SMILES: O=S1(=O)N=C(NCc2ccc(F)cc2)Nc2c(-c3ccnc(F)c3Cl)cccc21]

The title compound was prepared in a manner similar to Example 48, using 3-chloro-5-(3-chloro-2-fluoropyridin-4-yl)-4H-benzo[e][1,2,4]thiadiazine 1,1-dioxide (40 mg, 0.116 mmol), Et₃N (32.2 µL, 0.231 mmol), and (4-fluorophenyl)methanamine (17.35 mg, 0.139 mmol) dissolved in EtOH (500 µL), and was isolated as an orange solid (12.5 mg, 25%). ¹H NMR (400 MHz, DMSO-d₆) δ ppm 4.39-4.48 (m, 2H), 7.17-7.23 (m, 2H), 7.38 (dd, J=8.59, 5.56 Hz, 2H), 7.41-7.46 (m, 1H), 7.51-7.55 (m, 2H), 7.58 (d, J=4.80 Hz, 1H), 7.87 (dd, J=7.71, 1.14 Hz, 1H), 8.38 (d, J=4.80 Hz, 1H), 9.27 (s, 1H); ESI-MS m/z [M+H]⁺ 435.3.

Example 55: 2-(((5-(3-chloro-2-fluoropyridin-4-yl)-1,1-dioxido-4H-benzo[e][1,2,4]thiadiazin-3-yl)amino)methyl)thiazole-5-carbonitrile

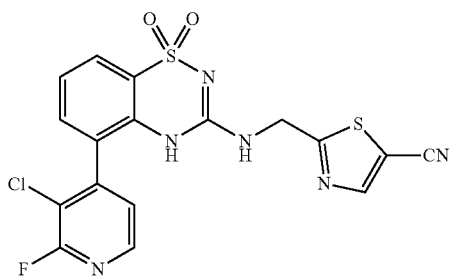 [SMILES: N#Cc1cnc(CNC2=NS(=O)(=O)c3cccc(-c4ccnc(F)c4Cl)c3N2)s1]

The title compound was prepared in a manner similar to Example 48, using 3-chloro-5-(3-chloro-2-fluoropyridin-4-yl)-4H-benzo[e][1,2,4]thiadiazine 1,1-dioxide (40 mg, 0.116 mmol), Et₃N (32.2 µL, 0.231 mmol), and 2-(aminomethyl)thiazole-5-carbonitrile, HCl (24.35 mg, 0.139 mmol) dissolved in EtOH (500 µL), and was isolated as a yellow solid (16.1 mg, 31%). ¹H NMR (400 MHz, DMSO-d₆) δ ppm 4.85 (br s, 2H), 7.47 (d, J=7.58 Hz, 1H), 7.55-7.66 (m, 2H), 7.89 (d, J=7.83 Hz, 2H), 8.40 (d, J=4.80 Hz, 1H), 8.63 (s, 1H), 9.73 (br s, 1H); ESI-MS m/z [M+H]⁺ 449.3.

Example 56: 5-(3-chloro-2-fluoropyridin-4-yl)-3-(methylamino)-4H-benzo[e][1,2,4]thiadiazine 1,1-dioxide

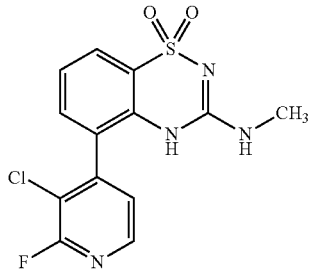 [SMILES: CNC1=NS(=O)(=O)c2cccc(-c3ccnc(F)c3Cl)c2N1]

The title compound was prepared in a manner similar to Example 48, using 3-chloro-5-(3-chloro-2-fluoropyridin-4-yl)-4H-benzo[e][1,2,4]thiadiazine 1,1-dioxide (19.25 mg, 0.056 mmol), Et$_3$N (23.25 µL, 0.167 mmol), and methanamine (33% in EtOH) (10.38 µL, 0.083 mmol) dissolved in EtOH (479 µL), and was isolated as a pale, beige film (2.2 mg, 12%). $^1$H NMR (400 MHz, CD$_3$OD) δ ppm 2.92 (s, 3H), 7.45-7.50 (m, 2H), 7.52-7.55 (m, 1H), 7.98 (d, J=7.58 Hz, 1H), 8.34 (d, J=4.80 Hz, 1H); ESI-MS m/z [M+H]$^+$ 341.0.

Example 57: 5-(2-chloro-3-fluorophenyl)-3-(((4-methylmorpholin-2-yl)methyl)amino)-4H-benzo[e][1,2,4]thiadiazine 1,1-dioxide

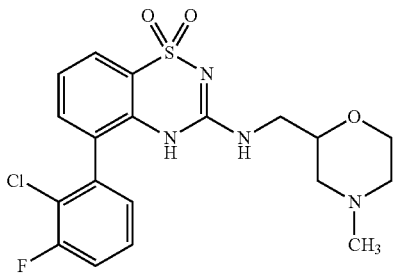 [SMILES: CN1CCOC(CNC2=NS(=O)(=O)c3cccc(-c4cccc(F)c4Cl)c3N2)C1]

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and 4-methylmorpholin-2-yl)methanamine, HCl (23.17 mg, 0.139 mmol) in DMA (232 µL), and was isolated as a pale, beige solid (24.8 mg, 49%). $^1$H NMR (400 MHz, DMSO-d$_6$) δ ppm 2.83 (br s, 3H), 3.01 (br s, 1H), 3.22-3.40 (m, 2H), 3.46-3.57 (m, 2H), 3.63-3.72 (m, 1H), 3.78 (br s, 1H), 3.98 (s, 1H), 4.06 (d, J=10.61 Hz, 1H), 7.32-7.36 (m, 1H), 7.38-7.42 (m, 1H), 7.45-7.48 (m, 1H), 7.56-7.68 (m, 3H), 7.82 (d, J=7.83 Hz, 1H), 9.19 (s, 1H); ESI-MS m/z [M+H]$^+$ 439.0.

Example 58: 5-(2-chloro-3-fluorophenyl)-3-((2-ethoxypropyl)amino)-4H-benzo[e][1,2,4]thiadiazine 1,1-dioxide

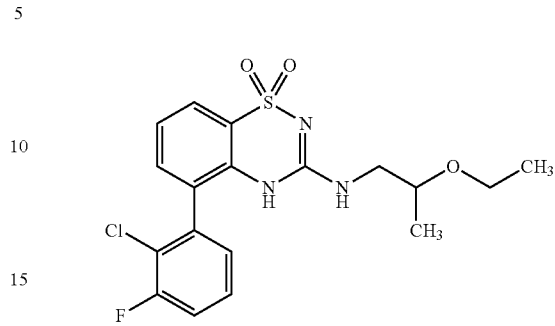

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and 2-ethoxypropan-1-amine, HCl (19.42 mg, 0.139 mmol) in DMA (232 µL), and was isolated as a pale, yellow film (15.4 mg, 32%). $^1$H NMR (400 MHz, DMSO-d$_6$) δ ppm 1.06-1.14 (m, 6H), 3.18-3.26 (m, 1H), 3.43 (dt, J=6.76, 3.32 Hz, 1H), 3.51 (ddd, J=9.85, 6.82, 3.28 Hz, 1H), 3.54-3.61 (m, 1H), 7.33-7.44 (m, 4H), 7.58-7.67 (m, 2H), 7.80 (dd, J=7.71, 1.39 Hz, 1H), 9.12 (d, J=4.04 Hz, 1H); ESI-MS m/z [M+H]$^+$ 412.0.

Example 59: 3-(((5-chloropyridin-2-yl)methyl)amino)-5-(1,3-dimethyl-1H-pyrazol-4-yl)-4H-benzo[e][1,2,4]thiadiazine 1,1-dioxide

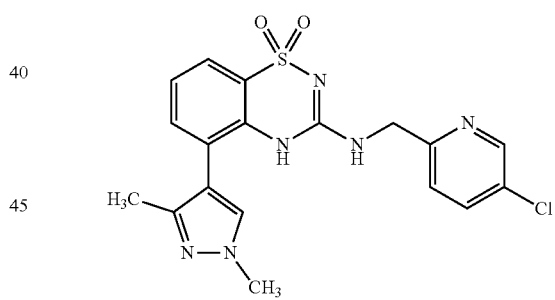

A 5 mL microwave vial equipped for stirring was charged with 3-chloro-5-(1,3-dimethyl-1H-pyrazol-4-yl)-4H-benzo[e][1,2,4]thiadiazine 1,1-dioxide (60 mg, 0.193 mmol), (5-chloropyridin-2-yl)methanamine (35.8 mg, 0.251 mmol), DIPEA (67.4 µL, 0.386 mmol) and DMA (386 µL). The reaction mixture was heated at 70° C. for 21 hours, then diluted in MeOH and filtered through a 12 mL fritted syringe containing a 0.5-inch pad of Celite®. The product was purified by column chromatography and dried on a Biotage TurboVap® II (water bath set at 60° C.) to afford the title compound as a pale, yellow solid (17.9 mg, 22%). $^1$H NMR (400 MHz, DMSO-d$_6$) δ ppm 2.07 (s, 3H), 3.87 (s, 3H), 4.57 (d, J=5.31 Hz, 2H), 7.26-7.34 (m, 1H), 7.40 (dd, J=7.58, 1.52 Hz, 1H), 7.47 (d, J=8.84 Hz, 1H), 7.67 (dd, J=7.83, 1.26 Hz, 1H), 7.86 (s, 1H), 7.96 (dd, J=8.59, 2.53 Hz, 1H), 8.22 (t, J=5.43 Hz, 1H), 8.62 (d, J=2.02 Hz, 1H), 9.44 (s, 1H); ESI-MS m/z [M+H]$^+$ 417.0.

Example 60: 5-(1,3-dimethyl-1H-pyrazol-4-yl)-3-((2-methoxypropyl)amino)-4H-benzo[e][1,2,4]thiadiazine 1,1-dioxide

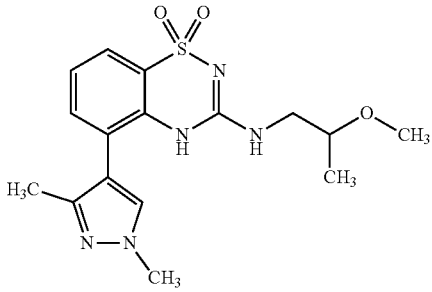

A 5 mL microwave vial equipped for stirring was charged with 3-chloro-5-(1,3-dimethyl-1H-pyrazol-4-yl)-4H-benzo[e][1,2,4]thiadiazine 1,1-dioxide (60 mg, 0.193 mmol), 2-methoxypropan-1-amine, HCl (29.1 mg, 0.232 mmol), DIPEA (67.4 µL, 0.386 mmol) and DMA (386 µL). The reaction mixture was heated at 70° C. for 15 hours, then diluted in MeOH and filtered through a 12 mL fritted syringe containing a 0.5-inch pad of Celite®. The product was purified by mass-triggered preparative LC/MS (Waters SunFire® C18, 5 µm, ID 30×75 mm column) eluting with a 20-45% gradient of ACN in water (acid mode). The product-containing fractions were collected, concentrated, and dried in vacuo to afford the title compound as a yellow-orange solid (17.9 mg, 26%). $^1$H NMR (400 MHz, DMSO-$d_6$) δ ppm 1.09 (d, J=6.06 Hz, 3H), 2.05 (s, 3H), 3.14-3.21 (m, 1H), 3.27 (s, 3H), 3.38-3.50 (m, 2H), 3.87 (s, 3H), 7.26-7.31 (m, 1H), 7.37 (dd, J=7.58, 1.52 Hz, 1H), 7.64-7.71 (m, 2H), 7.85 (s, 1H), 9.23 (s, 1H); ESI-MS m/z [M+H]$^+$ 364.0.

Example 61: 3-((cyclobutylmethyl)amino)-5-(1,3-dimethyl-1H-pyrazol-4-yl)-4H-benzo[e][1,2,4]thiadiazine 1,1-dioxide

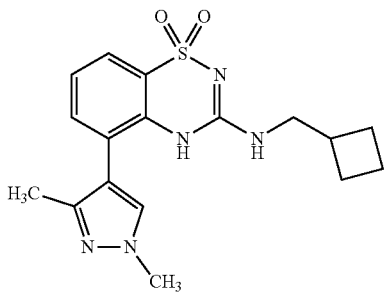 [SMILES: Cc1nn(C)cc1-c1cccc2c1NC(NCC1CCC1)=NS2(=O)=O]

The title compound was prepared in a manner similar to Example 60, using 3-chloro-5-(1,3-dimethyl-1H-pyrazol-4-yl)-4H-benzo[e][1,2,4]thiadiazine 1,1-dioxide (50 mg, 0.161 mmol), cyclobutylmethanamine, HCl (25.4 mg, 0.209 mmol) and DIPEA (28.1 µL, 0.161 mmol) in DMA (322 µL), and was isolated as colorless oil (34 mg, 56%). $^1$H NMR (400 MHz, CD$_3$OD) δ ppm 1.60-1.74 (m, 2H), 1.78-1.90 (m, 2H), 1.94-2.02 (m, 2H), 2.03 (s, 3H), 2.40-2.47 (m, 1H), 3.24 (dd, J=7.20, 5.43 Hz, 2H), 3.85 (s, 3H), 7.26 (s, 1H), 7.33-7.37 (m, 1H), 7.52-7.58 (m, 1H), 7.62-7.68 (m, 1H), 7.83 (s, 1H), 9.02-9.06 (m, 1H).

Example 62: 2-((5-(2-chloro-3-fluorophenyl)-1,1-dioxido-4H-benzol[e][1,2,4]thiadiazin-3-yl)amino)-N,N-dimethylacetamide

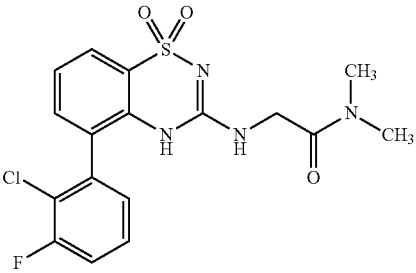 [SMILES: CN(C)C(=O)CNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (40.5 µL, 0.232 mmol), and 2-amino-N,N-dimethylacetamide (14.20 mg, 0.139 mmol) in DMA (232 µL), and was isolated as a pale, beige solid (12.2 mg, 26%). $^1$H NMR (400 MHz, DMSO-$d_6$) δ ppm 2.88 (s, 3H), 2.97 (s, 3H), 4.11 (d, J=4.29 Hz, 2H), 7.33-7.46 (m, 3H), 7.57-7.66 (m, 2H), 7.76 (t, J=4.29 Hz, 1H), 7.81 (dd, J=7.71, 1.39 Hz, 1H), 9.53 (s, 1H); ESI-MS m/z [M+H]$^+$ 411.0.

Example 63: 5-(2-cyclopropylphenyl)-3-((2-methoxyethyl)amino)-4H-benzo[e][1,2,4]thiadiazine 1,1-dioxide

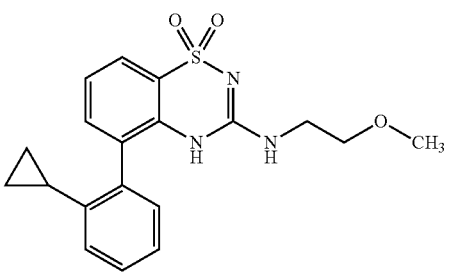 [SMILES: COCCNC1=NS(=O)(=O)c2cccc(-c3ccccc3C3CC3)c2N1]

The title compound was prepared in a manner similar to Example 35, using 5-iodo-3-((2-methoxyethyl)amino)-4H-benzo[e][1,2,4]thiadiazine 1,1-dioxide (60 mg, 0.157 mmol), (2-cyclopropylphenyl)boronic acid (28.0 mg, 0.173 mmol), Cs$_2$CO$_3$ (2M, 197 µL, 0.394 mmol), and Pd(dppf)$_2$·CH$_2$Cl$_2$ adduct (12.85 mg, 0.016 mmol) in dioxane (787 µL), and was isolated as a pale, yellow solid (21.2 mg, 36.3%). $^1$H NMR (400 MHz, DMSO-$d_6$) δ ppm 0.66-0.78 (m, 4H), 1.37-1.46 (m, 1H), 3.26 (s, 3H), 3.36-3.45 (m, 4H), 7.08 (d, J=7.58 Hz, 1H), 7.22 (dd, J=7.45, 1.14 Hz, 1H), 7.32-7.37 (m, 2H), 7.39-7.47 (m, 2H), 7.68-7.76 (m, 2H), 8.93 (s, 1H); ESI-MS m/z [M+H]$^+$ 372.0.

Example 64: 5-(2-chloro-3-fluorophenyl)-3-((isothiazol-3-ylmethyl)amino)-4H-benzo[e][1,2,4]thiadiazine 1,1-dioxide

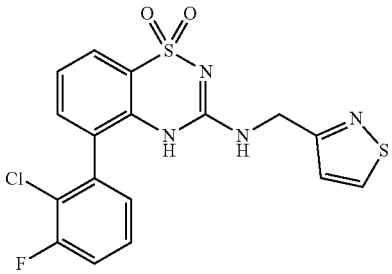 [SMILES: O=S1(=O)N=C(NCc2ccsn2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 µL, 0.217 mmol), and isothiazol-3-ylmethanamine (10.75 mg, 0.094 mmol) in EtOH (2 mL), and was isolated as a white solid (2 mg, 7%). $^1$H NMR (400 MHz, DMSO-d$_6$) δ ppm 4.54-4.66 (m, 2H) 7.28-7.49 (m, 4H), 7.53-7.67 (m, 2H), 7.75-7.84 (m, 1H), 7.92 (s, 1H), 9.06 (d, J=4.55 Hz, 1H), 9.29 (s, 1H); ESI-MS m/z [M+H]$^+$ 423.0.

Example 65: 5-(2-chloro-3-fluorophenyl)-3-((thiazol-2-ylmethyl)amino)-4H-benzo[e][1,2,4]thiadiazine 1,1-dioxide

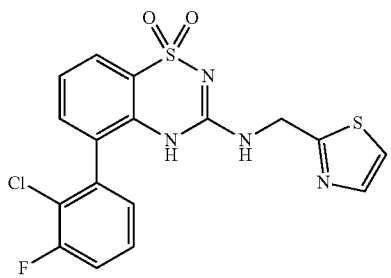 [SMILES: O=S1(=O)N=C(NCc2nccs2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (75.0 mg, 0.217 mmol), Et$_3$N (91 µL, 0.652 mmol), and thiazol-2-ylmethanamine hydrochloride (120 mg, 0.796 mmol) in EtOH (3.0 mL), and was isolated as a white solid (115 mg, 46%). $^1$H NMR (400 MHz, DMSO-d$_6$) δ ppm 9.32 (br s, 1H), 8.00 (br s, 1H), 7.85-7.79 (m, 1H), 7.76 (d, J=3.2 Hz, 1H), 7.67 (d, J=3.2 Hz, 1H), 7.65-7.53 (m, 2H), 7.48-7.43 (m, 1H), 7.40 (d, J=7.8 Hz, 1H), 7.38-7.32 (m, 1H), 4.75 (d, J=6.0 Hz, 2H); ESI-MS m/z [M+H]$^+$ 423.0.

Example 66: 5-(2-chloro-3-fluorophenyl)-3-((pyrimidin-2-ylmethyl)amino)-4H-benzo[e][1,2,4]thiadiazine 1,1-dioxide

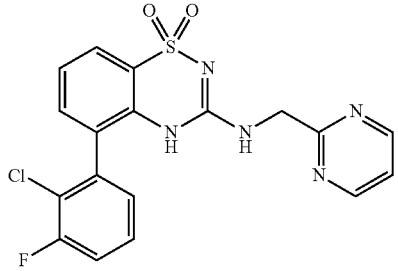 [SMILES: O=S1(=O)N=C(NCc2ncccn2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 µL, 0.217 mmol), and pyrimidine-2-ylmethylamine (15.8 mg, 0.109 mmol) in EtOH (2 mL), and was isolated as a yellow oil (12 mg, 40%). $^1$H NMR (400 MHz, DMSO-d$_6$) δ ppm 4.66 (br s, 2H), 7.30-7.49 (m, 4H), 7.55-7.68 (m, 2H), 7.79 (dd, J=7.96, 1.39 Hz, 1H), 8.01 (s, 1H), 8.81 (d, J=4.80 Hz, 2H), 9.47 (s, 1H); ESI-MS m/z [M+H]$^+$ 418.0.

Example 67: 5-(2-chloro-3-fluorophenyl)-3-((2-(pyridin-2-yl)ethyl)amino)-4H-benzo[e][1,2,4]thiadiazine 1,1-dioxide

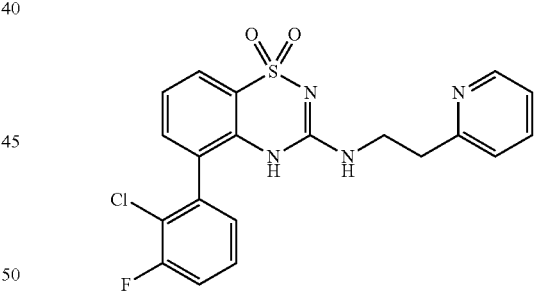

A TFA salt of the title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), Et$_3$N (61 µL, 0.435 mmol), and 2-(pyridin-2-yl)ethanamine (26.5 mg, 0.217 mmol) in EtOH (2 mL), and was isolated as an off-white solid (30 mg, 48%). $^1$H NMR (400 MHz, DMSO-d$_6$) δ ppm 3.09 (t, J=6.69 Hz, 2H), 3.60-3.69 (t, J=6.69 Hz, 2H), 7.26-7.48 (m, 4H), 7.49-7.66 (m, 4H), 7.78 (dd, J=7.71, 1.39 Hz, 1H), 8.07 (br s, 1H), 8.66 (d, J=4.55 Hz, 1H), 9.08 (s, 1H); ESI-MS m/z [M+H]$^+$ 431.1.

Example 68: 5-(2-chloro-3-fluorophenyl)-3-((2-(pyridin-4-yl)ethyl)amino)-4H-benzo[e][1,2,4]thiadiazine 1,1-dioxide

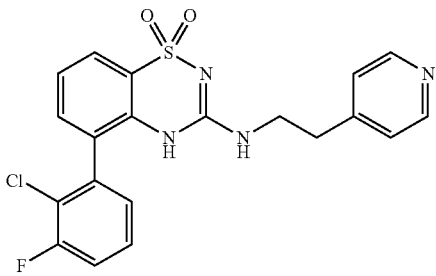 [SMILES: O=S1(=O)N=C(NCCc2ccncc2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(pyridine-4-yl)ethanamine (13.3 mg, 0.109 mmol) in EtOH (2 mL), and was isolated as a white solid (9 mg, 29%). $^1$H NMR (400 MHz, DMSO-d$_6$) δ ppm 2.94-3.07 (m, 2H), 3.51-3.63 (m, 2H), 7.26-7.50 (m, 4H), 7.52-7.64 (m, 2H), 7.67 (d, J=5.31 Hz, 2H), 7.78 (dd, J=7.83, 1.26 Hz, 1H), 8.69 (d, J=6.32 Hz, 2H), 9.07 (s, 1H); ESI-MS m/z [M+H]$^+$ 431.1.

Example 69: 5-(2-chloro-3-fluorophenyl)-3-((2-(pyridin-3-yl)ethyl)amino)-4H-benzo[e][1,2,4]thiadiazine 1,1-dioxide

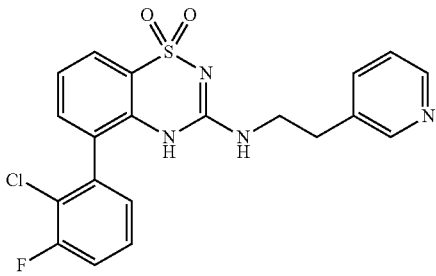 [SMILES: O=S1(=O)N=C(NCCc2cccnc2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(pyridine-3-yl)ethanamine (13 mg, 0.109 mmol) in EtOH (2 mL), and was isolated as a white solid (10 mg, 32%); ESI-MS m/z [M+H]$^+$ 431.1.

Example 70: 5-(2-chloro-3-fluorophenyl)-3-((3-methoxyphenethyl)amino)-4H-benzo[e][1,2,4]thiadiazine 1,1-dioxide

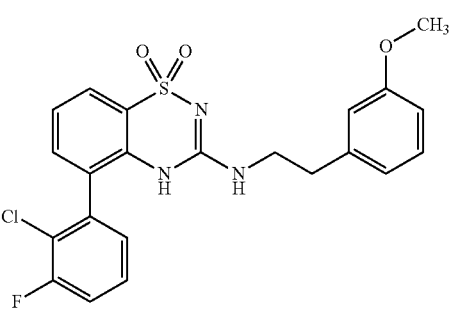 [SMILES: COc1cccc(CCNC2=NS(=O)(=O)c3cccc(-c4cccc(F)c4Cl)c3N2)c1]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(3-methoxyphenyl)ethanamine (16.4 mg, 0.109 mmol) in EtOH (2 mL), and was isolated as a white solid (5 mg, 14%); ESI-MS m/z [M+H]$^+$ 460.1.

Example 71: 5-(2-chloro-3-fluorophenyl)-3-((2-methoxyphenethyl)amino)-4H-benzo[e][1,2,4]thiadiazine 1,1-dioxide

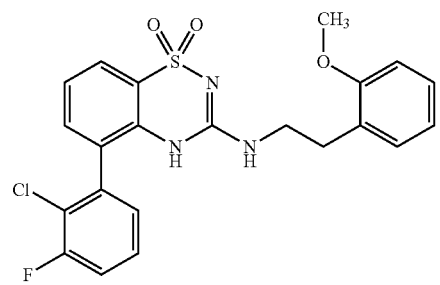 [SMILES: COc1ccccc1CCNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(2-methoxyphenyl)ethanamine (16.4 mg, 0.109 mmol) in EtOH (2 mL), and was isolated as a white solid (4 mg, 12%); ESI-MS m/z [M+H]$^+$ 460.1.

Example 72: 5-(2-chloro-3-fluorophenyl)-3-((4-methoxyphenethyl)amino)-4H-benzo[e][1,2,4]thiadiazine 1,1-dioxide

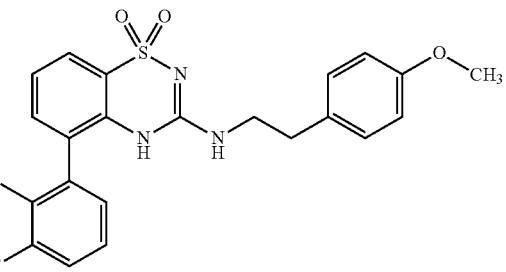

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(4-methoxyphenyl)ethanamine (16.4 mg, 0.109 mmol) in EtOH (2 mL), and was isolated as a white solid (3.0 mg, 9%); ESI-MS m/z [M+H]$^+$ 460.1.

Example 73: 5-(2-chloro-3-fluorophenyl)-3-((2-(tetrahydrofuran-2-yl)ethyl)amino)-4H-benzo[e][1,2,4]thiadiazine 1,1-dioxide

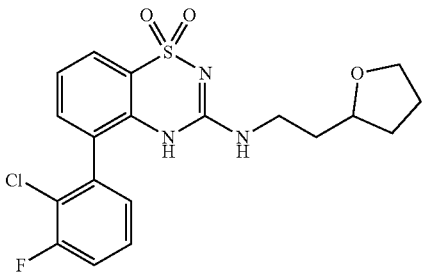 [SMILES: O=S1(=O)N=C(NCCC2CCCO2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 2-(tetrahydrofuran-2-yl)ethanamine (12.5 mg, 0.109 mmol) in EtOH (2 mL), and was isolated as a brown film (2.0 mg, 7%); ESI-MS m/z [M+H]$^+$ 424.1.

Example 74: 5-(2-chloro-3-fluorophenyl)-3-((1-isopropyl-5-methyl-1H-pyrazol-3-yl)amino)-4H-benzo[e][1,2,4]thiadiazine 1,1-dioxide

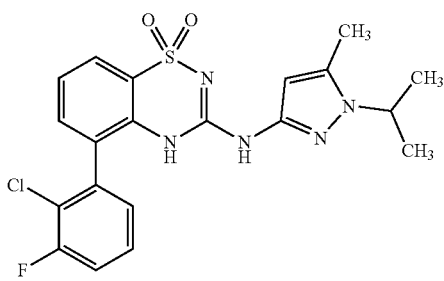 [SMILES: Cc1cc(NC2=NS(=O)(=O)c3cccc(-c4cccc(F)c4Cl)c3N2)nn1C(C)C]

The title compound was prepared in a manner similar to Example 1, using 3-chloro-5-(2-chloro-3-fluorophenyl)-4H-benzo[e][1,2,4]thiadiazine 1,1-dioxide (25 mg, 0.072 mmol), Et$_3$N (30 μL, 0.217 mmol), and 1-isopropyl-5-methyl-1H-pyrazol-3-amine (15 mg, 0.109 mmol) in EtOH (2 mL), and was isolated as a white solid (1 mg, 3%); ESI-MS m/z [M+H]$^+$ 448.1.

Example 75: 5-(3,5-difluorophenyl)-3-((4-fluorobenzyl)amino)-4H-benzo[e][1,2,4]thiadiazine 1,1-dioxide

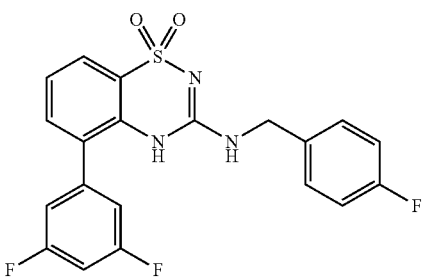 [SMILES: O=S1(=O)N=C(NCc2ccc(F)cc2)Nc2c(-c3cc(F)cc(F)c3)cccc21]

An 8 mL vial was charged with 3-chloro-5-(3,5-difluorophenyl)-4H-benzo[e][1,2,4]thiadiazine 1,1-dioxide (25 mg, 0.076 mmol), (4-fluorophenyl)methanamine (19.03 mg, 0.152 mmol), Et$_3$N (0.032 mL, 0.228 mmol) and EtOH (2 mL). The reaction mixture was heated to 65° C. and stirred overnight. LC/MS indicated the reaction was complete. The solvent was removed and the product was taken up in DMF (1 mL), filtered, and purified by supercritical fluid chromatography. The purified fractions were evaporated on a TurboVap® to give the title compound as a white solid (6.7 mg, 21%). $^1$H NMR (400 MHz, DMSO-d$_6$) δ ppm 4.42 (d, J=5.56 Hz, 2H), 7.13-7.23 (m, 2H), 7.23-7.31 (m, 2H), 7.31-7.45 (m, 4H), 7.48 (dd, J=7.58, 1.52 Hz, 1H), 7.77 (dd, J=7.83, 1.01 Hz, 1H), 7.84 (t, J=5.56 Hz, 1H), 9.19 (s, 1H); ESI-MS m/z [M+H]$^+$ 418.1.

Example 76: 3-((2,5-difluorobenzyl)amino)-5-(3,5-difluorophenyl)-4H-benzo[e][1,2,4]thiadiazine 1,1-dioxide

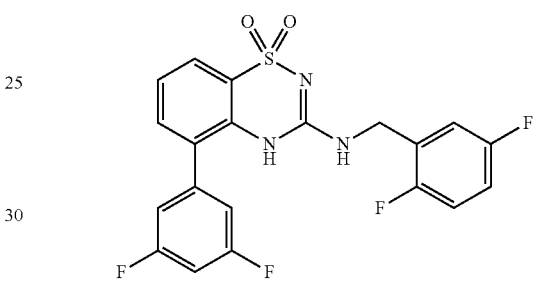

The title compound was prepared in a manner similar to Example 75, using 3-chloro-5-(3,5-difluorophenyl)-4H-benzo[e][1,2,4]thiadiazine 1,1-dioxide (25 mg, 0.076 mmol), (2,5-difluorophenyl)methanamine (21.8 mg, 0.152 mmol) and Et$_3$N (0.032 mL, 0.228 mmol) in EtOH (2 mL), and was isolated as a white solid (2.7 mg, 8%). $^1$H NMR (400 MHz, DMSO-d$_6$) δ ppm 4.47 (d, J=5.31 Hz, 2H), 7.13-7.23 (m, 1H), 7.23-7.33 (m, 4H), 7.33-7.39 (m, 1H), 7.39-7.46 (m, 1H), 7.49 (dd, J=7.58, 1.52 Hz, 1H), 7.77 (dd, J=7.83, 1.01 Hz, 1H), 7.89 (t, J=5.68 Hz, 1H), 9.29 (s, 1H); ESI-MS m/z [M+H]$^+$ 436.0.

Example 77: 5-(3,5-difluorophenyl)-3-((2-fluorobenzyl)amino)-4H-benzo[e][1,2,4]thiadiazine 1,1-dioxide

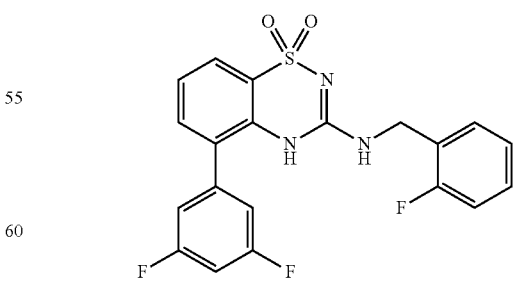

The title compound was prepared in a manner similar to Example 75, using 3-chloro-5-(3,5-difluorophenyl)-4H-benzo[e][1,2,4]thiadiazine 1,1-dioxide (25 mg, 0.076 mmol), (2-fluorophenyl)methanamine (19 mg, 0.152 mmol)

and Et₃N (0.032 mL, 0.228 mmol) in EtOH (2 mL), and was isolated as a white solid (3.5 mg, 11%). ¹H NMR (400 MHz, DMSO-d₆) δ ppm 4.47 (d, J=5.31 Hz, 2H), 7.14-7.24 (m, 2H), 7.24-7.31 (m, 2H), 7.31-7.46 (m, 4H), 7.48 (dd, J=7.45, 1.39 Hz, 1H), 7.77 (d, J=6.82 Hz, 1H), 7.83-7.91 (m, 1H), 9.19 (s, 1H); ESI-MS m/z [M+H]⁺ 418.1.

Example 78: 3-((2,6-difluorobenzyl)amino)-5-(3,5-difluorophenyl)-4H-benzo[e][1,2,4]thiadiazine 1,1-dioxide

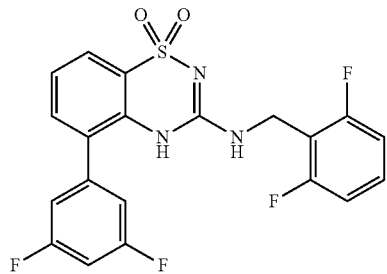 [SMILES: O=S1(=O)N=C(NCc2c(F)cccc2F)Nc2c(-c3cc(F)cc(F)c3)cccc21]

The title compound was prepared in a manner similar to Example 75, using 3-chloro-5-(3,5-difluorophenyl)-4H-benzo[e][1,2,4]thiadiazine 1,1-dioxide (25 mg, 0.076 mmol), (2,6-difluorophenyl)methanamine (22 mg, 0.152 mmol) and Et₃N (0.032 mL, 0.228 mmol) in EtOH (2 mL), and was isolated as a white solid (2 mg, 6%). ESI-MS m/z [M+H]⁺ 436.0.

Example 79: 5-(3,5-difluorophenyl)-3-(((6-methylpyridin-2-yl)methyl)amino)-4H-benzo[e][1,2,4]thiadiazine 1,1-dioxide

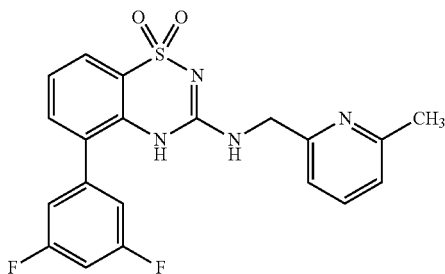 [SMILES: Cc1cccc(CNC2=NS(=O)(=O)c3cccc(-c4cc(F)cc(F)c4)c3N2)n1]

The title compound was prepared in a manner similar to Example 75, using 3-chloro-5-(3,5-difluorophenyl)-4H-benzo[e][1,2,4]thiadiazine 1,1-dioxide (25 mg, 0.076 mmol), (6-methylpyridin-2yl)methanamine (19 mg, 0.152 mmol) and Et₃N (0.032 mL, 0.228 mmol) in EtOH (2 mL), and was isolated as a white solid (10 mg, 32%). ESI-MS m/z [M+H]⁺ 415.0.

Example 80: 5-(3,5-difluorophenyl)-3-((2-(pyridin-2-yl)ethyl)amino)-4H-benzo[e][1,2,4]thiadiazine 1,1-dioxide

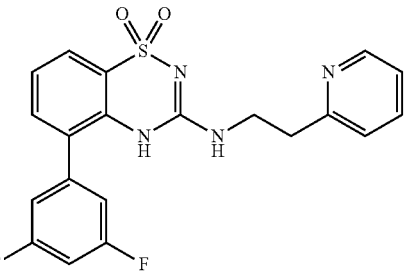

A TFA salt of the title compound was prepared in a manner similar to Example 75, using 3-chloro-5-(3,5-difluorophenyl)-4H-benzo[e][1,2,4]thiadiazine 1,1-dioxide (75 mg, 0.228 mmol), 2-(pyridine-2-yl)ethanamine (42.0 mg, 0.342 mmol) and Et₃N (0.095 mL, 0.684 mmol) in EtOH (3 mL), and was isolated as an orange oil (21 mg, 23%). ¹H NMR (400 MHz, DMSO-d₆) δ ppm 3.07 (t, J=6.82 Hz, 2H), 3.59-3.70 (m, 2H), 7.24 (d, J=6.06 Hz, 2H), 7.30-7.37 (m, 1H), 7.41 (t, J=9.60 Hz, 1H), 7.44-7.65 (m, 4H), 7.75 (dd, J=7.83, 1.26 Hz, 1H), 8.00 (br s, 1H), 8.62 (br s, 1H), 9.18 (s, 1H); ESI-MS m/z [M+H]⁺ 415.5.

Example 81: 3-((cyclobutylmethyl)amino)-5-(3,5-difluorophenyl)-4H-benzo[e][1,2,4]thiadiazine 1,1-dioxide

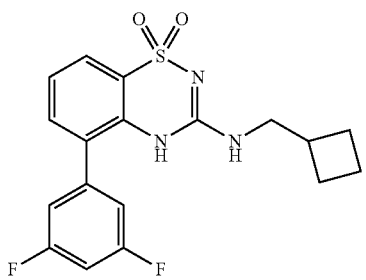 [SMILES: O=S1(=O)N=C(NCC2CCC2)Nc2c(-c3cc(F)cc(F)c3)cccc21]

The title compound was prepared in a manner similar to Example 75, using 3-chloro-5-(3,5-difluorophenyl)-4H-benzo[e][1,2,4]thiadiazine 1,1-dioxide (50 mg, 0.152 mmol), cyclobutylmethanamine, HCl (37.0 mg, 0.304 mmol) and Et₃N (0.0636 mL, 0.456 mmol) in EtOH (3.5 mL), and was isolated as a white semi solid (33.0 mg, 58%). ¹H NMR (400 MHz, CD₃OD) δ ppm 1.68-1.80 (m, 2H), 1.83-1.99 (m, 2H), 2.07 (d, J=8.08 Hz, 2H), 2.53 (dt, J=15.22, 7.67 Hz, 1H), 3.33 (d, J=7.33 Hz, 2H), 7.01-7.17 (m, 3H), 7.30-7.40 (m, 1H), 7.47 (d, J=7.33 Hz, 1H), 7.83 (d, J=7.58 Hz, 1H); ESI-MS m/z [M+H]⁺ 378.1.

Example 82: 5-(3,5-difluorophenyl)-3-((pyridin-4-ylmethyl)amino)-4H-benzo[e][1,2,4]thiadiazine 1,1-dioxide

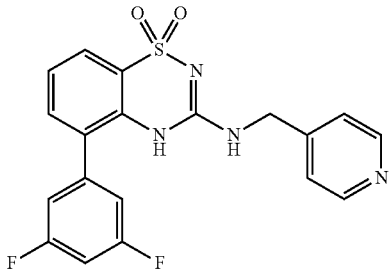 [SMILES: O=S1(=O)N=C(NCc2ccncc2)Nc2c(-c3cc(F)cc(F)c3)cccc21]

A formic acid salt of the title compound was prepared in a manner similar to Example 75, using 3-chloro-5-(3,5-difluorophenyl)-4H-benzo[e][1,2,4]thiadiazine 1,1-dioxide (25.0 mg, 0.076 mmol), pyridin-4-ylmethanamine (32.90 mg, 0.304 mmol) and Et$_3$N (0.032 mL, 0.228 mmol) in EtOH (2.0 mL), and was isolated as a yellow solid (23.92 mg, 35%). $^1$H NMR (400 MHz, DMSO-d$_4$) δ ppm 4.48 (d, J=5.2 Hz, 2H), 7.42-7.28 (m, 6H), 7.48 (d, J=8.4 Hz, 1H), 7.75 (d, J=7.6 Hz, 1H), 7.99 (s, 1H), 8.51 (d, J=5.6 Hz, 2H); ESI-MS m/z [M+H]$^+$ 401.1.

Example 83: 5-(3,5-difluorophenyl)-3-((pyridin-2-ylmethyl)amino)-4H-benzo[e][1,2,4]thiadiazine 1,1-dioxide

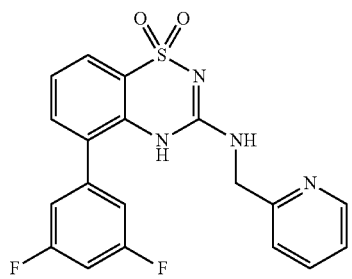 [SMILES: O=S1(=O)N=C(NCc2ccccn2)Nc2c(-c3cc(F)cc(F)c3)cccc21]

The title compound was prepared in a manner similar to Example 75, using 3-chloro-5-(3,5-difluorophenyl)-4H-benzo[e][1,2,4]thiadiazine 1,1-dioxide (50 mg, 0.152 mmol), pyridin-2-ylmethanamine (21.4 mg, 0.198 mmol) and DIPEA (26.6 μL, 0.152 mmol) in DMA (304 μL), and was isolated as white solid (31 mg, 51%). $^1$H NMR (400 MHz, CD$_3$OD) δ ppm 4.67-4.82 (m, 2H), 7.05-7.22 (m, 3H), 7.35-7.43 (m, 1H), 7.46-7.57 (m, 1H) 7.57-7.69 (m, 1H), 7.73-7.82 (m, 1H), 7.80-7.88 (m, 1H), 8.12-8.27 (m, 1H), 8.54-8.66 (m, 1H); ESI-MS m/z [M+H]$^+$ 401.0.

Example 84: 5-(3,5-difluorophenyl)-3-((2-methoxypropyl)amino)-4H-benzo[e][1,2,4]thiadiazine 1,1-dioxide

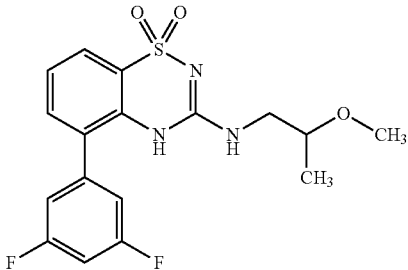 [SMILES: COC(C)CNC1=NS(=O)(=O)c2cccc(-c3cc(F)cc(F)c3)c2N1]

The title compound was prepared in a manner similar to Example 75, using 3-chloro-5-(3,5-difluorophenyl)-4H-benzo[e][1,2,4]thiadiazine 1,1-dioxide (100 mg, 0.304 mmol), 2-methoxypropan-1-amine, HCl (45.8 mg, 0.365 mmol) and DIPEA (106 μL, 0.608 mmol) in DMA (608 μL), and was isolated as a white solid (56.1 mg, 48%). $^1$H NMR (400 MHz, DMSO-d$_6$) δ ppm 1.10 (d, J=6.32 Hz, 3H), 3.15-3.21 (m, 1H), 3.26 (s, 3H), 3.38-3.50 (m, 2H), 7.28 (d, J=6.32 Hz, 2H), 7.33-7.37 (m, 1H), 7.42-7.49 (m, 2H), 7.59 (t, J=5.05 Hz, 1H), 7.77 (dd, J=7.71, 1.14 Hz, 1H), 9.22 (s, 1H); ESI-MS m/z [M+H]$^+$ 382.1.

Example 85: (R)-5-(3,5-difluorophenyl)-3-((2-methoxypropyl)amino)-4H-benzo[e][1,2,4]thiadiazine 1,1-dioxide

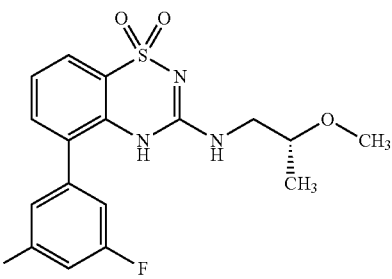

The racemate prepared in Example 84 was resolved by 2D separation using SFC/UV, PIC system (Chiral Technology AS-H column, 5 μm, ID 20×150 mm, flow rate at 100 mL/min) eluting with 30% IPA. The title compound, which was the first eluting peak and arbitrarily assigned R-stereochemical configuration, was isolated as a white solid (15.4 mg, 27.5%). $^1$H NMR (400 MHz, DMSO-d$_6$) δ ppm 1.10 (d, J=6.32 Hz, 3H), 3.15-3.21 (m, 1H), 3.26 (s, 3H), 3.38-3.50 (m, 2H), 7.28 (d, J=6.32 Hz, 2H), 7.33-7.37 (m, 1H), 7.42-7.49 (m, 2H), 7.59 (t, J=5.05 Hz, 1H), 7.77 (dd, J=7.71, 1.14 Hz, 1H), 9.22 (s, 1H); ESI-MS m/z [M+H]$^+$ 382.1.

Example 86: (S)-5-(3,5-difluorophenyl)-3-((2-methoxypropyl)amino)-4H-benzo[e][1,2,4]thiadiazine 1,1-dioxide

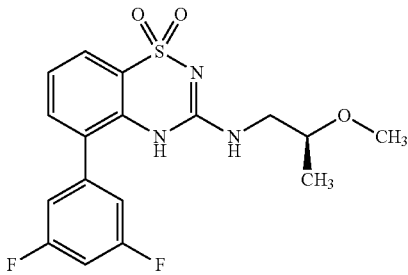 [SMILES: CO[C@@H](C)CNC1=NS(=O)(=O)c2cccc(-c3cc(F)cc(F)c3)c2N1]

The racemate prepared in Example 84 was resolved by 2D separation using SFC/UV, PIC system (Chiral Technology AS-H column, 5 μm, ID 20×150 mm, flow rate at 100 mL/min) eluting with 30% IPA. The title compound, which was the second eluting peak and arbitrarily assigned S-stereochemical configuration, was isolated as a white solid (21.2 mg, 37.8%). $^1$H NMR (400 MHz, DMSO-d$_6$) δ ppm 1.10 (d, J=6.32 Hz, 3H), 3.14-3.22 (m, 1H), 3.26 (s, 3H), 3.37-3.51 (m, 2H), 7.29 (d, J=6.06 Hz, 2H), 7.32-7.37 (m, 1H), 7.41-7.50 (m, 2H), 7.59 (t, J=5.18 Hz, 1H), 7.77 (dd, J=7.83, 1.26 Hz, 1H), 9.22 (s, 1H); ESI-MS m/z [M+H]$^+$ 382.1.

Example 87: 5-(3,5-difluorophenyl)-3-((2-methoxybutyl)amino)-4H-benzo[e][1,2,4]thiadiazine 1,1-dioxide

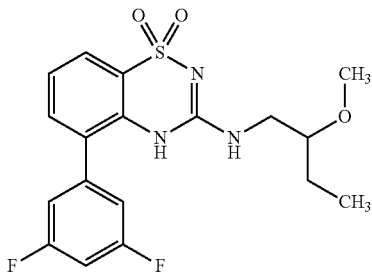 [SMILES: CCC(CNC1=NS(=O)(=O)c2cccc(-c3cc(F)cc(F)c3)c2N1)OC]

The title compound was prepared in a manner similar to Example 75, using 3-chloro-5-(3,5-difluorophenyl)-4H-benzo[e][1,2,4]thiadiazine 1,1-dioxide (50 mg, 0.152 mmol), 2-methoxybutan-1-amine, HCl (27.6 mg, 0.198 mmol) and DIPEA (26.6 μL, 0.152 mmol) in DMA (304 μL), and was isolated as tan solid (12 mg, 20%). $^1$H NMR (400 MHz, CD$_3$OD) δ ppm 0.93 (td, J=7.39, 1.64 Hz, 3H), 1.43-1.64 (m, 2H), 3.35 (d, J=2.27 Hz, 2H), 3.53-3.62 (m, 1H), 7.07-7.17 (m, 3H), 7.33-7.40 (m, 1H), 7.45-7.50 (m, 1H), 7.82-7.86 (m, 1H); ESI-MS m/z [M+H]$^+$ 396.0.

Example 88: 3-(benzylamino)-5-(3,5-difluorophenyl)-4H-benzo[e][1,2,4]thiadiazine 1,1-dioxide

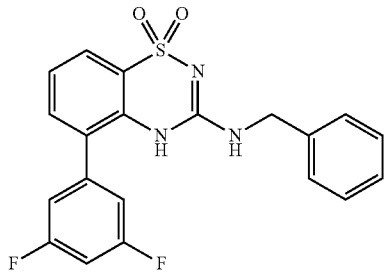 [SMILES: O=S1(=O)N=C(NCc2ccccc2)Nc2c(-c3cc(F)cc(F)c3)cccc21]

The title compound was prepared in a manner similar to Example 75, using 3-chloro-5-(3,5-difluorophenyl)-4H-benzo[e][1,2,4]thiadiazine 1,1-dioxide (25.0 mg, 0.076 mmol), benzylamine (32.60 mg, 0.304 mmol) and Et$_3$N (32.0 μL, 0.028 mmol) in EtOH (2.0 mL), and was isolated as a white solid (32.00 mg, 54%). $^1$H NMR (400 MHz, CDCl$_3$) δ ppm 4.40 (d, J=5.6 Hz, 2H), 6.06 (t, J=5.6 Hz, 1H), 6.74 (d, J=5.2 Hz, 2H), 6.82 (t, J=8.8 Hz, 1H), 7.20-7.18 (m, 2H), 7.28-7.26 (m, 3H), 7.35-7.34 (m, 2H), 7.88-7.86 (dd, J=6.4 Hz, J=3.2 Hz, 2H); ESI-MS m/z [M+H]$^+$ 400.0.

Example 89: 2-fluoro-6-(3-(methylamino)-1,1-dioxido-4H-benzo[e][1,2,4]thiadiazin-5-yl)benzonitrile

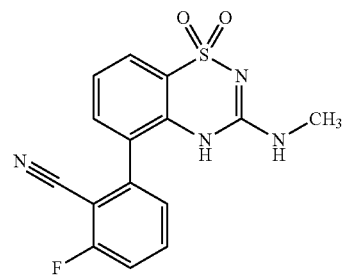 [SMILES: CNC1=NS(=O)(=O)c2cccc(-c3cccc(F)c3C#N)c2N1]

To a 10 mL vial were added 5-iodo-3-(methylamino)-4H-benzo[e][1,2,4]thiadiazine 1,1-dioxide (20 mg, 0.059 mmol), 2-fluoro-6-(4,4,5,5-tetramethyl-1,3,2-dioxaborolan-2-yl)benzonitrile (19 mg, 0.077 mmol), saturated (aq) NaHCO$_3$ aq (2 mL) and PdCl$_2$(dppf) (4.34 mg, 5.93 μmol) in dioxane (2 mL). The reaction mixture was heated to 80° C. and stirred overnight. LC/MS indicated the reaction was complete. The solvent was boiled off with mild heating. The crude product was taken up in MeOH, filtered using a 0.45p PTFE syringe filter, and purified by preparative LC/MS (Waters SunFire® C18, 5 μm, ID 4×50 mm column) eluting with a gradient of ACN in water (acid mode). The pure fractions were combined and lyophilized to give a TFA salt of the tile compound as a white solid (1 mg, 5%). ESI-MS m/z [M+H]$^+$ 331.0.

Example 90: 4-chloro-2-(3-(methylamino)-1,1-di-oxido-4H-benzo[e][1,2,4]thiadiazin-5-yl)benzonitrile

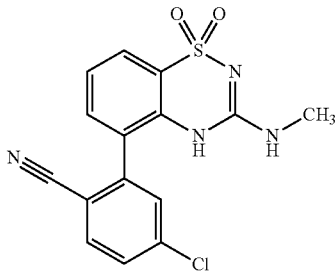 [SMILES: CNC1=NS(=O)(=O)c2cccc(-c3cc(Cl)ccc3C#N)c2N1]

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (5-chloro-2-cyanophenyl)boronic acid (14 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (1.0 mg, 5%). ESI-MS m/z [M+H]$^+$ 347.0.

Example 91: 5-(2-ethylphenyl)-3-(methylamino)-4H-benzo[e][1,2,4]thiadiazine 1,1-dioxide

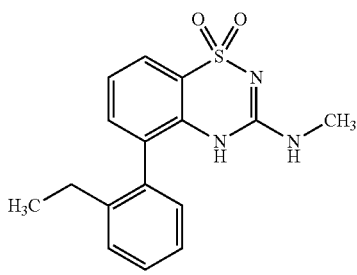 [SMILES: CCc1ccccc1-c1cccc2c1NC(NC)=NS2(=O)=O]

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (2-ethylphenyl)boronic acid (12 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (1 mg, 5%). ESI-MS m/z [M+H]$^+$ 316.1.

Example 92: 5-(2-chloro-4-methylphenyl)-3-(methylamino)-4H-benzo[e][1,2,4]thiadiazine 1,1-dioxide

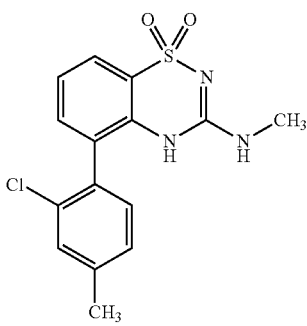 [SMILES: CNC1=NS(=O)(=O)c2cccc(-c3ccc(C)cc3Cl)c2N1]

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (2-chloro-4-methylphenyl)boronic acid (13 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (2 mg, 8%). ESI-MS m/z [M+H]$^+$ 336.0.

Example 93: 5-(2-chloro-5-fluorophenyl)-3-(methylamino)-4H-benzo[e][1,2,4]thiadiazine 1,1-dioxide

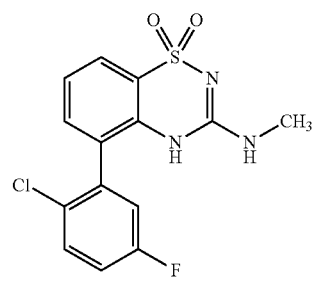 [SMILES: CNC1=NS(=O)(=O)c2cccc(-c3cc(F)ccc3Cl)c2N1]

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (2-chloro-5-fluorophenyl boronic acid (13 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (1 mg, 5%); ESI-MS m/z [M+H]$^+$ 340.0.

Example 94: 5-(2-chloro-4-fluorophenyl)-3-(methylamino)-4H-benzo[e][1,2,4]thiadiazine 1,1-dioxide

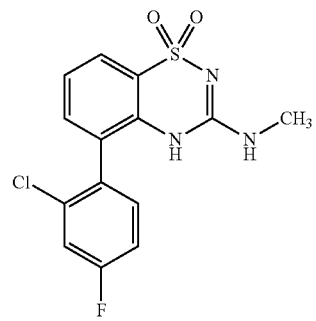 [SMILES: CNC1=NS(=O)(=O)c2cccc(-c3ccc(F)cc3Cl)c2N1]

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (2-chloro-4-fluorophenyl)boronic acid (13 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (2 mg, 10%). ESI-MS m/z [M+H]$^+$ 340.0.

Example 95: 5-(3-fluoro-2-methylphenyl)-3-(methylamino)-4H-benzo[e][1,2,4]thiadiazine 1,1-dioxide

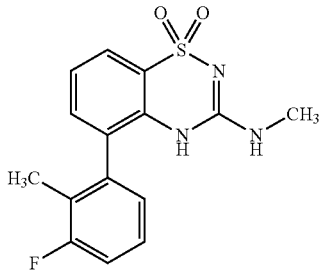

A TFA salt of the title compound was prepared in a manner similar to Example 89, using 5-iodo-3-(methylamino)-4H-benzo[e][1,2,4]thiadiazine 1,1-dioxide (20 mg, 0.059 mmol), (3-fluoro-2-methylphenyl)boronic acid (12 mg, 0.077 mmol), saturated (aq) NaHCO$_3$ aq (2 mL) and PdCl$_2$(dppf) (4.34 mg, 5.93 µmol) in dioxane (2 mL), and was isolated as a white solid (1 mg, 5%). ESI-MS m/z [M+H]$^+$ 320.1.

Example 96: 3-(methylamino)-5-(2,3,5-trifluorophenyl)-4H-benzo[e][1,2,4]thiadiazine 1,1-dioxide

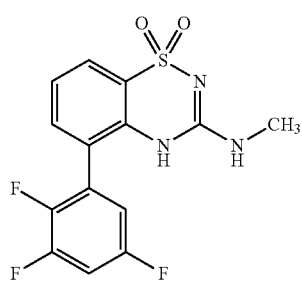 [SMILES: CNC1=NS(=O)(=O)c2cccc(-c3cc(F)cc(F)c3F)c2N1]

To a 2-5 mL microwave vial were added 5-iodo-3-(methylamino)-4H-benzo[e][1,2,4]thiadiazine 1,1-dioxide (150 mg, 0.445 mmol), (2,3,5-trifluorophenyl)boronic acid (82 mg, 0.467 mmol), and dioxane (2.225 mL), followed by Cs$_2$CO$_3$ (2M, 890 µL, 1.780 mmol) and Pd(dppf)$_2$·CH$_2$Cl$_2$ adduct (36.3 mg, 0.044 mmol). The mixture was purged with nitrogen and then heated in a microwave reactor for 45 minutes at 120° C. The reaction mixture was then poured into water and extracted with EtOAc (3×). The combined organic layers were washed with brine, dried over MgSO$_4$, filtered, and concentrated. The resulting brown oil was dissolved in MeOH (2 mL), filtered, and purified by preparative LC/MS (Waters SunFire® C18, 5 µm, ID 30×75 mm column) eluting with a gradient of 30-50% ACN in water (acid mode). The title compound was isolated as a white solid (23.6 mg, 16%). $^1$H NMR (400 MHz, DMSO-d$_6$) δ ppm 2.69 (d, J=4.55 Hz, 3H), 7.14 (br s, 1H), 7.22-7.36 (m, 2H), 7.46 (dd, J=7.58, 1.52 Hz, 1H), 7.64-7.81 (m, 2H), 9.24 (s, 1H); ESI-MS m/z [M+H]$^+$ 342.0.

Example 97: 5-(2-chloro-3-fluorophenyl)-7-methyl-3-(methylamino)-4H-benzo[e][1,2,4]thiadiazine 1,1-dioxide

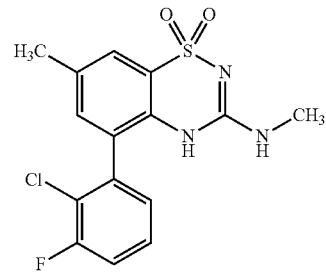 [SMILES: CNC1=NS(=O)(=O)c2cc(C)cc(-c3cccc(F)c3Cl)c2N1]

To a 10 mL vial were added 3-chloro-5-(2-chloro-3-fluorophenyl)-7-methyl-4H-benzo[e][1,2,4]thiadiazine 1,1-dioxide (44 mg, 0.122 mmol) in EtOH (9 mL) along with methanamine (2M in MeOH, 0.122 mL, 0.245 mmol) and Et$_3$N (0.051 mL, 0.367 mmol). The resulting yellow solution was heated to 65° C. and stirred for 16 hours. The mixture was subsequently concentrated and purified by preparative HPLC (Waters XSelect® C18, 5 µm, ID 30×75 mm column) eluting with a gradient of ACN (0.1% TFA) in water (0.1% TFA). The title compound was isolated as a white solid (26 mg, 60%). $^1$H NMR (400 MHz, DMSO-d$_6$) δ ppm 2.36 (s, 3H), 2.73 (d, J=4.55 Hz, 3H), 7.13 (d, J=4.29 Hz, 1H), 7.24 (d, J=1.52 Hz, 1H), 7.27-7.33 (m, 1H), 7.52-7.64 (m, 3H), 8.99 (s, 1H); ESI-MS m/z [M+H]$^+$ 354.5.

Example 98: 3-((4-isopropylphenyl)amino)-5-(5-methyl-1H-pyrazol-3-yl)-4H-benzo[e][1,2,4]thiadiazine 1,1-dioxide

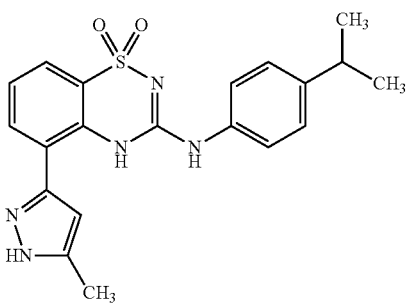 [SMILES: Cc1cc(-c2cccc3c2NC(Nc2ccc(C(C)C)cc2)=NS3(=O)=O)n[nH]1]

An 8 mL vial was charged with 5-iodo-3-((4-isopropylphenyl)amino)-4H-benzo[e][1,2,4]thiadiazine 1,1-dioxide (25 mg, 0.057 mmol), (5-methyl-1H-pyrazol-3-yl)boronic acid (10.7 mg, 0.085 mmol), saturated (aq) NaHCO$_3$ (1.5 mL), PdCl$_2$(dppf) (2.073 mg, 2.83 µmol) and dioxane (1.5 mL). The reaction mixture was heated to 80° C. and stirred overnight. LC/MS indicated the reaction was complete. The reaction mixture was diluted with EtOAc and the organic layer was separated and introduced into a 4 mL vial. The solvent was boiled off. The residue was diluted with MeOH, filtered, and purified to give the title compound as a white solid (1.0 mg, 5%); ESI-MS m/z [M+H]$^+$ 396.5.

Example 99: 5-(1-(difluoromethyl)-1H-pyrazol-4-yl)-3-((4-isopropylphenyl)amino)-4H-benzo[e][1,2,4]thiadiazine 1,1-dioxide

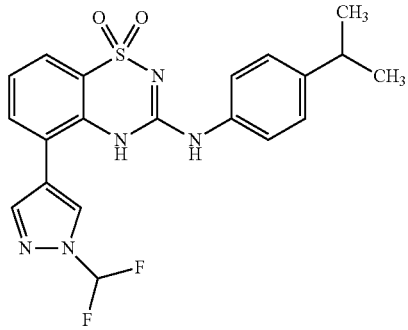 [SMILES: CC(C)c1ccc(NC2=NS(=O)(=O)c3cccc(-c4cnn(C(F)F)c4)c3N2)cc1]

The title compound was prepared in a manner similar to Example 98, using 5-iodo-3-((4-isopropylphenyl)amino)-4H-benzo[e][1,2,4]thiadiazine 1,1-dioxide (25 mg, 0.057 mmol), 1-(difluoromethyl)-4-(4,4,5,5-tetramethyl-1,3,2-dioxaborolan-2-yl)-1H-pyrazole (20.74 mg, 0.085 mmol), saturated (aq) NaHCO₃ (1.5 mL) and PdCl₂(dppf) (2.073 mg, 2.83 μmol) in dioxane (1.5 mL), and was isolated as a white solid (1.0 mg, 5%); ESI-MS m/z [M+H]⁺ 432.0.

Example 100: 3-((4-isopropylphenyl)amino)-5-(1H-pyrazol-1-yl)-4H-benzo[e][1,2,4]thiadiazine 1,1-dioxide

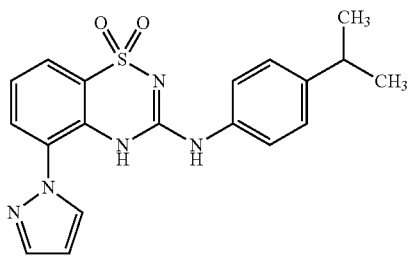 [SMILES: CC(C)c1ccc(NC2=NS(=O)(=O)c3cccc(-n4cccn4)c3N2)cc1]

An oven-dried 8 mL vial was charged with 5-iodo-3-((4-isopropylphenyl)amino)-4H-benzo[e][1,2,4]thiadiazine 1,1-dioxide (25 mg, 0.057 mmol), 1H-pyrazole (7.71 mg, 0.113 mmol), K₂CO₃ (15.66 mg, 0.113 mmol), copper(I) iodide (1.079 mg, 5.67 μmol) and DMF (2 mL). The reaction mixture was degassed with N2 and then heated to 125° C. and stirred for 18 hours. The reaction mixture was subsequently diluted with DMF (1 mL), filtered through a 0.45 μm PTFE syringe filter, and purified by preparative HPLC (Phenomenex Gemini® C18, 10 μm, ID 50×250 mm column) eluting with a gradient of 40-55% ACN in water (acid mode). The pure fractions were combined and lyophilized to give a TFA salt of the title compound as a white solid (6 mg, 28%). ¹H NMR (400 MHz, DMSO-d₆) δ ppm 1.22 (d, J=6.82 Hz, 6H), 2.91 (quin, J=6.88 Hz, 1H), 6.54 (s, 1H), 6.70 (s, 1H), 7.25-7.42 (m, 4H), 7.45 (t, J=8.08 Hz, 1H), 7.72-7.81 (m, 1H), 7.95 (d, J=8.08 Hz, 1H), 8.55 (d, J=2.53 Hz, 1H), 10.25 (s, 1H), 11.21 (br s, 1H); ESI-MS m/z [M+H]⁺ 382.1.

Example 101: 3-((4-isopropylphenyl)amino)-5-(1-(oxetan-3-yl)-1H-pyrazol-4-yl)-4H-benzo[e][1,2,4]thiadiazine 1,1-dioxide

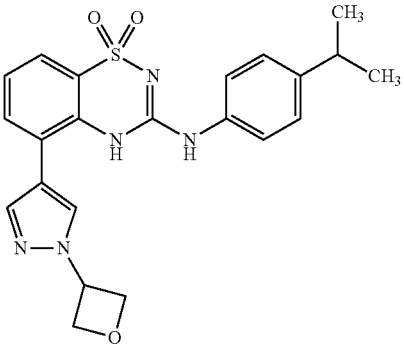 [SMILES: CC(C)c1ccc(NC2=NS(=O)(=O)c3cccc(-c4cnn(C5COC5)c4)c3N2)cc1]

To a stirring solution of 5-iodo-3-((4-isopropylphenyl)amino)-4H-benzo[e][1,2,4]thiadiazine 1,1-dioxide (40 mg, 0.091 mmol) and 1-(oxetan-3-yl)-4-(4,4,5,5-tetramethyl-1,3,2-dioxaborolan-2-yl)-1H-pyrazole (34.0 mg, 0.136 mmol) in water (1 mL) and dioxane (3 mL), were added PdCl₂(dppf)·CH₂Cl₂ adduct (7.40 mg, 9.06 μmol) and K₂CO₃ (27.6 mg, 0.199 mmol). The reaction mixture was heated at 100° C. for 18 hours, then washed with brine (2×) and extracted with EtOAc. The organic layers were combined, dried over MgSO₄, concentrated, filtered, and purified via reverse phase preparative LC/MS (Phenomenex Gemini® C18, 5 μm, ID 30×75 mm column) eluting with a gradient of 35-60% 10 mM NH₄HCO₃ (aq) in water/ACN (20/80 v/v containing 10 mM NH₄HCO₃) to give the title compound as a white solid (3.2 mg, 8%). ¹H NMR (400 MHz, CD₃OD) δ ppm 1.21-1.26 (m, 6H), 2.89 (spt, J=6.82 Hz, 1H), 5.06-5.16 (m, 4H), 5.62-5.70 (m, 1H), 7.21 (d, J=8.59 Hz, 2H), 7.35 (t, J=7.71 Hz, 1H), 7.40 (d, J=8.59 Hz, 2H), 7.52-7.55 (m, 1H), 7.78 (dd, J=7.96, 1.39 Hz, 1H), 7.86 (s, 1H), 8.08 (s, 1H); ESI-MS m/z [M+H]⁺ 438.3.

Example 102: 5-(1-ethyl-1H-pyrazol-4-yl)-3-((4-isopropylphenyl)amino)-4H-benzo[e][1,2,4]thiadiazine 1,1-dioxide

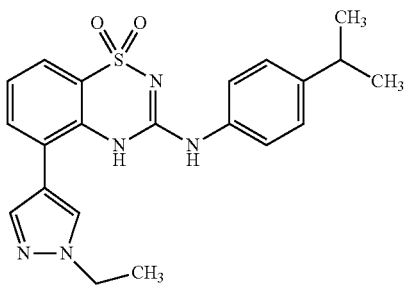 [SMILES: CCn1cc(-c2cccc3c2NC(Nc2ccc(C(C)C)cc2)=NS3(=O)=O)cn1]

A TFA salt of the title compound was prepared in a manner similar to Example 101, using 5-iodo-3-((4-isopropylphenyl)amino)-4H-benzo[e][1,2,4]thiadiazine 1,1-dioxide (40 mg, 0.091 mmol), 1-ethyl-4-(4,4,5,5-tetramethyl-1,3,2-dioxaborolan-2-yl)-1H-pyrazole (30.20 mg, 0.13 mmol), K₂CO₃ (27.6 mg, 0.199 mmol) and PdCl₂(dppf)·CH₂Cl₂ adduct (7.40 mg, 9.06 μmol) in water (1 mL) and dioxane (3 mL), and was isolated as a tan solid (14.7 mg, 31%). ¹H NMR (400 MHz, CD₃OD) δ ppm 1.24 (d, J=6.82 Hz, 6H), 1.54 (t, J=7.33 Hz, 3H), 2.89 (spt, J=6.86 Hz, 1H), 4.29 (q, J=7.33 Hz, 2H), 7.22 (d, J=8.34 Hz, 2H), 7.32-7.37 (m, 1H), 7.40 (d, J=8.34 Hz, 2H), 7.53 (dd, J=7.58, 1.52 Hz, 1H), 7.73 (s, 1H), 7.77 (dd, J=7.96, 1.39 Hz, 1H), 7.96 (s, 1H); ESI-MS m/z [M+H]⁺ 410.2.

Example 103: 5-(1,3-dimethyl-1H-pyrazol-4-yl)-3-((4-isopropylphenyl)amino)-4H-benzo[e][1,2,4]thiadiaazne 1,1-dioxide

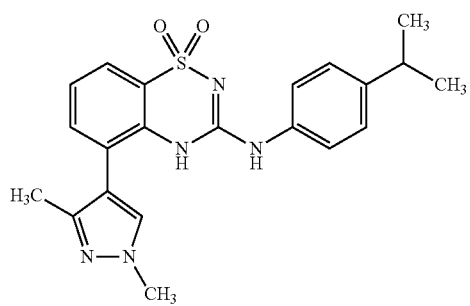 [SMILES: Cc1nn(C)cc1-c1cccc2c1NC(Nc1ccc(C(C)C)cc1)=NS2(=O)=O]

The title compound was prepared in a manner similar to Example 101, using 5-iodo-3-((4-isopropylphenyl)amino)-4H-benzo[e][1,2,4]thiadiazine 1,1-dioxide (45 mg, 0.102 mmol), 1,3-dimethyl-4-(4,4,5,5-tetramethyl-1,3,2-dioxaborolan-2-yl)-1H-pyrazole (27.2 mg, 0.122 mmol), K₂CO₃ (31 mg, 0.224 mmol) and PdCl₂(dppf)·CH₂Cl₂ adduct (8.33 mg, 10.20 μmol) in water (1 mL) and dioxane (3 mL), and was isolated as an off-white solid (7.0 mg, 17%). ¹H NMR (400 MHz, DMSO-d₆) δ ppm 1.14-1.22 (m, 6H), 2.09 (s, 3H), 2.86 (dt, J=13.58, 6.98 Hz, 1H), 3.28-3.36 (m, 3H), 7.18-7.34 (m, 3H), 7.41 (d, J=7.83 Hz, 3H), 7.68 (d, J=6.32 Hz, 1H), 7.90 (s, 1H), 9.08-9.44 (m, 1H), 9.47-9.83 (m, 1H); ESI-MS m/z [M+H]⁺ 410.2.

Example 104: 5-(1-(3,3-difluorocyclobutyl)-1H-pyrazol-4-yl)-3-((4-isopropylphenyl)amino)-4H-benzo[e][1,2,4]thiadiazine 1,1-dioxide

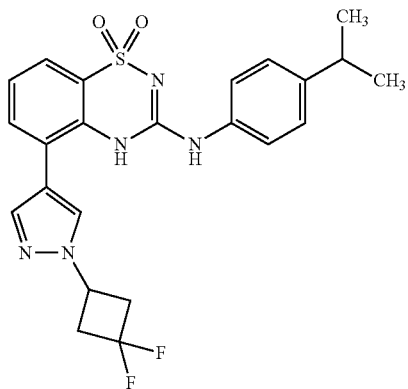 [SMILES: CC(C)c1ccc(NC2=NS(=O)(=O)c3cccc(-c4cnn(C5CC(F)(F)C5)c4)c3N2)cc1]

A TFA salt of the title compound was prepared in a manner similar to Example 101, using 5-iodo-3-((4-isopropylphenyl)amino)-4H-benzo[e][1,2,4]thiadiazine 1,1-dioxide (55 mg, 0.125 mmol), 1-(3,3-difluorocyclobutyl)-4-(4, 4,5,5-tetramethyl-1,3,2-dioxaborolan-2-yl)-1H-pyrazole (53.10 mg, 0.187 mmol), K₂CO₃ (37.9 mg, 0.274 mmol) and PdCl₂(dppf)·CH₂Cl₂ adduct (10.18 mg, 0.012 mmol) in water (1 mL) and dioxane (3 mL), and was isolated as an off-white solid (15.9 mg, 22%). ¹H NMR (400 MHz, DMSO-d₆) δ ppm 1.20 (d, J=7.07 Hz, 6H), 2.81-2.95 (m, 1H), 3.19-3.30 (m, 4H), 4.97-5.08 (m, 1H), 7.26 (d, J=8.34 Hz, 2H), 7.34 (t, J=7.71 Hz, 1H), 7.40 (d, J=8.59 Hz, 2H), 7.53 (dd, J=7.71, 1.39 Hz, 1H), 7.69 (dd, J=7.83, 1.01 Hz, 1H), 7.93 (s, 1H), 8.32 (s, 1H), 9.43 (s, 1H), 9.72 (s, 1H); ESI-MS m/z [M+H]⁺ 472.2.

Example 105: 5-(1-cyclobutyl-1H-pyrazol-4-yl)-3-((4-isopropylphenyl)amino)-4H-benzo[e][1,2,4]thiadiazine 1,1-dioxide

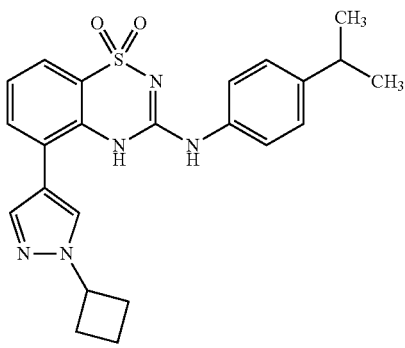 [SMILES: CC(C)c1ccc(NC2=NS(=O)(=O)c3cccc(-c4cnn(C5CCC5)c4)c3N2)cc1]

A TFA salt of the title compound was prepared in a manner similar to Example 101, using 5-iodo-3-((4-isopropylphenyl)amino)-4H-benzo[e][1,2,4]thiadiazine 1,1-dioxide (40 mg, 0.091 mmol), 1-cyclobutyl-4-(4,4,5,5-tetramethyl-1,3,2-dioxaborolan-2-yl)-1H-pyrazole (33.70 mg, 0.136 mmol), K₂CO₃ (27.6 mg, 0.199 mmol) and PdCl₂(dppf)·CH₂Cl₂ adduct (7.40 mg, 9.06 μmol) in water (1 mL) and dioxane (3 mL), and was isolated as a white solid (7.2 mg, 14%). ¹H NMR (400 MHz, CD₃OD) δ ppm 1.24 (d, J=6.82 Hz, 6H), 1.89-1.98 (m, 2H), 2.48-2.57 (m, 2H), 2.59-2.71 (m, 2H), 2.89 (dt, J=13.77, 7.01 Hz, 1H), 4.91-4.98 (m, 1H), 7.22 (d, J=8.34 Hz, 2H), 7.35 (t, J=7.71 Hz, 1H), 7.41 (d, J=8.59 Hz, 2H), 7.53 (dd, J=7.58, 1.52 Hz, 1H), 7.75-7.79 (m, 2H), 8.01 (s, 1H); ESI-MS m/z [M+H]⁺ 436.3.

Example 106: 3-((4-isopropylphenyl)amino)-5-(3-methyl-1H-pyrazol-4-yl)-4H-benzo[e][1,2,4]thiadiazine 1,1-dioxide

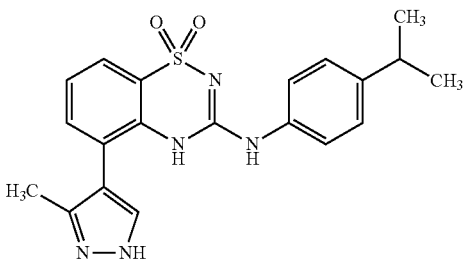 [SMILES: Cc1n[nH]cc1-c1cccc2c1NC(Nc1ccc(C(C)C)cc1)=NS2(=O)=O]

To a solution of 5-iodo-3-((4-isopropylphenyl)amino)-4H-benzo[e][1,2,4]thiadiazine 1,1-dioxide (25 mg, 0.057 mmol) and 3-methyl-4-(4,4,5,5-tetramethyl-1,3,2-dioxaborolan-2-yl)-1H-pyrazole (50 mg, 0.240 mmol) in dioxane (3 mL) were added PdCl$_2$(dppf) (5 mg, 6.83 μmol) and saturated (aq) NaHCO$_3$ (1 mL). The mixture was sparged with nitrogen for 30 seconds. The stirred reaction mixture was heated at 135° C. in a microwave reactor for 60 minutes and then allowed to cool to room temperature. The solution was decanted away from the salts and the product purified by preparative HPLC (Waters XSelect® C18, 5 μm, ID 30×75 mm column) eluting with a gradient of ACN (0.1% formic acid) in water (0.1% formic acid). The product-containing fractions were combined and dried to give the title compound as a white solid (7.2 mg, 32%). $^1$H NMR (400 MHz, CD$_3$OD) δ ppm 1.26-1.32 (m, 6H), 2.87-3.03 (m, 1H), 3.18 (s, 1H), 3.38-3.42 (m, 1H), 4.88 (s, 1H), 7.25-7.32 (m, 2H), 7.41-7.47 (m, 3H), 7.50-7.55 (m, 1H), 7.87 (dd, J=8.08, 1.52 Hz, 1H); ESI-MS m/z [M+H]$^+$ 396.2.

Example 107: 3-((4-isopropylphenyl)amino)-5-(1-methyl-1H-pyrazol-4-yl)-4H-benzo[e][1,2,4]thiadiazine 1,1-dioxide

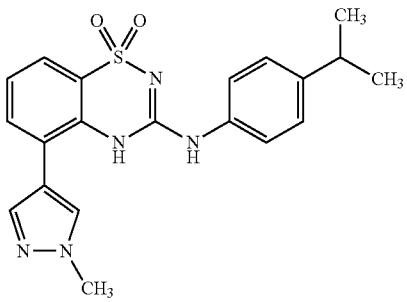 [SMILES: CC(C)c1ccc(NC2=NS(=O)(=O)c3cccc(-c4cnn(C)c4)c3N2)cc1]

The title compound was prepared in a manner similar to Example 106, using 5-iodo-3-((4-isopropylphenyl)amino)-4H-benzo[e][1,2,4]thiadiazine 1,1-dioxide (25 mg, 0.057 mmol), 1-methyl-4-(4,4,5,5-tetramethyl-1,3,2-dioxaborolan-2-yl)-1H-pyrazole (50 mg, 0.240 mmol), PdCl$_2$(dppf) (5 mg, 6.83 μmol) and saturated (aq) NaHCO$_3$ (1 mL) in dioxane (3 mL), and was isolated as a white solid (10 mg, 45%). $^1$H NMR (400 MHz, CD$_3$OD) δ ppm 1.22-1.26 (m, 6H), 2.89 (dt, J=13.83, 6.85 Hz, 1H), 4.00 (s, 3H), 7.22 (d, J=8.34 Hz, 2H), 7.32-7.44 (m, 3H), 7.53 (dd, J=7.58, 1.26 Hz, 1H), 7.70 (s, 1H), 7.77 (dd, J=7.83, 1.52 Hz, 1H), 7.92 (s, 1H); ESI-MS m/z [M+H]$^+$ 396.2.

Example 108: 3-((4-isopropylphenyl)amino)-5-(1-methyl-1H-pyrazol-3-yl)-4H-benzo[e][1,2,4]thiadiazine 1,1-dioxide

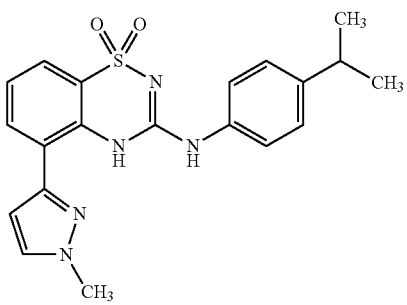 [SMILES: CC(C)c1ccc(NC2=NS(=O)(=O)c3cccc(-c4ccn(C)n4)c3N2)cc1]

The title compound was prepared in a manner similar to Example 106, using 5-iodo-3-((4-isopropylphenyl)amino)-4H-benzo[e][1,2,4]thiadiazine 1,1-dioxide (25 mg, 0.057 mmol), 1-methyl-3-(4,4,5,5-tetramethyl-1,3,2-dioxaborolan-2-yl)-1H-pyrazole (50 mg, 0.240 mmol), PdCl$_2$(dppf) (5 mg, 6.83 μmol) and saturated (aq) NaHCO$_3$ (1 mL) in dioxane (3 mL), and was isolated as a white solid (6.4 mg, 29%). $^1$H NMR (400 MHz, DMSO-d$_6$) δ ppm 1.21 (d, J=7.07 Hz, 6H), 2.89 (dt, J=13.77, 7.01 Hz, 1H), 3.72 (s, 3H), 6.58 (d, J=1.52 Hz, 1H), 7.27 (d, J=8.59 Hz, 2H), 7.37-7.46 (m, 3H), 7.61 (d, J=6.57 Hz, 1H), 7.69 (d, J=1.77 Hz, 1H), 7.88 (d, J=7.83 Hz, 1H), 9.28 (s, 1H), 9.71 (s, 1H); ESI-MS m/z [M+H]$^+$ 396.2.

Example 109: 5-cyclopropyl-3-((4-isopropylphenyl)amino)-4H-benzo[e][1,2,4]thiadiazine 1,1-dioxide

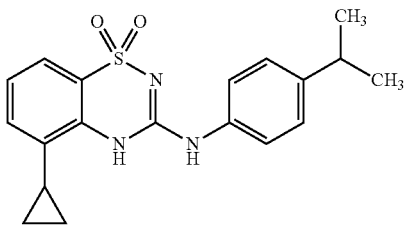

The title compound was prepared in a manner similar to Example 106, using 5-iodo-3-((4-isopropylphenyl)amino)-4H-benzo[e][1,2,4]thiadiazine 1,1-dioxide (25.0 mg, 0.057 mmol), cyclopropylboronic acid (16.35 mg, 0.190 mmol), PdCl$_2$(dppf) (10.92 mg, 0.013 μmol) and saturated (aq) NaHCO$_3$ (1.5 mL mL) in dioxane (1.5 mL), and was isolated as an off-white solid (11.19 mg, 19%). $^1$H NMR (400 MHz, CDCl$_3$) δ ppm 0.42-0.46 (m, 2H), 0.72-0.74 (m, 2H), 1.25 (d, J=6.9 Hz, 6H), 1.43~ 1.58 (m, 1H), 2.88-2.98 (m, 1H), 7.17~7.25 (m, 6H), 7.79 (d, J=7.6 Hz, 1H), 8.49 (s, 1H); ESI-MS m/z [M+H]$^+$ 356.0.

Example 110: 5-isopropyl-3-((4-isopropylphenyl)amino)-4H-benzo[e][1,2,4]thiadiazine 1,1-dioxide

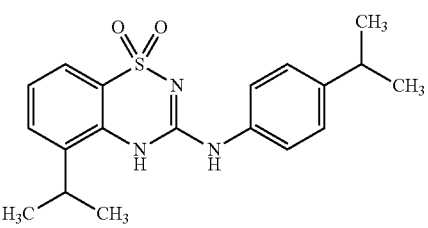 [SMILES: CC(C)c1ccc(NC2=NS(=O)(=O)c3cccc(C(C)C)c3N2)cc1]

Step A: 3-((4-isopropylphenyl)amino)-5-(prop-1-en-2-yl)-4H-benzo[e][1,2,4]thiadiazine 1,1-dioxide

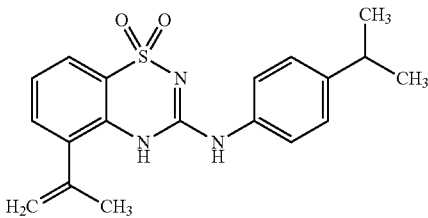 [SMILES: C=C(C)c1cccc2c1NC(Nc1ccc(C(C)C)cc1)=NS2(=O)=O]

The title compound was prepared in a manner similar to Example 106, using 5-iodo-3-((4-isopropylphenyl)amino)-4H-benzo[e][1,2,4]thiadiazine 1,1-dioxide (113.5 mg, 259 mmol), 2-isopropenyl-4,4,5,5-tetramethyl-1,3,2-dioxaborolane (74.25 mg, 441.88 µmol), PdCl$_2$(dppf) (49.58 mg, 0.059 µmol) and saturated (aq) NaHCO$_3$ (7.0 mL) in dioxane (7.0 mL), and was isolated as a (crude) brown solid (120 mg); ESI-MS m/z [M+H]$^+$ 356.1.

Step B: 5-isopropyl-3-((4-isopropylphenyl)amino)-4H-benzo[e][1,2,4]thiadiazine 1,1-dioxide To a solution of 5-isopropyl-3-((4-isopropylphenyl)amino)-4H-benzo[e][1,2,4]thiadiazine 1,1-dioxide (120.00 mg, 337.60 µmol) in MeOH (40 mL) was added Pd/C (50 mg, 5%). The reaction mixture was stirred under a hydrogen atmosphere (H2-filled balloon) at 15 psi and 25° C. for 20 hours. Additional Pd/C (100.00 mg, 5%) was added to the reaction mixture which was stirred under H2 at 15 psi and 25° C. for another 20 hours. Following the hydrogenation, the reaction mixture was filtered and the filtrate was concentrated in vacuo. The residue was purified by preparative HPLC (Phenomenex Synergi™ C18, 4 µm, ID 30×150 mm column) eluting with a gradient of 50-80% water (0.225% formic acid) in ACN. The product-containing fractions were combined and dried to give the title compound as a white solid (15.67 mg, 13%). $^1$H NMR (400 MHz, DMSO-d$_6$) δ ppm 1.22 (d, J=6.8 Hz, 6H), 1.28 (d, J=6.4 Hz, 6H), 2.85-2.90 (m, 1H), 3.23-3.29 (m, 1H), 7.25-7.27 (m, 3H), 7.49 (d, J=7.6 Hz, 2H), 7.57 (d, J=5.8 Hz, 2H), 9.43 (s, 1H), 9.83 (s, 1H); ESI-MS m/z [M+H]$^+$ 358.2.

Example 111: 5-cyclobutyl-3-((4-isopropylphenyl)amino)-4H-benzo[e][1,2,4]thiadiazine 1,1-dioxide

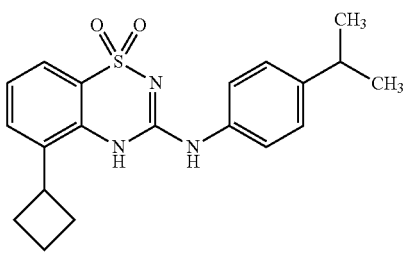 [SMILES: CC(C)c1ccc(NC2=NS(=O)(=O)c3cccc(C4CCC4)c3N2)cc1]

To a mixture of 5-iodo-3-((4-isopropylphenyl)amino)-4H-benzo[e][1,2,4]thiadiazine 1,1-dioxide (160 mg, 0.362 mmol), bromo(cyclobutyl)zinc (0.5 M, 725.14 µL), S-Phos (29.77 mg, 0.073 mmol) in THF (2.00 mL) was added Pd(OAc)$_2$ (16.28 mg, 0.073 mmol). The resulting mixture was heated to 65° C. for 16 hours. The reaction mixture was subsequently poured into saturated (aq) NH$_4$Cl (40 mL) and extracted with EtOAc (2×30 mL). The organic phase was dried over Na$_2$SO$_4$ and then concentrated in vacuo. The crude product was purified by preparative HPLC (Welch Ultimate AQ-C18, 5 µm, ID 30×150 mm column) eluting with a gradient of 50-80% water in ACN (acid mode). The title compound was isolated as a white solid (3.83 mg, 3%). $^1$H NMR (400 MHz, DMSO-d$_6$) δ ppm 1.21 (d, J=6.8 Hz, 6H), 1.85-1.88 (m, 1H), 2.03-2.17 (m, 3H), 2.41-2.55 (m, 2H), 2.85-2.90 (m, 1H), 3.77-3.79 (m, 1H), 7.24-7.27 (m, 3H), 7.47 (d, J=7.6 Hz, 2H), 7.56 (d, J=7.6 Hz, 2H), 9.39 (s, 1H), 9.56 (s, 1H); ESI-MS m/z [M+H]$^+$ 370.1.

Example 112: 5-(2-chlorophenyl)-3-((4-isopropylphenyl)amino)-4H-benzo[e][1,2,4]thiadiazine 1,1-dioxide

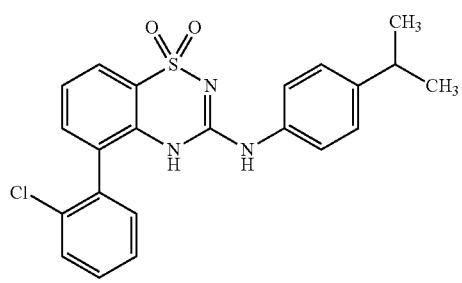 [SMILES: CC(C)c1ccc(NC2=NS(=O)(=O)c3cccc(-c4ccccc4Cl)c3N2)cc1]

The title compound was prepared in a manner similar to Example 101, using 5-iodo-3-((4-isopropylphenyl)amino)-4H-benzo[e][1,2,4]thiadiazine 1,1-dioxide (50 mg, 0.113 mmol), (2-chlorophenyl)boronic acid (21.26 mg, 0.136 mmol), K$_2$CO$_3$ (34.5 mg, 0.249 mmol) and PdCl$_2$(dppf)·CH$_2$Cl$_2$ adduct (9.25 mg, 0.011 mmol) in water (1 mL) and dioxane (3 mL), and was isolated as a white solid (28 mg, 59%). $^1$H NMR (400 MHz, DMSO-d$_6$) δ ppm 1.19 (d, J=6.82 Hz, 6H), 2.86 (dt, J=13.71, 6.92 Hz, 1H), 7.23 (br s, 2H), 7.33-7.46 (m, 4H), 7.49-7.64 (m, 3H), 7.72 (d, J=7.33 Hz, 1H), 7.81 (d, J=7.07 Hz, 1H), 9.12 (br s, 1H), 9.50 (br s, 1H); ESI-MS m/z [M+H]$^+$ 426.1.

Example 113: 3-((4-isopropylphenyl)amino)-5-(3-methylpyridin-4-yl)-4H-benzo[e][1,2,4]thiadiazine 1,1-dioxide

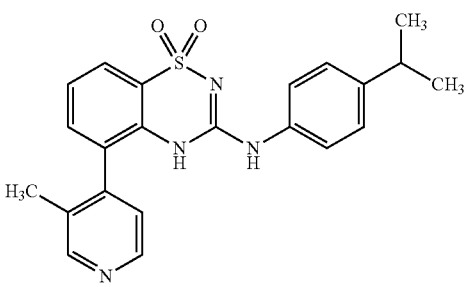 [SMILES: Cc1cnccc1-c1cccc2c1NC(Nc1ccc(C(C)C)cc1)=NS2(=O)=O]

The title compound was prepared in a manner similar to Example 101, using 5-iodo-3-((4-isopropylphenyl)amino)-4H-benzo[e][1,2,4]thiadiazine 1,1-dioxide (50 mg, 0.113 mmol), (3-methylpyridin-4-yl)boronic acid (23.27 mg, 0.170 mmol), K₂CO₃ (34.5 mg, 0.249 mmol) and PdCl₂(dppf)·CH₂Cl₂ adduct (9.25 mg, 0.011 mmol) in water (1 mL) and dioxane (3 mL), and was isolated as a tan solid (10.8 mg, 23%). ¹H NMR (400 MHz, CD₃OD) δ ppm 1.23 (d, J=7.07 Hz, 6H), 2.18 (s, 3H), 2.88 (spt, J=6.99 Hz, 1H), 7.20 (d, J=8.59 Hz, 2H), 7.33-7.41 (m, 3H), 7.44-7.49 (m, 2H), 7.89-7.94 (m, 1H), 8.49-8.71 (m, 2H); ESI-MS m/z [M+H]⁺ 407.2.

Example 114: 5-(1,5-dimethyl-1H-pyrazol-4-yl)-3-((4-isopropylphenyl)amino)-4H-benzo[e][1,2,4]thiadiazine 1,1-dioxide

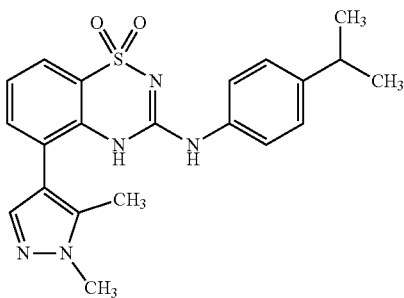 [SMILES: Cc1c(-c2cccc3c2NC(Nc2ccc(C(C)C)cc2)=NS3(=O)=O)cnn1C]

A TFA salt of the title compound was prepared in a manner similar to Example 101, using 5-iodo-3-((4-isopropylphenyl)amino)-4H-benzo[e][1,2,4]thiadiazine 1,1-dioxide (40 mg, 0.091 mmol), (1,5-dimethyl-1H-pyrazol-4-yl)boronic acid (19.03 mg, 0.136 mmol), K₂CO₃ (27.6 mg, 0.199 mmol) and PdCl₂(dppf)·CH₂Cl₂ adduct (7.40 mg, 9.06 μmol) in water (1 mL) and dioxane (3 mL), and was isolated as a tan solid (4.7 mg, 9%). ¹H NMR (400 MHz, CD₃OD) δ ppm 1.24 (d, J=7.07 Hz, 6H), 2.20 (s, 3H), 2.89 (spt, J=6.99 Hz, 1H), 3.90 (s, 3H), 7.22 (d, J=8.59 Hz, 2H), 7.34-7.42 (m, 3H), 7.42-7.47 (m, 1H), 7.57 (br s, 1H), 7.81 (dd, J=7.83, 1.52 Hz, 1H); ESI-MS m/z [M+H]⁺ 410.2.

Example 115: 5-(1,3-dimethyl-1H-pyrazol-4-yl)-3-((3-isopropylphenyl)amino)-4H-benzo[e][1,2,4]thiadiazine 1,1-dioxide

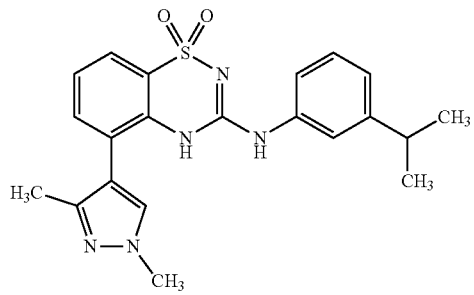 [SMILES: Cc1nn(C)cc1-c1cccc2c1NC(Nc1cccc(C(C)C)c1)=NS2(=O)=O]

To a stirring solution of 5-iodo-3-((3-isopropylphenyl)amino)-4H-benzo[e][1,2,4]thiadiazine 1,1-dioxide (59 mg, 0.134 mmol) and 1,3-dimethyl-4-(4,4,5,5-tetramethyl-1,3,2-dioxaborolan-2-yl)-1H-pyrazole (35.6 mg, 0.160 mmol) in water (1 mL) and dioxane (3 mL), were added PdCl₂(dppf)·CH₂Cl₂ adduct (10.92 mg, 0.013 mmol) and K₂CO₃ (40.7 mg, 0.294 mmol). The reaction mixture was heated at 100° C. for 6 hours. The mixture was neutralized with 1N (aq) HCl and extracted with EtOAc. The organic layers were combined, dried over anhydrous MgSO₄, and concentrated under vacuum. The product was purified by reverse phase LC/MS (Waters XSelect® C18, 5 μm, ID 30×75 mm column) eluting with a gradient of 30-55% (aq) formic acid in ACN (containing 1% formic acid) to give the title compound as an off-white solid (16 mg, 29%). ¹H NMR (400 MHz, CD₃OD) δ ppm 1.24 (d, J=6.82 Hz, 6H), 2.14 (s, 3H), 2.88 (dt, J=13.83, 6.85 Hz, 1H), 3.92 (s, 3H), 7.03 (d, J=7.33 Hz, 1H), 7.22-7.28 (m, 1H), 7.29-7.34 (m, 1H), 7.36 (s, 2H), 7.45 (d, J=7.33 Hz, 1H), 7.71 (s, 1H), 7.80 (d, J=7.83 Hz, 1H); ESI-MS m/z [M+H]⁺ 410.2.

Example 116: 5-cyclopropyl-3-((3-isopropylphenyl)amino)-4H-benzo[e][1,2,4]thiadiazine 1,1-dioxide

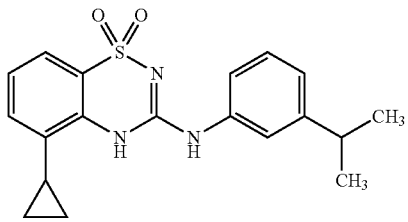 [SMILES: CC(C)c1cccc(NC2=NS(=O)(=O)c3cccc(C4CC4)c3N2)c1]

The title compound was prepared in a manner similar to Example 115, using 5-iodo-3-((3-isopropylphenyl)amino)-4H-benzo[e][1,2,4]thiadiazine 1,1-dioxide (59 mg, 0.134 mmol), cyclopropylboronic acid (13.78 mg, 0.160 mmol), K₂CO₃ (40.7 mg, 0.294 mmol) and PdCl₂(dppf)·CH₂Cl₂ adduct (10.92 mg, 0.013 mmol) in water (1 mL) and dioxane (3 mL), and was isolated as a tan solid (11.3 mg, 24%). ¹H NMR (400 MHz, CD₃OD) δ ppm 0.74 (br s, 2H), 1.09 (d, J=6.06 Hz, 2H), 1.27 (d, J=6.57 Hz, 6H), 1.89 (br s, 1H), 2.85-3.00 (m, 1H), 7.05 (d, J=7.07 Hz, 1H), 7.22-7.33 (m, 2H), 7.37-7.50 (m, 3H), 7.66 (d, J=7.58 Hz, 1H); ESI-MS m/z [M+H]⁺ 356.2.

Example 117: 5-(2-chlorophenyl)-3-((6-isopropylpyridin-3-yl)amino)-4H-benzo[e][1,2,4]thiadiazine 1,1-dioxide

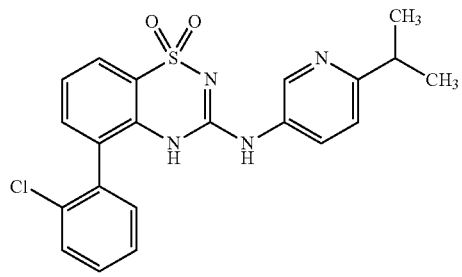 [SMILES: CC(C)c1ccc(NC2=NS(=O)(=O)c3cccc(-c4ccccc4Cl)c3N2)cn1]

To a stirring solution of 5-iodo-3-((6-isopropylpyridin-3-yl)amino)-4H-benzo[e][1,2,4]thiadiazine 1,1-dioxide (43 mg, 0.097 mmol) and (2-chlorophenyl)boronic acid (18.24 mg, 0.117 mmol) in water (1 mL) and dioxane (3 mL), were added PdCl₂(dppf)·CH₂Cl₂ adduct (7.94 mg, 9.72 μmol) and K₂CO₃ (29.6 mg, 0.214 mmol). The reaction mixture was heated at 100° C. for 3 hours. The reaction mixture was subsequently neutralized with 1 N HCl (aq) and extracted with EtOAc. The organic layers were combined, dried over anhydrous MgSO$_4$, and concentrated under vacuum. The product was purified by reverse phase chromatography (Waters XSelect® C18, 5 μm, ID 30×75 mm column) eluting with a gradient of 20-45% water (1% formic acid) in ACN (1% formic acid). The titled compound was isolated as a white solid (8 mg, 19%). $^1$H NMR (400 MHz, DMSO-d$_6$) δ ppm 1.20 (d, J=6.82 Hz, 6H), 2.96 (br s, 1H), 7.40 (br s, 3H), 7.45-7.62 (m, 3H), 7.69 (d, J=6.57 Hz, 1H), 7.78 (br s, 1H), 7.90 (dd, J=8.59, 2.27 Hz, 1H), 8.41 (br s, 1H); ESI-MS m/z [M+H]$^+$ 427.1.

Example 118: 5-cyclopropyl-3-((6-isopropylpyridin-3-yl)amino)-4H-benzo[e][1,2,4]thiadiazine 1,1-dioxide

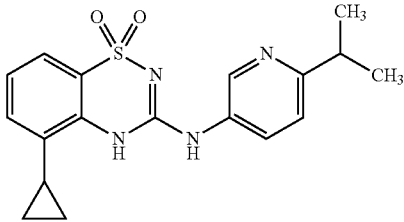 [SMILES: CC(C)c1ccc(NC2=NS(=O)(=O)c3cccc(C4CC4)c3N2)cn1]

The title compound was prepared in a manner similar to Example 117, using 5-iodo-3-((6-isopropylpyridin-3-yl)amino)-4H-benzo[e][1,2,4]thiadiazine 1,1-dioxide (63 mg, 0.142 mmol), cyclopropylboronic acid (18.35 mg, 0.21 mmol), PdCl$_2$(dppf)·CH$_2$Cl$_2$ adduct (11.63 mg, 0.014 mmol) and K$_2$CO$_3$ (43.3 mg, 0.313 mmol) in water (1 mL) and dioxane (3 mL), and was isolated as a light yellow solid (6.0 mg, 12%). $^1$H NMR (400 MHz, CD$_3$OD) δ ppm 0.73-0.79 (m, 2H), 1.10-1.16 (m, 2H), 1.30 (d, J=7.07 Hz, 6H), 1.88-1.97 (m, 1H), 3.00-3.12 (m, 1H), 7.23-7.29 (m, 1H), 7.35 (d, J=8.59 Hz, 1H), 7.43 (dt, J=7.64, 1.11 Hz, 1H), 7.66 (dd, J=7.83, 0.76 Hz, 1H), 8.10 (dd, J=8.59, 2.53 Hz, 1H), 8.56 (d, J=2.27 Hz, 1H); ESI-MS m/z [M+H]$^+$ 357.2.

Example 119: 5-cyclopropyl-3-(((3-fluoropyridin-2-yl)methyl)amino)-4H-benzo[e][1,2,4]thiadiazine 1,1-dioxide

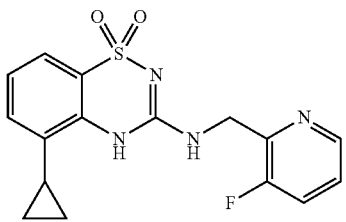 [SMILES: O=S1(=O)N=C(NCc2ncccc2F)Nc2c(C3CC3)cccc21]

To a stirring solution of 3-(((3-fluoropyridin-2-yl)methyl)amino)-5-iodo-4H-benzo[e][1,2,4]thiadiazine 1,1-dioxide (53 mg, 0.123 mmol) and cyclopropylboronic acid (13.69 mg, 0.159 mmol) in water (1 mL) and dioxane (3 mL), were added PdCl$_2$(dppf)·CH$_2$Cl$_2$ adduct (10.01 mg, 0.012 mmol) and K$_2$CO$_3$ (37.3 mg, 0.270 mmol). The reaction mixture was heated at 100° C. for 29 hours, then neutralized with 1N HCl (aq) and extracted with EtOAc. The organic layers were combined, dried over anhydrous MgSO$_4$, and concentrated under vacuum. The product was purified by reverse phase column chromatography (Phenomenex Gemini® C18, 5 μm, ID 30×75 mm column) eluting with a gradient of 25-50% water in ACN (basic mode). The title compound was isolated as a light yellow solid (4.5 mg, 11%). $^1$H NMR (400 MHz, CD$_3$OD) δ ppm 0.71-0.77 (m, 2H), 1.06-1.15 (m, 2H), 1.85-1.96 (m, 1H), 4.78 (d, J=1.52 Hz, 2H), 7.19-7.24 (m, 1H), 7.37-7.44 (m, 2H), 7.59-7.66 (m, 2H), 8.41 (d, J=4.55 Hz, 1H); ESI-MS m/z [M+H]$^+$ 347.1.

Example 120: 5-cyclopropyl-3-(((6-methoxypyridin-2-yl)methyl)amino)-4H-benzo[e][1,2,4]thiadiazine 1,1-dioxide

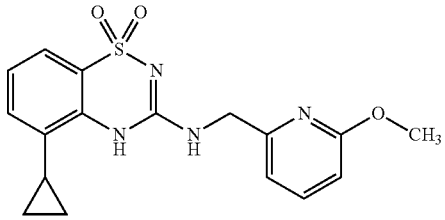 [SMILES: COc1cccc(CNC2=NS(=O)(=O)c3cccc(C4CC4)c3N2)n1]

The title compound was prepared in a manner similar to Example 119, using 5-iodo-3-(((6-methoxypyridin-2-yl)methyl)amino)-4H-benzo[e][1,2,4]thiadiazine 1,1-dioxide (25 mg, 0.056 mmol), cyclopropylboronic acid (5.80 mg, 0.068 mmol), PdCl$_2$(dppf)·CH$_2$Cl$_2$ adduct (4.60 mg, 5.63 μmol) and K$_2$CO$_3$ (17.11 mg, 0.124 mmol) in water (1 mL) and dioxane (3 mL), and was isolated as a tan semi-solid (2.6 mg, 13%). $^1$H NMR (400 MHz, CD$_3$OD) δ ppm 0.69-0.75 (m, 2H), 1.05-1.14 (m, 2H), 1.83-1.92 (m, 1H), 3.93 (s, 3H), 4.60 (s, 2H), 6.69 (d, J=8.08 Hz, 1H), 6.99 (d, J=7.33 Hz, 1H), 7.19-7.25 (m, 1H), 7.39 (dt, J=7.58, 1.14 Hz, 1H), 7.61-7.68 (m, 2H); ESI-MS m/z [M+H]$^+$ 359.1.

Example 121: 5-cyclopropyl-3-(phenylamino)-4H-benzo[e][1,2,4]thiadiazine 1,1-dioxide

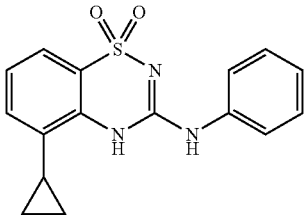 [SMILES: O=S1(=O)N=C(Nc2ccccc2)Nc2c(C3CC3)cccc21]

The title compound was prepared in a manner similar to Example 119, using 5-iodo-3-(phenylamino)-4H-benzo[e][1,2,4]thiadiazine 1,1-dioxide (35 mg, 0.088 mmol), cyclopropylboronic acid (11.30 mg, 0.132 mmol), PdCl$_2$(dppf)·CH$_2$Cl$_2$ adduct (7.16 mg, 8.77 μmol) and K$_2$CO$_3$ (26.7 mg, 0.193 mmol) in water (1 mL) and dioxane (3 mL), and was isolated as a light yellow solid (5.7 mg, 21%). $^1$H NMR (400 MHz, CD$_3$OD) δ ppm 0.73-0.78 (m, 2H), 1.08-1.14 (m, 2H), 1.87-1.95 (m, 1H), 7.14-7.20 (m, 1H), 7.26 (t, J=7.71 Hz, 1H), 7.35-7.41 (m, 2H), 7.44 (d, J=7.58 Hz, 1H), 7.59 (dd, J=8.59, 1.01 Hz, 2H), 7.67 (dd, J=7.96, 0.88 Hz, 1H); ESI-MS m/z [M+H]$^+$ 314.1.

Example 122: 5-(2-chloro-3-fluorophenyl)-3-(((3-methoxypyridin-2-yl)methyl)amino)-4H-benzo[e][1,2,4]thiadiazine 1,1-dioxide

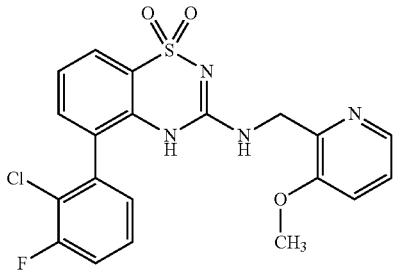 [SMILES: COc1cccnc1CNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (50.0 mg, 0.014 mmol), Et₃N (56 μL, 0.760 mmol), and (3-methoxypyridin-2-yl)methanamine hydrochloride (50.60 mg, 0.29 mmol) in EtOH (2.0 mL), and was isolated as an off-white solid (29.8 mg, 46%). $^1$H NMR (400 MHz, DMSO-$d_6$) δ ppm 3.86-3.95 (m, 4H), 4.54 (dd, J=7.58, 4.80 Hz, 2H), 7.30-7.45 (m, 4H), 7.51 (dd, J=8.34, 1.01 Hz, 1H), 7.54-7.67 (m, 2H), 7.80 (dd, J=7.83, 1.52 Hz, 1H), 8.03 (t, J=4.42 Hz, 1H), 8.13 (d, J=4.29 Hz, 1H), 9.54 (s, 1H); ESI-MS m/z [M+H]⁺ 447.1.

Example 123: 5-(2-chloro-3-fluorophenyl)-3-(((tetrahydrofuran-2-yl)methyl)amino)-4H-benzo[e][1,2,4]thiadiazine 1,1-dioxide

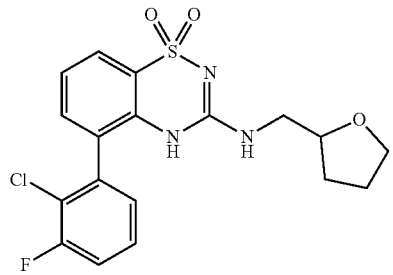 [SMILES: O=S1(=O)N=C(NCC2CCCO2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), DIPEA (16.7 μL, 0.096 mmol), and (tetrahydrofuran-2-yl)methanamine (8.79 mg, 0.087 mmol) in DMA (435 μL), and was isolated as a pale beige solid (8.3 mg, 23%). $^1$H NMR (400 MHz, DMSO-$d_6$) δ ppm 1.44-1.56 (m, 1H), 1.77-1.86 (m, 2H), 1.89-2.00 (m, 1H), 3.06-3.19 (m, 1H), 3.36-3.49 (m, 1H), 3.89 (td, J=7.20, 3.54 Hz, 1H), 7.30-7.39 (m, 2H), 7.39-7.45 (m, 1H), 7.51 (q, J=5.98 Hz, 1H), 7.54-7.65 (m, 2H), 7.78 (dd, J=7.83, 1.26 Hz, 1H), 9.05 (s, 1H); ESI-MS m/z [M+H]⁺ 410.0.

Example 124: 3-((2-methoxyethyl)amino)-5-(2-(trifluoromethyl)phenyl)-4H-benzo[e][1,2,4]thiadiazine 1,1-dioxide

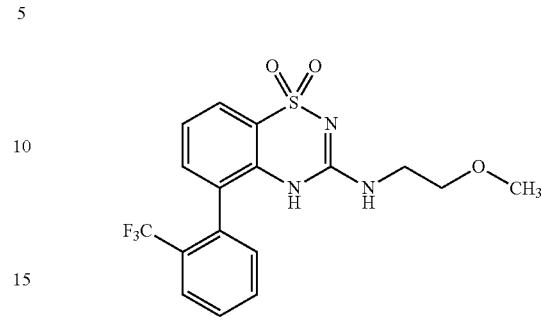

The title compound was prepared in a manner similar to Example 35, using 5-iodo-3-((2-methoxyethyl)amino)-4H-benzo[e][1,2,4]thiadiazine 1,1-dioxide (100 mg, 0.262 mmol), (2-(trifluoromethyl)phenyl)boronic acid (52.3 mg, 0.275 mmol), calcium carbonate (2M 525 μL, 1.049 mmol), and Pd(dppf)₂·CH₂Cl₂ adduct (21.42 mg, 0.026 mmol) in dioxane (1312 μL), and was isolated as a light brown solid (34.3 mg, 33%). $^1$H NMR (400 MHz, DMSO-$d_6$) δ ppm 3.26 (s, 3H), 3.39-3.48 (m, 3H), 7.30-7.41 (m, 3H), 7.43-7.55 (m, 2H), 7.74-7.89 (m, 3H), 7.98 (d, J=7.33 Hz, 1H), 8.96 (s, 1H); ESI-MS m/z [M+H]⁺ 400.1.

Example 125: 2-fluoro-6-(3-((2-methoxyethyl)amino)-1,1-dioxido-4H-benzo[e][1,2,4]thiadiazin-5-yl)benzonitrile

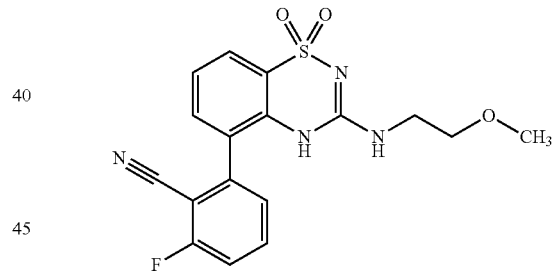

A 20 mL microwave vial equipped for stirring was charged with 5-iodo-3-((2-methoxyethyl)amino)-4H-benzo[e][1,2,4]thiadiazine 1,1-dioxide (0.03 g, 0.079 mmol), 2-fluoro-6-(4,4,5,5-tetramethyl-1,3,2-dioxaborolan-2-yl)benzonitrile (0.025 g, 0.102 mmol), Cs₂CO₃ (0.157 ml, 0.315 mmol) and dioxane (0.394 mL). Next, Pd(dppf)₂·CH₂Cl₂ adduct (6.43 mg, 7.87 μmol) was added under nitrogen, and the reaction mixture was heated to 90° C. for 12 hours. The mixture was subsequently cooled, diluted with MeOH (1 mL) and filtered over Celite®. The residue was purified by preparative LC/MS on (Waters SunFire® C18, 5 μm, ID 30×75 mm column) eluting with a gradient of 25-90% ACN in water (acid mode). The fractions were collected, concentrated, and dried in vacuo to give the title compound as a tan solid (5 mg, 17%). $^1$H NMR (400 MHz, DMSO-$d_6$) δ ppm 3.26 (s, 3H), 3.43 (d, J=4.29 Hz, 4H), 7.40 (s, 4H), 7.50-7.57 (m, 2H), 7.69-7.80 (m, 1H), 7.82-7.88 (m, 1H), 7.92-8.01 (m, 1H), 9.23-9.33 (m, 1H); ESI-MS m/z [M+H]⁺ 375.0.

Example 126: 2-(1,1-dioxido-3-((thiazol-2-ylmethyl)amino)-4H-benzo[e][1,2,4]thiadiazin-5-yl)-6-fluorobenzonitrile

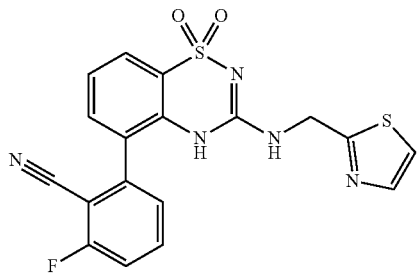 [SMILES: N#Cc1c(F)cccc1-c1cccc2c1NC(NCc1nccs1)=NS2(=O)=O]

To a 2-5 mL microwave vial were added 5-iodo-3-((thiazol-2-ylmethyl)amino)-4H-benzo[e][1,2,4]thiadiazine 1,1-dioxide (150 mg, 0.357 mmol), 2-fluoro-6-(4,4,5,5-tetramethyl-1,3,2-dioxaborolan-2-yl)benzonitrile (211.65 mg, 0.856 mmol), $Cs_2CO_3$ (0.759 mL, 1.518 mmol), $Pd(dppf)_2 \cdot CH_2Cl_2$ adduct (31.0 mg, 0.038 mmol) in dioxane (1.898 mL). The reaction mixture was heated in a microwave reactor at 120° C. for 30 minutes, then poured into water, and extracted with EtOAc (3×). The organic layers were combined, dried over $MgSO_4$, filtered, and concentrated to give a light brown oil. The oil was dissolved in MeOH (2 mL), filtered and purified by supercritical fluid chromatography (SFC) to give, after removal of the solvent, a formic acid salt of the title compound as a white solid (10.37 mg, 4%). $^1$H NMR (400 MHz, DMSO-$d_6$) δ ppm 4.58 (s, 2H), 7.02 (t, J=7.6 Hz, 1H), 7.24-7.49 (m, 4H), 7.56-7.76 (m, 3H), 8.28 (s, 1H); ESI-MS m/z [M+H]$^+$ 414.0.

Example 127: 3-((2-methoxypropyl)amino)-5-(2,3,5-trifluorophenyl)-4H-benzo[e][1,2,4]thiadiazine 1,1-dioxide

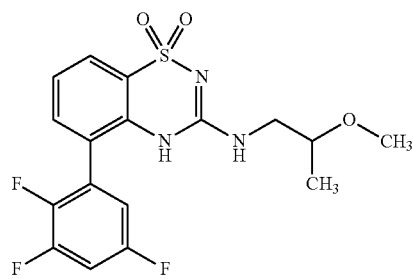 [SMILES: COC(C)CNC1=NS(=O)(=O)c2cccc(-c3cc(F)cc(F)c3F)c2N1]

To a 2-5 mL microwave vial were added (crude) 5-iodo-3-((2-methoxypropyl)amino)-4H-benzo[e][1,2,4]thiadiazine 1,1-dioxide (150 mg, 0.380 mmol), (2,3,5-trifluorophenyl)boronic acid (70.1 mg, 0.399 mmol), and dioxane (1.898 mL), followed by $Cs_2CO_3$ (759 µL, 1.518 mmol) and $Pd(dppf)_2 \cdot CH_2Cl_2$ adduct (31.0 mg, 0.038 mmol). The mixture was purged with nitrogen and then heated in microwave reactor at 120° C. for 45 minutes. The reaction mixture was poured into water and then extracted with EtOAc (3×). The organic layers were combined, washed with brine, dried over $MgSO_4$, filtered, and concentrated to give a brown oil. The oil was dissolved in MeOH (2 mL), filtered and purified by supercritical fluid chromatography (SFC) to give, after removal of the solvent, the title compound as a clear oil (8.5 mg, 6%). $^1$H NMR (400 MHz, CD$_3$OD) δ ppm 1.07-1.21 (m, 3H), 3.11-3.24 (m, 1H), 3.31 (dt, J=3.28, 1.64 Hz, 3H), 3.46-3.62 (m, 2H), 7.09 (br s, 1H), 7.32-7.44 (m, 2H), 7.51 (d, J=7.33 Hz, 1H), 7.89 (dd, J=7.96, 1.39 Hz, 1H); ESI-MS m/z [M+H]$^+$ 400.0.

Example 128: (S)-3-((2-methoxypropyl)amino)-5-(2,3,5-trifluorophenyl)-4H-benzo[e][1,2,4]thiadiazne 1,1-dioxide

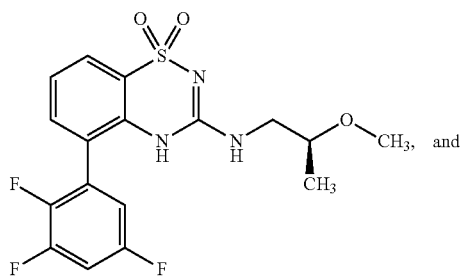 [SMILES: CO[C@@H](C)CNC1=NS(=O)(=O)c2cccc(-c3cc(F)cc(F)c3F)c2N1 ; "and"]

and

Example 129: (R)-3-((2-methoxypropyl)amino)-5-(2,3,5-trifluorophenyl)-4H-benzo[e][1,2,4]thiadiazine 1,1-dioxide

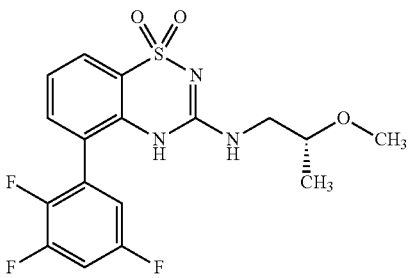 [SMILES: CO[C@H](C)CNC1=NS(=O)(=O)c2cccc(-c3cc(F)cc(F)c3F)c2N1]

To a 10-20 mL microwave vial were added 5-iodo-3-((2-methoxypropyl)amino)-4H-benzo[e][1,2,4]thiadiazine 1,1-dioxide (400 mg, 1.012 mmol), (2,3,5-trifluorophenyl)boronic acid (214 mg, 1.215 mmol), and dioxane (5.061 mL), followed by $Cs_2CO_3$ (2.024 mL, 4.05 mmol) and $Pd(dppf)_2 \cdot CH_2Cl_2$ adduct (83 mg, 0.101 mmol). The mixture was purged with nitrogen and then heated at 120° C. for 80 minutes. The reaction mixture was poured into water and extracted with EtOAc (3×). The organic layers were combined, washed with brine, dried over $MgSO_4$, filtered, and concentrated. The resulting brown oil was filtered oil through a pad of Celite® and purified by supercritical fluid chromatography (SFC) to give, following removal of solvent, the racemate of the title compounds as a clear oil. The racemate was resolved by chiral chromatography using SFC/UV 04 system (Chiral Technology AS-H column, 5 µm, ID 2.1×150 mm, flow rate at 1.25 mL/min) eluting with 30% EtOH.

Example 128, which was the first eluting peak and was arbitrarily assigned S-stereochemical configuration, was isolated as a clear oil (15.7 mg, 3.9%). $^1$H NMR (400 MHz, CD$_3$OD) δ ppm 1.14 (s, 3H), 3.13-3.23 (m, 1H), 3.32-3.36 (m, 2H), 3.46-3.56 (m, 2H), 7.10 (br s, 1H), 7.31-7.46 (m, 2H), 7.51 (d, J=7.33 Hz, 1H), 7.90 (dd, J=7.83, 1.52 Hz, 1H); ESI-MS m/z [M+H]$^+$ 400.1.

Example 129, which was the second eluting peak and was arbitrarily assigned R-stereochemical configuration, was isolated as a clear oil (17.3 mg, 4.3%). $^1$H NMR (400 MHz, CD$_3$OD) δ ppm 1.14 (s, 3H), 3.08-3.24 (m, 1H), 3.32-3.35 (m, 3H), 3.45-3.57 (m, 2H), 7.10 (br s, 1H), 7.32-7.45 (m, 2H), 7.51 (d, J=7.07 Hz, 1H), 7.90 (dd, J=7.83, 1.52 Hz, 1H); ESI-MS m/z [M+H]$^+$ 400.1.

Example 130: 3-((cyclobutylmethyl)amino)-5-(2,3,5-trifluorophenyl)-4H-benzo[e][1,2,4]thiadiazine 1,1-dioxide

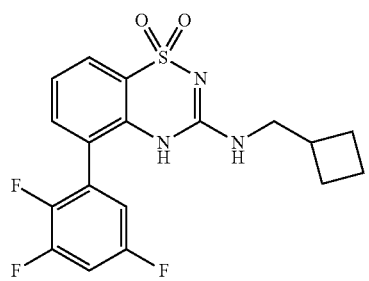 [SMILES: O=S1(=O)N=C(NCC2CCC2)Nc2c(-c3cc(F)cc(F)c3F)cccc21]

The title compound was prepared in a manner similar to Example 127, using 3-((cyclobutylmethyl)amino)-5-iodo-4H-benzo[e][1,2,4]thiadiazine 1,1-dioxide (150 mg, 0.383 mmol), (2,3,5-trifluorophenyl)boronic acid (70.8 mg, 0.403 mmol), Pd(dppf)$_2$·CH$_2$Cl$_2$ adduct (31.3 mg, 0.038 mmol) and Cs$_2$CO$_3$ (767 μL, 1.534 mmol) in dioxane (1.917 mL), and was isolated as a tan solid (5.1 mg, 3%). $^1$H NMR (400 MHz, DMSO-d$_6$) δ ppm 1.61-1.74 (m, 2H), 1.78-1.89 (m, 2H), 1.93-2.06 (m, 2H), 3.22-3.30 (m, 2H), 7.27-7.40 (m, 3H), 7.52 (dd, J=7.58, 1.52 Hz, 1H), 7.71-7.86 (m, 2H), 9.21 (s, 1H); ESI-MS m/z [M+H]$^+$ 396.1.

Example 131: 3-((pyridin-2-ylmethyl)amino)-5-(2,3,5-trifluorophenyl)-4H-benzo[e][1,2,4]thiadiazine 1,1-dioxide

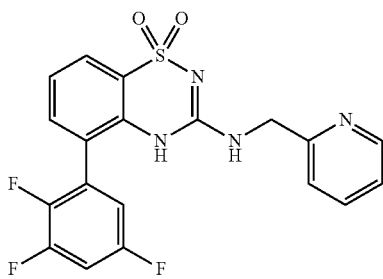

The title compound was prepared in a manner similar to Example 127, using 5-iodo-3-((pyridin-2-ylmethyl)amino)-4H-benzo[e][1,2,4]thiadiazine 1,1-dioxide (120 mg, 0.290 mmol), (2,3,5-trifluorophenyl)boronic acid (53.5 mg, 0.304 mmol), Pd(dppf)$_2$·CH$_2$Cl$_2$ adduct (23.66 mg, 0.029 mmol) and Cs$_2$CO$_3$ (579 μL, 1.159 mmol) in dioxane (1.449 mL), and was isolated as a white solid (3.4 mg, 3%). $^1$H NMR (400 MHz, DMSO-d$_6$) δ ppm 4.60 (br s, 2H), 7.34-7.44 (m, 3H), 7.46 (d, J=7.58 Hz, 1H), 7.57 (d, J=6.57 Hz, 1H), 7.73-7.93 (m, 3H), 7.99 (br s, 1H), 8.59 (d, J=4.55 Hz, 1H), 9.54-9.66 (m, 1H); ESI-MS m/z [M+H]$^+$ 419.0.

Example 132: 5-(2-chloro-3-(trifluoromethyl)phenyl)-3-((2-methoxyethyl)amino)-4H-benzo[e][1,2,4]thiadiazine 1,1-dioxide

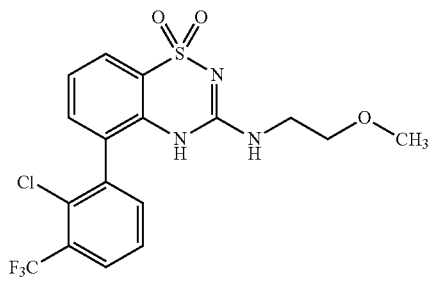 [SMILES: COCCNC1=NS(=O)(=O)c2cccc(-c3cccc(C(F)(F)F)c3Cl)c2N1]

The title compound was prepared in a manner similar to Example 35, using 5-iodo-3-((2-methoxyethyl)amino)-4H-benzo[e][1,2,4]thiadiazine 1,1-dioxide (100 mg, 0.262 mmol), (2-chloro-3-(trifluoromethyl)phenyl)boronic acid (61.8 mg, 0.275 mmol), Cs$_2$CO$_3$ (2M, 525 μL, 1.049 mmol), and Pd(dppf)$_2$·CH$_2$Cl$_2$ adduct (21.42 mg, 0.026 mmol) in dioxane (1312 μL), and was isolated as a white solid (1.0 mg, 1%). $^1$H NMR (400 MHz, CD$_3$OD) δ ppm 3.49-3.58 (m, 4H), 7.46 (br s, 2H), 7.72 (d, J=4.80 Hz, 2H), 7.92-7.97 (m, 1H), 8.02 (t, J=4.67 Hz, 1H); ESI-MS m/z [M+H]$^+$ 434.0.

Example 133: 5-(2-chloro-4-fluorophenyl)-3-((2-methoxyethyl)amino)-4H-benzo[e][1,2,4]thiadiazine 1,1-dioxide

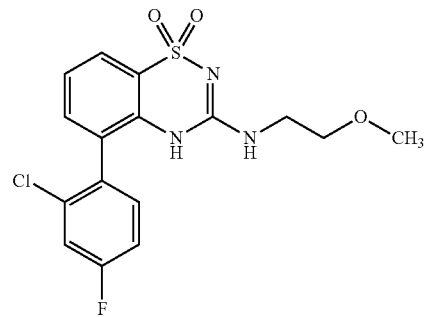 [SMILES: COCCNC1=NS(=O)(=O)c2cccc(-c3ccc(F)cc3Cl)c2N1]

Step A: 3-chloro-5-(2-chloro-4-fluorophenyl)-4H-benzo[e][1,2,4]thiadiazine 1,1-dioxide

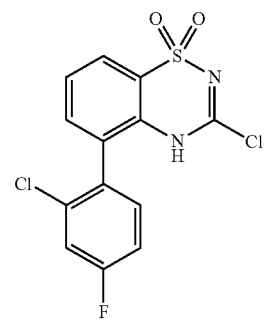 [SMILES: O=S1(=O)N=C(Cl)Nc2c(-c3ccc(F)cc3Cl)cccc21]

To a 2-5 mL microwave vial were added 3-chloro-5-iodo-4H-benzo[e][1,2,4]thiadiazine 1,1-dioxide (120 mg, 0.350 mmol), (2-chloro-4-fluorophenyl)boronic acid (64.1 mg, 0.368 mmol), Pd(dppf)$_2$·CH$_2$Cl$_2$ adduct (28.6 mg, 0.035 mmol), Cs$_2$CO$_3$ (0.701 mL, 1.401 mmol), and dioxane (1.7 mL). The mixture was purged with nitrogen, heated in a microwave reactor at 120° C. for 30 minutes, and then cooled. The reaction mixture was poured into water (10 mL) and acidified with 1N HCl (aq) (5 mL), forming a precipitate which was difficult to filter. The filtrate was extracted with EtOAc (2×20 mL) and the organic layers were combined, dried over MgSO$_4$, and filtered. The solvent was removed to give the title compound as reddish-brown oil, which was used without further purification. ESI-MS m/z [M+H]$^+$ 344.9.

Step B: 5-(2-chloro-4-fluorophenyl)-3-((2-methoxyethyl)amino)-4H-benzo[e][1,2,4]thiadiazine 1,1-dioxide To (crude) 3-chloro-5-(2-chloro-4-fluorophenyl)-4H-benzo[e][1,2,4]thiadiazine 1,1-dioxide (20 mg, 0.058 mmol) were added DMA (290 µL), followed by DIPEA (11.13 µL, 0.064 mmol) and 2-methoxyethanamine (5.49 µL, 0.064 mmol). The reaction mixture was heated at 70° C. overnight, then filtered and purified by preparative LC/MS (Waters SunFire® C18, 5 µm, ID 30×75 mm column) eluting with a gradient 30-50% ACN in water (acid mode). The product-containing fractions were collected and the solvent removed to give the title compound as a white solid (13 mg, 59%). $^1$H NMR (400 MHz, DMSO-d$_6$) δ ppm 3.26 (s, 3H), 3.35-3.40 (m, 2H), 3.42 (d, J=5.31 Hz, 2H), 7.31-7.46 (m, 3H), 7.48 (br s, 1H), 7.54 (dd, J=8.46, 6.19 Hz, 1H), 7.70-7.79 (m, 2H), 9.03 (s, 1H); ESI-MS m/z [M+H]$^+$ 384.0.

Example 134: 5-(2-chloro-5-(trifluoromethyl)phenyl)-3-((2-methoxyethyl)amino)-4H-benzo[e][1,2,4]thiadiazine 1,1-dioxide

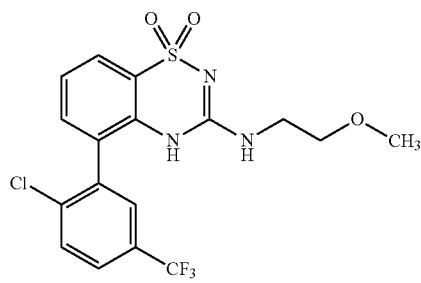 [SMILES: COCCNC1=NS(=O)(=O)c2cccc(-c3cc(C(F)(F)F)ccc3Cl)c2N1]

The title compound was prepared in a manner similar to Example 35, using 5-iodo-3-((2-methoxyethyl)amino)-4H-benzo[e][1,2,4]thiadiazine 1,1-dioxide (100 mg, 0.262 mmol), (2-chloro-5-(trifluoromethyl)phenyl)boronic acid (61.8 mg, 0.275 mmol), Cs$_2$CO$_3$ (2M, 525 µL, 1.049 mmol), and Pd(dppf)$_2$·CH$_2$Cl$_2$ adduct (21.42 mg, 0.026 mmol) in dioxane (1312 µL), and was isolated as a brown solid (5.5 mg, 5%). $^1$H NMR (400 MHz, DMSO-d$_6$) δ ppm 3.26 (br s, 3H), 3.43 (br s, 2H), 7.19-7.56 (m, 3H), 7.66-8.13 (m, 5H), 9.15 (br s, 1H); ESI-MS m/z [M+H]$^+$ 434.0.

Example 135: 5-(3-chloro-2-fluorophenyl)-3-((2-methoxyethyl)amino)-4H-benzo[e][1,2,4]thiadiazine 1,1-dioxide

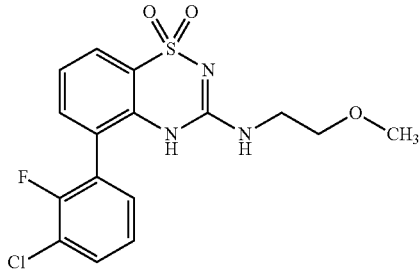 [SMILES: COCCNC1=NS(=O)(=O)c2cccc(-c3cccc(Cl)c3F)c2N1]

The title compound was prepared in a manner similar to Example 35, using 5-iodo-3-((2-methoxyethyl)amino)-4H-benzo[e][1,2,4]thiadiazine 1,1-dioxide (100 mg, 0.262 mmol), 2-(3-chloro-2-fluorophenyl)-4,4,5,5-tetramethyl-1,3,2-dioxaborolane (70.7 mg, 0.276 mmol), Cs$_2$CO$_3$ (2M, 328 µL, 0.656 mmol), and Pd(dppf)$_2$·CH$_2$Cl$_2$ adduct (21.42 mg, 0.026 mmol) in dioxane (1312 µL), and was isolated as a white film (5.0 mg, 5%). $^1$H NMR (400 MHz, CD$_3$OD) δ ppm 3.33 (br s, 2H), 3.49 (br s, 4H), 7.30-7.43 (m, 3H), 7.47 (d, J=7.07 Hz, 1H), 7.61-7.73 (m, 1H), 7.87 (dd, J=7.83, 1.52 Hz, 1H); ESI-MS m/z [M+H]$^+$ 384.0.

Example 136: 3-((4-ethylphenyl)amino)-5-(1-methyl-1H-pyrazol-4-yl)-4H-benzo[e][1,2,4]thiadiazine 1,1-dioxide

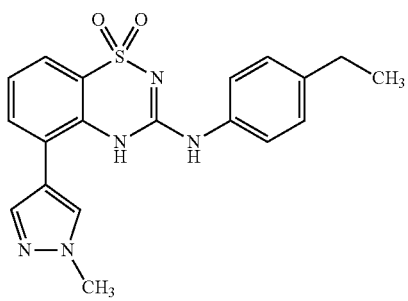 [SMILES: CCc1ccc(NC2=NS(=O)(=O)c3cccc(-c4cnn(C)c4)c3N2)cc1]

To a solution of 3-chloro-5-(1-methyl-1H-pyrazol-4-yl)-4H-benzo[e][1,2,4]thiadiazine 1,1-dioxide (50 mg, 0.169 mmol) in DMA (1 mL) was added 4-ethylaniline (0.063 mL, 0.506 mmol). The reaction mixture was heated at 120° C. for 15 hours. The reaction mixture was cooled to room temperature, extracted with EtOAc, and washed with brine (3×). The organic layers were combined, concentrated, filtered, and purified by preparative LC/MS (Waters XSelect® C18, 5 µm, ID 30×75 mm column) eluting with a gradient of 20-70% water in ACN (basic mode). The product-containing fractions were collected and concentrated to give the title compound as a brown solid (3.2 mg, 5%). $^1$H NMR (400 MHz, CD$_3$OD) δ ppm 1.22-1.26 (m, 3H), 2.64 (qd, J=7.62, 3.41 Hz, 2H), 3.98 (s, 3H), 7.16-7.23 (m, 2H), 7.29-7.34 (m, 1H), 7.42 (d, J=8.34 Hz, 2H), 7.53-7.57 (m, 1H), 7.72-7.76 (m, 1H), 7.98 (br s, 1H), 8.55 (br s, 1H); ESI-MS m/z [M+H]$^+$ 382.1.

Example 137: 3-((furan-2-ylmethyl)amino)-5-(o-tolyl)-4H-benzo[e][1,2,4]thiadiazine 1,1-dioxide

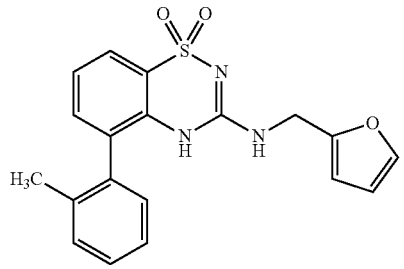 [SMILES: Cc1ccccc1-c1cccc2c1NC(NCc1ccco1)=NS2(=O)=O]

Step A: 3-chloro-5-(o-tolyl)-4H-benzo[e][1,2,4]thiadiazine 1,1-dioxide

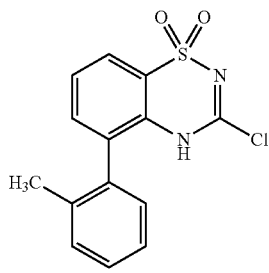 [SMILES: Cc1ccccc1-c1cccc2c1NC(Cl)=NS2(=O)=O]

To a stirred solution of 3-chloro-5-iodo-2H-benzo[e][1,2,4]thiadiazine 1,1-dioxide (0.034 g, 0.1 mmol) and o-tolylboronic acid (0.014 g, 0.1 mmol) in water (0.5 mL) and dioxane (0.5 mL) were added tetrakis(triphenylphosphine)palladium(0) (5.78 mg, 5 μmol) and $Na_2CO_3$ (0.089 g, 0.837 mmol). The (first) reaction mixture was heated at 100° C. for 1 hour and then cooled to room temperature and set aside. To a (second) stirred solution of 3-chloro-5-iodo-2H-benzo[e][1,2,4]thiadiazine 1,1-dioxide (68.5 mg, 0.2 mmol) and o-tolylboronic acid (27.2 mg, 0.2 mmol) in water (1 mL) and dioxane (1 mL) were added tetrakis(triphenylphosphine)palladium(0) (11.56 mg, 10 μmol) and $Na_2CO_3$ (177 mg, 1.674 mmol). The reaction mixture was heated at 70° C. for 0.5 hours and at 80° C. for 1 hour, then cooled to room temperature, and combined with the first reaction mixture. The combined mixtures were neutralized with a 1 N HCl (aq) and extracted with EtOAc. The organic layers were combined, dried over anhydrous $NaSO_4$, and concentrated under vacuum. The crude product was purified on a silica gel column, eluting with 50% EtOAc in hexanes. The product-containing fractions were collected and concentrated in vacuo to give the title compound as an off-white solid (49 mg, 53%). ESI-MS m/z [M+H]$^+$ 307.0.

Step B: 3-((furan-2-ylmethyl)amino)-5-(o-tolyl)-4H-benzo[e][1,2,4]thiadiazine 1,1-dioxide To a mixture of 3-chloro-5-(o-tolyl)-4H-benzo[e][1,2,4]thiadiazine 1,1-dioxide (50 mg, 0.163 mmol) and furan-2-ylmethanamine (200 mg, 2.059 mmol) dissolved in n-butanol (5 mL) was added $Cs_2CO_3$ (100 mg, 0.307 mmol). The reaction mixture stirred at 150° C. for 2 hours in a microwave reactor, then cooled, and purified by preparative LC/MS (Waters XSelect® C18, 5 μm, ID 30×75 mm column). The title compound was isolated as a white solid (50 mg, 44%). $^1$H NMR (400 MHz, $CD_3OD$) δ ppm 2.08 (s, 3H), 4.46 (s, 2H), 6.29-6.35 (m, 2H), 7.17-7.23 (m, 1H), 7.32-7.44 (m, 6H), 7.79-7.87 (m, 1H); ESI-MS m/z [M+H]$^+$ 368.1.

Example 138: 5-(2-chlorophenyl)-6-fluoro-3-(methylamino)-4H-benzo[e][1,2,4]thiadiazine 1,1-dioxide

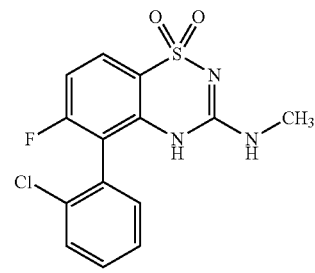 [SMILES: CNC1=NS(=O)(=O)c2ccc(F)c(-c3ccccc3Cl)c2N1]

Step A: 2'-chloro-6-fluoro-[1,1'-biphenyl]-2-amine

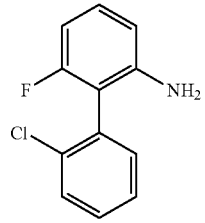 [SMILES: Nc1cccc(F)c1-c1ccccc1Cl]

To a solution of 2-bromo-3-fluoroaniline (1.00 g, 5.26 mmol) and (2-chlorophenyl)boronic acid (1.23 g, 7.89 mmol) in dioxane (10 mL) and water (1 mL), was added bis(di-tert-butyl(4-dimethylaminophenyl)phosphine)dichloropalladium(II) (171.50 mg, 263.00 μmol) and $K_2CO_3$ (1.82 g, 13.15 mmol). The reaction mixture was stirred at 100° C. under nitrogen for 1 hour, then poured into water (20 mL) and extracted with EtOAc (2×2 mL). The organic layers were combined, dried over anhydrous $Na_2SO_4$, and concentrated. The crude material was purified by column chromatography ($SiO_2$) eluting with petroleum ether/EtOAc (20:1) to afford the title compound as a colorless oil (800.00 mg, 69%). $^1$H NMR (400 MHz, DMSO-$d_6$) δ ppm 5.07-4.62 (m, 2H), 6.44-6.36 (m, 1H), 6.61-6.56 (m, 1H), 7.13-7.05 (m, 1H), 7.35-7.29 (m, 1H), 7.47-7.40 (m, 2H), 7.64-7.56 (m, 1H); ESI-MS m/z [M+H]$^+$ 222.1.

Step B: 5-(2-chlorophenyl)-6-fluoro-2H-benzo[e][1,2,4]thiadiazin-3(4H)-one 1,1-dioxide

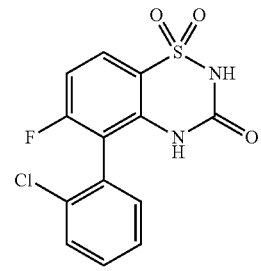 [SMILES: O=C1Nc2c(ccc(F)c2-c2ccccc2Cl)S(=O)(=O)N1]

To a solution of sulfurisocyanatidic chloride (536.96 mg, 3.79 mmol) in nitromethane (9.00 mL), was added 2'-chloro-6-fluoro-[1,1'-biphenyl]-2-amine (6 mL). The reaction mixture was stirred at a temperature of −20° C. to 0° C. for 30 minutes. AlCl₃ (433.62 mg, 3.25 mmol) was added slowly and the temperature of the mixture was gradually raised to 100° C. to 110° C. The reaction mixture was stirred at this temperature for an additional hour under nitrogen atmosphere. The reaction mixture was allowed to cool to room temperature and then poured into water (30.00 mL), and extracted with EtOAc (2×30 mL). The combined organic fractions were dried over anhydrous Na₂SO₄ and filtered. The filtrate was concentrated to dryness under vacuum and the remaining residue purified by preparative TLC (DCM/MeOH) to afford the title compound as a white solid (300 mg, 34% yield).

Step C: 3-chloro-5-(2-chlorophenyl)-6-fluoro-4H-benzo[e][1,2,4]thiadiazine 1,1-dioxide

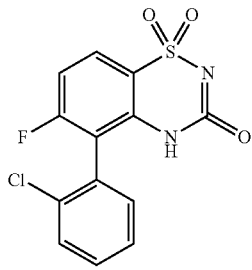

A solution of 5-(2-chlorophenyl)-6-fluoro-2H-benzo[e][1,2,4]thiadiazin-3(4H)-one 1,1-dioxide (300 mg, 0.918 mmol), N,N-diethylaniline (137.02 mg, 0.918 mmol) and POCl₃ (5.00 mL) was stirred at 120° C. for 3 hours and then allowed to cool to room temperature. The volatiles were removed under vacuum to give the title (crude) compound as a brown oil which was used without additional purification (300 mg). ESI-MS m/z [M+H]⁺ 345.1.

Step D: 5-(2-chlorophenyl)-6-fluoro-3-(methylamino)-4H-benzo[e][1,2,4]thiadiazine 1,1-dioxide To a solution of 3-chloro-5-(2-chlorophenyl)-6-fluoro-4H-benzo[e][1,2,4]thiadiazine 1,1-dioxide (320.00 mg, 0.927 mmol) and methanamine, HCl (93.89 mg, 1.39 mmol) in IPA (5.00 mL) was added Et₃N (469.04 mg, 4.64 mmol). The resulting mixture was stirred at 70° C. for 2 hours. The solvents were removed and the crude material purified by preparative HPLC (Phenomenex Synergi™ C18, 10 μm, ID 25×150 mm) eluting with a gradient of water (0.225% formic acid) in ACN. The product-containing fractions were combined and dried to give the title compound as a yellow solid (36 mg, 11%). ¹H NMR (400 MHz, DMSO-d₆) δ ppm 2.71 (s, 3H), 7.32-7.20 (m, 2H), 7.59-7.47 (m, 4H), 7.71-7.69 (m, 1H), 7.81-7.78 (m, 1H); ESI-MS m/z [M+H]⁺ 340.0.

Example 139: 5-(2,5-difluorophenyl)-3-((pyridin-2-ylmethyl)amino)-4H-benzo[e][1,2,4]thiadiazine 1,1-dioxide

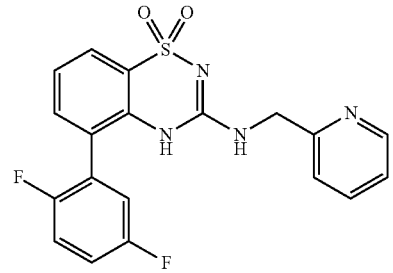 [SMILES: O=S1(=O)N=C(NCc2ccccn2)Nc2c(-c3cc(F)ccc3F)cccc21]

To a solution of 3-chloro-5-(2,5-difluorophenyl)-4H-benzo[e][1,2,4]thiadiazine 1,1-dioxide (100 mg, 0.304 mmol) and pyridin-2-ylmethanamine (33.2 mg, 0.307 mmol) in DMA (5 mL) was added Cs₂CO₃ (100 mg, 0.307 mmol). The reaction mixture was stirred and heated at 150° C. for 2 hours in a microwave reactor. The product was purified by preparative HPLC (Waters XSelect® C18, 5 μm, ID 30×75 mm column) eluting with a gradient of ACN (0.1% formic acid) in water (0.1% formic acid). The title compound was isolated as a white solid (18 mg, 15%). ¹H NMR (400 MHz, CD₃OD) δ ppm 4.62 (br s, 2H), 7.19-7.56 (m, 1H), 7.88 (dd, J=7.96, 1.64 Hz, 1H), 8.36-8.56 (m, 1H); ESI-MS m/z [M+H]⁺ 401.0.

Example 140: 3-((cyclopropylmethyl)amino)-5-(2,5-difluorophenyl)-4H-benzo[e][1,2,4]thiadiazine 1,1-dioxide

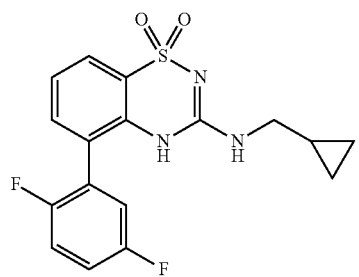 [SMILES: O=S1(=O)N=C(NCC2CC2)Nc2c(-c3cc(F)ccc3F)cccc21]

The title compound was prepared in a manner similar to Example 139, using 3-chloro-5-(2,5-difluorophenyl)-4H-benzo[e][1,2,4]thiadiazine 1,1-dioxide (100 mg, 0.304 mmol), cyclopropylmethanamine (200 mg, 2.81 mmol) and Cs₂CO₃ (100 mg, 0.307 mmol) in DMA (5 mL), and was isolated as a white solid (22 mg, 20%). ¹H NMR (400 MHz, CD₃OD) δ ppm 0.21-0.30 (m, 2H), 0.46-0.58 (m, 2H), 1.03 (qt, J=7.64, 7.64, 7.64, 7.64, 4.80, 4.80 Hz, 1H), 3.17 (d, J=7.33 Hz, 2H), 7.19-7.43 (m, 3H), 7.48 (dd, J=7.58, 1.52 Hz, 1H), 7.86 (dd, J=7.83, 1.52 Hz, 1H); ESI-MS m/z [M+H]⁺ 364.1.

Example 141: 5-(2,5-difluorophenyl)-3-((2-methoxyethyl)amino)-4H-benzo[e][1,2,4]thiadiazine 1,1-dioxide

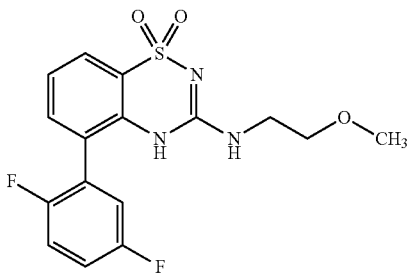 [SMILES: COCCNC1=NS(=O)(=O)c2cccc(-c3cc(F)ccc3F)c2N1]

The title compound was prepared in a manner similar to Example 139, using 3-chloro-5-(2,5-difluorophenyl)-4H-benzo[e][1,2,4]thiadiazine 1,1-dioxide (100 mg, 0.304 mmol), methoxyethanamine (400 mg, 5.33 mmol) and Cs$_2$CO$_3$ (100 mg, 0.307 mmol) in DMA (5 mL), and was isolated as a white solid (65 mg, 58%). $^1$H NMR (400 MHz, CD$_3$OD) δ ppm 3.49 (br s, 4H) 7.22 (br s, 1H) 7.26-7.44 (m, 3H) 7.48 (d, J=6.57 Hz, 1H) 7.87 (dd, J=7.83, 1.52 Hz, 1H); ESI-MS m/z [M+H]$^+$ 368.1.

Example 142: 5-(2,5-difluorophenyl)-3-((2-methoxypropyl)amino)-4H-benzo[e][1,2,4]thiadiazine 1,1-dioxide

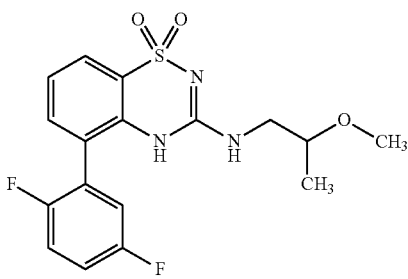 [SMILES: COC(C)CNC1=NS(=O)(=O)c2cccc(-c3cc(F)ccc3F)c2N1]

The title compound was prepared in a manner similar to Example 139, using 3-chloro-5-(2,5-difluorophenyl)-4H-benzo[e][1,2,4]thiadiazine 1,1-dioxide (70 mg, 0.213 mmol), 2-methoxypropan-1-amine, HCl (34.8 mg, 0.277 mmol) and DIPEA (37.2 μL, 0.213 mmol) in DMA (426 μL), and was isolated as a white solid (31 mg, 38%). $^1$H NMR (400 MHz, CD$_3$OD) δ ppm 1.07 (d, J=6.06 Hz, 3H), 3.10-3.21 (m, 1H), 3.24 (s, 3H), 3.38 (br s, 2H), 3.40-3.43 (m, 1H), 7.30-7.39 (m, 1H), 7.40-7.56 (m, 5H), 7.74-7.82 (m, 1H), 9.26 (s, 1H); ESI-MS m/z [M+H]$^+$ 401.4.

Example 143: 5-(2,5-difluorophenyl)-3-(ethylamino)-4H-benzo[e][1,2,4]thiadiazine 1,1-dioxide

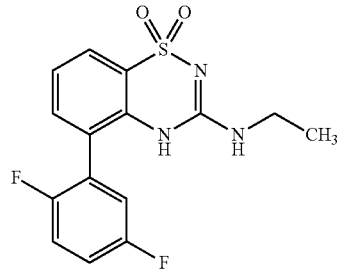 [SMILES: CCNC1=NS(=O)(=O)c2cccc(-c3cc(F)ccc3F)c2N1]

The title compound was prepared in a manner similar to Example 139, using 3-chloro-5-(2,5-difluorophenyl)-4H-benzo[e][1,2,4]thiadiazine 1,1-dioxide (70 mg, 0.213 mmol), ethanamine, HCl (22.57 mg, 0.277 mmol) and DIPEA (37.2 μL, 0.213 mmol) in DMA (426 μL), and was isolated as a tan solid (14 mg, 20%). $^1$H NMR (400 MHz, CD$_3$OD) δ ppm 1.10 (t, J=7.20 Hz, 3H), 3.22 (dd, J=7.33, 5.31 Hz, 2H), 7.31-7.55 (m, 6H), 7.78 (dd, J=7.83, 1.01 Hz, 1H), 9.12 (s, 1H); ESI-MS m/z [M+H]$^+$ 338.0.

Example 144: 5-(2-chloro-5-fluorophenyl)-3-((2-methoxyethyl)amino)-4H-benzo[e][1,2,4]thiadiazine 1,1-dioxide

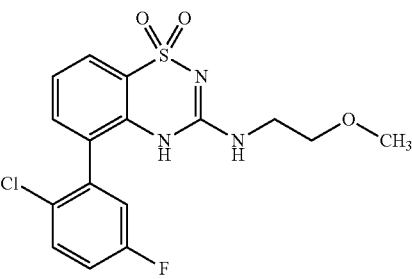 [SMILES: COCCNC1=NS(=O)(=O)c2cccc(-c3cc(F)ccc3Cl)c2N1]

The title compound was prepared in a manner similar to Example 35, using 5-iodo-3-((2-methoxyethyl)amino)-4H-benzo[e][1,2,4]thiadiazine 1,1-dioxide (100 mg, 0.262 mmol), (2-chloro-5-fluorophenyl)boronic acid (46 mg, 0.262 mmol), Cs$_2$CO$_2$ (2M, 525 μL, 1.049 mmol), and Pd(dppf)$_2$·CH$_2$Cl$_2$ adduct (32 mg, 0.039 mmol) in dioxane (1312 μL), and was isolated as a pale, yellow oil (5 mg, 5%); ESI-MS m/z [M+H]$^+$ 384.0.

Example 145: 2-(3-((2-methoxypropyl)amino)-1,1-dioxido-4H-benzo[e][1,2,4]thiadiazin-5-yl)benzonitrile

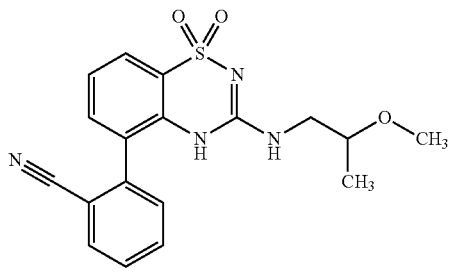 [SMILES: COC(C)CNC1=NS(=O)(=O)c2cccc(-c3ccccc3C#N)c2N1]

To a solution of 2-methoxypropan-1-amine, HCl (36.0 mg, 0.286 mmol) and DIPEA (38.5 µL, 0.220 mmol) in DMA (441 µL) was added 2-(3-chloro-1,1-dioxido-4H-benzo[e][1,2,4]thiadiazin-5-yl)benzonitrile (70 mg, 0.220 mmol). The reaction mixture was heated at 70° C. for 24 hours, then diluted with MeOH (1 mL) and filtered. the residue was purified by preparative LC/MS on (ZQ3) eluting with a gradient of 25-90% ACN in water (acid mode). The product-containing fractions were collected, concentrated, and dried in vacuo to give the title compound as a tan solid (3 mg, 4%). $^1$H NMR (400 MHz, CD$_3$OD) δ ppm 1.05-1.10 (m, 3H), 3.24 (s, 3H), 3.43 (s, 3H), 7.33-7.40 (m, 1H), 7.43-7.53 (m, 2 H), 7.63-7.68 (m, 1H), 7.71-7.85 (m, 2H), 7.87-7.93 (m, 1H), 8.05-8.13 (m, 1H), 9.20-9.29 (m, 1H).

Example 146: 2-(3-((cyclobutylmethyl)amino)-1,1-dioxido-4H-benzo[e][1,2,4]thiadiazin-5-yl)benzonitrile

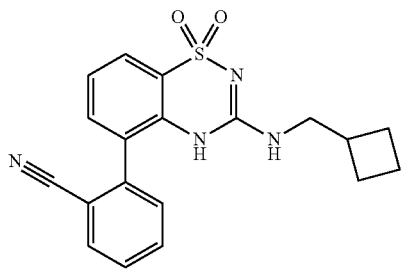 [SMILES: N#Cc1ccccc1-c1cccc2c1NC(NCC1CCC1)=NS2(=O)=O]

The title compound was prepared in a manner similar to Example 145, using 2-(3-chloro-1,1-dioxido-4H-benzo[e][1,2,4]thiadiazin-5-yl)benzonitrile (70 mg, 0.220 mmol), cyclobutylmethanamine, HCl (34.8 mg, 0.286 mmol) and DIPEA (38.5 µL, 0.220 mmol) in DMA (441 µL), and was isolated as a tan solid (32 mg, 40%). $^1$H NMR (400 MHz, CD$_3$OD) δ ppm 1.61-1.72 (m, 2H), 1.83 (s, 2H), 1.94-2.03 (m, 2H), 2.40-2.46 (m, 1H), 3.24 (br s, 2H), 7.30-7.41 (m, 2H), 7.45-7.51 (m, 1H), 7.46-7.50 (m, 1H), 7.63-7.67 (m, 1H), 7.71-7.77 (m, 1H), 7.79-7.83 (m, 1H), 7.86-7.93 (m, 1H), 8.05-8.11 (m, 1H), ESI-MS m/z [M+H]$^+$ 367.1.

Example 147: 5-(2-chloro-3-fluorophenyl)-3-((2-fluoroethyl)amino)-4H-benzo[e][1,2,4]thiadiazine 1,1-dioxide

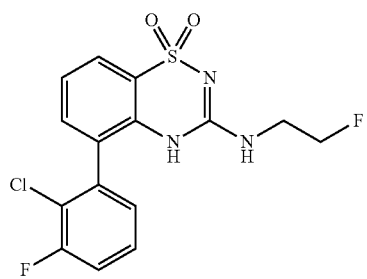 [SMILES: O=S1(=O)N=C(NCCF)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (40 mg, 0.116 mmol), DIPEA (20.24 µL, 0.116 mmol), and 2-fluoroethanamine, HCl (15 mg, 0.151 mmol) in DMA (232 µL), and was isolated as a tan solid (11 mg, 26%). $^1$H NMR (400 MHz, CD$_3$OD) δ ppm 3.47-3.52 (m, 1H), 3.53-3.60 (m, 1H), 4.44-4.50 (m, 1H), 4.56-4.62 (m, 1H), 7.30-7.36 (m, 1H), 7.37-7.41 (m, 1H), 7.42-7.46 (m, 1H), 7.54-7.66 (m, 3H), 7.77-7.83 (m, 1H), 9.07-9.11 (m, 1H).

Example 148: 5-(2-chloro-3-fluorophenyl)-3-(((6-fluoropyridin-2-yl)methyl)amino)-4H-benzo[e][1,2,4]thiadiazine 1,1-dioxide

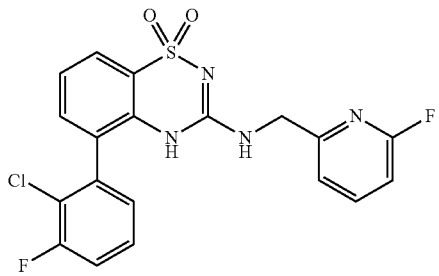 [SMILES: O=S1(=O)N=C(NCc2cccc(F)n2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), DIPEA (25.3 µL, 0.145 mmol), and (6-fluoropyridin-2-yl)methanamine (23.8 mg, 0.188 mmol) in DMA (290 µL), and was isolated as a tan solid (1.2 mg, 2%). $^1$H NMR (400 MHz, CD$_3$OD) δ ppm 4.48-4.55 (m, 2H), 7.06-7.14 (m, 1H), 7.30-7.40 (m, 4H), 7.43-7.47 (m, 1H), 7.56-7.66 (m, 2H), 7.77-7.82 (m, 1H), 7.86-7.92 (m, 1H), 7.95-8.04 (m, 1H), 9.29-9.40 (m, 1H).

Example 149: 2-fluoro-6-(3-((2-fluoroethyl)amino)-1,1-dioxido-4H-benzo[e][1,2,4]thiadiazin-5-yl)benzonitrile

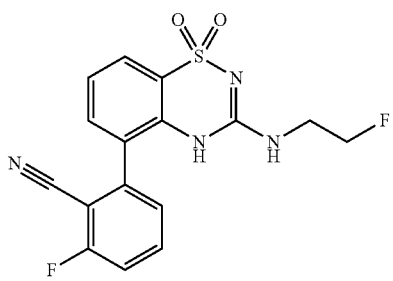 [SMILES: N#Cc1c(F)cccc1-c1cccc2c1NC(NCCF)=NS2(=O)=O]

To a solution of 2-fluoroethanamine, HCl (16.31 mg, 0.164 mmol) and DIPEA (26.0 µL, 0.149 mmol) in DMA (298 µL) was added 2-(3-chloro-1,1-dioxido-4H-benzo[e][1,2,4]thiadiazin-5-yl)-6-fluorobenzonitrile (50 mg, 0.149 mmol). The reaction mixture was heated at 70° C. for 24 hours, then diluted with MeOH (1 mL) and filtered. This residue was purified by preparative LC/MS on (Waters SunFire® C18, 5 µm, ID 30×75 mm column) eluting with a gradient of 25-90% ACN in water (acid mode). The fractions were collected, concentrated, and dried in vacuo to give the title compound as a tan solid (5 mg, 9%). $^1$H NMR (400 MHz, CD$_3$OD) δ ppm 3.49-3.60 (m, 2H), 4.45-4.50 (m, 1H), 4.59 (s, 1H), 7.39-7.46 (m, 1H), 7.51-7.61 (m, 3H), 7.70-7.78 (m, 1H), 7.83-7.88 (m, 1H), 7.94-8.01 (m, 1H), 9.25-9.38 (m, 1H); ESI-MS m/z [M+H]$^+$ 363.0.

Example 150: 2-fluoro-6-(3-((2-methoxypropyl)amino)-1,1-dioxido-4H-benzo[e][1,2,4]thiadiazin-5-yl)benzonitrile

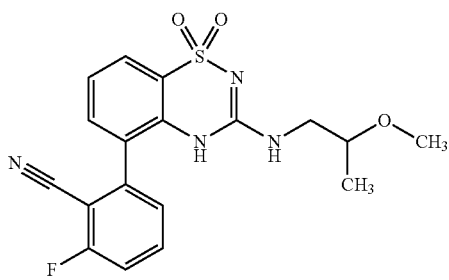 [SMILES: COC(C)CNC1=NS(=O)(=O)c2cccc(-c3cccc(F)c3C#N)c2N1]

The title compound was prepared in a manner similar to Example 149, using 2-(3-chloro-1,1-dioxido-4H-benzo[e][1,2,4]thiadiazin-5-yl)-6-fluorobenzonitrile (50 mg, 0.149 mmol), 2-methoxypropan-1-amine, HCl (20.57 mg, 0.164 mmol) and DIPEA (26.0 μL, 0.149 mmol) in DMA (298 μL), and was isolated as a brown oil (17 mg, 29%); ESI-MS m/z [M+H]$^+$ 389.1.

Example 151: 5-(2-chloro-3-fluorophenyl)-3-((3-methoxypropyl)amino)-4H-benzo[e][1,2,4]thiadiazine 1,1-dioxide

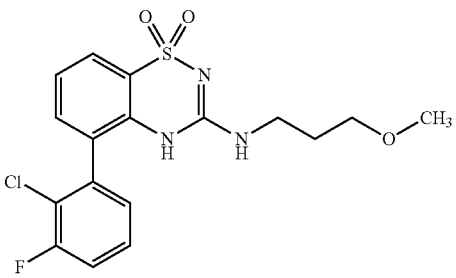 [SMILES: COCCCNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), DIPEA (25.3 μL, 0.145 mmol), and 3-methoxypropan-1-amine, HCl (24 mg, 0.188 mmol) in DMA (290 μL), and was isolated as a tan solid (20 mg, 35%). $^1$H NMR (400 MHz, CD$_3$OD) δ ppm 4.48-4.55 (m, 2H), 7.06-7.14 (m, 1H), 7.30-7.40 (m, 4H), 7.43-7.47 (m, 1H), 7.56-7.66 (m, 2H), 7.77-7.82 (m, 1H), 7.86-7.92 (m, 1H), 7.95-8.04 (m, 1H), 9.29-9.40 (m, 1H); ESI-MS m/z [M+H]$^+$ 398.0.

Example 152: 5-(2-chloro-3-fluorophenyl)-3-((3-fluoropropyl)amino)-4H-benzo[e][1,2,4]thiadiazine 1,1-dioxide

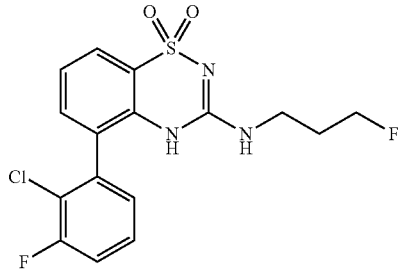 [SMILES: O=S1(=O)N=C(NCCCF)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), DIPEA (25.3 μL, 0.145 mmol), and 3-fluoropropan-1-amine, HCl (18.1 mg, 0.159 mmol) in DMA (290 μL), and was isolated as a tan solid (37 mg, 66%); ESI-MS m/z [M+H]$^+$ 386.0.

Example 153: 5-(2-chloro-3-fluorophenyl)-3-((3-methoxybutyl)amino)-4H-benzo[e][1,2,4]thiadiazine 1,1-dioxide

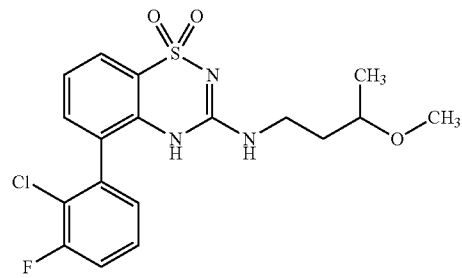 [SMILES: COC(C)CCNC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (50 mg, 0.145 mmol), DIPEA (25.3 μL, 0.145 mmol), and 3-methoxybutan-1-amine, HCl (26.3 mg, 0.188 mmol) in DMA (290 μL), and was isolated as a colorless oil (19 mg, 32%); ESI-MS m/z [M+H]$^+$ 412.1.

Example 154: (R)-5-(2-chloro-3-fluorophenyl)-3-((3-methoxybutyl)amino)-4H-benzo[e][1,2,4]thiadiazine 1,1-dioxide

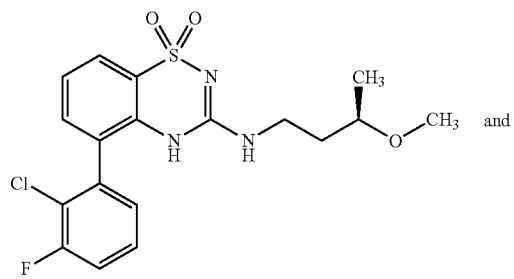 [SMILES: CO[C@H](C)CCNC1=NS(=O)(=O)c2cccc(-c3cccc(F)c3Cl)c2N1]

and

Example 155: (S)-5-(2-chloro-3-fluorophenyl)-3-((3-methoxybutyl)amino)-4H-benzo[e][1,2,4]thiadiazine 1,1-dioxide

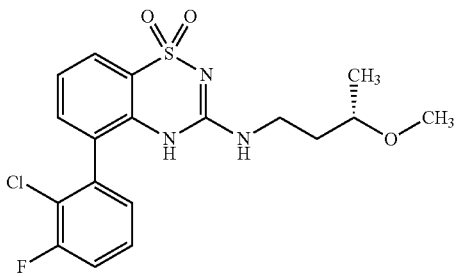 [SMILES: CO[C@@H](C)CCNC1=NS(=O)(=O)c2cccc(-c3cccc(F)c3Cl)c2N1]

The racemate prepared in Example 153 was resolved by chiral chromatography. The first eluting peak was arbitrarily assigned R-stereochemical configuration (Example 154) and the second eluting peak was assign S-stereochemical configuration (Example 155). Each of the title compounds was isolated as a colorless semisolid.

Example 156: 5-(2-cyclopropyl-3-fluorophenyl)-3-((2-methoxyethyl)amino)-4H-benzo[e][1,2,4]thiadiazine 1,1-dioxide

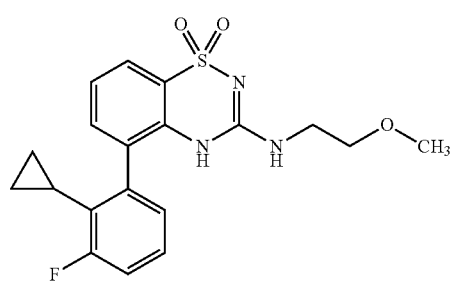 [SMILES: COCCNC1=NS(=O)(=O)c2cccc(-c3cccc(F)c3C3CC3)c2N1]

To a solution of 2-methoxyethan-1-amine (13.92 mg, 0.185 mmol) and DIPEA (24.89 µL, 0.143 mmol) in DMA (285 µL) was added 3-chloro-5-(2-cyclopropyl-3-fluorophenyl)-4H-benzo[e][1,2,4]thiadiazine 1,1-dioxide (50 mg, 0.143 mmol). The reaction mixture was heated at 70° C. for 24 hours, then diluted with MeOH (1 mL) and filtered. The product was purified by preparative LC/MS (Waters SunFire® C18, 5 µm, ID 30×75 mm column) eluting with a gradient of 25-90% ACN in water (acid mode). The product-containing fractions were collected, concentrated, and dried in vacuo to give the title compound as a tan glassy solid (14 mg, 25% yield). ESI-MS m/z [M+H]⁺ 390.1

Example 157: 5-(2-cyclopropyl-3-fluorophenyl)-3-(methylamino)-4H-benzo[e][1,2,4]thiadiazine 1,1-dioxide

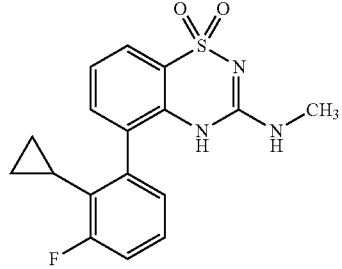 [SMILES: CNC1=NS(=O)(=O)c2cccc(-c3cccc(F)c3C3CC3)c2N1]

The title compound was prepared in a manner similar to Example 156, using 3-chloro-5-(2-cyclopropyl-3-fluorophenyl)-4H-benzo[e][1,2,4]thiadiazine 1,1-dioxide (50 mg, 0.143 mmol), methanamine (93 µL, 0.185 mmol) and DIPEA (24.89 µL, 0.143 mmol) in DMA (285 µL), and was isolated as a tan, glassy solid (10 mg, 20%). ESI-MS m/z [M+H]⁺ 346.3.

Example 158: 5-(2-chloro-3-fluorophenyl)-3-(isopropylamino)-4H-benzo[e][1,2,4]thiadiazine 1,1-dioxide

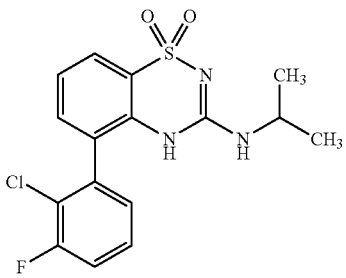 [SMILES: CC(C)NC1=NS(=O)(=O)c2cccc(-c3cccc(F)c3Cl)c2N1]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), DIPEA (15.2 µL, 0.087 mmol), and propan-2-amine, HCl (10.8 mg, 0.113 mmol) in DMA (174 µL), and was isolated as a yellow film (32 mg, 95%); ESI-MS m/z [M+H]⁺ 368.8.

Example 159: 5-(2-chloro-3-fluorophenyl)-3-(cyclopropylamino)-4H-benzo[e][1,2,4]thiadiazine 1,1-dioxide

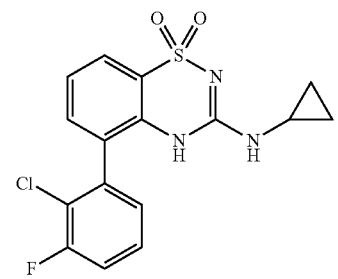 [SMILES: O=S1(=O)N=C(NC2CC2)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), cyclopropanamine, HCl (10.6 mg, 0.113 mmol) and DIPEA (15.2 μL, 0.087 mmol) in DMA (174 μL), and was isolated as a clear film (32 mg, 95%); ESI-MS m/z [M+H]+ 366.8.

Example 160: 5-(2-chloro-3-fluorophenyl)-3-((2-(2,2-difluoroethoxy)ethyl)amino)-4H-benzo[e][1,2,4]thiadiazine 1,1-dioxide

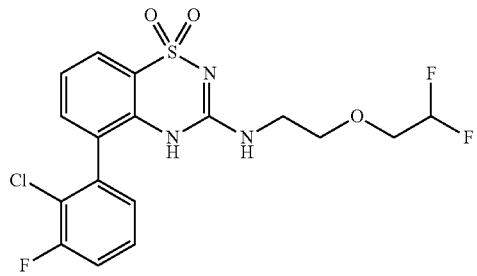 [SMILES: O=S1(=O)N=C(NCCOCC(F)F)Nc2c(-c3cccc(F)c3Cl)cccc21]

The title compound was prepared in a manner similar to Example 1, using 3-chloro-5-(2-chloro-3-fluorophenyl)-4H-benzo[e][1,2,4]thiadiazine 1,1-dioxide (30 mg, 0.087 mmol), 2-(2,2-difluoroethoxy)ethanamine, HCl (18.3 mg, 0.113 mmol) and DIPEA (15.2 μL, 0.087 mmol) in DMA (174 μL), and was isolated as a yellow film (32 mg, 85%); ESI-MS m/z [M+H]+ 434.8.

Each of the compounds shown in Examples 161 to 170, below, are prepared like the compounds above.

Example 161: 2-fluoro-6-(3-((oxazol-2-ylmethyl)amino)-1,1-dioxido-4H-benzo[e][1,2,4]thiadiazin-5-yl)benzonitrile

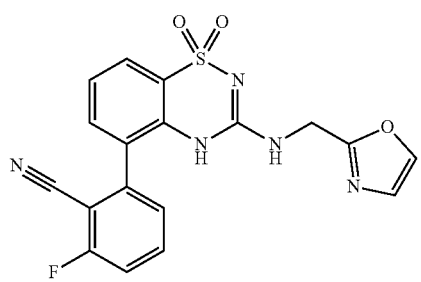 [SMILES: N#Cc1c(F)cccc1-c1cccc2c1NC(NCc1ncco1)=NS2(=O)=O]

ESI-MS m/z [M+H]+ 402.1.

Example 162: 3-((pyridin-2-ylmethyl)amino)-5-(o-tolyl)-4H-benzo[e][1,2,4]thiadiazine 1,1-dioxide

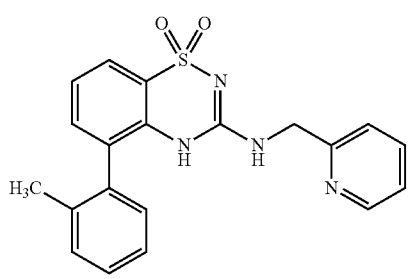 [SMILES: Cc1ccccc1-c1cccc2c1NC(NCc1ccccn1)=NS2(=O)=O]

$^1$H NMR (400 MHz, DMSO-$d_6$) δ ppm 2.05 (s, 3H), 4.52 (t, J=5.31 Hz, 2H), 7.23 (d, J=7.58 Hz, 1H), 7.30-7.44 (m, 7H), 7.71-7.75 (m, 1H), 7.79 (td, J=7.71, 1.77 Hz, 1H), 8.17 (br s, 1H), 8.53 (d, J=4.04 Hz, 1H), 9.16 (br s, 1H); ESI-MS m/z [M+H]+ 379.2.

Example 163: 5-(2-ethylphenyl)-3-((2-methoxyethyl)amino)-4H-benzo[e][1,2,4]thiadiazine 1,1-dioxide

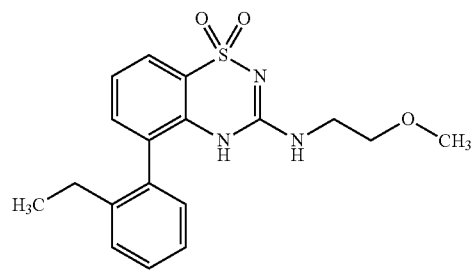 [SMILES: CCc1ccccc1-c1cccc2c1NC(NCCOC)=NS2(=O)=O]

$^1$H NMR (400 MHz, CD$_3$OD) δ ppm 1.03 (t, J=7.58 Hz, 3H), 2.29-2.41 (m, 1H), 2.42-2.54 (m, 1H), 3.46 (br s, 4H), 7.18 (d, J=7.33 Hz, 1H), 7.32-7.40 (m, 3H), 7.45 (d, J=1.52 Hz, 2H), 7.82 (dd, J=6.82, 2.78 Hz, 1H); ESI-MS m/z [M+H]+ 360.1.

Example 164: 5-(3,5-difluorophenyl)-3-((furan-2-ylmethyl)amino)-4H-benzo[e][1,2,4]thiadiazine 1,1-dioxide

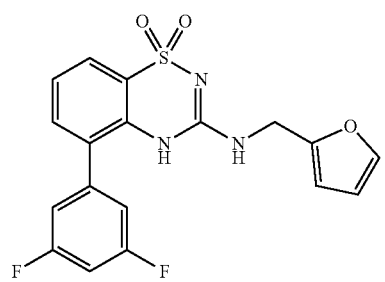 [SMILES: O=S1(=O)N=C(NCc2ccco2)Nc2c(-c3cc(F)cc(F)c3)cccc21]

$^1$H NMR (400 MHz, DMSO-$d_6$) δ ppm 4.44 (d, J=5.31 Hz, 2H) 6.33-6.52 (m, 1H) 7.25-7.30 (m, 2H) 7.34-7.34 (m, 1H) 7.36 (s, 1H) 7.39-7.47 (m, 1H) 7.48-7.51 (m, 1H) 7.64-7.67 (m, 1H) 7.75-7.81 (m, 1H) 7.83-7.89 (m, 1H) 9.14 (s, 1H); ESI-MS m/z [M+H]+ 390.4

Example 165: 5-(2,3-difluorophenyl)-3-(ethyl-amino)-4H-benzo[e][1,2,4]thiadiazine 1,1-dioxide

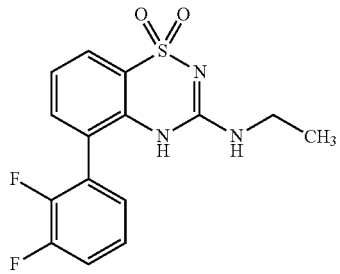 [SMILES: CCNC1=NS(=O)(=O)c2cccc(-c3cccc(F)c3F)c2N1]

¹H NMR (400 MHz, DMSO-d₆) δ ppm 1.10 (t, J=7.20 Hz, 3H) 3.19-3.28 (m, 2H) 7.24-7.34 (m, 2H) 7.34-7.37 (m, 1H) 7.39-7.45 (m, 1H) 7.49 (dd, J=7.58, 1.52 Hz, 1H) 7.59-7.69 (m, 1H) 7.76-7.82 (m, 1H) 9.14 (s, 1H); ESI-MS m/z [M+H]⁺ 338.0.

Example 166: 5-(3,5-difluorophenyl)-3-((2-methoxypropyl)amino)-4H-benzo[e][1,2,4]thiadiazine 1,1-dioxide

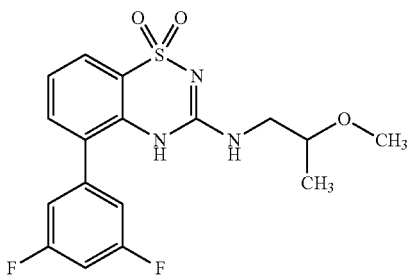 [SMILES: COC(C)CNC1=NS(=O)(=O)c2cccc(-c3cc(F)cc(F)c3)c2N1]

ESI-MS m/z [M+H]⁺ 382.4

Example 167: 5-(2-chloro-3-fluorophenyl)-3-((3-methoxycyclobutyl)amino)-4H-benzo[e][1,2,4]thiadiazine 1,1-dioxide

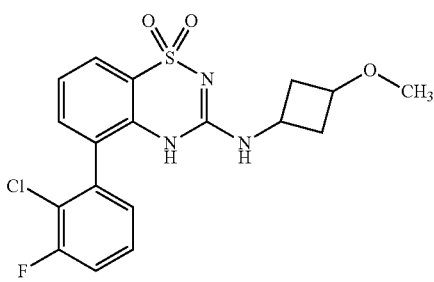 [SMILES: COC1CC(NC2=NS(=O)(=O)c3cccc(-c4cccc(F)c4Cl)c3N2)C1]

ESI-MS m/z [M]⁺ 410.6

Example 168: 3-((2-methoxyethyl)amino)-5-(2,3,5-trifluorophenyl)-4H-benzo[e][1,2,4]thiadiazine 1,1-dioxide

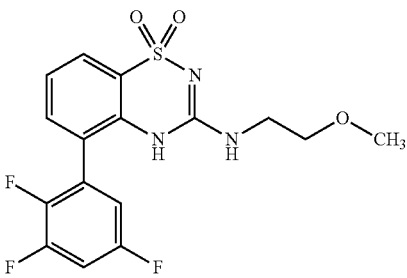 [SMILES: COCCNC1=NS(=O)(=O)c2cccc(-c3cc(F)cc(F)c3F)c2N1]

¹H NMR (400 MHz, CD₃OD) δ ppm 3.32-3.38 (m, 3H), 3.50 (br s, 4H), 7.07-7.14 (m, 1H), 7.40 (s, 2H), 7.47-7.55 (m, 1H), 7.87-7.92 (m, 1H); ESI-MS m/z [M+H]⁺ 386.4

Example 169: 3-((4-isopropylphenyl)amino)-5-(methoxymethyl)-4H-benzo[e][1,2,4]thiadiazine 1,1-dioxide

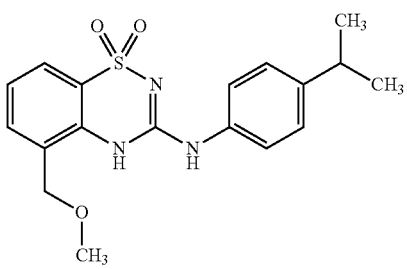 [SMILES: COCc1cccc2c1NC(Nc1ccc(C(C)C)cc1)=NS2(=O)=O]

¹H NMR (400 MHz, DMSO-d₆) (9.81 (s, 1H), 9.66 (s, 1H), 7.72 (d, J=7.6 Hz, 1H), 7.70 (d, J=8.0 Hz, 1H), 7.43 (d, J=8.4 Hz, 2H), 7.33-7.28 (m, 3H), 4.64 (s, 2H), 3.32 (s, 3H), 2.92-2.86 (m, 1H), 1.21 (d, J=6.8 Hz, 6H); ESI-MS m/z [M+H]⁺ 360.1.

Example 170: 5-(3,4-difluoro-2-methylphenyl)-3-((2-methoxyethyl)amino)-4H-benzo[e][1,2,4]thiadiazine, 1,1-dioxide

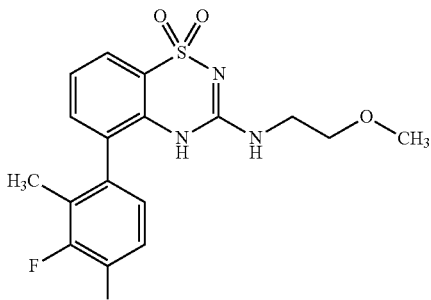

¹H NMR (400 MHz, CD₃OD) δ ppm 2.10 (d, J=2.78 Hz, 3H), 3.36 (td, J=3.47, 1.89 Hz, 5H), 3.53 (d, J=3.28 Hz, 2H), 4.90-4.91 (m, 1H), 7.07-7.15 (m, 1H), 7.26-7.37 (m, 1H), 7.40-7.46 (m, 2H), 7.87-7.92 (m, 1H); ESI-MS m/z [M+H]$^+$ 382.1.

Table 1 lists hMRGX2 cellular potency (pEC$_{50}$) and binding affinity (pK$_d$) for the compounds shown in the examples, where larger pEC$_{50}$ values represent higher activity or potency, and larger pK$_d$ values represent higher binding affinity. The methods used to measure cellular potency and binding affinity are described in the specification, above, under the heading Biological Activity.

TABLE 1 hMRGX2 Cellular Potency (pEC$_{50}$) and Binding Affinity (pK$_d$)

| Ex. | pEC$_{50}$ | pK$_d$ |
|---|---|---|
| 1 | 7.159 | 6.724 |
| 2 | 7.285 | 6.984 |
| 3 | 7.939 | 6.58 |
| 4 | 7.813 | 6.975 |
| 5 | 7.699 | — |
| 6 | 7.666 | 6.78 |
| 7 | 7.633 | 7.27 |
| 8 | 6.960 | — |
| 9 | 6.836 | — |
| 10 | 7.406 | — |
| 11 | 6.895 | — |
| 12 | 7.867 | 7.45 |
| 13 | 7.450 | — |
| 14 | 7.392 | — |
| 15 | 7.205 | — |
| 16 | 7.986 | 7.5 |
| 17 | 7.683 | — |
| 18 | 7.671 | — |
| 19 | 7.630 | — |
| 20 | 6.067 | — |
| 21 | 6.132 | — |
| 22 | 7.094 | — |
| 23 | 7.386 | — |
| 24 | 7.193 | — |
| 25 | 5.56 | — |
| 26 | 6.410 | — |
| 27 | 6.464 | — |
| 28 | 7.618 | 7.03 |
| 29 | 7.572 | — |
| 30 | 7.544 | — |
| 31 | 7.524 | — |
| 32 | 7.447 | — |
| 33 | 7.418 | — |
| 34 | 7.415 | 7.025 |
| 35 | 7.036 | 4.7 |
| 36 | 7.298 | — |
| 37 | 6.405 | — |
| 38 | 7.285 | — |
| 39 | 7.284 | 7.055 |
| 40 | 7.118 | — |
| 41 | 7.579 | — |
| 42 | 7.113 | — |
| 43 | 6.992 | 6.47 |
| 44 | 6.731 | — |
| 45 | 6.516 | — |
| 46 | 7.056 | — |
| 47 | 7.030 | — |
| 48 | 7.444 | — |
| 49 | 7.617 | — |
| 50 | 7.150 | — |
| 51 | 7.722 | — |
| 52 | 6.882 | — |
| 53 | 6.240 | — |
| 54 | 7.878 | — |
| 55 | 6.865 | — |
| 56 | 6.550 | — |
| 57 | 6.763 | — |
| 58 | 6.747 | — |
| 59 | 6.606 | — |
| 60 | 6.063 | — |
| 61 | 6.367 | — |
| 62 | 6.555 | — |
| 63 | 6.021 | — |
| 64 | 7.807 | — |
| 65 | 7.971 | 7.055 |
| 66 | 7.531 | 7.22 |
| 67 | 7.436 | — |
| 68 | 6.516 | — |
| 69 | 6.221 | — |
| 70 | 7.237 | — |
| 71 | 7.082 | — |
| 72 | 7.400 | — |
| 73 | 6.856 | — |
| 74 | 6.127 | — |
| 75 | 7.461 | — |
| 76 | 7.458 | — |
| 77 | 7.457 | — |
| 78 | 6.649 | — |
| 79 | 6.434 | — |
| 80 | 6.047 | — |
| 81 | 6.416 | — |
| 82 | 5.996 | — |
| 83 | 6.374 | — |
| 84 | | — |
| 85 | 6.603 | — |
| 86 | <4.3 | — |
| 87 | 6.620 | — |
| 88 | 7.124 | — |
| 89 | 7.160 | 6.35 |
| 90 | 6.012 | — |
| 91 | 7.087 | — |
| 92 | 7.033 | — |
| 93 | 6.742 | — |
| 94 | 6.629 | — |
| 95 | 6.456 | — |
| 96 | 6.223 | — |
| 97 | 6.230 | — |
| 98 | 6.539 | — |
| 99 | 6.119 | — |
| 100 | 6.116 | — |
| 101 | 7.340 | — |
| 102 | 7.068 | 6.28 |
| 103 | 7.291 | 6.755 |
| 104 | 7.050 | — |
| 105 | 6.926 | 6.06 |
| 106 | 7.154 | — |
| 107 | 6.881 | 6.52 |
| 108 | 6.228 | — |
| 109 | 6.974 | 6.575 |
| 110 | 7.454 | — |
| 111 | 6.974 | — |
| 112 | 6.782 | — |
| 113 | 6.633 | — |
| 114 | 6.582 | 6.095 |
| 115 | 7.261 | — |
| 116 | 7.260 | 6.685 |
| 117 | 6.705 | — |
| 118 | 6.422 | — |
| 119 | 6.315 | — |
| 120 | 6.238 | — |
| 121 | 6.366 | — |
| 122 | 7.518 | — |
| 123 | 7.216 | — |
| 124 | 7.191 | — |
| 125 | 7.107 | 6.545 |
| 126 | 7.155 | — |
| 127 | 7.060 | — |
| 128 | 7.604 | — |
| 129 | 5.57 | — |
| 130 | 7.056 | — |
| 131 | 7.053 | — |
| 132 | 6.551 | — |
| 133 | 6.529 | — |
| 134 | 6.141 | — |
| 135 | 6.075 | — |
| 136 | 6.924 | 6.535 |

TABLE 1-continued hMRGX2 Cellular Potency (pEC$_{50}$) and Binding Affinity (pK$_d$)

| Ex. | pEC$_{50}$ | pK$_d$ |
|---|---|---|
| 137 | 7.102 | 6.54 |
| 138 | 6.721 | — |
| 139 | 6.609 | — |
| 140 | 6.160 | — |
| 141 | 6.436 | — |
| 142 | 6.612 | — |
| 143 | 6.354 | — |
| 144 | 6.665 | — |
| 145 | 6.850 | — |
| 146 | 6.790 | — |
| 147 | 7.292 | 6.67 |
| 148 | 7.770 | — |
| 149 | 6.495 | — |
| 150 | 6.381 | — |
| 151 | 6.250 | — |
| 152 | 6.651 | — |
| 153 | 7.564 | — |
| 154 | 7.492 | — |
| 155 | 7.454 | — |
| 156 | 7.323 | — |
| 157 | 7.250 | — |
| 158 | 6.640 | — |
| 159 | 7.271 | — |
| 160 | 7.030 | — |
| 161 | 7.211 | — |
| 162 | 6.998 | 6.51 |
| 163 | 6.745 | — |
| 164 | 6.648 | — |
| 165 | 6.540 | — |
| 166 | 6.468 | — |
| 167 | 6.404 | — |
| 168 | 6.328 | — |
| 169 | 6.324 | 5.95 |
| 170 | 6.195 | — |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A compound of Formula 1,

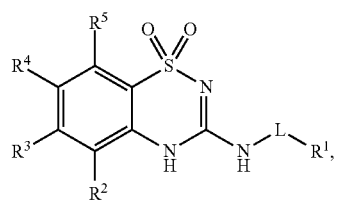

or a tautomer thereof, or a pharmaceutically acceptable salt of the compound of Formula 1 or tautomer thereof, wherein:

L is selected from a bond and $C_{1-4}$ alkanediyl;

$R^1$ is selected from
(a) $C_{1-4}$ alkyl which is substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl; and
(b) a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl;

$R^2$ is a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl;

$R^3$, $R^4$, and $R^5$ are each independently selected from hydrogen, halo, cyano, and $C_{1-3}$ alkyl;

wherein each of the aforementioned heterocyclyl and heteroaryl moieties independently has 1 to 4 heteroatoms as ring members, each independently selected from N, O, and S.

2. The compound, tautomer or pharmaceutically acceptable salt according to claim 1, wherein $R^1$ is $C_{1-4}$ alkyl which is substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

3. The compound, tautomer or pharmaceutically acceptable salt according to claim 2, wherein the $R^1$ $C_{1-4}$ alkyl is methyl or ethyl, each substituted with from 0 to 3 optional substituents independently selected from halo, hydroxy, cyano, $C_{1-4}$ alkoxy, amino and aminocarbonyl, wherein each of the $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

4. The compound, tautomer or pharmaceutically acceptable salt according to claim 2, wherein the $R^1$ $C_{1-4}$ alkyl is substituted with from 0 to 3 optional substituents independently selected from halo, $C_{1-4}$ alkoxy and aminocarbonyl, wherein each of the $C_{1-4}$ alkoxy optional substituents is independently substituted with from 0 to 3 substituents independently selected from halo, and wherein each of the aminocarbonyl optional substituents is independently substituted with from 0 to 2 substituents independently selected from $C_{1-4}$ alkyl.

5. The compound, tautomer or pharmaceutically acceptable salt according to claim 1, wherein $R^1$ is a cyclic group selected from $C_{3-8}$ cycloalkyl, $C_{2-9}$ heterocyclyl, $C_{6-14}$ aryl and $C_{1-9}$ heteroaryl, wherein the cyclic group is substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

6. The compound, tautomer or pharmaceutically acceptable salt according to claim 1, wherein $R^1$ is a cyclic group which is phenyl substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

7. The compound, tautomer or pharmaceutically acceptable salt according to claim 1, wherein $R^1$ is a cyclic group which is selected from pyrrolyl, furanyl, thienyl, pyrazolyl, imidazolyl, isoxazolyl, oxazolyl, isothiazolyl, thiazolyl, pyridinyl, pyridazinyl, pyrimidinyl, and pyrazinyl, each substituted with from 0 to 3 optional substituents independently selected from halo, hydroxy, cyano, $C_{1-4}$ alkyl, $C_{1-4}$ alkoxy, amino and aminocarbonyl, wherein each of the $C_{1-4}$ alkyl and $C_{1-4}$ alkoxy optional substituents is independently substituted with from 0 to 3 substituents independently selected from halo, and wherein each of the amino and aminocarbonyl optional substituents is independently substituted with from 0 to 2 substituents independently selected from $C_{1-4}$ alkyl.

8. The compound, tautomer or pharmaceutically acceptable salt according to claim 5, wherein the $R^1$ cyclic group is substituted with from 0 to 3 optional substituents independently selected from halo, hydroxy, cyano, $C_{1-4}$ alkyl, and $C_{1-4}$ alkoxy, wherein each of the $C_{1-4}$ alkyl and $C_{1-4}$ alkoxy optional substituents is independently substituted with from 0 to 3 substituents independently selected from halo.

9. The compound, tautomer or pharmaceutically acceptable salt according to claim 1, wherein L is selected from a bond, —$CH_2$—, —$CH_2CH_2$—, and —$CH(CH_3)$—.

10. The compound, tautomer or pharmaceutically acceptable salt according to claim 1, wherein L is —$CH_2$—.

11. The compound, tautomer or pharmaceutically acceptable salt according to claim 1, wherein L is a bond.

12. The compound, tautomer or pharmaceutically acceptable salt according to claim 1, wherein $R^2$ is a cyclic group which is phenyl substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

13. The compound, tautomer or pharmaceutically acceptable salt according to claim 1, wherein $R^2$ is a cyclic group which is selected from pyrazolyl, pyridinyl, and pyrimidinyl, each substituted with from 0 to 3 optional substituents independently selected from halo, hydroxy, cyano, $C_{1-4}$ alkyl, $C_{1-4}$ alkoxy, amino, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo, and wherein the amino optional substituent is independently substituted with from 0 to 2 substituents independently selected from $C_{1-4}$ alkyl.

14. The compound, tautomer or pharmaceutically acceptable salt according to claim 1, wherein the $R^2$ cyclic group is substituted with from 0 to 3 optional substituents independently selected from halo, cyano, $C_{1-4}$ alkyl, $C_{1-4}$ alkoxy, $C_{3-8}$ cycloalkyl and $C_{3-5}$ heterocyclyl, provided the cyclic group has no more than one optional substituent which is selected from $C_{3-8}$ cycloalkyl and $C_{3-5}$ heterocyclyl, and wherein each of the $C_{1-4}$ alkyl, $C_{1-4}$ alkoxy, $C_{3-8}$ cycloalkyl and $C_{3-5}$ heterocyclyl optional substituents is independently substituted with from 0 to 3 substituents independently selected from halo.

15. The compound, tautomer or pharmaceutically acceptable salt according to claim 1, wherein $R^3$, $R^4$ and $R^5$ are each independently selected from hydrogen, halo and $C_{1-3}$ alkyl.

16. The compound, tautomer or pharmaceutically acceptable salt according to claim 1, wherein $R^3$, $R^4$ and $R^5$ are each hydrogen.

17. A compound selected from the following compounds and tautomers thereof:
  5-(2-chloro-3-fluorophenyl)-3-(methylamino)-4H-benzo[e][1,2,4]thiadiazine 1,1-dioxide;
  5-(2-chloro-3-fluorophenyl)-3-((2-methoxyethyl)amino)-4H-benzo[e][1,2,4]thiadiazine 1,1-dioxide;
  5-(2-chloro-3-fluorophenyl)-7-fluoro-3-(methylamino)-4H-benzo[e][1,2,4]thiadiazine 1,1-dioxide;
  5-(2-chloro-3-fluorophenyl)-7-fluoro-3-((2-methoxyethyl)amino)-4H-benzo[e][1,2,4]thiadiazine 1,1-dioxide;
  5-(2-chloro-3-fluorophenyl)-7-fluoro-3-((thiazol-2-ylmethyl)amino)-4H-benzo[e][1,2,4]thiadiazine 1,1-dioxide;
  5-(2-chloro-3-fluorophenyl)-3-(ethylamino)-7-fluoro-4H-benzo[e][1,2,4]thiadiazine 1,1-dioxide;
  5-(2-chloro-3-fluorophenyl)-3-((cyclopropylmethyl)amino)-7-fluoro-4H-benzo[e][1,2,4]thiadiazine 1,1-dioxide;
  5-(2-chloro-3-fluorophenyl)-7-fluoro-3-((1-(thiazol-2-yl)ethyl)amino)-4H-benzo[e][1,2,4]thiadiazine 1,1-dioxide;
  5-(2-chloro-3-fluorophenyl)-7-fluoro-3-((1-(thiazol-4-yl)ethyl)amino)-4H-benzo[e][1,2,4]thiadiazine 1,1-dioxide;

5-(2-chloro-3-fluorophenyl)-3-((2,2-difluoroethyl) amino)-7-fluoro-4H-benzo[e][1,2,4]thiadiazine 1,1-dioxide;

5-(2-chloro-3-fluorophenyl)-7-fluoro-3-((2-fluoroethyl) amino)-4H-benzo[e][1,2,4]thiadiazine 1,1-dioxide;

5-(2-chloro-3-fluorophenyl)-3-(((3-fluoropyridin-2-yl) methyl)amino)-4H-benzo[e][1,2,4]thiadiazine 1,1-dioxide;

5-(2-chlorophenyl)-7-fluoro-3-(methylamino)-4H-benzo [e][1,2,4]thiadiazine 1,1-dioxide;

5-(2-chlorophenyl)-7-fluoro-3-((2-methoxyethyl)amino)-4H-benzo[e][1,2,4]thiadiazine 1,1-dioxide;

5-(2-chlorophenyl)-3-(ethylamino)-7-fluoro-4H-benzo[e][1,2,4]thiadiazine 1,1-dioxide;

5-(2-chlorophenyl)-7-fluoro-3-(((3-fluoropyridin-2-yl) methyl)amino)-4H-benzo[e][1,2,4]thiadiazine 1,1-dioxide;

5-(2-chloro-3-fluorophenyl)-3-((cyclobutylmethyl) amino)-4H-benzo[e][1,2,4]thiadiazine 1,1-dioxide;

5-(2-chloro-3-fluorophenyl)-3-(((6-methoxypyridin-2-yl) methyl)amino)-4H-benzo[e][1,2,4]thiadiazine 1,1-dioxide;

5-(2,3-difluorophenyl)-3-(((6-methoxypyridin-2-yl) methyl)amino)-4H-benzo[e][1,2,4]thiadiazine 1,1-dioxide;

3-(((5-(2,3-difluorophenyl)-1,1-dioxido-4H-benzo[e][1,2,4]thiadiazin-3-yl)amino)methyl)-1-methylpyridin-2(1H)-one;

5-(2,3-difluorophenyl)-3-((2-fluoroethyl)amino)-4H-benzo[e][1,2,4]thiadiazine 1,1-dioxide;

3-((cyclobutylmethyl)amino)-5-(2,3-difluorophenyl)-4H-benzo[e][1,2,4]thiadiazine 1,1-dioxide;

5-(2,3-difluorophenyl)-3-((2-methoxypropyl)amino)-4H-benzo[e][1,2,4]thiadiazine 1,1-dioxide;

(R)-5-(2,3-difluorophenyl)-3-((2-methoxypropyl)amino)-4H-benzo[e][1,2,4]thiadiazine 1,1-dioxide;

(S)-5-(2,3-difluorophenyl)-3-((2-methoxypropyl)amino)-4H-benzo[e][1,2,4]thiadiazine 1,1-dioxide;

5-(2,3-difluorophenyl)-3-(methylamino)-4H-benzo[e][1,2,4]thiadiazine 1,1-dioxide;

5-(2,3-difluorophenyl)-3-((oxazol-2-ylmethyl)amino)-4H-benzo[e][1,2,4]thiadiazine 1,1-dioxide;

5-(2-chloro-3-fluorophenyl)-3-((oxazol-2-ylmethyl) amino)-4H-benzo[e][1,2,4]thiadiazine 1,1-dioxide;

5-(2-chloro-3-fluorophenyl)-3-((cyclopropylmethyl) amino)-4H-benzo[e][1,2,4]thiadiazine 1,1-dioxide;

5-(2-chloro-3-fluorophenyl)-3-(((4-methyloxazol-2-yl) methyl)amino)-4H-benzo[e][1,2,4]thiadiazine 1,1-dioxide;

5-(2-chloro-3-fluorophenyl)-3-((pyridin-2-ylmethyl) amino)-4H-benzo[e][1,2,4]thiadiazine 1,1-dioxide;

5-(2-chloro-3,5-difluorophenyl)-3-((2-methoxyethyl) amino)-4H-benzo[e][1,2,4]thiadiazine 1,1-dioxide;

5-(2-chloro-3-fluorophenyl)-3-((2-methoxypropyl) amino)-4H-benzo[e][1,2,4]thiadiazine 1,1-dioxide;

5-(2-chloro-3-fluorophenyl)-3-((2,2-difluoroethyl) amino)-4H-benzo[e][1,2,4]thiadiazine 1,1-dioxide;

5-(2-chlorophenyl)-3-((2-methoxyethyl)amino)-4H-benzo[e][1,2,4]thiadiazine 1,1-dioxide;

5-(3-chloro-2-fluoropyridin-4-yl)-3-((2-methoxyethyl) amino)-4H-benzo[e][1,2,4]thiadiazine 1,1-dioxide;

5-(2,3-difluorophenyl)-3-((2-methoxyethyl)amino)-4H-benzo[e][1,2,4]thiadiazine 1,1-dioxide;

5-(2-chloro-3-fluorophenyl)-3-(((5-methyloxazol-2-yl) methyl)amino)-4H-benzo[e][1,2,4]thiadiazine 1,1-dioxide;

5-(2-chloro-3-fluorophenyl)-3-(ethylamino)-4H-benzo[e][1,2,4]thiadiazine 1,1-dioxide;

5-(2-chlorophenyl)-3-((2-methoxypropyl)amino)-4H-benzo[e][1,2,4]thiadiazine 1,1-dioxide;

5-(2-chlorophenyl)-3-((pyridin-2-ylmethyl)amino)-4H-benzo[e][1,2,4]thiadiazine 1,1-dioxide;

5-(2-chlorophenyl)-3-(ethylamino)-4H-benzo[e][1,2,4]thiadiazine 1,1-dioxide;

5-(2-chlorophenyl)-3-(methylamino)-4H-benzo[e][1,2,4]thiadiazine 1,1-dioxide;

5-(2-chlorophenyl)-3-((2,2-difluoroethyl)amino)-4H-benzo[e][1,2,4]thiadiazine 1,1-dioxide;

5-(2-chlorophenyl)-3-((2-fluoroethyl)amino)-4H-benzo[e][1,2,4]thiadiazine 1,1-dioxide;

3-(((5-(2-chloro-3-fluorophenyl)-1,1-dioxido-4H-benzo[e][1,2,4]thiadiazin-3-yl)amino)methyl)-1-methylpyridin-2(1H)-one;

(R)-5-(2-chloro-3-fluorophenyl)-3-((2-methoxypropyl) amino)-4H-benzo[e][1,2,4]thiadiazine 1,1-dioxide;

5-(3-chloro-2-fluoropyridin-4-yl)-3-((oxazol-2-ylmethyl) amino)-4H-benzo[e][1,2,4]thiadiazine 1,1-dioxide;

5-(3-chloro-2-fluoropyridin-4-yl)-3-((thiazol-2-ylmethyl) amino)-4H-benzo[e][1,2,4]thiadiazine 1,1-dioxide;

5-(3-chloro-2-fluoropyridin-4-yl)-3-((cyclopropylmethyl)amino)-4H-benzo[e][1,2,4]thiadiazine 1,1-dioxide;

5-(3-chloro-2-fluoropyridin-4-yl)-3-(((3-fluoropyridin-2-yl)methyl)amino)-4H-benzo[e][1,2,4]thiadiazine 1,1-dioxide;

5-(3-chloro-2-fluoropyridin-4-yl)-3-(ethylamino)-4H-benzo[e][1,2,4]thiadiazine 1,1-dioxide;

5-(3-chloro-2-fluoropyridin-4-yl)-3-((2,2-difluoroethyl) amino)-4H-benzo[e][1,2,4]thiadiazine 1,1-dioxide;

5-(3-chloro-2-fluoropyridin-4-yl)-3-((4-fluorobenzyl) amino)-4H-benzo[e][1,2,4]thiadiazine 1,1-dioxide;

2-(((5-(3-chloro-2-fluoropyridin-4-yl)-1,1-dioxido-4H-benzo[e][1,2,4]thiadiazin-3-yl)amino)methyl)thiazole-5-carbonitrile;

5-(3-chloro-2-fluoropyridin-4-yl)-3-(methylamino)-4H-benzo[e][1,2,4]thiadiazine 1,1-dioxide;

5-(2-chloro-3-fluorophenyl)-3-(((4-methylmorpholin-2-yl)methyl)amino)-4H-benzo[e][1,2,4]thiadiazine 1,1-dioxide;

5-(2-chloro-3-fluorophenyl)-3-((2-ethoxypropyl)amino)-4H-benzo[e][1,2,4]thiadiazine 1,1-dioxide;

3-(((5-chloropyridin-2-yl)methyl)amino)-5-(1,3-dimethyl-1H-pyrazol-4-yl)-4H-benzo[e][1,2,4]thiadiazine 1,1-dioxide;

5-(1,3-dimethyl-1H-pyrazol-4-yl)-3-((2-methoxypropyl) amino)-4H-benzo[e][1,2,4]thiadiazine 1,1-dioxide;

3-((cyclobutylmethyl)amino)-5-(1,3-dimethyl-1H-pyrazol-4-yl)-4H-benzo[e][1,2,4]thiadiazine 1,1-dioxide;

2-((5-(2-chloro-3-fluorophenyl)-1,1-dioxido-4H-benzo[e][1,2,4]thiadiazin-3-yl)amino)-N,N-dimethylacetamide;

5-(2-cyclopropylphenyl)-3-((2-methoxyethyl)amino)-4H-benzo[e][1,2,4]thiadiazine 1,1-dioxide;

5-(2-chloro-3-fluorophenyl)-3-((isothiazol-3-ylmethyl) amino)-4H-benzo[e][1,2,4]thiadiazine 1,1-dioxide;

5-(2-chloro-3-fluorophenyl)-3-((thiazol-2-ylmethyl) amino)-4H-benzo[e][1,2,4]thiadiazine 1,1-dioxide;

5-(2-chloro-3-fluorophenyl)-3-((pyrimidin-2-ylmethyl) amino)-4H-benzo[e][1,2,4]thiadiazine 1,1-dioxide;

5-(2-chloro-3-fluorophenyl)-3-((2-(pyridin-2-yl)ethyl) amino)-4H-benzo[e][1,2,4]thiadiazine 1,1-dioxide;

5-(2-chloro-3-fluorophenyl)-3-((2-(pyridin-4-yl)ethyl) amino)-4H-benzo[e][1,2,4]thiadiazine 1,1-dioxide;

5-(2-chloro-3-fluorophenyl)-3-((2-(pyridin-3-yl)ethyl)amino)-4H-benzo[e][1,2,4]thiadiazine 1,1-dioxide;
5-(2-chloro-3-fluorophenyl)-3-((3-methoxyphenethyl)amino)-4H-benzo[e][1,2,4]thiadiazine 1,1-dioxide;
5-(2-chloro-3-fluorophenyl)-3-((2-methoxyphenethyl)amino)-4H-benzo[e][1,2,4]thiadiazine 1,1-dioxide;
5-(2-chloro-3-fluorophenyl)-3-((4-methoxyphenethyl)amino)-4H-benzo[e][1,2,4]thiadiazine 1,1-dioxide;
5-(2-chloro-3-fluorophenyl)-3-((2-(tetrahydrofuran-2-yl)ethyl)amino)-4H-benzo[e][1,2,4]thiadiazine 1,1-dioxide;
5-(2-chloro-3-fluorophenyl)-3-((1-isopropyl-5-methyl-1H-pyrazol-3-yl)amino)-4H-benzo[e][1,2,4]thiadiazine 1,1-dioxide;
5-(3,5-difluorophenyl)-3-((4-fluorobenzyl)amino)-4H-benzo[e][1,2,4]thiadiazine 1,1-dioxide;
3-((2,5-difluorobenzyl)amino)-5-(3,5-difluorophenyl)-4H-benzo[e][1,2,4]thiadiazine 1,1-dioxide;
5-(3,5-difluorophenyl)-3-((2-fluorobenzyl)amino)-4H-benzo[e][1,2,4]thiadiazine 1,1-dioxide;
3-((2,6-difluorobenzyl)amino)-5-(3,5-difluorophenyl)-4H-benzo[e][1,2,4]thiadiazine 1,1-dioxide;
5-(3,5-difluorophenyl)-3-(((6-methylpyridin-2-yl)methyl)amino)-4H-benzo[e][1,2,4]thiadiazine 1,1-dioxide;
5-(3,5-difluorophenyl)-3-((2-(pyridin-2-yl)ethyl)amino)-4H-benzo[e][1,2,4]thiadiazine 1,1-dioxide;
3-((cyclobutylmethyl)amino)-5-(3,5-difluorophenyl)-4H-benzo[e][1,2,4]thiadiazine 1,1-dioxide;
5-(3,5-difluorophenyl)-3-((pyridin-4-ylmethyl)amino)-4H-benzo[e][1,2,4]thiadiazine 1,1-dioxide;
5-(3,5-difluorophenyl)-3-((pyridin-2-ylmethyl)amino)-4H-benzo[e][1,2,4]thiadiazine 1,1-dioxide;
5-(3,5-difluorophenyl)-3-((2-methoxypropyl)amino)-4H-benzo[e][1,2,4]thiadiazine 1,1-dioxide;
(R)-5-(3,5-difluorophenyl)-3-((2-methoxypropyl)amino)-4H-benzo[e][1,2,4]thiadiazine 1,1-dioxide;
(S)-5-(3,5-difluorophenyl)-3-((2-methoxypropyl)amino)-4H-benzo[e][1,2,4]thiadiazine 1,1-dioxide;
5-(3,5-difluorophenyl)-3-((2-methoxybutyl)amino)-4H-benzo[e][1,2,4]thiadiazine 1,1-dioxide;
3-(benzylamino)-5-(3,5-difluorophenyl)-4H-benzo[e][1,2,4]thiadiazine 1,1-dioxide;
2-fluoro-6-(3-(methylamino)-1,1-dioxido-4H-benzo[e][1,2,4]thiadiazin-5-yl)benzonitrile;
4-chloro-2-(3-(methylamino)-1,1-dioxido-4H-benzo[e][1,2,4]thiadiazin-5-yl)benzonitrile;
5-(2-ethylphenyl)-3-(methylamino)-4H-benzo[e][1,2,4]thiadiazine 1,1-dioxide;
5-(2-chloro-4-methylphenyl)-3-(methylamino)-4H-benzo[e][1,2,4]thiadiazine 1,1-dioxide;
5-(2-chloro-5-fluorophenyl)-3-(methylamino)-4H-benzo[e][1,2,4]thiadiazine 1,1-dioxide;
5-(2-chloro-4-fluorophenyl)-3-(methylamino)-4H-benzo[e][1,2,4]thiadiazine 1,1-dioxide;
5-(3-fluoro-2-methylphenyl)-3-(methylamino)-4H-benzo[e][1,2,4]thiadiazine 1,1-dioxide;
3-(methylamino)-5-(2,3,5-trifluorophenyl)-4H-benzo[e][1,2,4]thiadiazine 1,1-dioxide;
5-(2-chloro-3-fluorophenyl)-7-methyl-3-(methylamino)-4H-benzo[e][1,2,4]thiadiazine 1,1-dioxide;
3-((4-isopropylphenyl)amino)-5-(5-methyl-1H-pyrazol-3-yl)-4H-benzo[e][1,2,4]thiadiazine 1,1-dioxide;
5-(1-(difluoromethyl)-1H-pyrazol-4-yl)-3-((4-isopropylphenyl)amino)-4H-benzo[e][1,2,4]thiadiazine 1,1-dioxide;
3-((4-isopropylphenyl)amino)-5-(1H-pyrazol-1-yl)-4H-benzo[e][1,2,4]thiadiazine 1,1-dioxide;
3-((4-isopropylphenyl)amino)-5-(1-(oxetan-3-yl)-1H-pyrazol-4-yl)-4H-benzo[e][1,2,4]thiadiazine 1,1-dioxide;
5-(1-ethyl-1H-pyrazol-4-yl)-3-((4-isopropylphenyl)amino)-4H-benzo[e][1,2,4]thiadiazine 1,1-dioxide;
5-(1,3-dimethyl-1H-pyrazol-4-yl)-3-((4-isopropylphenyl)amino)-4H-benzo[e][1,2,4]thiadiazine 1,1-dioxide;
5-(1-(3,3-difluorocyclobutyl)-1H-pyrazol-4-yl)-3-((4-isopropylphenyl)amino)-4H-benzo[e][1,2,4]thiadiazine 1,1-dioxide;
5-(1-cyclobutyl-1H-pyrazol-4-yl)-3-((4-isopropylphenyl)amino)-4H-benzo[e][1,2,4]thiadiazine 1,1-dioxide;
3-((4-isopropylphenyl)amino)-5-(3-methyl-1H-pyrazol-4-yl)-4H-benzo[e][1,2,4]thiadiazine 1,1-dioxide;
3-((4-isopropylphenyl)amino)-5-(1-methyl-1H-pyrazol-4-yl)-4H-benzo[e][1,2,4]thiadiazine 1,1-dioxide;
3-((4-isopropylphenyl)amino)-5-(1-methyl-1H-pyrazol-3-yl)-4H-benzo[e][1,2,4]thiadiazine 1,1-dioxide;
5-cyclopropyl-3-((4-isopropylphenyl)amino)-4H-benzo[e][1,2,4]thiadiazine 1,1-dioxide;
5-isopropyl-3-((4-isopropylphenyl)amino)-4H-benzo[e][1,2,4]thiadiazine 1,1-dioxide;
5-cyclobutyl-3-((4-isopropylphenyl)amino)-4H-benzo[e][1,2,4]thiadiazine 1,1-dioxide;
5-(2-chlorophenyl)-3-((4-isopropylphenyl)amino)-4H-benzo[e][1,2,4]thiadiazine 1,1-dioxide;
3-((4-isopropylphenyl)amino)-5-(3-methylpyridin-4-yl)-4H-benzo[e][1,2,4]thiadiazine 1,1-dioxide;
5-(1,5-dimethyl-1H-pyrazol-4-yl)-3-((4-isopropylphenyl)amino)-4H-benzo[e][1,2,4]thiadiazine 1,1-dioxide;
5-(1,3-dimethyl-1H-pyrazol-4-yl)-3-((3-isopropylphenyl)amino)-4H-benzo[e][1,2,4]thiadiazine 1,1-dioxide;
5-cyclopropyl-3-((3-isopropylphenyl)amino)-4H-benzo[e][1,2,4]thiadiazine 1,1-dioxide;
5-(2-chlorophenyl)-3-((6-isopropylpyridin-3-yl)amino)-4H-benzo[e][1,2,4]thiadiazine 1,1-dioxide;
5-cyclopropyl-3-((6-isopropylpyridin-3-yl)amino)-4H-benzo[e][1,2,4]thiadiazine 1,1-dioxide;
5-cyclopropyl-3-(((3-fluoropyridin-2-yl)methyl)amino)-4H-benzo[e][1,2,4]thiadiazine 1,1-dioxide;
5-cyclopropyl-3-(((6-methoxypyridin-2-yl)methyl)amino)-4H-benzo[e][1,2,4]thiadiazine 1,1-dioxide;
5-cyclopropyl-3-(phenylamino)-4H-benzo[e][1,2,4]thiadiazine 1,1-dioxide;
5-(2-chloro-3-fluorophenyl)-3-(((3-methoxypyridin-2-yl)methyl)amino)-4H-benzo[e][1,2,4]thiadiazine 1,1-dioxide;
5-(2-chloro-3-fluorophenyl)-3-(((tetrahydrofuran-2-yl)methyl)amino)-4H-benzo[e][1,2,4]thiadiazine 1,1-dioxide;
3-((2-methoxyethyl)amino)-5-(2-(trifluoromethyl)phenyl)-4H-benzo[e][1,2,4]thiadiazine 1,1-dioxide;
2-fluoro-6-(3-((2-methoxyethyl)amino)-1,1-dioxido-4H-benzo[e][1,2,4]thiadiazin-5-yl)benzonitrile;
2-(1,1-dioxido-3-((thiazol-2-ylmethyl)amino)-4H-benzo[e][1,2,4]thiadiazin-5-yl)-6-fluorobenzonitrile;
3-((2-methoxypropyl)amino)-5-(2,3,5-trifluorophenyl)-4H-benzo[e][1,2,4]thiadiazine 1,1-dioxide;
(S)-3-((2-methoxypropyl)amino)-5-(2,3,5-trifluorophenyl)-4H-benzo[e][1,2,4]thiadiazine 1,1-dioxide;
(R)-3-((2-methoxypropyl)amino)-5-(2,3,5-trifluorophenyl)-4H-benzo[e][1,2,4]thiadiazine 1,1-dioxide;
3-((cyclobutylmethyl)amino)-5-(2,3,5-trifluorophenyl)-4H-benzo[e][1,2,4]thiadiazine 1,1-dioxide;

3-((pyridin-2-ylmethyl)amino)-5-(2,3,5-trifluorophenyl)-4H-benzo[e][1,2,4]thiadiazine 1,1-dioxide;

5-(2-chloro-3-(trifluoromethyl)phenyl)-3-((2-methoxyethyl)amino)-4H-benzo[e][1,2,4]thiadiazine 1,1-dioxide;

5-(2-chloro-4-fluorophenyl)-3-((2-methoxyethyl)amino)-4H-benzo[e][1,2,4]thiadiazine 1,1-dioxide;

5-(2-chloro-5-(trifluoromethyl)phenyl)-3-((2-methoxyethyl)amino)-4H-benzo[e][1,2,4]thiadiazine 1,1-dioxide;

5-(3-chloro-2-fluorophenyl)-3-((2-methoxyethyl)amino)-4H-benzo[e][1,2,4]thiadiazine 1,1-dioxide;

3-((4-ethylphenyl)amino)-5-(1-methyl-1H-pyrazol-4-yl)-4H-benzo[e][1,2,4]thiadiazine 1,1-dioxide;

3-((furan-2-ylmethyl)amino)-5-(o-tolyl)-4H-benzo[e][1,2,4]thiadiazine 1,1-dioxide;

5-(2-chlorophenyl)-6-fluoro-3-(methylamino)-4H-benzo[e][1,2,4]thiadiazine 1,1-dioxide;

5-(2,5-difluorophenyl)-3-((pyridin-2-ylmethyl)amino)-4H-benzo[e][1,2,4]thiadiazine 1,1-dioxide;

3-((cyclopropylmethyl)amino)-5-(2,5-difluorophenyl)-4H-benzo[e][1,2,4]thiadiazine 1,1-dioxide;

5-(2,5-difluorophenyl)-3-((2-methoxyethyl)amino)-4H-benzo[e][1,2,4]thiadiazine 1,1-dioxide;

5-(2,5-difluorophenyl)-3-((2-methoxypropyl)amino)-4H-benzo[e][1,2,4]thiadiazine 1,1-dioxide;

5-(2,5-difluorophenyl)-3-(ethylamino)-4H-benzo[e][1,2,4]thiadiazine 1,1-dioxide;

5-(2-chloro-5-fluorophenyl)-3-((2-methoxyethyl)amino)-4H-benzo[e][1,2,4]thiadiazine 1,1-dioxide;

2-(3-((2-methoxypropyl)amino)-1,1-dioxido-4H-benzo[e][1,2,4]thiadiazin-5-yl)benzonitrile;

2-(3-((cyclobutylmethyl)amino)-1,1-dioxido-4H-benzo[e][1,2,4]thiadiazin-5-yl)benzonitrile;

5-(2-chloro-3-fluorophenyl)-3-((2-fluoroethyl)amino)-4H-benzo[e][1,2,4]thiadiazine 1,1-dioxide;

5-(2-chloro-3-fluorophenyl)-3-(((6-fluoropyridin-2-yl)methyl)amino)-4H-benzo[e][1,2,4]thiadiazine 1,1-dioxide;

2-fluoro-6-(3-((2-fluoroethyl)amino)-1,1-dioxido-4H-benzo[e][1,2,4]thiadiazin-5-yl)benzonitrile;

2-fluoro-6-(3-((2-methoxypropyl)amino)-1,1-dioxido-4H-benzo[e][1,2,4]thiadiazin-5-yl)benzonitrile;

5-(2-chloro-3-fluorophenyl)-3-((3-methoxypropyl)amino)-4H-benzo[e][1,2,4]thiadiazine 1,1-dioxide;

5-(2-chloro-3-fluorophenyl)-3-((3-fluoropropyl)amino)-4H-benzo[e][1,2,4]thiadiazine 1,1-dioxide;

5-(2-chloro-3-fluorophenyl)-3-((3-methoxybutyl)amino)-4H-benzo[e][1,2,4]thiadiazine 1,1-dioxide;

(R)-5-(2-chloro-3-fluorophenyl)-3-((3-methoxybutyl)amino)-4H-benzo[e][1,2,4]thiadiazine 1,1-dioxide;

(S)-5-(2-chloro-3-fluorophenyl)-3-((3-methoxybutyl)amino)-4H-benzo[e][1,2,4]thiadiazine 1,1-dioxide;

5-(2-cyclopropyl-3-fluorophenyl)-3-((2-methoxyethyl)amino)-4H-benzo[e][1,2,4]thiadiazine 1,1-dioxide;

5-(2-cyclopropyl-3-fluorophenyl)-3-(methylamino)-4H-benzo[e][1,2,4]thiadiazine 1,1-dioxide;

5-(2-chloro-3-fluorophenyl)-3-(isopropylamino)-4H-benzo[e][1,2,4]thiadiazine 1,1-dioxide;

5-(2-chloro-3-fluorophenyl)-3-(cyclopropylamino)-4H-benzo[e][1,2,4]thiadiazine 1,1-dioxide;

5-(2-chloro-3-fluorophenyl)-3-((2-(2,2-difluoroethoxy)ethyl)amino)-4H-benzo[e][1,2,4]thiadiazine 1,1-dioxide;

2-fluoro-6-(3-((oxazol-2-ylmethyl)amino)-1,1-dioxido-4H-benzo[e][1,2,4]thiadiazin-5-yl)benzonitrile;

3-((pyridin-2-ylmethyl)amino)-5-(o-tolyl)-4H-benzo[e][1,2,4]thiadiazine 1,1-dioxide;

5-(2-ethylphenyl)-3-((2-methoxyethyl)amino)-4H-benzo[e][1,2,4]thiadiazine 1,1-dioxide;

5-(3,5-difluorophenyl)-3-((furan-2-ylmethyl)amino)-4H-benzo[e][1,2,4]thiadiazine 1,1-dioxide;

5-(2,3-difluorophenyl)-3-(ethylamino)-4H-benzo[e][1,2,4]thiadiazine 1,1-dioxide;

5-(3,5-difluorophenyl)-3-((2-methoxypropyl)amino)-4H-benzo[e][1,2,4]thiadiazine 1,1-dioxide;

5-(2-chloro-3-fluorophenyl)-3-((3-methoxycyclobutyl)amino)-4H-benzo[e][1,2,4]thiadiazine 1,1-dioxide;

3-((2-methoxyethyl)amino)-5-(2,3,5-trifluorophenyl)-4H-benzo[e][1,2,4]thiadiazine 1,1-dioxide;

3-((4-isopropylphenyl)amino)-5-(methoxymethyl)-4H-benzo[e][1,2,4]thiadiazine 1,1-dioxide;

5-(3,4-difluoro-2-methylphenyl)-3-((2-methoxyethyl)amino)-4H-benzo[e][1,2,4]thiadiazine 1,1-dioxide; and a pharmaceutically acceptable salt of any one of the aforementioned compounds and tautomers.

18. A pharmaceutical composition comprising:
a compound, tautomer or pharmaceutically acceptable salt as defined in claim 1; and
a pharmaceutically acceptable excipient.

19. A method for inhibiting MRGX2 in a subject, the method comprising administering to the subject a compound, tautomer or pharmaceutically acceptable salt as defined in claim 1.

20. A method of treating a disease, disorder or condition in a subject, the method comprising administering to the subject a compound, tautomer or pharmaceutically acceptable salt as defined in claim 1, wherein the disease, disorder or condition is selected from systemic lupus erythematosus (SLE), psoriasis, psoriatic arthritis, rosacea, chronic urticaria, atopic dermatitis, rheumatoid arthritis, bronchial asthma, irritable bowel syndrome (IBS), systemic mastocytosis, cutaneous mastocytosis, mastocytic enterocolitis, mast cell activation syndrome (MCAS), interstitial cystitis, food allergy, pruiritis, allergic rhinitis, microbial infection, eosinophilic esophagitis (EOE) and chronic pain.

21. A combination comprising a compound, tautomer or pharmaceutically acceptable salt as defined in claim 1, and at least one additional pharmacologically active agent.

22. The combination according to claim 21, wherein the additional pharmacologically active agent is selected from anti-inflammatory agents, analgesics, biological response modifiers, disease modifying antirheumatic drugs (DMARDs), antihistamines, mast cell stabilizers, prokinetic agents, antidiarrheals, prosecretory agents, antibiotics, antidepressants, anxiolytics, antipsychotics and anticonvulsants.

* * * * *